US010752609B2

(12) United States Patent
Hartz et al.

(10) Patent No.: US 10,752,609 B2
(45) Date of Patent: Aug. 25, 2020

(54) GSK-3 INHIBITORS

(71) Applicant: BRISTOL-MYERS SQUIBB COMPANY, Princeton, NJ (US)

(72) Inventors: Richard A. Hartz, Ewing, NJ (US); Vijay T. Ahuja, Princeton, NJ (US); Guanglin Luo, Newtown, PA (US); Ling Chen, Doylestown, PA (US); Prasanna Sivaprakasam, Lawrenceville, NJ (US); Gene M. Dubowchik, Middlefield, CT (US); Swanee E. Jacutin-Porte, Madison, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/463,467

(22) PCT Filed: Nov. 27, 2017

(86) PCT No.: PCT/US2017/063231

§ 371 (c)(1),
(2) Date: May 23, 2019

(87) PCT Pub. No.: WO2018/098412

PCT Pub. Date: May 31, 2018

(65) Prior Publication Data

US 2019/0315714 A1 Oct. 17, 2019

Related U.S. Application Data

(60) Provisional application No. 62/426,631, filed on Nov. 28, 2016.

(51) Int. Cl.

| | |
|---|---|
| ***C07D 401/12*** | (2006.01) |
| ***A61P 25/28*** | (2006.01) |
| ***C07D 401/14*** | (2006.01) |
| ***C07D 403/12*** | (2006.01) |
| ***C07D 405/14*** | (2006.01) |
| ***C07D 417/14*** | (2006.01) |

(52) U.S. Cl.

CPC ............ *C07D 401/12* (2013.01); *A61P 25/28* (2018.01); *C07D 401/14* (2013.01); *C07D 403/12* (2013.01); *C07D 405/14* (2013.01); *C07D 417/14* (2013.01)

(58) Field of Classification Search

CPC .................................................... C07D 401/12
USPC ........................................................ 514/272
See application file for complete search history.

(56) References Cited

FOREIGN PATENT DOCUMENTS

| | | | |
|---|---|---|---|
| WO | WO2009014637 | A3 | 3/2009 |
| WO | WO2015069594 | A1 | 5/2015 |

*Primary Examiner* — Kahsay Habte
(74) *Attorney, Agent, or Firm* — Elliott Korsen; Shrikant M. Kulkarni

(57) ABSTRACT

The disclosure generally relates to compounds of formula I, including their salts, as well as compositions and methods of using the compounds to treat disorders associated with GSK-3.

I

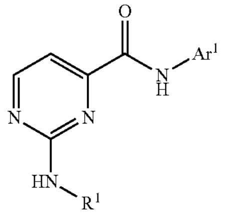

10 Claims, No Drawings

GSK-3 INHIBITORS

CROSS REFERENCE TO RELATED APPLICATION

This application claims the priority of U.S. provisional Ser. No. 62/426,631 filed Nov. 28, 2016 which is herein incorporated by reference.

BACKGROUND OF THE INVENTION

The disclosure generally relates to compounds of formula I, including their salts, as well as compositions and methods of using the compounds. The compounds inhibit GSK-3 and may be useful for the treatment of various disorders of the central nervous system.

GSK-3 is a proline directed serine/threonine kinase that carries out the phosphorylation of multiple protein substrates. Many of these proteins are involved in the regulation of numerous diverse cellular functions, including metabolism, differentiation, proliferation and apoptosis. GSK-3 is constitutively active, with its base level of activity being positively modulated by phosphorylation on Tyr216/219, depending on isoform. GSK-3 has a unique substrate selectivity profile that is distinguished by the strong preference for the presence of a phosphorylated residue optimally located four amino acids C-terminal to the site of GSK-3 phosphorylation. Most commonly, GSK-3 activity is associated with inducing a loss of substrate function, such that GSK-3 inhibition will frequently result in increased downstream substrate activity.

GSK-3 exists in two isoforms, GSK-3α (51 kDa) and GSK-3β (47 kDa), that share 84% overall identity and greater than 98% identity within their respective catalytic domains. Both primary isoforms are ubiquitously expressed, with high levels observed in the brain, particularly in the cortex and hippocampus. In most brain areas, GSK-3β is the predominant isoform. However, some studies suggest that GKS-3α and GSK-3β share very similar, if not entirely redundant functions in a number of cellular processes. The activity of GSK-3β is significantly reduced by phosphorylation at Ser9 in the N-terminal domain, most notably by protein kinase B (PKB or AKT). This inhibitory pathway has been proposed to result in neuroprotection, neurogenesis, and favorable outcomes following pharmacological treatment in various mood disorders.

Alzheimer's disease (AD) pathology is prominently associated with the formation of beta-amyloid (Aβ) plaques, soluble forms of Aβ such as Aβ1-42 that are associated with increased neuronal toxicity, and neurofibrillary tangles (NFTs). There is evidence to suggest that certain pathological mechanisms in AD, such as Aβ1-42, cause increases in GSK-3 activity in the brain. A principal consequence of this dysregulation is the hyperphosphorylation of the microtubule associated protein tau. This function of GSK-3 has been demonstrated both in cell culture, and in in vivo studies looking at tau and NFT formation. Hyper-phosphorylated tau disengages from microtubules resulting in structural destabilization of microtubules with concomitant negative effects on intracellular structures and transport mechanisms. In addition, the uncomplexed hyperphosphorylated tau assembles into paired helical filaments (PHFs) that aggregate to produce the stereotypic intracellular NFTs associated with AD. Other potential pathological consequences of over-activation of GSK-3 include neuroinflammation and neuronal apoptosis. In addition, GSK-3 has been demonstrated to be involved in mechanisms underlying memory and learning, and dysregulation of GSK-3 function may explain some of the early cognitive deficits observed in AD.

GSK-3 is also known to play a key role in glucose metabolism, and was first identified as the enzyme responsible for effecting the inhibitory phosphorylation of glycogen synthase, the result of which is to reduce the rate of conversion of glucose to glycogen, giving rise to elevated blood glucose levels. This function of GSK-3 is controlled by insulin. Binding of insulin to its receptor leads indirectly to the activation of AKT and subsequent inhibitory Ser9 phosphorylation of GSK-3.

These results and observations suggest that modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral schlerosis, stroke, Huntington's disease, peripheral neuropathies, traumatic brain injury, spinal cord trauma, and vascular dementias.

Compounds that inhibit GSK-3 may also have utility in the treatment of diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma. Inhibition of GSK-3 has also been shown to downregulate PD-1 in T-reg cells, enhancing viral clearance in vivo (*Immunity*, Volume 44, Issue 2, 16 Feb. 2016).

Recent reviews on the functions of GSK-3, potential therapeutic applications, and other compounds that inhibit the enzyme are listed below: Kaidanovich-Beilin O and Woodgett JR (2011) GSK-3: functional insights from cell biology and animal models. *Front. Mol. Neurosci.* 4:40. doi: 10.3389/fnmol.2011.00040; "Glycogen Synthase Kinase 3 (GSK-3) and Its Inhibitors", Martinez, Ana/Castro, Ana/Medina, Miguel (eds.), John Wiley and Sons (2006); and Gentles, R G, Hu, S. and Dubowchik, G M (2009) Recent Advances in the Discovery of GSK-3 Inhibitors and a Perspective on their Utility for the Treatment of Alzheimer's Disease. *Annual Reports in Medicinal Chemistry* 44, 3-26.

The invention provides technical advantages, for example, the compounds are novel inhibitors of GSK-3 and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders associated with GSK-3.

One aspect of the invention is a compound of formula I

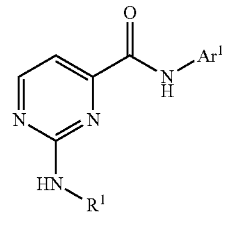

I where:

$R^1$ is hydrogen, alkyl, (cycloalkyl)alkyl, alkoxyalkyl, ($Ar^2$)alkyl, (($Ar^2$)cycloalkyl)alkyl, cycloalkyl, (alkyl)cycloalkyl, $Ar^2$, or $Ar^3$;

or $R^1$ is (adamantyl)alkyl, (oxetanyl)alkyl, (tetrahydropyranyl)alkyl, (benzodioxolanyl)alkyl, oxetanyl, (alkyl)piperidinyl, (pentaalkyl)piperidinyl, alkoxytetrahydrofuranyl, tetrahydropyranyl, dialkyltetrahydropyranyl, (dihalophenyl)pyrazolyl, acetamidopyridinyl, (dialkylamino)alkoxypyridinyl, pyridazinyl, (imidizolyl)phenyl, tetrahydroisoquinolinyl, isoquinolinyl, quinolinyl, or naphthyl;

$R^2$ is $N(R^3)(R^4)$, dioxolanyl, (alkyl)dioxolanyl, or tetrahydropyranyl;

$R^3$ is hydrogen, alkyl, (cycloalkyl)alkyl, cycloalkyl, or is $Ar^2$ is phenyl substituted with 0-3 substituents selected from the group consisting of halo, alkyl, haloalkyl, alkoxy, haloalkoxy;

$R^4$ is hydrogen or alkyl;

or $N(R^3)(R^4)$ taken together is azetdinyl, pyrrolidinyl, piperidinyl, piperazinyl, or morpholinyl, and is substituted with 0-4 substituents selected from alkyl and halo;

$Ar^1$ is 3-pyridinyl, 3-pyridazinyl, 4-pyridazinyl, 5-pyrimidinyl, or 2-pyrazinyl, and is substituted with 0-3 substituents selected from the group consisting of cyano, halo, alkyl, haloalkyl, ($R^2$)alkyl, alkoxy, haloalkoxy, $R^2$, and $Ar^2$;

$Ar^2$ is phenyl or pyridinyl and is substituted with 0-3 substituents selected from the group consisting of cyano, halo, alkyl, haloalkyl, alkoxy, haloalkoxy, alkylsulfinyl, alkylsulfonyl, and phenyl that is in turn substituted with 0-3 substituents selected from the group consisting of halo, alkyl, haloalkyl, and alkoxy; and $Ar^3$ is pyrazolyl, isothiazolyl, imidazolyl, thiadiazolyl, or triazolyl, and is substituted with 0-3 substituents selected from the group consisting of cyano, halo, alkyl, cycloalkyl, haloalkyl, alkoxy, and haloalkoxy;

or a pharmaceutically acceptable salt thereof.

Another aspect of the invention is a compound of formula I where $R^1$ is $Ar^2$.

Another aspect of the invention is a compound of formula I where $Ar^1$ is 3-pyridinyl or 5-pyrimidinyl and is substituted with 0-3 substituents selected from the group consisting of cyano, halo, alkyl, haloalkyl, ($R^2$)alkyl, alkoxy, haloalkoxy, $R^2$, and $Ar^2$.

Another aspect of the invention is a compound of formula I where $Ar^1$ is 3-pyridinyl substituted with 0-3 substituents selected from the group consisting of cyano, halo, alkyl, haloalkyl, ($R^2$)alkyl, alkoxy, haloalkoxy, $R^2$, and $Ar^2$.

Another aspect of the invention is a compound of formula I where $Ar^1$ is 5-pyrimidinyl substituted with 0-3 substituents selected from the group consisting of cyano, halo, alkyl, haloalkyl, ($R^2$)alkyl, alkoxy, haloalkoxy, $R^2$, and $Ar^2$.

Another aspect of the invention is a compound of formula I where $Ar^2$ is phenyl substituted with 0-3 substituents selected from the group consisting of cyano, halo, alkyl, haloalkyl, alkoxy, haloalkoxy, alkylsulfinyl, and alkylsulfonyl.

For a compound of formula I, the scope of any instance of a variable substituent, including $R^1$, $R^2$, $R^3$, $R^4$, $Ar^1$, $Ar^2$, and $Ar^3$, can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

The kinase assay was performed in V-bottom 384-well plates. The final assay volume was 30 μl prepared from 15 μl additions of enzyme, substrates (fluoresceinated peptide FL-KRREILSRRP[ps]ERYR-NH2 and ATP) and test compounds in assay buffer (100 mM HEPES pH 7.4, 10 mM $MgCl_2$, 25 mM Beta-Glycerolphosphate, 0.015% Brij35 and 0.25 mM DTT). The reaction was incubated at room temperature for 20 hours and terminated by adding 45 μl of 35 mM EDTA to each sample. The reaction mixture was analyzed on the Caliper LabChip3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 250 pM GSK3α or GSK3β, 20 uM ATP, 1.5 uM FL-KRREILSRRP[ps]ERYR-NH2, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

| Example | GSK3β/GSK3α (nM) | pTau (nM) |
|---|---|---|
| 1 | 57/— | 10,000 |
| 2 | 30/18 | 1,100 |
| 3 | 0.20/0.15 | 8.5 |
| 4 | 0.43/0.31 | 104 |
| 5 | 0.26/0.19 | 37 |
| 6 | 0.64/0.40 | 51 |
| 7 | 16/1.1 | 140 |
| 8 | 0.31/0.22 | 71 |
| 9 | 2.0/1.2 | 240 |
| 10 | 0.35/0.28 | 78 |
| 11 | 0.18/0.35 | 12 |
| 12 | 1.9/0.9 | 210 |
| 13 | 0.45/0.30 | 60 |
| 14 | 0.39/0.18 | 14 |
| 15 | 0.27/0.19 | 10 |
| 16 | 54/36 | 5,700 |
| 17 | 0.64/0.47 | 60 |
| 18 | 0.23/0.32 | 37 |
| 19 | 0.18/0.17 | 17 |
| 20 | 24/16 | 5,700 |
| 21 | 0.43/0.35 | 97 |
| 22 | 0.31/0.21 | — |
| 23 | 6.2/4.8 | 1,600 |
| 24 | 3.8/1.6 | 170 |
| 25 | 3.3/2.2 | 4,800 |
| 26 | 0.57/0.33 | 110 |
| 27 | 0.24/0.16 | 20 |
| 28 | 1.5/0.9 | 170 |
| 29 | 4.6/2.6 | 1,400 |
| 30 | 3.9/1.8 | 350 |
| 31 | 0.89/0.52 | 320 |
| 32 | 0.48/0.56 | 100 |
| 33 | 2.3/2.1 | 700 |
| 34 | 1.2/0.69 | 46 |
| 35 | 1.1/0.63 | 30 |
| 36 | 0.84/0.55 | 36 |
| 37 | 0.54/0.51 | 33 |
| 38 | 3.1/1.1 | 130 |
| 39 | 3.4/1.5 | 470 |
| 40 | 22/21 | 5,200 |
| 41 | 1.6/1.9 | 290 |
| 42 | 0.88/0.59 | 93 |
| 43 | 0.25/0.19 | 34 |
| 44 | 0.26/0.46 | 34 |
| 45 | 0.35/0.29 | 10 |
| 46 | 0.50/0.44 | 77 |
| 47 | 2.1/0.70 | 100 |
| 48 | 1.5/1.3 | 170 |
| 49 | 0.48/0.29 | 74 |
| 50 | 4.0/1.5 | 180 |
| 51 | 0.25/0.16 | 13 |
| 52 | 0.07/0.06 | 6.0 |
| 53 | 0.35/0.22 | 10 |
| 54 | 0.12/0.08 | 5.1 |
| 55 | 0.26/0.16 | 7.6 |

-continued

| Example | GSK3β/GSK3α (nM) | pTau (nM) |
|---|---|---|
| 56 | 0.25/0.15 | 5.9 |
| 57 | 0.08/0.07 | 1.4 |
| 58 | 0.30/0.18 | 10 |
| 59 | 0.18/0.21 | 8.2 |
| 60 | —/— | 5.5 |
| 61 | 0.72/0.39 | 230 |
| 62 | 0.08/0.09 | 230 |
| 63 | 0.18/0.13 | 3.0 |
| 64 | 0.20/0.19 | 8.5 |
| 65 | 2.0/1.4 | 86 |
| 66 | 1.0/0.67 | 22 |
| 67 | 0.97/0.36 | 90 |
| 68 | 0.73/1.3 | 90 |
| 69 | 0.56/0.60 | 160 |
| 70 | —/— | 52 |
| 71 | 8.0/4.2 | 1,000 |
| 72 | 1.6/1.1 | 290 |
| 73 | 0.26/0.18 | 22 |
| 74 | 5.9/4.5 | 890 |
| 75 | 48/33 | 4,500 |
| 76 | 1.1/0.56 | 77 |
| 77 | 0.79/0.47 | 100 |
| 78 | 28/15 | 2,900 |
| 79 | 160/98 | 8,000 |
| 80 | 2.4/0.65 | 86 |
| 81 | 9.8/6.6 | 520 |
| 82 | 0.18/0.09 | 2.8 |
| 83 | 0.22/0.16 | 5.1 |
| 84 | 0.24/0.11 | 4.8 |
| 85 | 0.51/0.41 | 17 |
| 86 | 0.80/0.40 | 68 |
| 85 | 1.4/0.92 | 150 |
| 88 | 2.6/1.4 | 150 |
| 89 | 3.0/1.5 | 73 |
| 90 | 3.0/2.2 | 120 |
| 91 | 3.5/2.3 | 270 |
| 92 | 3.8/2.2 | 250 |
| 93 | 4.3/3.1 | 390 |
| 94 | 5.1/3.5 | 210 |
| 95 | 5.7/0.70 | 78 |
| 96 | 18/11 | 900 |
| 97 | 29/30 | 870 |
| 98 | 46/37 | 2,600 |
| 99 | 78/190 | 10,000 |
| 100 | 93/65 | 10,000 |
| 101 | 100/42 | 9,000 |
| 102 | 260/170 | 10,000 |
| 103 | 3.1/1.3 | 510 |
| 104 | 4.8/2.1 | 660 |
| 105 | 31/15 | 2,100 |
| 106 | 0.11/0.09 | 1.9 |
| 107 | 0.17/0.24 | 9.4 |
| 108 | 0.24/0.17 | — |
| 109 | 0.88/0.43 | 44 |
| 110 | 1.1/0.68 | 65 |
| 111 | 2.9/2.2 | 220 |
| 112 | 3.6/2.1 | — |
| 113 | 5.3/4.0 | 300 |
| 114 | 20/14 | 210 |
| 115 | 2,000/2,000 | 23 |
| 116 | 0.19/0.16 | 12 |
| 117 | 0.25/0.21 | 28 |
| 118 | 0.30/0.28 | 14 |
| 119 | 0.34/— | 20 |
| 120 | 0.44/1.4 | 26 |
| 121 | 0.46/0.35 | 61 |
| 122 | 8.4/12 | 4,200 |
| 123 | 0.92/4.5 | 55 |
| 124 | 0.99/0.95 | 68 |
| 125 | 1.1/0.84 | 55 |
| 126 | 1.1/0.41 | 110 |
| 127 | 1.2/— | 140 |
| 128 | 1.2/1.3 | 210 |
| 129 | 1.5/1.8 | 180 |
| 130 | 1.6/1.5 | 46 |
| 131 | 1.8/2.2 | 160 |

-continued

| Example | GSK3β/GSK3α (nM) | pTau (nM) |
|---|---|---|
| 132 | 1.9/2.2 | 220 |
| 133 | 1.9/38 | 380 |
| 134 | 2.8/5.4 | 310 |
| 135 | 3.6/14 | 400 |
| 136 | 3.7/— | 320 |
| 137 | 4.1/2.3 | 350 |
| 138 | 6.1/3.2 | 430 |
| 139 | 6.3/5.4 | 570 |
| 140 | 1.3/1.6 | 280 |
| 141 | 7.8/8.0 | 300 |
| 142 | 14/12 | 1,000 |
| 143 | 33/73 | 4,900 |
| 144 | 210/200 | 10,000 |
| 145 | 250/460 | 10,000 |
| 146 | 2,000/2,000 | 320 |
| 147 | 0.14/0.14 | 20 |
| 148 | 0.35/0.30 | 51 |
| 149 | 0.65/0.36 | 110 |
| 150 | 0.66/0.57 | 120 |
| 151 | 0.67/0.32 | 44 |
| 152 | 0.71/— | 62 |
| 153 | 0.82/0.65 | 55 |
| 154 | 1.4/0.70 | 100 |
| 155 | 1.5/0.97 | 10,000 |
| 156 | 2.1/1.3 | 350 |
| 157 | 2.2/0.72 | 410 |
| 158 | 2.4/1.9 | 96 |
| 159 | 7.2/1.9 | 390 |
| 160 | 15/— | 4,900 |
| 161 | 22/20 | — |
| 162 | 32/39 | 2,200 |
| 163 | 310/210 | 10,000 |
| 164 | 1,500/780 | 10,000 |
| 165 | 91/110 | 3,300 |
| 166 | 0.73/1.7 | 220 |
| 167 | 0.43/0.47 | 69 |
| 168 | 0.17/0.20 | 21 |
| 169 | 0.27/0.15 | 34 |
| 170 | 0.34/0.21 | 48 |
| 171 | 0.58/0.47 | 59 |
| 172 | 0.89/0.46 | 160 |
| 173 | 1.1/0.49 | 69 |
| 174 | 1.1/1.6 | 54 |
| 175 | 46/27 | 2,100 |
| 176 | 0.32/0.28 | 28 |
| 177 | 0.47/0.41 | 60 |
| 178 | 0.67/0.57 | 69 |
| 179 | 0.70/0.61 | 94 |
| 180 | 0.90/0.39 | 68 |
| 181 | 1.2/1.6 | 77 |
| 182 | 2.5/1.0 | 220 |
| 183 | 2.9/3.1 | — |
| 184 | 11/6.0 | 400 |
| 185 | 5.9/2.3 | 530 |
| 186 | 6.0/9.9 | 5,000 |
| 187 | 13/7.9 | 2,500 |
| 188 | 0.83/1.0 | 180 |
| 189 | 1.43/0.80 | 410 |
| 190 | 3.1/2.6 | 190 |
| 191 | 3.3/4.3 | 240 |
| 192 | 4.8/4.8 | 480 |
| 193 | 3.4/1.8 | 620 |
| 194 | 4.4/2.9 | 390 |
| 195 | 8.9/7.2 | — |
| 196 | 5.2/3.9 | 840 |
| 197 | 24/21 | 5,100 |
| 198 | 35/28 | 6,500 |
| 199 | 40/33 | 6,100 |
| 200 | 53/59 | 6,400 |
| 201 | 71/45 | 4,200 |
| 202 | 120/57 | 2,300 |
| 203 | 8.7/6.1 | 600 |
| 204 | 13/11 | 1,100 |
| 205 | 19/22 | 1,800 |
| 206 | 74/99 | 4,700 |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment for modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral sclerosis, stroke, Huntington's disease, peripheral neuropathies, traumatic brain injury, spinal cord trauma, and vascular dementias, which comprises administering to a patient a therapeutically affective amount of a compound of formula I.

Another aspect of the invention is a method for the treatment for diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma, which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of Alzheimer's disease.

"Patient" means a person suitable for therapy as understood by practitioners in the field of affective disorders, neurodegenerative disorders, psychiatric disorders, cancer, metabolic disorders, or inflammatory disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, Remington's Pharmaceutical Sciences, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

The abbreviations used in the present application, including particularly in the illustrative schemes and examples which follow, are well-known to those skilled in the art. Some of the abbreviations used are as follows: RT or rt or r.t. for room temperature or retention time (context will dictate); $t_R$ for retention time; HATU for O-(7-azabenzotriazol-1-yl)-N,N,N',N'-tetramethyluronium hexafluorophosphate; BOP for benzotriazol-1-yloxytris(dimethylamino) phosphonium hexafluorophosphate; EDC or EDCI for 1-(3-dimethylaminopropyl)-3-ethylcarbodiimide hydrochloride; TBTU for O-benzotriazol-1-yl-N,N,N',N'-tetramethyluronium tetrafluoroborate; Xantphos for 4,5-bis(diphenylphosphino)-9,9-dimethylxanthene; Brettphos for 2-(dicyclohexylphosphino)3,6-dimethoxy-2',4',6'-triisopropyl-1,1'-biphenyl; SPhos for 2-dicyclohexylphosphino-2',6'-dimethoxybiphenyl; XPhos for 2-dicyclohexylphosphino-2',4',6'-triisopropylbiphenyl; i-Pr or iPr for isopropyl; THF for tetrahydrofuran; EtOH for ethanol; Ac for acetyl; DMAP for N,N-dimethylaminopyridine; TEA or $Et_3N$ for triethylamine; DIEA or i-$Pr_2NEt$ for N,N-diisopropylethylamine; Me for methyl; TFA for trifluoroacetic acid; Ph for phenyl; DMF for N,N-dimethylformamide; DMSO for dimethylsulfoxide; NMP for N-methylpyrrolidine; MeCN for acetonitrile; HOBt for 1-hydroxybenzotriazole; dppf for 1,1'-bis(diphenylphosphanyl) ferrocene; Et for ethyl; h or hr or hrs for hours; min or mins for minutes; EtOAc for ethyl acetate; DCM for dichloromethane; MeOH for methanol; AcOH for acetic acid; and MeOD for $CD_3OD$.

Compounds of Formula I can be prepared as described in Schemes 1-3. In Scheme 1, compound 2 can be prepared by a coupling reaction between 1 and various amines. The coupling reaction can be carried out using standard peptide coupling reagents such as HATU, BOP, EDC, T3P or TBTU in the presence of a base such as N,N-diisopropylethylamine and an appropriate solvent. Alternatively, compound 2 can also be formed by conversion of 1 to an acid chloride followed by treatment with the desired amine. Compounds of Formula I can be prepared from 2 coupling with an aryl halide or equivalent.

Scheme 1

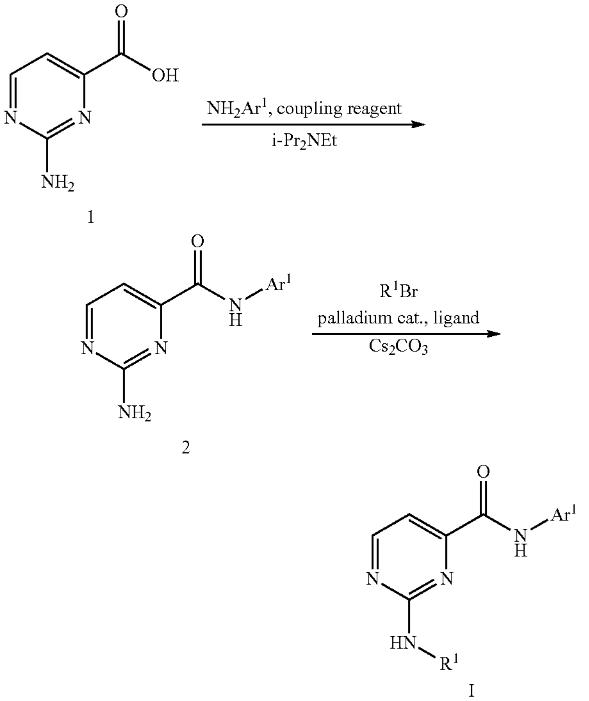

1

2

I

Alternatively as shown in Scheme 2, compounds of Formula I can be prepared starting with compound 3. Compound 4 can be prepared by a coupling reaction between 3 and various amines. Alternatively, compound 4 can also be formed by conversion of 3 to an acid chloride and coupling with the desired amine. Compounds of Formula I can be prepared from 4 by coupling with an amine. Alternatively, 4 can be subjected to Buchwald coupling reaction conditions whereby it is heated with an amine in the presence of a catalyst.

Scheme 2

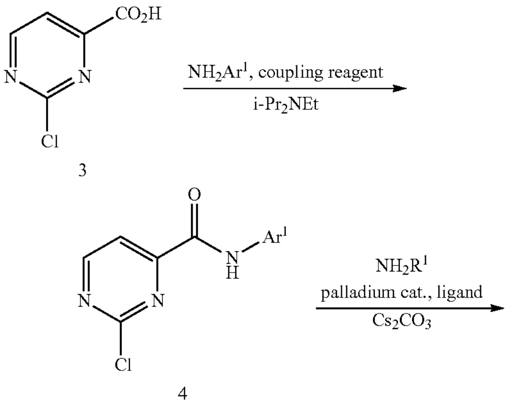

3

4

-continued

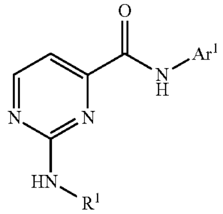

I

Another alternative method for the preparation of compounds of Formula I is shown in Scheme 3. Compound 5 can be subjected to Buchwald coupling reaction conditions to form 6, followed by hydrolysis of the ester and a coupling reaction between 7 and various amines. Alternatively, compounds of Formula I can be formed by conversion of 7 to an acid chloride followed by treatment with an amine.

Scheme 3

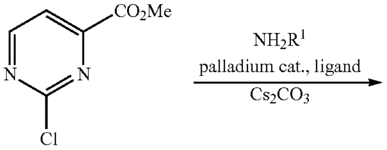

5

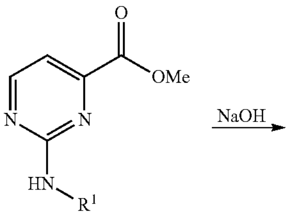

6

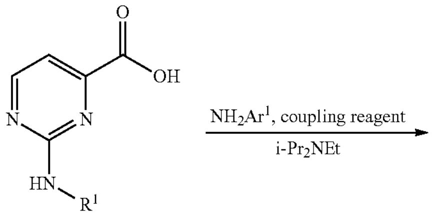

7

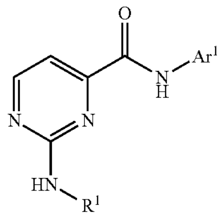

I

Various analogs synthesized using Schemes 1-3 are listed in Tables 1-7.

TABLE 1

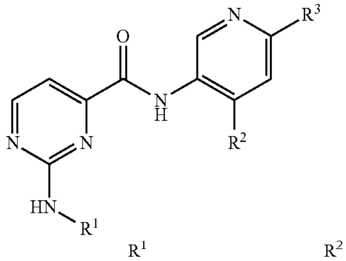

| Example | $R^1$ | $R^2$ | $R^3$ |
|---|---|---|---|
| 1 | H | H | Me |
| 2 | H | 4,4-difluoro-N-piperidine | H |
| 3 | Ph | 4,4-difluoro-N-piperidine | H |
| 4 | Ph | Ph | H |
| 5 | 4-F—Ph | Ph | H |
| 6 | 4-OMe—Ph | Ph | H |
| 7 | 4-OEt—Ph | Ph | H |
| 8 | 4-Me—Ph | Ph | H |
| 9 | 4-$CF_3$—Ph | Ph | H |
| 10 | 4-Cl—Ph | Ph | H |
| 11 | 4-CN—Ph | Ph | H |
| 12 | 4-$OCF_3$—Ph | Ph | H |
| 13 | 4-$OCHF_2$—Ph | Ph | H |
| 14 | 4-SOMe—Ph | Ph | H |
| 15 | 4-$SO_2$Me—Ph | Ph | H |
| 16 | 4-(1H-imidazol-1-yl)-Ph | Ph | H |
| 17 | 4-F-3-Me—Ph | Ph | H |
| 18 | 3-Cl-4-OMe—Ph | Ph | H |
| 19 | 3-Cl-4-OMe—Ph | Ph | H |
| 20 | 2-Cl-4-$CF_3$—Ph | Ph | H |
| 21 | 4-CN-2-Me—Ph | Ph | H |
| 22 | 4-CN-2-F—Ph | Ph | H |
| 23 | 2,4-$Cl_2$—Ph | Ph | H |
| 24 | 2-Cl-4-CN—Ph | Ph | H |
| 25 | 2-F-4-$CF_3$—Ph | Ph | H |
| 26 | 4-Cl-2-F—Ph | Ph | H |
| 27 | 3-Cl-4-CN—Ph | Ph | H |
| 28 | 4-CN-3-$CF_3$—Ph | Ph | H |
| 29 | 2-Cl-4-$OCHF_2$—Ph | Ph | H |
| 30 | 4-Cl-2,5-$Cl_2$—Ph | Ph | H |
| 31 | 4,5-$Cl_2$-2-F—Ph | Ph | H |
| 32 | 4-Cl-2,5-$F_2$—Ph | Ph | H |
| 33 | 4-Cl-5-$OCHF_2$-2-F—Ph | Ph | H |
| 34 | pyridin-3-yl | Ph | H |
| 35 | pyridin-4-yl | Ph | H |
| 36 | 2-Me-pyridin-4-yl | Ph | H |
| 37 | 2-OMe-pyridin-4-yl | Ph | H |
| 38 | 6-$OCHF_2$-pyridin-3-yl | Ph | H |
| 39 | 6-$CF_3$-pyridin-3-yl | Ph | H |
| 40 | 6-$OCHF_2$-2-Me-pyridin-3-yl | Ph | H |
| 41 | 6-$OCHF_2$-2,5-$Me_2$-pyridin-3-yl | Ph | H |
| 42 | 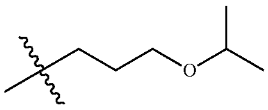 | Ph | H |
| 43 | Ph | 4-F—Ph | H |
| 44 | 4-F—Ph | 4-F—Ph | H |
| 45 | 4-CN—Ph | 4-F—Ph | H |
| 46 | 4-Cl—Ph | 4-F—PH | H |
| 47 | 4-$CF_3$—Ph | 4-F—Ph | H |
| 48 | 4-$OCF_3$—Ph | 4-F—Ph | H |
| 49 | 4-$OCHF_2$—Ph | 4-F—Ph | H |
| 50 | 6-$OCHF_2$-pyridin-3-yl | 4-F—Ph | H |
| 51 | Ph | $OCH_2CF_3$ | H |
| 52 | 4-OMe—Ph | $OCH_2CF_3$ | H |
| 53 | 4-OEt—Ph | $OCH_2CF_3$ | H |
| 54 | 4-Me—Ph | $OCH_2CF_3$ | H |
| 55 | 4-F—Ph | $OCH_2CF_3$ | H |

TABLE 1-continued

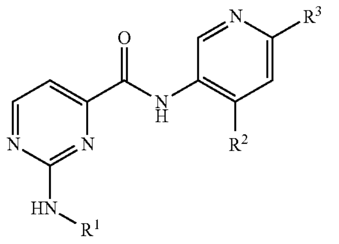

| Example | $R^1$ | $R^2$ | $R^3$ |
|---|---|---|---|
| 56 | 4-Cl—Ph | $OCH_2CF_3$ | H |
| 57 | 4-CN—Ph | $OCH_2CF_3$ | H |
| 58 | 4-$CF_3$—Ph | $OCH_2CF_3$ | H |
| 59 | 4-$OCF_3$—Ph | $OCH_2CF_3$ | H |
| 60 | 4-$OCHF_2$—Ph | $OCH_2CF_3$ | H |
| 61 | 4-Cl-2-F—Ph | $OCH_2CF_3$ | H |
| 62 | 3-F-4-OMe—Ph | $OCH_2CF_3$ | H |
| 63 | 6-$OCHF_2$-pyridin-3-yl | $OCH_2CF_3$ | H |
| 64 | 6-$CF_3$-pyridin-3-yl | $OCH_2CF_3$ | H |
| 65 | 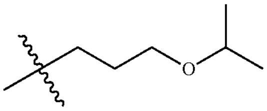 [SMILES: *CCCOC(C)C] | $OCH_2CF_3$ | H |

TABLE 2

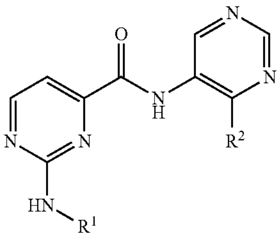

| Example | $R^1$ | $R^2$ |
|---|---|---|
| 66 | 4-CN—Ph | $OCH_2CF_3$ |
| 67 | 4-Cl—Ph | $OCH_2CF_3$ |
| 68 | 4-$CF_3$—Ph | $OCH_2CF_3$ |
| 69 | 4-$OCF_3$—Ph | $OCH_2CF_3$ |
| 70 | 4-$OCHF_2$—Ph | $OCH_2CF_3$ |
| 71 | 4-Cl-2-F—Ph | $OCH_2CF_3$ |
| 72 | 4-Cl-2,5-$F_2$—Ph | $OCH_2CF_3$ |
| 73 | 6-$OCHF_2$-pyridin-3-yl | $OCH_2CF_3$ |
| 74 | 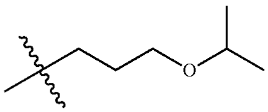 [SMILES: *CCCOC(C)C] | $OCH_2CF_3$ |
| 75 | Ph | NH—Ph |
| 76 | Ph | $OCH_2CF_3$ |
| 77 | 4-OMe—Ph | $OCH_2CF_3$ |
| 78 | 4-OMe—Ph | NH-4-OMe—Ph |
| 79 | Ph | NH—$CH_2$-cPr |

TABLE 3

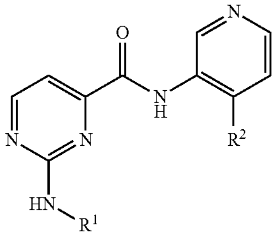

| Example | $R^1$ | $R^2$ |
|---|---|---|
| 80 | 6-$OCHF_2$-pyridin-3-yl | 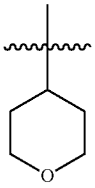 [SMILES: *C1CCOCC1] |
| 81 | 6-$OCHF_2$-pyridin-3-yl | 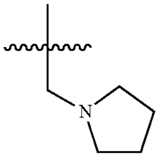 [SMILES: *CN1CCCC1] |

TABLE 4

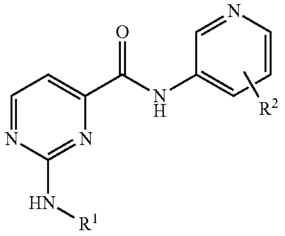

| Example | $R^1$ | $R^2$ |
|---|---|---|
| 82 | 6-CN-pyridin-3-yl | 4-$OCH_2CF_3$ |
| 83 | 6-Me-pyridin-3-yl | 4-$OCH_2CF_3$ |
| 84 | 6-F-pyridin-3-yl | 4-$OCH_2CF_3$ |
| 85 | 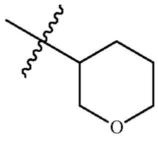 [SMILES: *C1CCCOC1] | 4-$OCH_2CF_3$ |
| 86 | 6-F-pyridin-3-yl | 4-Ph |
| 85 | 6-acetamido-pyridin-3-yl | 4-Ph |
| 88 | 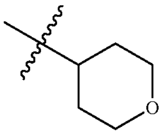 [SMILES: *C1CCOCC1] | 4-Ph |
| 89 | 6-Me-pyridin-3-yl | 4-Ph |
| 90 | 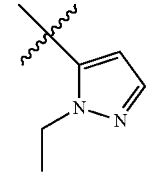 [SMILES: *c1ccnn1CC] | 4-Ph |

TABLE 4-continued
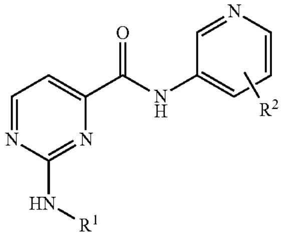
| Example | $R^1$ | $R^2$ |
| --- | --- | --- |
| 91 | 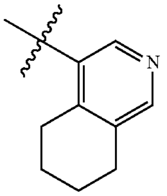 [SMILES: *c1cncc2c1CCCC2] | 4-Ph |
| 92 | 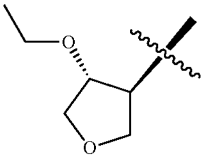 | 4-Ph |
| 93 | 6-$NMe_2$-pyridin-3-yl | 4-Ph |
| 94 | 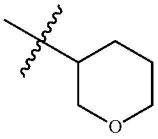 [SMILES: *C1CCCOC1] | 4-Ph |
| 95 | 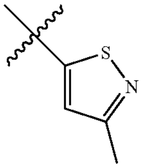 [SMILES: *c1cc(C)ns1] | 4-Ph |
| 96 | 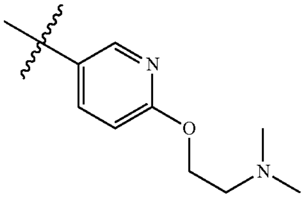 [SMILES: *c1ccc(OCCN(C)C)nc1] | 4-Ph |
| 97 | 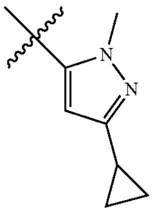 [SMILES: *c1cc(C2CC2)nn1C] | 4-Ph |
| 98 | 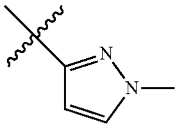 [SMILES: *c1ccn(C)n1] | 4-Ph |
| 99 | 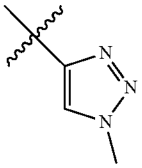 [SMILES: *c1cn(C)nn1] | 4-Ph |
| 100 | 6-(isobutylamino)pyridin-3-yl | 4-Ph |
| 101 | 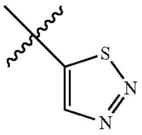 [SMILES: *c1cnns1] | 4-Ph |
| 102 | 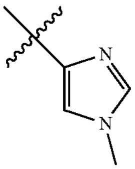 [SMILES: *c1cn(C)cn1] | 4-Ph |
| 103 | 6-Me-pyridin-3-yl | 5-(2-F—Ph) |
| 104 | 6-F-pyridin-3-yl | 5-(2-F—Ph) |
| 105 | 6-$OCHF_2$-pyridin-3-yl | 5-(2-F—Ph) |
TABLE 5
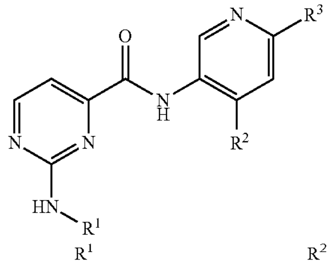
| Example | $R^1$ | $R^2$ | $R^3$ |
| --- | --- | --- | --- |
| 106 | 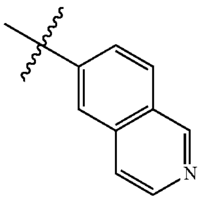 [SMILES: *c1ccc2cnccc2c1] | $OCH_2CF_3$ | H |

TABLE 5-continued

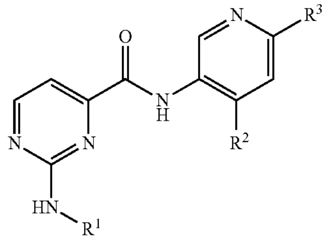

| Example | $R^1$ | $R^2$ | $R^3$ |
|---|---|---|---|
| 107 | 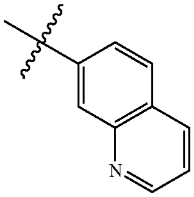 [SMILES: *c1ccc2cccnc2c1] | $OCH_2CF_3$ | H |
| 108 | 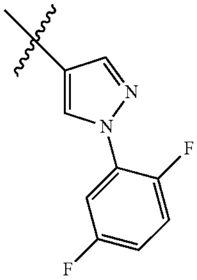 [SMILES: *c1cnn(-c2cc(F)ccc2F)c1] | $OCH_2CF_3$ | H |
| 109 | 4-$CF_3$—Ph | $OCH_2CF_3$ | F |
| 110 | 4-Cl—Ph | $OCH_2CF_3$ | F |
| 111 | 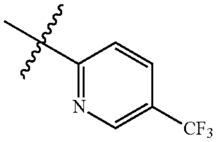 [SMILES: *c1ccc(C(F)(F)F)cn1] | $OCH_2CF_3$ | H |
| 112 | 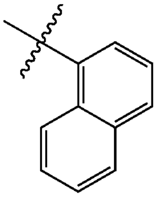 [SMILES: *c1cccc2ccccc12] | $OCH_2CF_3$ | H |
| 113 | 2,4-$F_2$—Ph | $OCH_2CF_3$ | H |
| 114 | 2-pyridyl | $OCH_2CF_3$ | H |
| 115 | 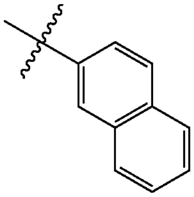 [SMILES: *c1ccc2ccccc2c1] | $OCH_2CF_3$ | H |
| 116 | cyclopentyl | $OCH_2CF_3$ | H |
| 117 | cyclohexyl | $OCH_2CF_3$ | H |

TABLE 5-continued

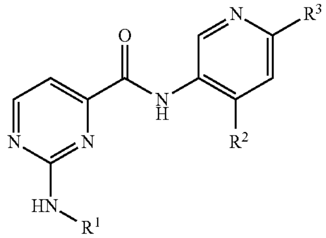

| Example | $R^1$ | $R^2$ | $R^3$ |
|---|---|---|---|
| 118 | 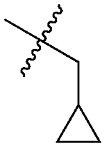 [SMILES: *CC1CC1] | $OCH_2CF_3$ | H |
| 119 | cyclobutyl | $OCH_2CF_3$ | H |
| 120 | isopropyl | $OCH_2CF_3$ | H |
| 121 | 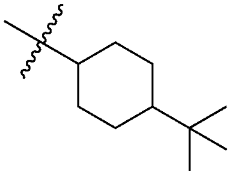 (cis) | $OCH_2CF_3$ | H |
| 122 | 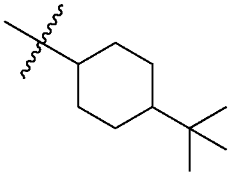 (trans) | $OCH_2CF_3$ | H |
| 123 | ethyl | $OCH_2CF_3$ | H |
| 124 | 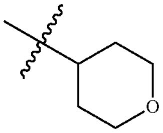 [SMILES: *C1CCOCC1] | $OCH_2CF_3$ | H |
| 125 | 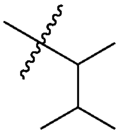 [SMILES: *C(C)C(C)C] | $OCH_2CF_3$ | H |
| 126 | 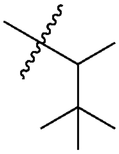 [SMILES: *C(C)C(C)(C)C] | $OCH_2CF_3$ | H |
| 127 | cyclobutyl | $OCH_2CF_3$ | F |

TABLE 5-continued
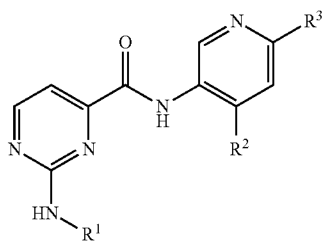
| Example | $R^1$ | $R^2$ | $R^3$ |
|---|---|---|---|
| 128 | 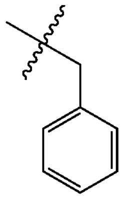 [SMILES: *Cc1ccccc1] | $OCH_2CF_3$ | H |
| 129 | 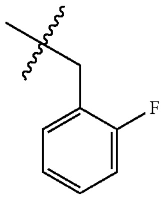 [SMILES: *Cc1ccccc1F] | $OCH_2CF_3$ | H |
| 130 | cyclopropyl | $OCH_2CF_3$ | H |
| 131 | 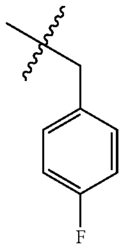 [SMILES: *Cc1ccc(F)cc1] | $OCH_2CF_3$ | H |
| 132 | 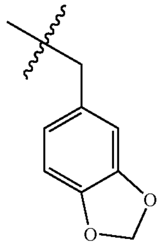 [SMILES: *Cc1ccc2c(c1)OCO2] | $OCH_2CF_3$ | H |
| 133 | 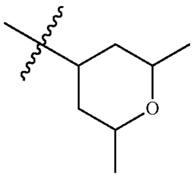 [SMILES: *C1CC(C)OC(C)C1] | $OCH_2CF_3$ | H |
TABLE 5-continued
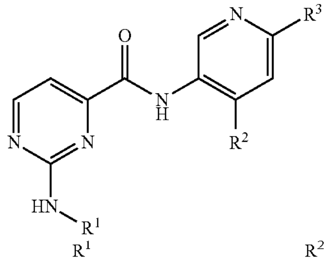
| Example | $R^1$ | $R^2$ | $R^3$ |
|---|---|---|---|
| 134 | 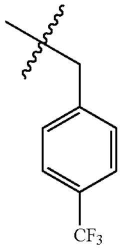 [SMILES: *Cc1ccc(C(F)(F)F)cc1] | $OCH_2CF_3$ | H |
| 135 | methyl | $OCH_2CF_3$ | H |
| 136 | isopropyl | $OCH_2CF_3$ | F |
| 137 | 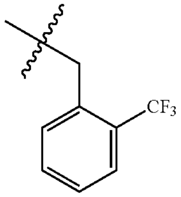 [SMILES: *Cc1ccccc1C(F)(F)F] | $OCH_2CF_3$ | H |
| 138 | 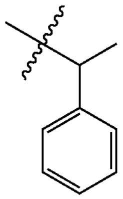 [SMILES: *C(C)c1ccccc1] | $OCH_2CF_3$ | H |
| 139 | 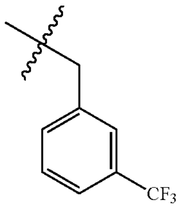 [SMILES: *Cc1cccc(C(F)(F)F)c1] | $OCH_2CF_3$ | H |
| 140 | 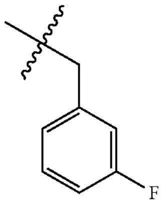 [SMILES: *Cc1cccc(F)c1] | $OCH_2CF_3$ | H |
| 141 | 2,2,2-trifluoroethyl | $OCH_2CF_3$ | H |
| 142 | 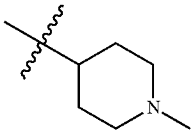 [SMILES: *C1CCN(C)CC1] | $OCH_2CF_3$ | H |

TABLE 5-continued
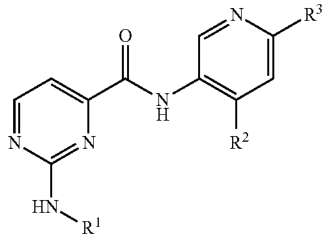
| Example | $R^1$ | $R^2$ | $R^3$ |
|---|---|---|---|
| 143 | 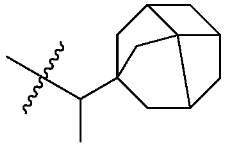 [SMILES: *C(C)C12CC3CC4CC(C1)C43C2] | $OCH_2CF_3$ | H |
| 144 | 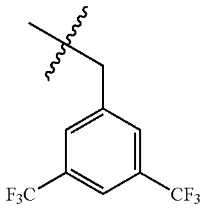 [SMILES: *Cc1cc(C(F)(F)F)cc(C(F)(F)F)c1] | $OCH_2CF_3$ | H |
| 145 | 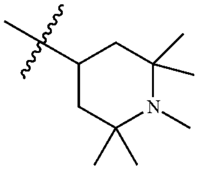 [SMILES: *C1CC(C)(C)N(C)C(C)(C)C1] | $OCH_2CF_3$ | H |
| 146 | 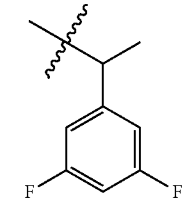 [SMILES: *C(C)c1cc(F)cc(F)c1] | $OCH_2CF_3$ | H |
| 147 | 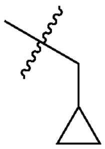 [SMILES: *CC1CC1] | Ph | H |
| 148 | cyclopentyl | 4-F—Ph | H |
| 149 | 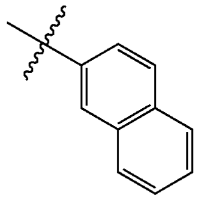 [SMILES: *c1ccc2ccccc2c1] | 2,4-$F_2$—Ph | H |
| 150 | cyclohexyl | 4-F—Ph | H |
| 151 | phenyl | 2,4-$F_2$—Ph | H |
| 152 | isopropyl | 4-F—Ph | H |
| 153 | cyclopropyl | 4-F—Ph | H |
TABLE 5-continued
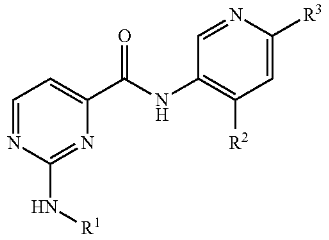
| Example | $R^1$ | $R^2$ | $R^3$ |
|---|---|---|---|
| 154 | 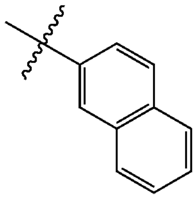 [SMILES: *c1ccc2ccccc2c1] | 2-F—Ph | H |
| 155 | 2,4-$F_2$—Ph | 2,4-$F_2$—Ph | H |
| 156 | cyclohexyl | Ph | H |
| 157 | 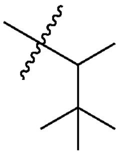 [SMILES: *C(C)C(C)(C)C] | 4-F—Ph | H |
| 158 | methyl | 2,4-$F_2$—Ph | H |
| 159 | 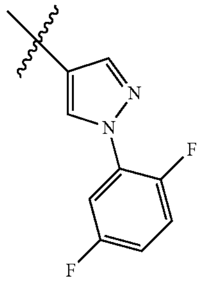 [SMILES: *c1cnn(-c2cc(F)ccc2F)c1] | Ph | H |
| 160 | 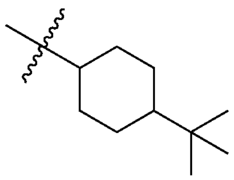 [SMILES: *C1CCC(C(C)(C)C)CC1] | 2-F—Ph | H |
| 161 | 2-pyridyl | 4-F—Ph | H |
| 162 | 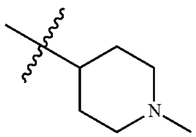 [SMILES: *C1CCN(C)CC1] | 2-F—Ph | H |
| 163 | 2-pyridyl | Ph | H |
| 164 | 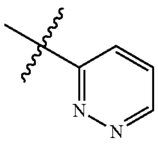 [SMILES: *c1cccnn1] | 2,4-$F_2$—Ph | H |

TABLE 5-continued

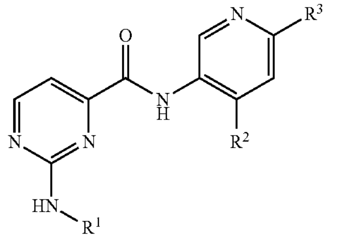

| Example | $R^1$ | $R^2$ | $R^3$ |
|---|---|---|---|
| 165 | 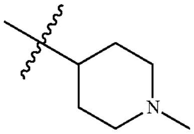 [SMILES: *C1CCN(C)CC1] | Ph | H |
| 166 | cyclopropyl | 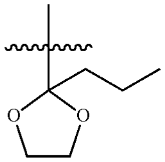 [SMILES: *C1(CCC)OCCO1] | Cl |
| 167 | 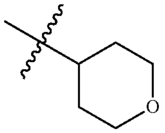 [SMILES: *C1CCOCC1] | 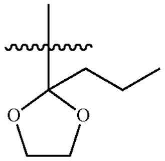 [SMILES: *C1(CCC)OCCO1] | Cl |
| 168 | 3-Cl—Ph | 4-morpholine | F |
| 169 | 4-Cl-3-F—Ph | 4-morpholine | F |
| 170 | 4-Cl—Ph | 4-morpholine | F |
| 171 | 4-Cl-2-F—Ph | 4-morpholine | F |
| 172 | 3-$OCF_3$—Ph | 4-morpholine | F |
| 173 | 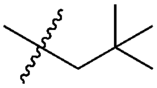 [SMILES: *CC(C)(C)C] | 4-morpholine | F |
| 174 | 4-CN—Ph | 4-morpholine | F |
| 175 | 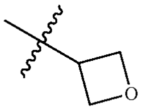 [SMILES: *C1COC1] | 4-morpholine | F |
| 176 | 4-CN—Ph | 4,4-difluoro-N-piperidine | F |
| 177 | Ph | 4,4-difluoro-N-piperidine | F |
| 178 | 4-Cl—Ph | 4,4-difluoro-N-piperidine | F |
| 179 | 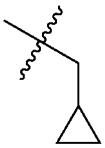 [SMILES: *CC1CC1] | 4,4-difluoro-N-piperidine | F |
| 180 | 4-F—Ph | 4,4-difluoro-N-piperidine | F |

TABLE 5-continued

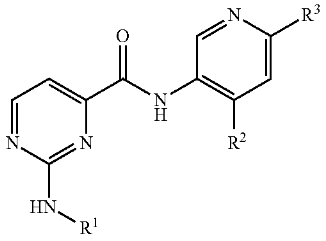

| Example | $R^1$ | $R^2$ | $R^3$ |
|---|---|---|---|
| 181 | 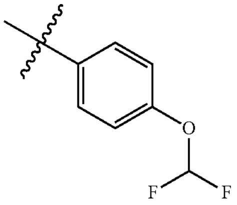 [SMILES: *c1ccc(OC(F)F)cc1] | 4,4-difluoro-N-piperidine | F |
| 182 | 4-Cl—Ph | 4,4-difluoro-N-piperidine | Me |
| 183 | 4-$CF_3$—Ph | 4,4-difluoro-N-piperidine | F |
| 184 | 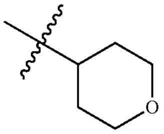 [SMILES: *C1CCOCC1] | 4,4-difluoro-N-piperidine | F |

TABLE 6

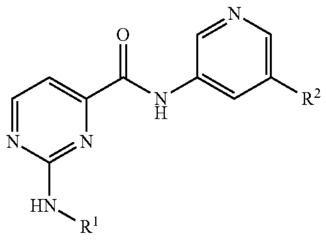

| Example | $R^1$ | $R^2$ |
|---|---|---|
| 185 | 3-$CF_3$—Ph | 2-F—Ph |
| 186 | 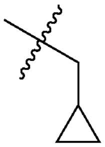 [SMILES: *CC1CC1] | 2-F—Ph |
| 187 | 3-$OCF_3$—Ph | 2-F—Ph |

TABLE 7
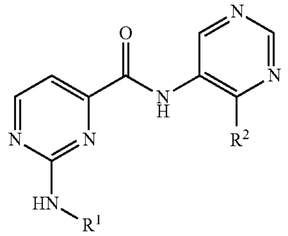
| Example | $R_1$ | $R_2$ |
|---|---|---|
| 188 | 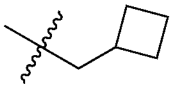 [SMILES: *CC1CCC1] | $OCH_2CF_3$ |
| 189 | 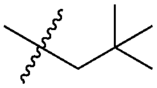 [SMILES: *CC(C)(C)C] | $OCH_2CF_3$ |
| 190 | 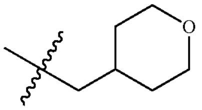 [SMILES: *CC1CCOCC1] | $OCH_2CF_3$ |
| 191 | 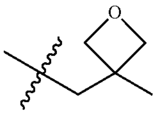 [SMILES: *CC1(C)COC1] | $OCH_2CF_3$ |
| 192 | 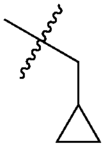 [SMILES: *CC1CC1] | $OCH_2CF_3$ |
| 193 | 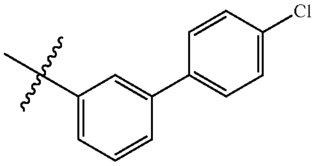 [SMILES: *c1cccc(-c2ccc(Cl)cc2)c1] | H |
| 194 | 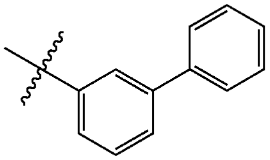 [SMILES: *c1cccc(-c2ccccc2)c1] | H |
| 195 | 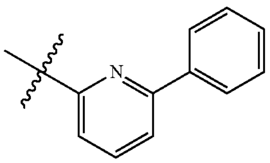 | H |
| 196 | 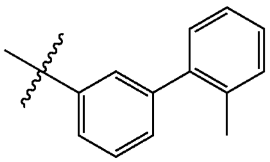 [SMILES: *c1cccc(-c2ccccc2C)c1] | H |
TABLE 7-continued
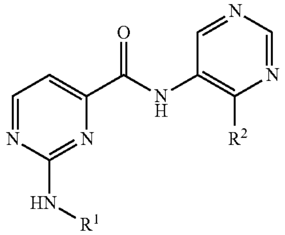
| Example | $R_1$ | $R_2$ |
|---|---|---|
| 197 | 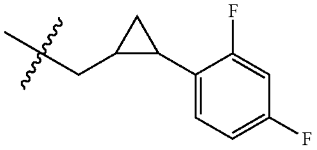 [SMILES: *CC1CC1c1ccc(F)cc1F] | H |
| 198 | 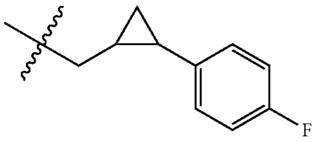 [SMILES: *CC1CC1c1ccc(F)cc1] | H |
| 199 | 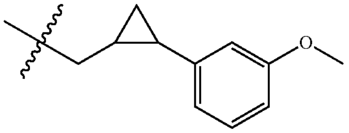 [SMILES: *CC1CC1c1cccc(OC)c1] | H |
| 200 | 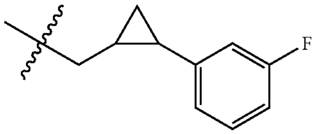 [SMILES: *CC1CC1c1cccc(F)c1] | H |
| 201 | phenyl | H |
| 202 | 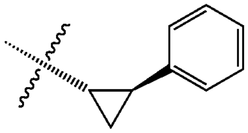 | H |
| 203 | 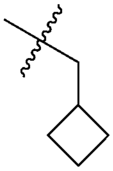 [SMILES: *CC1CCC1] | 4-morpholine |
| 204 | 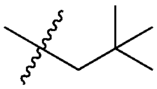 [SMILES: *CC(C)(C)C] | 4-morpholine |
| 205 | 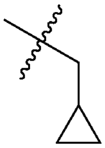 [SMILES: *CC1CC1] | 4-morpholine |
| 206 | 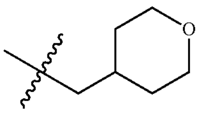 [SMILES: *CC1CCOCC1] | 4-morpholine |

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ. Preparative and analytical High Performance Liquid Chromatography (HPLC) was run on either a Varian or Shimadzu system.

Preparative HPLC Methods

Method A

Column: Waters XBridge C18, 19×200 mm, 5-μm
Mobile Phase A: Water with 20 mM ammonium acetate
Mobile Phase B: 95% methanol/5% water with 20 mM ammonium acetate
Gradient: See experimental procedures
Flow Rate: 20 mL/min
Detector Wavelength: 220 nm Method B Column: Waters XBridge C18, 19×200 mm, 5-μm
Mobile Phase A: Water with 20 mM ammonium acetate
Mobile Phase B: 95% acetonitrile/5% water with 20 mM ammonium acetate
Gradient: See experimental procedures
Flow Rate: 20 mL/min
Detector Wavelength: 220 nm Method C Column: Waters Sunfire 30×150 mm, 5 um
Mobile Phase A: 5% acetonitrile/95% water, 0.1% TFA
Mobile Phase B: 95% acetonitrile/5% water 0.1% TFA
Gradient: 10% B to 100% B over 20 minute gradient; hold at 100% B for 5 min
Flow Rate: 40 mL/min
Detector Wavelength: 254 nm Method D Column: Waters Sunfire 30×100 mm, 5 um
Mobile Phase A: 5% acetonitrile/95% water with 10 mM ammonium acetate
Mobile Phase B: 95% acetonitrile/5% water with 10 mM ammonium acetate
Gradient: 10% B to 100% B over 20 minute gradient; hold at 100% B for 5 min
Flow Rate: 40 mL/min
Detector Wavelength: 254 nm Analytical HPLC Methods Method A Column: Waters Sunfire C18, 4.6×150 mm, 3.5 μm
Mobile Phase A: Water with 0.1% TFA
Mobile Phase B: Acetonitrile with 0.1% TFA
Gradient: 10% B to 95% B over 15 min gradient; hold at 100% B for 5 min
Flow Rate: 1 mL/min
Detector Wavelength: 254 nm Method B Column: Waters Xbridge Phenyl, 4.6×150 mm, 3.5 m
Mobile Phase A: Water with 0.1% TFA
Mobile Phase B: Acetonitrile with 0.1% TFA
Gradient: 10% B to 95% B over 15 min gradient; hold at 100% B for 5 min
Flow Rate: 1 mL/min
Detector Wavelength: 254 nm LC/MS Methods Method A Column: Waters BEH C18, 2.0×50 mm, 1.7-μm particles
Mobile Phase A: 5% acetonitrile/95% water with 10 mM ammonium acetate
Mobile Phase B: 95% acetonitrile/5% water with 10 mM ammonium acetate
Gradient: 0.5 min hold at 0% B, 0 to 100% B over 4 minutes, then a 0.5-minute hold at 100% B Flow Rate: 1 mL/min
Detector Wavelength: 220 nm
Temperature: 40° C.

Method B

Column: Waters BEH C18, 2.0×50 mm, 1.7-μm particles
Mobile Phase A: 5% methanol/95% water with 10 mM ammonium acetate
Mobile Phase B: 95% methanol/5% water with 10 mM ammonium acetate
Gradient: 0.5 min hold at 0% B, 0 to 100% B over 4 minutes, then a 0.5-minute hold at 100% B
Flow Rate: 0.5 mL/min
Detector Wavelength: 220 nm
Temperature: 40° C.

Method C

Column: Phenomenex LUNA C18, 30×2 mm, 3 μm particles
Mobile Phase A: 5% methanol/95% water with 10 mM ammonium acetate
Mobile Phase B: 95% methanol/5% water with 10 mM ammonium acetate
Gradient: 0 to 100% B over 4 min, then 1 min hold at 100% B
Flow rate: 0.8 mL/min
Detector Wavelength: 220 nm Method D Column: Waters Acquity UPLC BEH C18, 2.1×50 mm, 1.7 um particles
Mobile Phase A: 5% acetonitrile/95% water with 0.1% TFA
Mobile Phase B: 95% acetonitrile/5% water with 0.1% TFA
Gradient: 0 to 100% B over 3 min, then 0.75 min hold at 100% B
Flow rate: 1.0 mL/min
Detector Wavelength: 220 nm
Temperature: 50° C.

The following abbreviations are used: THF (tetrahydrofuran), MeOH (methanol), DMF (N,N-dimethylformamide), EtOH (ethanol), MeCN (acetonitrile), DCE (dichloroethane), DCM (dichloromethane), NMP (N-methylpyrrolidinone), TFA (trifluoroacetic acid), HCl (hydrochloric acid), DMAP (dimethylaminopyridine), n-BuLi (n-butyllithium), DIPEA (N,N-diisopropylethylamine), HATU (O-(7-azabenzotriazol-1-yl)-N,N,N',N'-tetramethyluronium hexafluorophosphate), TBTU (N,N,N',N'-tetramethyl-O-(benzotriazol-1-yl)uronium tetrafluoroborate), TLC (thin layer chromatography), NMR (nuclear magnetic resonance), LC/MS or LCMS (liquid chromatography/mass spectrometry), HPLC (high pressure liquid chromatography).

Preparation of Intermediates

Preparation of 2-chloro-N-(4-phenylpyridin-3-yl)pyrimidine-4-carboxamide

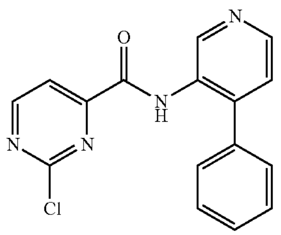 [SMILES: O=C(Nc1cnccc1-c1ccccc1)c1ccnc(Cl)n1]

Part A. 3-Nitro-4-phenylpyridine

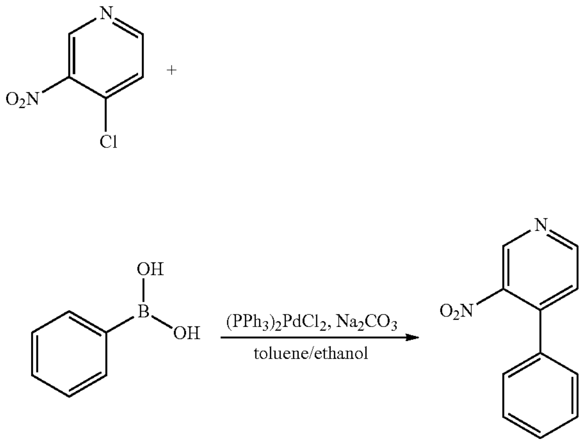

A mixture of 4-chloro-3-nitropyridine (500 mg, 3.15 mmol), phenylboronic acid (577 mg, 4.73 mmol) and $Na_2CO_3$ (2M) (3.94 mL, 7.88 mmol) in toluene (10 mL) and ethanol (2.00 mL) was degassed. Bis(triphenylphosphine) palladium(II) chloride (111 mg, 0.158 mmol) was added and the reaction mixture was heated to 100° C. for 4 h. The reaction mixture was transferred to a separatory funnel containing saturated aqueous $NaHCO_3$ solution (20 mL). The aqueous layer was extracted with ethyl acetate (3×20 mL). The combined organic layers were washed with brine (25 mL), dried over $MgSO_4$, filtered, and concentrated. The residue was purified by column chromatography on silica gel (30%→50% ethyl acetate in hexanes; 40 g column) to afford 3-nitro-4-phenylpyridine (600 mg, 3.00 mmol, 95% yield) as a tan solid: $^1H$ NMR (400 MHz, DMSO-$d_6$) 9.19 (s, 1H), 8.92 (d, J=5.0 Hz, 1H), 7.69 (dd, J=5.0, 0.5 Hz, 1H), 7.58-7.51 (m, 3H), 7.48-7.41 (m, 2H); LC/MS (APCI) m/e 201.1 $[(M+H)^+]$, calcd for $C_{11}H_9N_2O_2$ 201.1].

Part B. 4-Phenylpyridin-3-amine

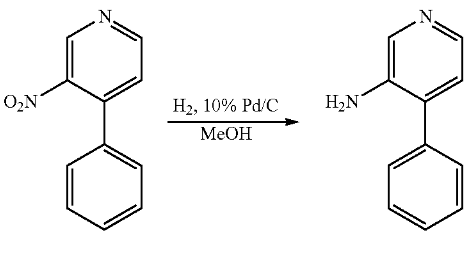 [SMILES: "MeOH" ; O=[N+]([O-])c1cnccc1-c1ccccc1 ; Nc1cnccc1-c1ccccc1]

A mixture of 3-nitro-4-phenylpyridine (600 mg, 3.00 mmol) and 10% palladium on carbon (319 mg, 0.150 mmol) in methanol (20 mL) was stirred under $H_2$ at 1 atm for 3 h. The catalyst was removed by filtration through a pad of Celite. The mixture was concentrated to afford 4-phenylpyridin-3-amine (420 mg, 2.468 mmol, 82% yield) as an off-white solid: $^1H$ NMR (400 MHz, DMSO-$d_6$) δ 8.11 (s, 1H), 7.85 (d, J=4.8 Hz, 1H), 7.54-7.47 (m, 4H), 7.45-7.38 (m, 1H), 7.00 (d, J=4.5 Hz, 1H), 5.10 (br. s., 2H); LC/MS (ESI) m/e 171.1 $[(M+H)^+]$, calcd for $C_{11}H_{11}N_2$ 171.1].

Part C. 2-Chloro-N-(4-phenylpyridin-3-yl)pyrimidine-4-carboxamide

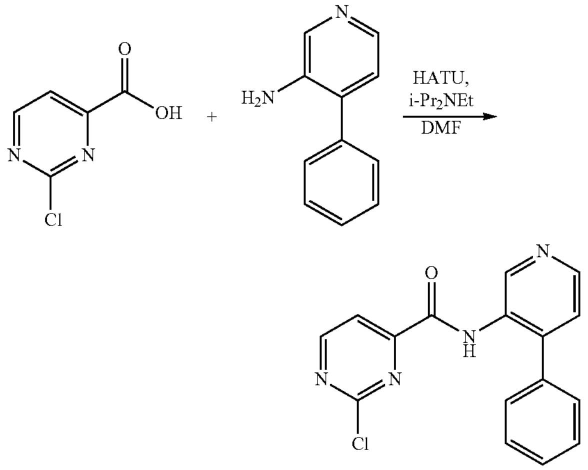

To a solution of 2-chloropyrimidine-4-carboxylic acid (60 mg, 0.378 mmol) and 4-phenylpyridin-3-amine (70.9 mg, 0.416 mmol) in DMF (1.5 mL) was added N,N-diisopropylethylamine (0.330 mL, 1.892 mmol) followed by HATU (173 mg, 0.454 mmol). The reaction mixture was stirred at room temperature for 1 h. The reaction mixture was transferred to a separatory funnel and was diluted with ethyl acetate (15 mL). The organic layer was washed with saturated aqueous $NaHCO_3$ solution (5 mL), water (3×5 mL), and brine (5 mL). The organic layer was dried over $MgSO_4$, filtered, and concentrated. The residue was purified by column chromatography on silica gel (70%→100% ethyl acetate in hexanes; 25 g column) to afford 2-chloro-N-(4-phenylpyridin-3-yl)pyrimidine-4-carboxamide (63 mg, 0.203 mmol, 54% yield) as a yellow solid: $^1H$ NMR (400 MHz, DMSO-$d_6$) δ 10.54 (s, 1H), 9.06 (d, J=5.0 Hz, 1H), 9.02 (s, 1H), 8.57 (d, J=5.0 Hz, 1H), 8.06 (d, J=5.0 Hz, 1H), 7.59-7.46 (m, 6H); LC/MS (ESI) m/e 311.0 $[(M+H)^+]$, calcd for $C_{16}H_{12}ClN_4O$ 311.1].

Preparation of 2-chloro-N-(4-(4-fluorophenyl)pyridin-3-yl)pyrimidine-4-carboxamide

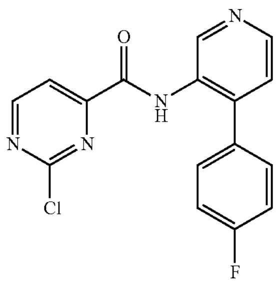 [SMILES: O=C(Nc1cnccc1-c1ccc(F)cc1)c1ccnc(Cl)n1]

Part A. 4-(4-Fluorophenyl)-3-nitropyridine

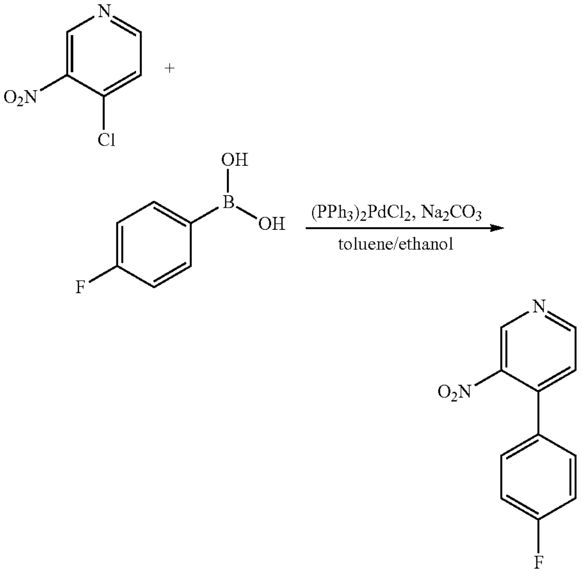

A mixture of 4-chloro-3-nitropyridine (1.00 g, 6.31 mmol), (4-fluorophenyl)boronic acid (1.32 g, 9.46 mmol) and $Na_2CO_3$ (2M) (7.88 mL, 15.77 mmol) in toluene (20 mL) and ethanol (4.00 mL) was degassed. Bis(triphenylphosphine)palladium(II) chloride (0.221 g, 0.315 mmol) was added and the reaction mixture was heated to 100° C. for 4 h. The reaction mixture was transferred to a separatory funnel containing saturated aqueous $NaHCO_3$ solution (20 mL). The aqueous layer was extracted with ethyl acetate (3x20 mL). The combined organic layers were washed with brine (25 mL), dried over $MgSO_4$, filtered, and concentrated. The residue was purified by column chromatography on silica gel (30%→50% ethyl acetate in hexanes; 40 g column) to afford 4-(4-fluorophenyl)-3-nitropyridine (1.1 g, 5.04 mmol, 80% yield) as a colorless solid: $^1H$ NMR (400 MHz, DMSO-$d_6$) δ 9.21 (s, 1H), 8.92 (d, J=5.3 Hz, 1H), 7.74-7.64 (m, 1H), 7.58-7.48 (m, 2H), 7.45-7.32 (m, 2H); LC/MS (ESI) m/e 219.0 $[(M+H)^+$, calcd for $C_{11}H_8N_2O_2F$ 219.1].

Part B. 4-(4-Fluorophenyl)pyridin-3-amine

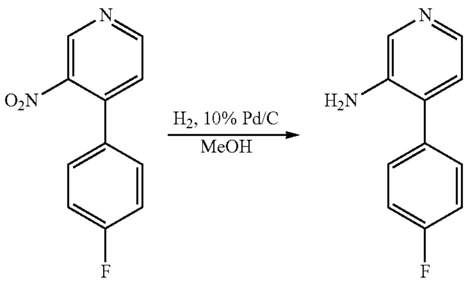 [SMILES: "MeOH" ; O=[N+]([O-])c1cnccc1-c1ccc(F)cc1 ; Nc1cnccc1-c1ccc(F)cc1]

A mixture of 4-(4-fluorophenyl)-3-nitropyridine (1.1 g, 5.04 mmol) and 10% palladium on carbon (0.537 g, 0.252 mmol) in methanol (30 mL) was stirred under $H_2$ at 1 atm for 3 h. The catalyst was removed by filtration through a pad of Celite. The mixture was concentrated to afford 4-(4-fluorophenyl)pyridin-3-amine (865 mg, 4.60 mmol, 91% yield) as a colorless solid: $^1H$ NMR (400 MHz, DMSO-$d_6$) δ 8.11 (s, 1H), 7.84 (d, J=5.0 Hz, 1H), 7.63-7.46 (m, 2H), 7.39-7.23 (m, 2H), 6.98 (d, J=4.8 Hz, 1H), 5.12 (s, 2H); LC/MS (APCI) m/e 189.1 $[(M+H)^+$, calcd for $C_{11}H_{11}N_2F$ 189.1].

Part C. 2-Chloro-N-(4-(4-fluorophenyl)pyridin-3-yl)pyrimidine-4-carboxamide

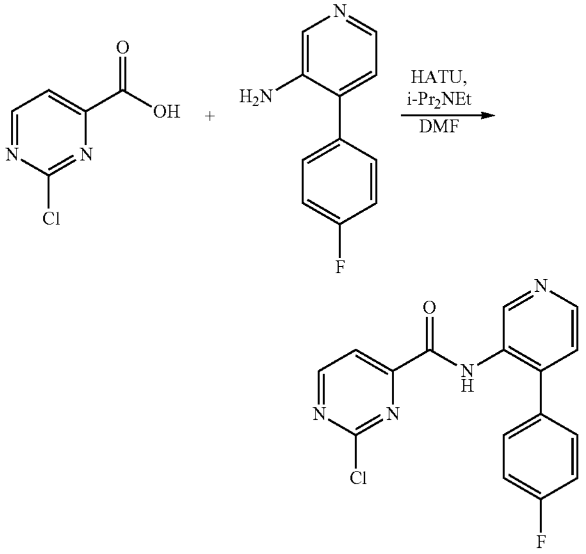

To a solution of 2-chloropyrimidine-4-carboxylic acid (200 mg, 1.261 mmol), 4-(4-fluorophenyl)pyridin-3-amine (285 mg, 1.514 mmol), and N—N-diisopropylethylamine (0.661 mL, 3.78 mmol) in DMF (3 mL) at rt was added HATU (528 mg, 1.388 mmol). The reaction mixture was stirred at rt for 5 h. The mixture was concentrated and the residue was purified by column chromatography on silica gel (30%→50% ethyl acetate in hexanes; 25 g column) to afford 2-chloro-N-(4-(4-fluorophenyl)pyridin-3-yl)pyrimidine-4-carboxamide (175 mg, 0.532 mmol, 42% yield) as a yellow solid: $^1H$ NMR (400 MHz, DMSO-$d_6$) δ 10.58 (s, 1H), 9.06 (d, J=5.0 Hz, 1H), 8.94 (s, 1H), 8.57 (d, J=5.0 Hz, 1H), 8.05 (d, J=5.0 Hz, 1H), 7.66-7.57 (m, 2H), 7.50 (d, J=5.0 Hz, 1H), 7.39-7.26 (m, 2H); LC/MS (ESI) m/e 329.0 $[(M+H)^+$, calcd for $C_{16}H_{11}N_4OClF$ 329.1].

Preparation of 2-chloro-N-(4-(2,2,2-trifluoroethoxy)pyridin-3-yl)pyrimidine-4-carboxamide

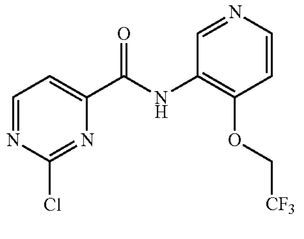 [SMILES: O=C(Nc1cnccc1OCC(F)(F)F)c1ccnc(Cl)n1]

Part A. 3-Nitro-4-(2,2,2-trifluoroethoxy)pyridine

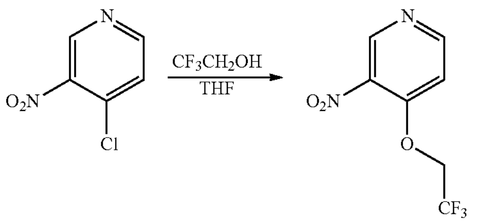

A mixture of 4-chloro-3-nitropyridine (1 g, 6.31 mmol), 2,2,2-trifluoroethanol (3.15 g, 31.5 mmol) and triethylamine (2.64 mL, 18.92 mmol) in THF (10 mL) was stirred at reflux for 12 h. The reaction mixture was transferred to a separatory funnel containing water (25 mL). The aqueous layer was extracted with ethyl acetate (3×20 mL). The combined organic layers were washed with brine (15 mL), dried over $MgSO_4$, filtered, and concentrated to afford 3-nitro-4-(2,2,2-trifluoroethoxy)pyridine (1.3 g, 5.85 mmol, 93% yield) as a tan solid: $^1H$ NMR (400 MHz, DMSO-$d_6$) δ 9.09 (s, 1H), 8.79 (d, J=6.0 Hz, 1H), 7.58 (d, J=6.0 Hz, 1H), 5.16 (q, J=8.7 Hz, 2H); LC/MS (ESI) m/e 223.0 [(M+H)$^+$, calcd for $C_7H_6N_2O_3F_3$ 223.0].

Part B. 4-(2,2,2-Trifluoroethoxy)pyridin-3-amine

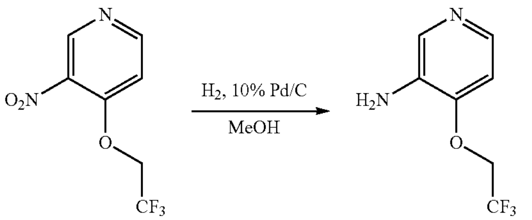 [SMILES: "MeOH" ; O=[N+]([O-])c1cnccc1OCC(F)(F)F ; Nc1cnccc1OCC(F)(F)F]

A mixture of 3-nitro-4-(2,2,2-trifluoroethoxy)pyridine (1.3 g, 5.85 mmol) and 10% palladium on carbon (0.623 g, 0.293 mmol) in methanol (20 mL) was stirred under a $H_2$ at 1 atm for 2 h. The mixture was filtered through a pad of Celite. The mixture was concentrated to afford 4-(2,2,2-trifluoroethoxy)pyridin-3-amine (1.0 g, 5.20 mmol, 89% yield) as a red oil: $^1H$ NMR (400 MHz, DMSO-$d_6$) δ 7.96 (s, 1H), 7.76 (d, J=5.5 Hz, 1H), 6.96 (d, J=5.3 Hz, 1H), 4.93 (s, 2H), 4.84 (q, J=8.9 Hz, 2H); LC/MS (ESI) m/e 193.1 [(M+H)$^+$, calcd for $C_7H_8N_2OF_3$ 193.1].

Part C. 2-Chloro-N-(4-(2,2,2-trifluoroethoxy)pyridin-3-yl)pyrimidine-4-carboxamide

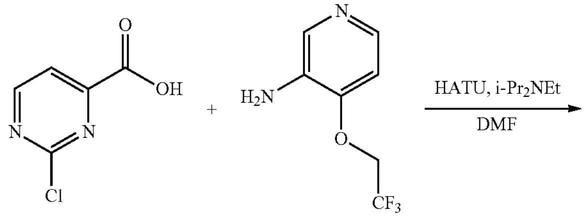

-continued

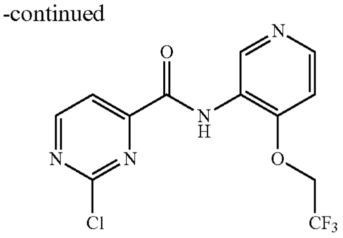

To a solution of 2-chloropyrimidine-4-carboxylic acid (50 mg, 0.315 mmol), 4-(2,2,2-trifluoroethoxy)pyridin-3-amine (91 mg, 0.473 mmol), and N,N-diisopropylethylamine (0.110 mL, 0.631 mmol) in DMF (1 mL) at rt, was added HATU (132 mg, 0.347 mmol). The reaction mixture was stirred at rt for 5 h. The mixture was concentrated and the residue was purified by column chromatography on silica gel (30%→50% ethyl acetate in hexanes; 25 g column) to afford 2-chloro-N-(4-(2,2,2-trifluoroethoxy)pyridin-3-yl) pyrimidine-4-carboxamide (40 mg, 0.120 mmol, 38% yield) as a yellow solid: LC/MS (ESI) m/e 333.0 [(M+H)$^+$, calcd for $C_{12}H_9ClF_3N_4O_2$ 333.0].

Preparation of 2-chloro-N-(4-(2,2,2-trifluoroethoxy) pyrimidin-5-yl)pyrimidine-4-carboxamide

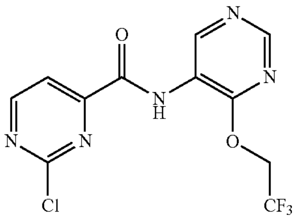 [SMILES: O=C(Nc1cncnc1OCC(F)(F)F)c1ccnc(Cl)n1]

Part A. 4-(2,2,2-Trifluoroethoxy)pyrimidin-5-amine

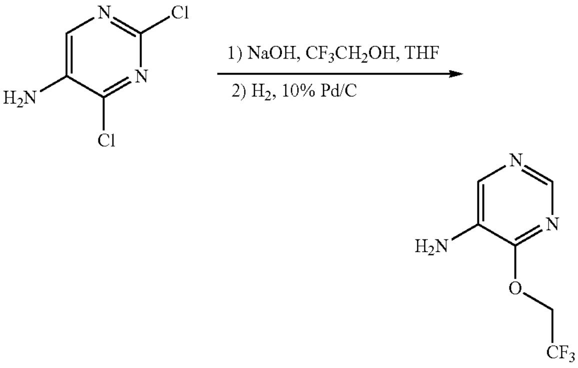

A mixture of 2,4-dichloropyrimidin-5-amine (1, 6.10 mmol), sodium hydroxide (0.976 g, 24.39 mmol), 2,2,2-trifluoroethanol (10.05 mL, 304 mmol) in THF (25 mL) was stirred at rt for 12 h. 10% palladium on carbon (0.649 g, 0.305 mmol) was then added and the reaction was stirred under a hydrogen atmosphere at room temperature for 6 h. The solvent was evaporated and the residue was purified by column chromatography on silica gel (40%→70% ethyl acetate in hexanes; 25 g column) to afford 4-(2,2,2-trifluoroethoxy)pyrimidin-5-amine (1 g, 5.18 mmol, 85% yield) as a yellow solid: $^1$H NMR (400 MHz, DMSO-$d_6$) δ 8.09 (s, 1H), 7.98 (s, 1H), 5.30 (s, 2H), 5.08 (q, J=9.0 Hz, 2H); LC/MS (ESI) m/e 194.0 [(M+H)$^+$, calcd for $C_6H_7N_3F_3O$ 194.1].

Part B. 2-Chloro-N-(4-(2,2,2-trifluoroethoxy)pyrimidin-5-yl)pyrimidine-4-carboxamide

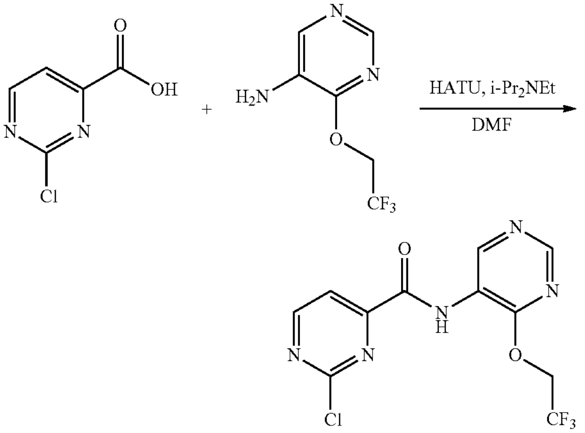

To a solution of 2-chloropyrimidine-4-carboxylic acid (200 mg, 1.261 mmol), 4-(2,2,2-trifluoroethoxy)pyrimidin-5-amine (244 mg, 1.261 mmol), and N,N-diisopropylethylamine (0.881 mL, 5.05 mmol) in DMF (6 mL) was added HATU (528 mg, 1.388 mmol). The reaction mixture was stirred at rt for 3 h. The mixture was concentrated and the residue was purified by column chromatography on silica gel (30%→50% ethyl acetate in hexanes; 25 g column) to afford 2-chloro-N-(4-(2,2,2-trifluoroethoxy)pyrimidin-5-yl)pyrimidine-4-carboxamide (220 mg, 0.659 mmol, 52% yield) as a yellow solid: $^1$H NMR (400 MHz, DMSO-$d_6$) δ 10.37 (s, 1H), 9.20-9.08 (m, 2H), 8.77 (s, 1H), 8.17 (d, J=5.0 Hz, 1H), 5.23 (q, J=8.8 Hz, 2H); LC/MS (ESI) m/e 334.0 [(M+H)$^+$, calcd for $C_{11}H_8N_5O_2ClF_3$ 334.0].

Preparation of 2-chloro-N-(5-(2-fluorophenyl)pyridin-3-yl)pyrimidine-4-carboxamide

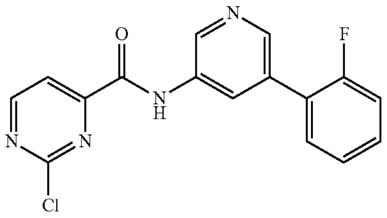 [SMILES: O=C(Nc1cncc(-c2ccccc2F)c1)c1ccnc(Cl)n1]

Part A. 5-(2-Fluorophenyl)pyridin-3-amine

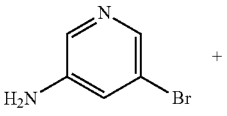

-continued

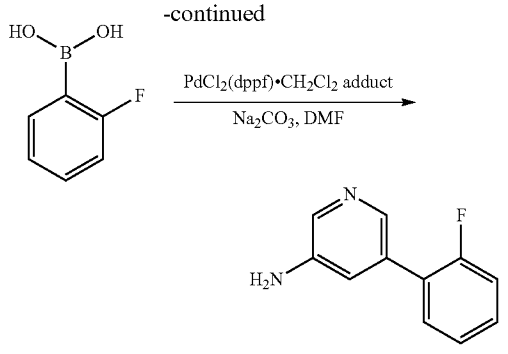

To a pressure vessel was added 5-bromopyridin-3-amine (1.0 g, 5.78 mmol), (2-fluorophenyl)boronic acid (0.809 g, 5.78 mmol) and $PdCl_2$(dppf).$CH_2Cl_2$ adduct (0.944 g, 1.156 mmol). The reaction mixture was degassed and flushed with $N_2$ (3×). DMF (10 mL) was added and the resulting mixture was degassed and flushed with $N_2$ (3×). Sodium carbonate (5.78 mL, 11.56 mmol) was added and the system was degassed and flushed with $N_2$ (3×). The reaction mixture was heated to 85° C. for 3 h. The reaction was diluted with ethyl acetate and saturated ammonium chloride. The organic layer was washed with water, brine, and dried over sodium sulfate. The crude product was dissolved in a small amount of dichloromethane and charged to a 120 g silica gel cartridge which was eluted with 0-100% ethyl acetate/hexanes over a period of 60 min. The desired fractions were combined and dried under vacuo to give 5-(2-fluorophenyl)pyridin-3-amine (1.0 g, 5.31 mmol, 92% yield): $^1$H NMR (400 MHz, DMSO-$d_6$) δ 7.96 (d, J=2.69 Hz, 1H), 7.89 (t, J=1.71 Hz, 1H), 7.51 (td, J=7.82, 1.71 Hz, 1H), 7.41-7.47 (m, 1H), 7.26-7.36 (m, 2H), 7.08 (q, J=1.87 Hz, 1H), 5.45 (s, 2H); $^{19}$F NMR (376 MHz, DMSO-$d_6$) δ −117.92 (s, 1F); MS (ESI) (m/z): 189.1 (M+H)$^+$.

Part B. 2-Chloro-N-(5-(2-fluorophenyl)pyridin-3-yl)pyrimidine-4-carboxamide

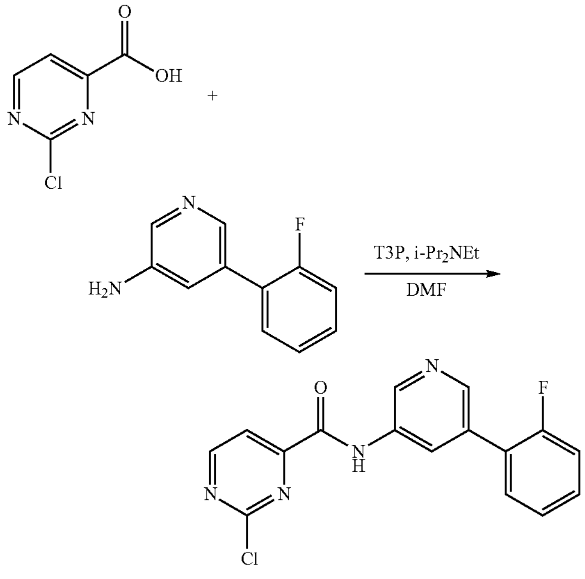

To 5-(2-fluorophenyl)pyridin-3-amine (0.187 g, 0.993 mmol) and 2-chloropyrimidine-4-carboxylic acid (0.15 g, 0.946 mmol) in ethyl acetate (2 mL) was added N, N-diisopropylethylamine (0.826 mL, 4.73 mmol) followed by 1-propanephosphonic acid cyclic anhydride (T3P), 50% in EtOAc (1.105 mL, 1.892 mmol) dropwise. The reaction was stirred overnight at rt. The reaction mixture was transferred to a separatory funnel containing saturated aqueous $NaHCO_3$ solution (20 mL). The aqueous layer was extracted with ethyl acetate (3×20 mL). The combined organic layers were washed with brine (25 mL), dried over $Na_2SO_4$, filtered, and concentrated to give 2-chloro-N-(5-(2-fluorophenyl)pyridin-3-yl)pyrimidine-4-carboxamide (0.31 g, 0.943 mmol, 100% yield): MS (ESI) (m/z): 329.0 $(M+H)^+$.

General Procedure (I) for Intermediate Synthesis for Examples 106-206

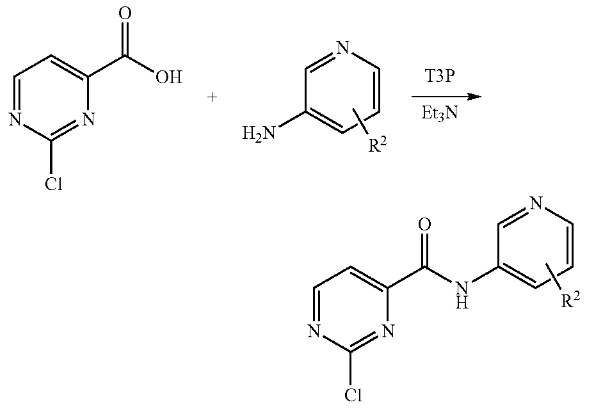

To a solution of the carboxylic acid, amine, and triethylamine in DMF (~0.3 M) at room temperature was added T3P. The reaction was stirred from 1.5 hours to overnight at room temperature depending on the substrate. After the reaction was complete, the mixture was diluted with ethyl acetate and washed with water three times. The ethyl acetate layer was separated, dried ($Na_2SO_4$), filtered, and concentrated. The crude was used directly in the next step.

Representative Experimental Procedure

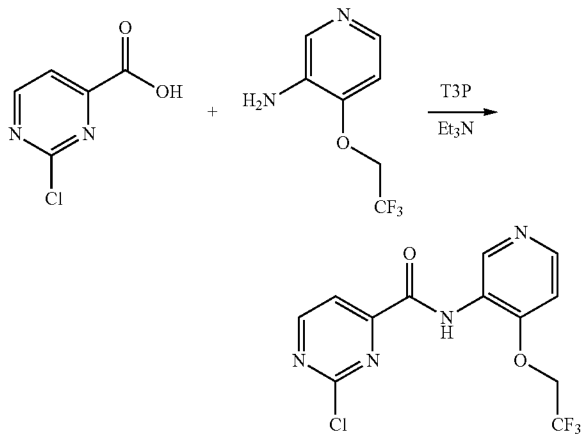

To a solution of 2-chloropyrimidine-4-carboxylic acid (0.094 g, 0.590 mmol), 4-(2,2,2-trifluoroethoxy)pyridin-3-amine (0.1134 g, 0.590 mmol), and triethylamine (0.247 mL, 1.771 mmol) in ethyl acetate (1.5 mL) at room temperature was added 2,4,6-tripropyl-1,3,5,2,4,6-trioxatriphosphinane 2,4,6-trioxide (T3P) (1.054 mL, 1.771 mmol). The reaction was stirred for 1.5 h at rt. The reaction was diluted with ethyl acetate and washed with water three times. The ethyl acetate layer was separated, dried ($Na_2SO_4$), filtered, and concentrated to afford 2-chloro-N-(4-(2,2,2-trifluoroethoxy)pyridin-3-yl)pyrimidine-4-carboxamide (0.126 g, 64% yield) as a brown solid: LCMS (ESI) m/e 333.0 $[(M+H)^+$, calcd $C_{12}H_9ClF_3N_4O_2$, 333.0].

Preparation of 2-chloro-N-(4-(2-fluorophenyl)pyridin-3-yl)pyrimidine-4-carboxamide

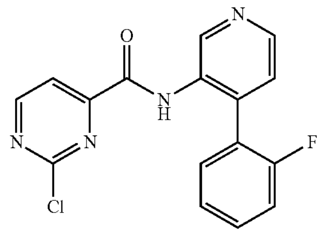 [SMILES: O=C(Nc1cnccc1-c1ccccc1F)c1ccnc(Cl)n1]

Prepared from 4-(2-fluorophenyl)pyridin-3-amine and 2-chloropyrimidine-4-carboxylic acid according to General procedure (I) described above to afford 2-chloro-N-(4-(2-fluorophenyl)pyridin-3-yl)pyrimidine-4-carboxamide (45 mg, 12% yield): LC/MS (ESI) m/e 329.1 $[(M+H)^+$, calcd $C_{16}H_{11}ClFN_4O$, 329.1]; LC/MS retention time (Method C): $t_R$=2.11 min.

Preparation of 2-chloro-N-(4-(2,4-difluorophenyl)pyridin-3-yl)pyrimidine-4-carboxamide

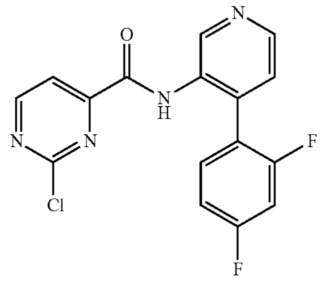 [SMILES: O=C(Nc1cnccc1-c1ccc(F)cc1F)c1ccnc(Cl)n1]

Prepared from 4-(2,4-difluorophenyl)pyridin-3-amine and 2-chloropyrimidine-4-carboxylic acid according to General procedure (I) described above to afford 2-chloro-N-(4-(2,4-difluorophenyl)pyridin-3-yl)pyrimidine-4-carboxamide (35 mg, 52% yield): $^1H$ NMR (400 MHz, CHLOROFORM-d) δ 9.72 (br. s., 1H), 9.67 (s, 1H), 8.91 (d, J=4.8 Hz, 1H), 8.57 (d, J=5.0 Hz, 1H), 8.11 (d, J=5.0 Hz, 1H), 7.39 (td, J=8.3, 6.1 Hz, 1H), 7.31 (d, J=4.8 Hz, 1H), 7.17-7.05 (m, 2H); $^{19}F$ NMR (376 MHz, CHLOROFORM-d) δ-106.82 (d, J=8.7 Hz, 1F), −109.09 (d, J=10.4 Hz, 1F); LC/MS (ESI) m/e 347.1 $[(M+H)^+$, calcd $C_{16}H_{10}ClF_2N_4O$, 347.1]; LC/MS retention time (Method C): $t_R$=2.42 min.

Preparation of 2-chloro-N-(6-fluoro-4-(2,2,2-trifluoroethoxy)pyridin-3-yl)pyrimidine-4-carboxamide

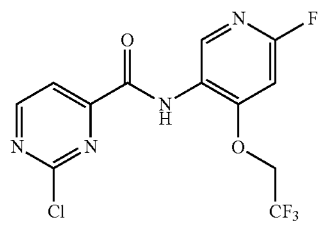 [SMILES: O=C(Nc1cnc(F)cc1OCC(F)(F)F)c1ccnc(Cl)n1]

Prepared from 6-fluoro-4-(2,2,2-trifluoroethoxy)pyridin-3-amine (Lou et al., WO 2015/069594) and 2-chloropyrimidine-4-carboxylic acid according to General procedure (I) described above to afford 2-chloro-N-(6-fluoro-4-(2,2,2-trifluoroethoxy)pyridin-3-yl)pyrimidine-4-carboxamide (153 mg, 72% yield): $^1H$ NMR (400 MHz, CHLOROFORM-d) δ 10.10 (br. s., 1H), 9.30 (s, 1H), 8.96 (d, J=5.0 Hz, 1H), 8.15 (d, J=4.8 Hz, 1H), 6.53 (d, J=1.8 Hz, 1H), 4.59 (q, J=7.5 Hz, 2H); 19F NMR (376 MHz, CHLOROFORM-d) δ -66.06 (s, 1F), −73.65 (s, 3F); LC/MS (ESI) m/e 351.0 [(M+H)$^+$, calcd $C_{12}H_{18}ClF_4N_4O_2$, 351.0]; LC/MS retention time (Method C): $t_R$=2.75 min.

Preparation of 2-chloro-N-(4-(2-propyl-1,3-dioxolan-2-yl)pyridin-3-yl)pyrimidine-4-carboxamide

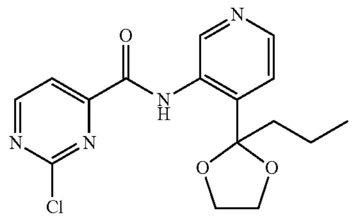 [SMILES: CCCC1(c2ccncc2NC(=O)c2ccnc(Cl)n2)OCCO1]

Prepared from 4-(2-propyl-1,3-dioxolan-2-yl)pyridin-3-amine (Lou et al., WO 2015/069594) and 2-chloropyrimidine-4-carboxylic acid according to General procedure (I) described above to afford 2-chloro-N-(4-(2-propyl-1,3-dioxolan-2-yl)pyridin-3-yl)pyrimidine-4-carboxamide (28 mg, 89% yield): LC/MS (ESI) m/e 383.1 [(M+H)$^+$, calcd $C_{16}H_{17}Cl_2N_4O_3$, 383.1]; LC/MS retention time (Method C): $t_R$=2.17 min.

Preparation of 2-chloro-N-(4-morpholinopyrimidin-5-yl)pyrimidine-4-carboxamide

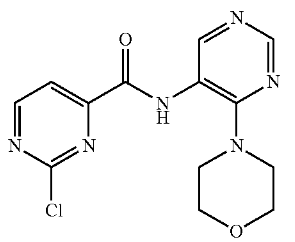 [SMILES: O=C(Nc1cncnc1N1CCOCC1)c1ccnc(Cl)n1]

Prepared from 4-morpholinopyrimidin-5-amine (Lou et al., WO 2015/069594) and 2-chloropyrimidine-4-carboxylic acid according to General procedure (I) described above to afford 2-chloro-N-(4-morpholinopyrimidin-5-yl)pyrimidine-4-carboxamide (20 mg, 60% yield): LC/MS (ESI) m/e 321.1 [(M+H)$^+$, calcd $C_{13}H_{14}ClN_6O_2$, 321.1]; LC/MS retention time (Method C): $t_R$=1.48 min.

Preparation of 2-chloro-N-(6-fluoro-4-morpholinopyridin-3-yl)pyrimidine-4-carboxamide

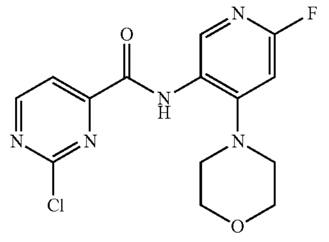 [SMILES: O=C(Nc1cnc(F)cc1N1CCOCC1)c1ccnc(Cl)n1]

Prepared from 6-fluoro-4-morpholinopyridin-3-amine (Lou et al., WO 2015/069594) and 2-chloropyrimidine-4-carboxylic acid according to General procedure (I) described above to afford 2-chloro-N-(6-fluoro-4-morpholinopyridin-3-yl)pyrimidine-4-carboxamide (173 mg, 95% yield): $^1H$ NMR (400 MHz, Chloroform-d) δ 10.12 (s, 1H), 9.21 (s, 1H), 8.96 (d, J=4.9 Hz, 1H), 8.16 (d, J=4.8 Hz, 1H), 6.64 (d, J=1.7 Hz, 1H), 4.06-3.97 (m, 4H), 3.09-3.03 (m, 4H); $^{19}F$ NMR (376 MHz, Chloroform-d) δ -68.62; LC/MS (ESI) m/e 338.1 [(M+H)$^+$, calcd $C_{14}H_{14}ClFN_5O_2$, 338.1]; LC/MS retention time (Method C): $t_R$=2.03 min.

Preparation of 2-chloro-N-(4-(4,4-difluoropiperidin-1-yl)-6-fluoropyridin-3-yl)pyrimidine-4-carboxamide

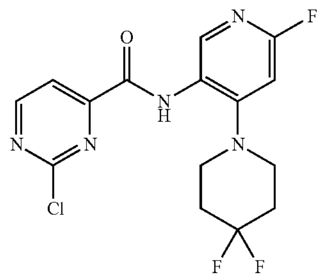 [SMILES: O=C(Nc1cnc(F)cc1N1CCC(F)(F)CC1)c1ccnc(Cl)n1]

Prepared from 4-(4,4-difluoropiperidin-1-yl)-6-fluoropyridin-3-amine (Lou et al., WO 2015/069594) and 2-chloropyrimidine-4-carboxylic acid according to General procedure (I) described above to afford 2-chloro-N-(4-(4,4-difluoropiperidin-1-yl)-6-fluoropyridin-3-yl)pyrimidine-4-carboxamide (73 mg, 99% yield): LC/MS (ESI) m/e 372.1 [(M+H)$^+$, calcd $C_{15}H_{14}ClF_3N_5O$, 372.1]; LC/MS retention time (Method C): $t_R$=2.22 min.

Preparation of 2-chloro-N-(4-(4,4-difluoropiperidin-1-yl)-6-methylpyridin-3-yl)pyrimidine-4-carboxamide

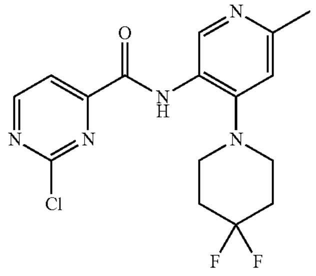 [SMILES: Cc1cc(N2CCC(F)(F)CC2)c(NC(=O)c2ccnc(Cl)n2)cn1]

Prepared from 4-(4,4-difluoropiperidin-1-yl)-6-methylpyridin-3-amine (Lou et al., WO 2015/069594) and 2-chloropyrimidine-4-carboxylic acid according to General procedure (I) described above to afford 2-chloro-N-(4-(4,4-difluoropiperidin-1-yl)-6-methylpyridin-3-yl)pyrimidine-4-carboxamide (20 mg, 60% yield): $^1$H NMR (400 MHz, Chloroform-d) δ 10.28 (s, 1H), 9.57 (s, 1H), 8.98 (d, J=4.9 Hz, 1H), 8.19 (d, J=4.9 Hz, 1H), 6.97 (s, 1H), 3.18 (t, J=5.7 Hz, 4H), 2.60 (s, 3H), 2.37 (tt, J=13.4, 5.6 Hz, 4H); $^{19}$F NMR (376 MHz, Chloroform-d) δ-98.32; LC/MS (ESI) m/e 368.1 $[(M+H)^+$, calcd $C_{16}H_{17}ClF_2N_5O$, 368.1]; LC/MS retention time (Method D): $t_R$=2.58 min.

Preparation of 2-chloro-N-(pyrimidin-5-yl)pyrimidine-4-carboxamide

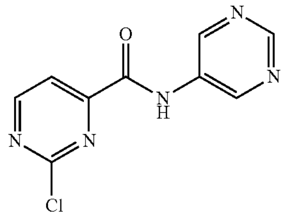 [SMILES: O=C(Nc1cncnc1)c1ccnc(Cl)n1]

Prepared from pyrimidin-5-amine according and 2-chloropyrimidine-4-carboxylic acid to General procedure (I) described above to afford 2-chloro-N-(pyrimidin-5-yl)pyrimidine-4-carboxamide (77 mg, 67% yield): LC/MS (ESI) m/e 236.1 $[(M+H)^+$, calcd $C_9H_7ClN_5O$, 236.0]; LC/MS retention time (Method D): $t_R$=2.21 min.

Preparation of Aniline and Pyridyl Intermediates

Preparation of 6-(difluoromethoxy)-2-methylpyridin-3-amine was completed as described by Hartz et al., (*Bioorg. Med. Chem. Lett.* 2010, 20, 1890-1894). Preparation of 6-(difluoromethoxy)-2,5-dimethylpyridin-3-amine was completed as described by Hartz et al., (*J. Med. Chem.* 2009, 52, 7653-7668). Preparation of 6-(difluoromethoxy)pyridin-3-amine was completed in a similar fashion as described for 6-(difluoromethoxy)-2-methylpyridin-3-amine and 6-(difluoromethoxy)-2,5-dimethylpyridin-3-amine.

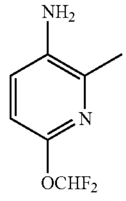
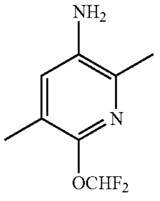
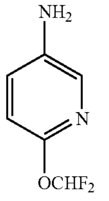

Preparation of 4-chloro-2,5-difluoroaniline

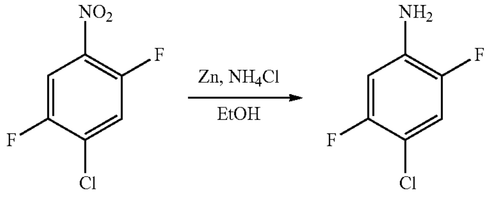 [SMILES: "EtOH" ; O=[N+]([O-])c1cc(F)c(Cl)cc1F ; Nc1cc(F)c(Cl)cc1F]

A mixture of 1-chloro-2,5-difluoro-4-nitrobenzene (500 mg, 2.58 mmol), zinc (845 mg, 12.92 mmol) and ammonium chloride (829 mg, 15.50 mmol) in ethanol (10 mL) was stirred at room temperature for 12 h. The mixture was filtered and the filtrate was concentrated. The residue was transferred to a separatory funnel containing saturated aqueous $NaHCO_3$ solution (20 mL). The aqueous layer was extracted with ethyl acetate (3×25 mL). The combined organic layers were washed with brine, dried over $MgSO_4$, filtered and concentrated to afford 4-chloro-2,5-difluoroaniline (302 mg, 1.847 mmol, 72% yield) as a red solid: $^1$H NMR (400 MHz, DMSO-$d_6$) δ 7.31 (dd, J=10.8, 7.0 Hz, 1H), 6.70 (dd, J=11.2, 7.9 Hz, 1H), 5.66 (s, 2H); LC/MS (ESI) m/e 164.0 $[(M+H)^+$, calcd for $C_6H_5ClF_2N$ 164.0].

Preparation of 4-chloro-5-(difluoromethoxy)-2-fluoroaniline

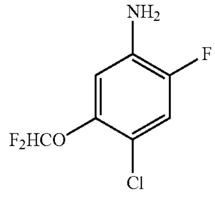 [SMILES: Nc1cc(OC(F)F)c(Cl)cc1F]

Part A. 1-Chloro-2-(difluoromethoxy)-5-fluoro-4-nitrobenzene

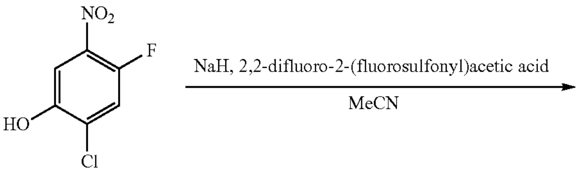

-continued

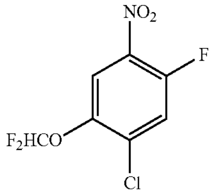

To a mixture of 2-chloro-4-fluoro-5-nitrophenol (1.00 g, 5.22 mmol) in acetonitrile (25 mL), was added NaH (0.564 g, 14.10 mmol) at rt. After stirring for 30 minutes, 2,2-difluoro-2-(fluorosulfonyl)acetic acid (0.917 mL, 8.88 mmol) was added. The mixture was stirred at rt for 12 h. TLC showed the formation of a new spot of higher rf. The reaction mixture was transferred to a separatory funnel containing saturated aqueous $NaHCO_3$ solution (20 mL). The aqueous layer was extracted with ethyl acetate (3×10 mL). The combined organic layers were washed with brine (20 mL), dried over $MgSO_4$, filtered, and concentrated. The residue was purified by column chromatography on silica gel (5%→15% ethyl acetate in hexanes; 25 g column) to afford 1-chloro-2-(difluoromethoxy)-5-fluoro-4-nitrobenzene (160 mg, 0.662 mmol, 12.69% yield) as an oil: $^1H$ NMR (400 MHz, CHLOROFORM-d) δ 8.03 (d, J=6.8 Hz, 1H), 7.48 (d, J=10.0 Hz, 1H), 6.63 (t, J=71.8 Hz, 1H)

Part B. 4-Chloro-5-(difluoromethoxy)-2-fluoroaniline

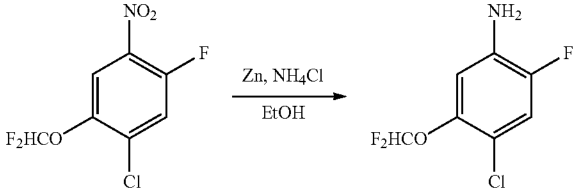 [SMILES: "EtOH" ; O=[N+]([O-])c1cc(OC(F)F)c(Cl)cc1F ; Nc1cc(OC(F)F)c(Cl)cc1F]

A mixture of 1-chloro-2-(difluoromethoxy)-5-fluoro-4-nitrobenzene (160 mg, 0.662 mmol), zinc (217 mg, 3.31 mmol), and ammonium chloride (213 mg, 3.97 mmol) in ethanol (10 mL) was stirred at room temperature for 12 h. The mixture was filtered through a pad of Celite and the filtrate was concentrated. The residue was transferred to a separatory funnel containing saturated aqueous $NaHCO_3$ solution (20 mL). The aqueous layer was extracted with ethyl acetate (3×25 mL). The combined organic layers were washed with brine, dried over $MgSO_4$, filtered and concentrated to afford 4-chloro-5-(difluoromethoxy)-2-fluoroaniline (120 mg, 0.567 mmol, 86% yield) as a red solid: $^1H$ NMR (400 MHz, CHLOROFORM-d) δ 7.09 (d, J=10.3 Hz, 1H), 6.69 (d, J=8.3 Hz, 1H), 6.65-6.19 (m, 1H), 3.84 (br. s., 2H); LC/MS (ESI) m/e 212.0 [(M+H)$^+$, calcd for $C_7H_6ClF_3NO$ 212.0].

Preparation of Final Products

General Procedure (II) for the Synthesis of Final Products

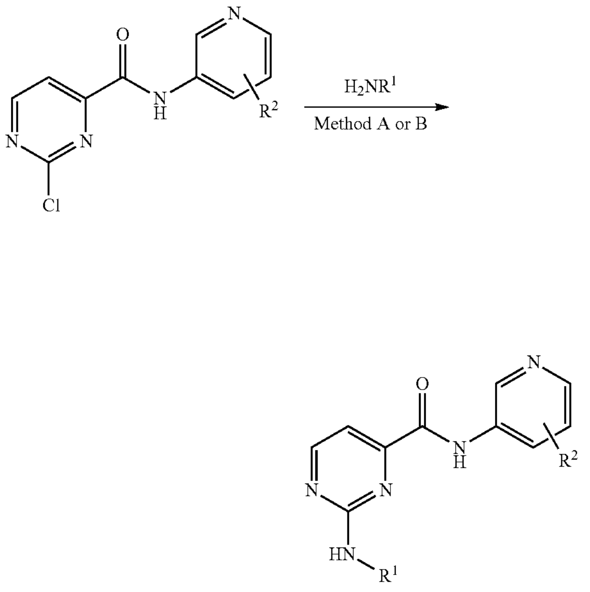

Method A:

A mixture of the amine and chloropyrimidine intermediate in NMP was heated at either 110° C. or 150° C. (the reaction time is included in the example section). The product was purified by reverse phase HPLC.

Methods B-D:

A mixture of amine, chloropyrimidine intermediate, cesium carbonate or potassium carbonate, palladium catalyst, and ligand in the indicated solvent was heated under nitrogen for the time and temperature indicated. The mixture was cooled to room temperature and was filtered through a pad of Celite and was concentrated. The reaction mixture was transferred to a separatory funnel containing saturated aqueous $NaHCO_3$ solution. The aqueous layer was extracted with either ethyl acetate or 5% methanol in dichloromethane. The combined organic layers were washed with brine, dried over $MgSO_4$ or $NaSO_4$, filtered, and concentrated. The product was purified either by reverse phase HPLC or by column chromatography on silica gel.

Representative Procedures:

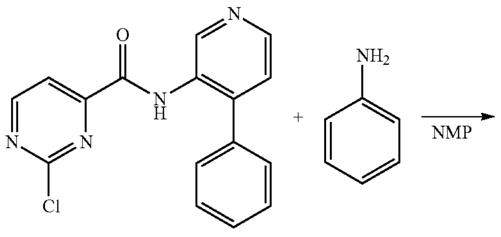

-continued

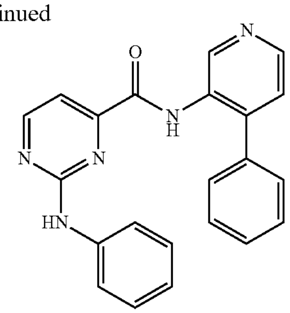

Method A:

A mixture of 2-chloro-N-(4-phenylpyridin-3-yl)pyrimidine-4-carboxamide (28 mg, 0.090 mmol) and aniline (0.066 mL, 0.721 mmol) in NMP (0.4 mL) was heated at 150° C. for 45 min. The mixture was cooled to room temperature and was transferred to a separatory funnel containing ethyl acetate (15 mL). The organic layer was washed with water (3×5 mL) and was concentrated. The product was purified by reverse phase HPLC (Method C) to afford 2-(phenylamino)-N-(4-phenylpyridin-3-yl)pyrimidine-4-carboxamide, TFA (16.8 mg, 0.034 mmol, 38% yield) as a yellow amorphous solid: $^1$H NMR (500 MHz, DMSO-$d_6$) δ 10.01 (s, 1H), 9.83 (s, 1H), 9.14 (s, 1H), 8.75 (d, J=4.7 Hz, 1H), 8.61 (d, J=5.0 Hz, 1H), 7.62-7.57 (m, 3H), 7.54 (d, J=7.8 Hz, 2H), 7.44-7.37 (m, 3H), 7.36 (d, J=4.9 Hz, 1H), 7.20 (t, J=7.9 Hz, 2H), 6.98 (t, J=7.3 Hz, 1H); LC/MS (ESI) m/e 368.1 [(M+H)$^+$, calcd for $C_{22}H_{18}N_5O$ 368.2]; HPLC retention time (Method A): $t_R$=10.19 min; (Method B) $t_R$=10.26 min.

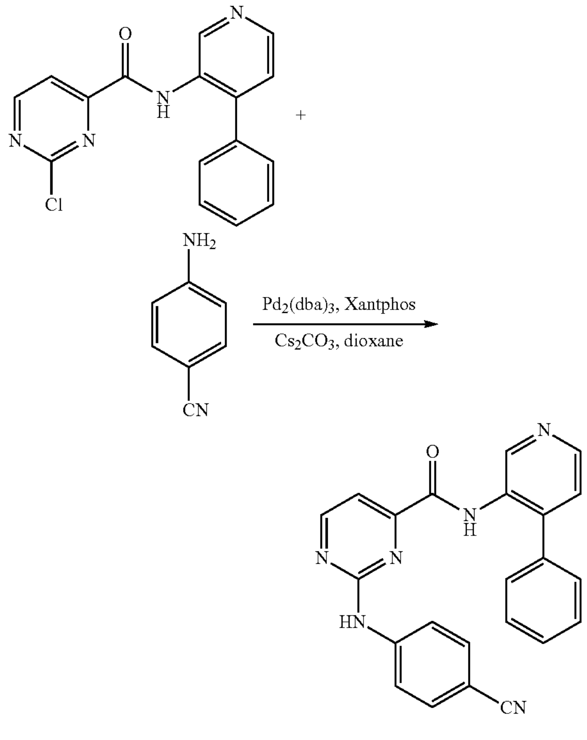

Method B:

2-Chloro-N-(4-phenylpyridin-3-yl)pyrimidine-4-carboxamide (20 mg, 0.064 mmol), 4-aminobenzonitrile (30.4 mg, 0.257 mmol), cesium carbonate (41.9 mg, 0.129 mmol) and dioxane (0.5 mL) were combined in a 2 mL microwave vial. The mixture was degassed under nitrogen for 5 min. Tris(dibenzylideneacetone)dipalladium(0) (5.89 mg, 6.44 μmol) and Xantphos (7.45 mg, 0.013 mmol) were added. The vial was sealed under nitrogen and the mixture was heated at 100° C. for 2 h. The mixture was cooled to room temperature and was filtered through a pad of Celite and was concentrated. The reaction mixture was transferred to a separatory funnel containing saturated aqueous $NaHCO_3$ solution (5 mL). The aqueous layer was extracted with 5% methanol in dichloromethane (3×5 mL). The combined organic layers were washed with brine (5 mL), dried over $MgSO_4$, filtered, and concentrated. The crude material was purified by reverse phase HPLC (Method B, Gradient: 40-80% B over 12 minutes, then a 5-minute hold at 100% B) to afford 2-((4-cyanophenyl)amino)-N-(4-phenylpyridin-3-yl)pyrimidine-4-carboxamide (14.2 mg, 0.034 mmol, 52% yield): $^1$H NMR (500 MHz, DMSO-$d_6$) δ 10.42 (s, 1H), 10.03 (s, 1H), 9.09 (s, 1H), 8.84 (d, J=4.6 Hz, 1H), 8.56 (d, J=5.2 Hz, 1H), 7.77 (d, J=8.9 Hz, 2H), 7.61 (d, J=8.5 Hz, 2H), 7.58-7.55 (m, 2H), 7.49 (d, J=4.9 Hz, 2H), 7.39-7.35 (m, 2H), 7.34-7.29 (m, 1H); LC/MS (ESI) m/e 393.2 [(M+H)$^+$, calcd for $C_{23}H_{17}N_6O$ 393.1]; LC/MS retention time (Method A): $t_R$=2.51 min; (Method B) $t_R$=3.74 min.

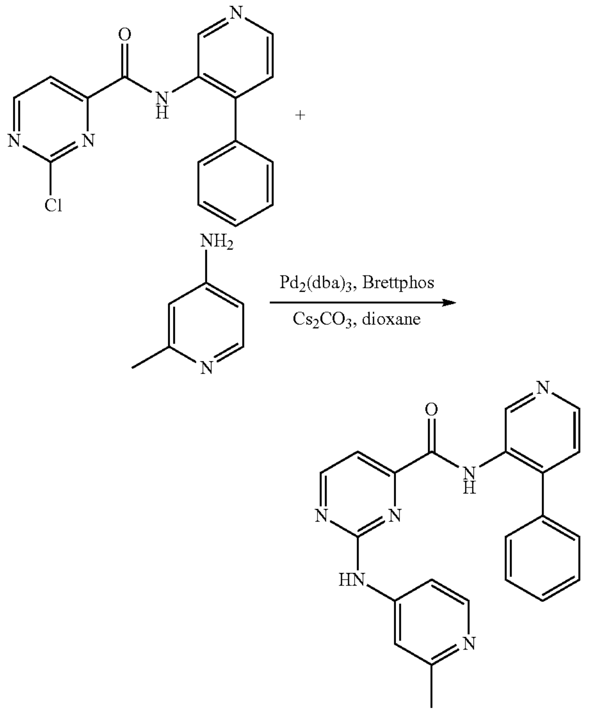

Method C:

2-Chloro-N-(4-phenylpyridin-3-yl)pyrimidine-4-carboxamide (30 mg, 0.097 mmol), 2-methylpyridin-4-amine (17.75 mg, 0.164 mmol), cesium carbonate (62.9 mg, 0.193 mmol) and dioxane (0.8 mL) were combined in a vial. The mixture was degassed by sonication under nitrogen for 5 min. Tris(dibenzylideneacetone)dipalladium(0) (8.84 mg, 9.65 μmol) and BrettPhos (51.8 mg, 0.097 mmol) were added. The vial was sealed under nitrogen and the mixture was heated at 100° C. for 2 h. The mixture was cooled to room temperature and was filtered through a pad of Celite and was concentrated. The reaction mixture was transferred to a separatory funnel containing saturated aqueous $NaHCO_3$ solution (5 mL). The aqueous layer was extracted with 5% methanol in dichloromethane (3×5 mL). The combined organic layers were washed with brine (5 mL), dried over $MgSO_4$, filtered, and concentrated. The product was purified by reverse phase HPLC (Method B, Gradient: 20-100% B over 12 minutes, then a 5-minute hold at 100% B) to afford 2-((2-methylpyridin-4-yl)amino)-N-(4-phenylpyridin-3-yl)pyrimidine-4-carboxamide (27 mg, 71% yield): $^1H$ NMR (500 MHz, DMSO-$d_6$) δ 10.22 (s, 1H), 10.10 (br. s., 1H), 9.01 (s, 1H), 8.84 (d, J=4.9 Hz, 1H), 8.57 (d, J=4.9 Hz, 1H), 8.14 (d, J=5.5 Hz, 1H), 7.57 (d, J=7.3 Hz, 2H), 7.50 (d, J=4.9 Hz, 1H), 7.48-7.42 (m, 3H), 7.42-7.38 (m, 2H), 7.37-7.32 (m, 1H), 2.37 (s, 3H); LC/MS (ESI) m/e 383.2 [(M+H)$^+$, calcd for $C_{22}H_{19}N_6O$ 383.2]; LC/MS retention time (Method A): $t_R$=1.74 min; (Method B) $t_R$=3.50 min.

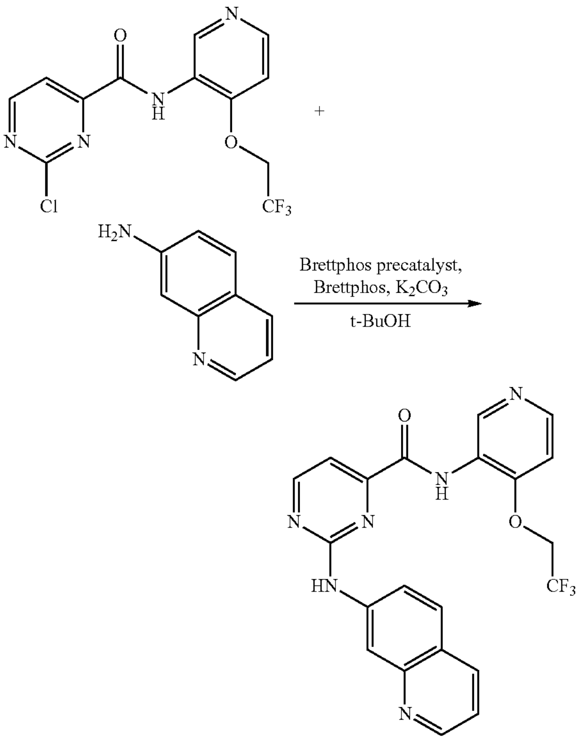

Method D:

A mixture of 2-chloro-N-(4-(2,2,2-trifluoroethoxy)pyridin-3-yl)pyrimidine-4-carboxamide (14.9 mg, 0.045 mmol), quinolin-7-amine (7.75 mg, 0.054 mmol), potassium carbonate (9.29 mg, 0.067 mmol), dicyclohexyl(2',4',6'-triisopropyl-3,6-dimethoxy-[1,1'-biphenyl]-2-yl)phosphine (Brettphos) (0.240 mg, 0.448 μmol), and Brettphos precatalyst (0.358 mg, 0.448 μmol) in t-butanol (1 mL) (degassed) was heated at 110° C. for 18 h. The mixture was filtered through a tiny silica plug and washed with methanol. The product was purified reverse phase HPLC (Method B, Gradient: 30-100% B over 16 minutes, then a 5-minute hold at 100% B) to afford 2-(quinolin-7-ylamino)-N-(4-(2,2,2-trifluoroethoxy)pyridin-3-yl)pyrimidine-4-carboxamide (0.7 mg, 3% yield): $^1H$ NMR (500 MHz, METHANOL-$d_4$) δ 9.41 (s, 1H), 8.85 (d, J=4.9 Hz, 1H), 8.77 (dd, J=4.3, 1.5 Hz, 1H), 8.64 (d, J=1.8 Hz, 1H), 8.35 (d, J=5.8 Hz, 1H), 8.31 (d, J=7.3 Hz, 1H), 7.92 (d, J=8.9 Hz, 1H), 7.81 (dd, J=8.9, 2.1 Hz, 1H), 7.63 (d, J=4.9 Hz, 1H), 7.42 (dd, J=8.2, 4.3 Hz, 1H), 7.32 (d, J=5.8 Hz, 1H), 4.80 (q, J=8.2 Hz, 2H); LCMS (ESI) m/e 441.1 [(M+H)$^+$, calcd $C_{21}H_{16}F_3N_6O_2$, 441.1]; LC/MS retention time (Method A): $t_R$=2.31 min.

EXAMPLES

Example 1

2-Amino-N-(6-methylpyridin-3-yl)pyrimidine-4-carboxamide

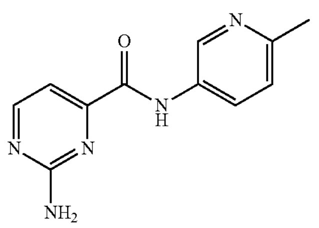 [SMILES: Cc1ccc(NC(=O)c2ccnc(N)n2)cn1]

To a solution of 2-aminopyrimidine-4-carboxylic acid (20 mg, 0.144 mmol) and 2-aminopyrimidine-4-carboxylic acid (20 mg, 0.144 mmol) in DMF (1 mL) was added N,N-diisopropylethylamine (0.126 mL, 0.719 mmol) followed by HATU (65.6 mg, 0.173 mmol). The reaction mixture was stirred at rt for 14 h. The mixture was concentrated and the residue was dissolved in DMF (1.5 mL) and was purified by reverse phase HPLC (Method A, Gradient: 30-100% B over 12 minutes, then a 5-minute hold at 100% B) to afford 2-amino-N-(6-methylpyridin-3-yl)pyrimidine-4-carboxamide (10.1 mg, 30% yield): $^1H$ NMR (500 MHz, DMSO-$d_6$) δ 10.44 (s, 1H), 8.83 (d, J=2.4 Hz, 1H), 8.54 (d, J=4.6 Hz, 1H), 8.12 (dd, J=8.2, 2.4 Hz, 1H), 7.28 (d, J=8.5 Hz, 1H), 7.16 (d, J=4.9 Hz, 1H), 6.96 (br. s., 2H), 2.46 (s, 3H); LC/MS (ESI) m/e 230.2 [(M+H)$^+$, calcd for $C_{11}H_{12}N_5O$ 230.1]; LC/MS retention time (Method A): $t_R$=1.46 min; (Method B) $t_R$=2.62 min.

Example 2

2-Amino-N-(4-(4,4-difluoropiperidin-1-yl)pyridin-3-yl)pyrimidine-4-carboxamide

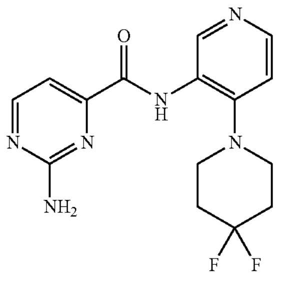 [SMILES: Nc1nccc(C(=O)Nc2cnccc2N2CCC(F)(F)CC2)n1]

To a solution of 2-aminopyrimidine-4-carboxylic acid (20 mg, 0.144 mmol) and 4-(4,4-difluoropiperidin-1-yl)pyridin-3-amine (36.8 mg, 0.173 mmol) in DMF (1 mL) was added N,N-diisopropylethylamine (0.126 mL, 0.719 mmol) followed by HATU (65.6 mg, 0.173 mmol). The reaction mixture was stirred at rt for 14 h. The mixture was concentrated and the residue was dissolved in DMF (1.5 mL) and was purified by reverse phase HPLC (Method A, Gradient: 30-95% B over 8.3 minutes, then a 6.7 minute hold at 95% B) to afford 2-amino-N-(4-(4,4-difluoropiperidin-1-yl)pyridin-3-yl)pyrimidine-4-carboxamide (28.2 mg, 58% yield): $^1$H NMR (500 MHz, DMSO-$d_6$) δ 10.13 (s, 1H), 9.32 (s, 1H), 8.60 (d, J=4.6 Hz, 1H), 8.31 (d, J=5.5 Hz, 1H), 7.25 (d, J=4.9 Hz, 2H), 7.17 (s, 2H), 3.10 (t, J=5.5 Hz, 4H), 2.35-2.19 (m, 4H); LC/MS (ESI) m/e 335.2 [(M+H)$^+$, calcd for $C_{15}H_{17}F_2N_6O$ 335.1]; LC/MS retention time (Method A): $t_R$=1.98 min; (Method B) $t_R$=3.01 min.

Example 3

N-(4-(4,4-Difluoropiperidin-1-yl)pyridin-3-yl)-2-(phenylamino)pyrimidine-4-carboxamide

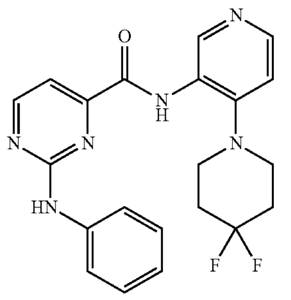 [SMILES: O=C(Nc1cnccc1N1CCC(F)(F)CC1)c1ccnc(Nc2ccccc2)n1]

Part A. 2-Amino-N-(4-(4,4-difluoropiperidin-1-yl)pyridin-3-yl)pyrimidine-4-carboxamide

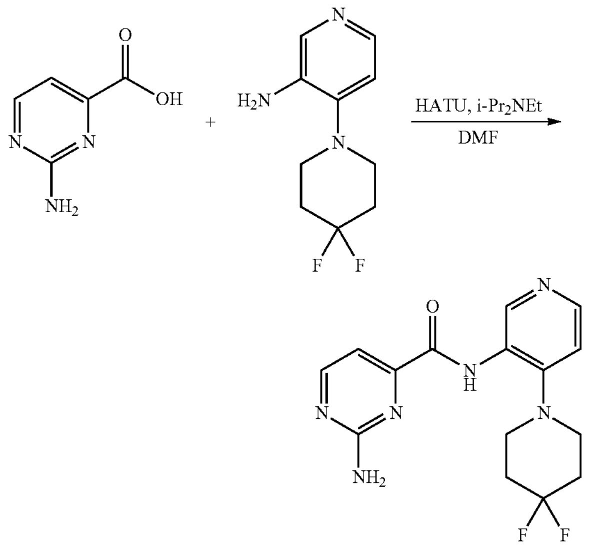

To a solution of 2-aminopyrimidine-4-carboxylic acid (150 mg, 1.078 mmol) and 4-(4,4-difluoropiperidin-1-yl)pyridin-3-amine (276 mg, 1.294 mmol) in DMF (5 mL) was added N,N-diisopropylethylamine (0.942 mL, 5.39 mmol) followed by HATU (492 mg, 1.294 mmol). The reaction mixture was stirred at rt for 18 h. The mixture was concentrated and the residue was purified by column chromatography on silica gel (5%→8% methanol in $CH_2Cl_2$; 40 g column) to afford 2-amino-N-(4-(4,4-difluoropiperidin-1-yl)pyridin-3-yl)pyrimidine-4-carboxamide (455 mg, 1.361 mmol, 126% yield) as a yellow solid. (An impurity was present in the product.) $^1$H NMR (500 MHz, DMSO-$d_6$) δ 10.13 (s, 1H), 9.32 (s, 1H), 8.60 (d, J=4.6 Hz, 1H), 8.31 (d, J=5.5 Hz, 1H), 7.25 (d, J=4.9 Hz, 2H), 7.17 (s, 2H), 3.10 (t, J=5.5 Hz, 4H), 2.35-2.19 (m, 4H); LC/MS (ESI) m/e 335.2 [(M+H)$^+$, calcd for $C_{15}H_{17}F_2N_6O$ 335.1].

Part B. N-(4-(4,4-Difluoropiperidin-1-yl)pyridin-3-yl)-2-(phenylamino)pyrimidine-4-carboxamide

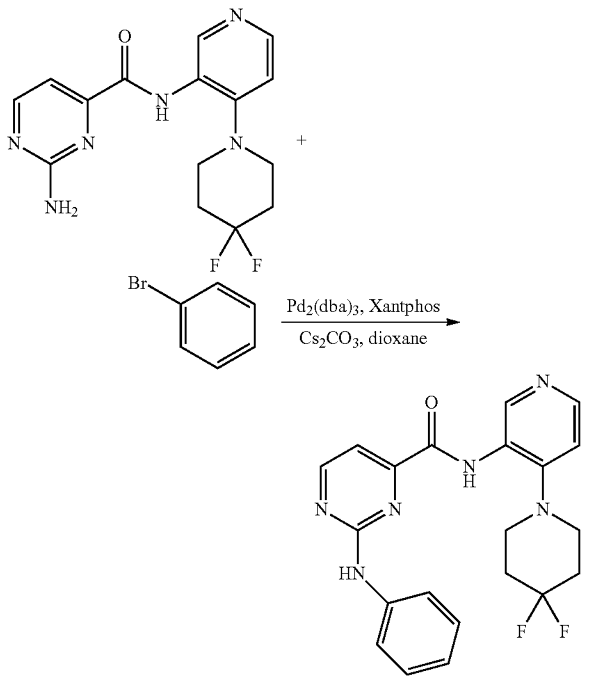

2-Amino-N-(4-(4,4-difluoropiperidin-1-yl)pyridin-3-yl)pyrimidine-4-carboxamide (40 mg, 0.120 mmol), bromobenzene (31.9 mg, 0.203 mmol), cesium carbonate (78 mg, 0.239 mmol) and dioxane (1.0 mL) were combined in a 2 mL conical vial. The mixture was degassed by sonication under nitrogen for 5 min. Tris(dibenzylideneacetone)dipalladium(0) (10.96 mg, 0.012 mmol) and Xantphos (13.85 mg, 0.024 mmol) were added. The vial was sealed under nitrogen and the mixture was heated at 100° C. for 14 h. The reaction mixture was cooled to room temperature and was transferred to a separatory funnel containing saturated aqueous $NaHCO_3$ solution (5 mL). The aqueous layer was extracted with 5% methanol in dichloromethane (3×10 mL). The combined organic layers were washed with brine (5 mL), dried over $MgSO_4$, filtered, and concentrated. The residue was taken up in methanol and filtered and the product was purified by reverse phase HPLC (Method C) to afford N-(4-(4,4-difluoropiperidin-1-yl)pyridin-3-yl)-2-(phenylamino)pyrimidine-4-carboxamide, TFA (14.5 mg, 0.027 mmol, 23% yield) as a yellow amorphous solid: $^1$H NMR (500 MHz, DMSO-$d_6$) δ 10.10 (s, 1H), 9.93 (s, 1H), 8.93 (s, 1H), 8.81 (d, J=4.7 Hz, 1H), 8.43 (d, J=6.6 Hz, 1H), 7.72 (d, J=7.6 Hz, 2H), 7.48 (d, J=6.7 Hz, 1H), 7.44 (d, J=4.7 Hz, 1H), 7.34 (t, J=7.9 Hz, 2H), 7.04 (t, J=7.4 Hz, 1H), 3.55-3.50 (m, 4H), 2.08-1.99 (m, 4H); LC/MS (ESI) m/e 411.2 [(M+H)$^+$, calcd for $C_{21}H_{21}F_2N_6O$ 411.2]; HPLC retention time (Method A): $t_R$=9.45 min; (Method B) $t_R$=9.90 min.

Example 4

2-(Phenylamino)-N-(4-phenylpyridin-3-yl)pyrimidine-4-carboxamide

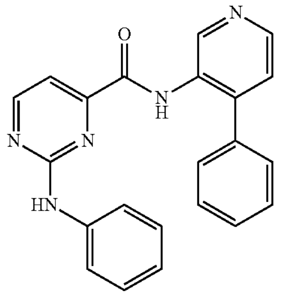

Prepared by Method A (heated at 150° C. for 45 min), obtained 16.8 mg, 38% yield as a yellow amorphous solid: $^1$H NMR (500 MHz, DMSO-$d_6$) δ 10.01 (s, 1H), 9.83 (s, 1H), 9.14 (s, 1H), 8.75 (d, J=4.7 Hz, 1H), 8.61 (d, J=5.0 Hz, 1H), 7.62-7.57 (m, 3H), 7.54 (d, J=7.8 Hz, 2H), 7.44-7.37 (m, 3H), 7.36 (d, J=4.9 Hz, 1H), 7.20 (t, J=7.9 Hz, 2H), 6.98 (t, J=7.3 Hz, 1H); LC/MS (ESI) m/e 368.1 [(M+H)$^+$, calcd for $C_{22}H_{18}N_5O$ 368.2]; HPLC retention time (Method A): $t_R$=10.19 min; (Method B) $t_R$=10.26 min.

Example 5

2-((4-Fluorophenyl)amino)-N-(4-phenylpyridin-3-yl)pyrimidine-4-carboxamide

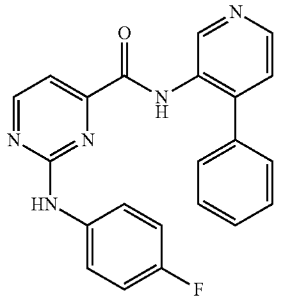

Prepared by Method A (heated at 150° C. for 40 min), obtained 9.7 mg, 50% yield: $^1$H NMR (500 MHz, DMSO-$d_6$) δ 9.94 (s, 1H), 9.88 (s, 1H), 9.09 (s, 1H), 8.74 (d, J=4.9 Hz, 1H), 8.55 (d, J=4.9 Hz, 1H), 7.57-7.51 (m, 4H), 7.48 (d, J=4.9 Hz, 1H), 7.42-7.33 (m, 4H), 7.01 (t, J=8.7 Hz, 2H); LC/MS (ESI) m/e 386.1 [(M+H)$^+$, calcd for $C_{22}H_{17}FN_5O$ 386.1]; LC/MS retention time (Method A): $t_R$=2.73 min; (Method B) $t_R$=4.02 min.

Example 6

2-((4-Methoxyphenyl)amino)-N-(4-phenylpyridin-3-yl)pyrimidine-4-carboxamide

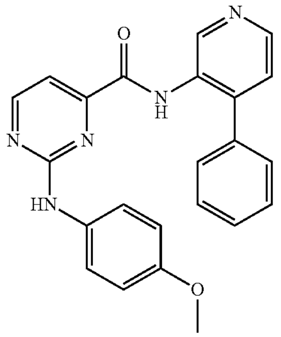

Prepared by Method A (heated at 150° C. for 30 min), obtained 12.7 mg, 66% yield: $^1$H NMR (500 MHz, DMSO-$d_6$) δ 9.89 (s, 1H), 9.65 (br. s., 1H), 9.09 (s, 1H), 8.70 (d, J=4.6 Hz, 1H), 8.54 (d, J=4.9 Hz, 1H), 7.56 (dd, J=7.6, 1.5 Hz, 2H), 7.47 (d, J=4.9 Hz, 1H), 7.44-7.35 (m, 5H), 7.31 (d, J=4.6 Hz, 1H), 6.75 (d, J=8.9 Hz, 2H), 3.74 (s, 3H); LC/MS (ESI) m/e 398.2 [(M+H)$^+$, calcd for $C_{23}H_{20}N_5O_2$ 398.2]; LC/MS retention time (Method A): $t_R$=2.60 min; (Method B) $t_R$=3.88 min.

Example 7

2-((4-Ethoxyphenyl)amino)-N-(4-phenylpyridin-3-yl)pyrimidine-4-carboxamide

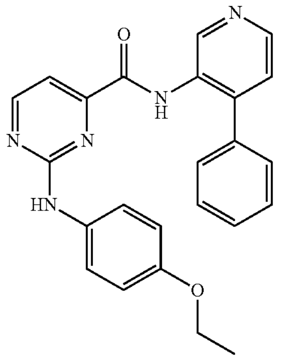 [SMILES: CCOc1ccc(Nc2nccc(C(=O)Nc3cnccc3-c3ccccc3)n2)cc1]

Prepared by Method A (heated at 150° C. for 30 min), obtained 10.7 mg, 54% yield: $^1$H NMR (500 MHz, DMSO-$d_6$) δ 9.90 (br. s., 1H), 9.64 (br. s., 1H), 9.08 (s, 1H), 8.69 (d, J=4.6 Hz, 1H), 8.54 (d, J=4.9 Hz, 1H), 7.56 (dd, J=7.5, 1.7 Hz, 2H), 7.47 (d, J=4.9 Hz, 1H), 7.43-7.35 (m, 5H), 7.31 (d, J=4.9 Hz, 1H), 6.74 (d, J=8.9 Hz, 2H), 3.99 (q, J=6.9 Hz, 2H), 1.34 (t, J=7.0 Hz, 3H); LC/MS (ESI) m/e 412.2 [(M+H)$^+$, calcd for $C_{24}H_{22}N_5O_2$ 412.2]; LC/MS retention time (Method A): $t_R$=2.76 min; (Method B) $t_R$=4.03 min.

Example 8

N-(4-Phenylpyridin-3-yl)-2-(p-tolylamino)pyrimidine-4-carboxamide

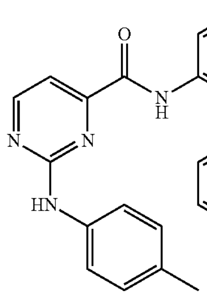

Prepared by Method A (heated at 150° C. for 30 min), obtained 12.1 mg, 64% yield: $^1$H NMR (500 MHz, DMSO-$d_6$) δ 9.94 (s, 1H), 9.72 (s, 1H), 9.08 (s, 1H), 8.72 (d, J=4.6 Hz, 1H), 8.55 (d, J=5.2 Hz, 1H), 7.58-7.53 (m, 2H), 7.47 (d, J=4.9 Hz, 1H), 7.43-7.35 (m, 5H), 7.33 (d, J=4.9 Hz, 1H), 7.00 (d, J=8.2 Hz, 2H), 2.27 (s, 3H); LC/MS (ESI) m/e 382.2 $[(M+H)^+$, calcd for $C_{23}H_{20}N_5O$ 382.2]; LC/MS retention time (Method A): $t_R$=2.86 min; (Method B) $t_R$=4.12 min.

Example 9

N-(4-Phenylpyridin-3-yl)-2-((4-(trifluoromethyl)phenyl)amino)pyrimidine-4-carboxamide

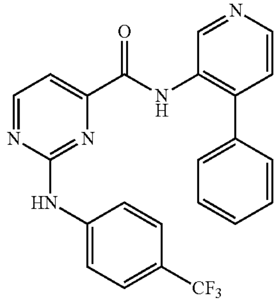 [SMILES: O=C(Nc1cnccc1-c1ccccc1)c1ccnc(Nc2ccc(C(F)(F)F)cc2)n1]

Prepared by Method A (heated at 150° C. for 40 min), obtained 2 mg, 10% yield as an off-white solid: $^1$H NMR (400 MHz, CHLOROFORM-d) δ 9.87 (s, 1H), 9.80 (s, 1H), 8.75 (d, J=4.8 Hz, 1H), 8.55 (d, J=4.8 Hz, 1H), 7.70 (d, J=4.8 Hz, 1H), 7.52-7.49 (m, 4H), 7.47 (s, 4H), 7.45-7.40 (m, 1H), 7.35 (d, J=5.0 Hz, 1H), 7.05 (s, 1H); LC/MS (ESI) m/e 436.1 $[(M+H)^+$, calcd for $C_{23}H_{17}F_3N_5O$ 436.1]; HPLC retention time (Method A): $t_R$=11.16 min; (Method B) $t_R$=11.26 min.

Example 10

2-((4-Chlorophenyl)amino)-N-(4-phenylpyridin-3-yl)pyrimidine-4-carboxamide

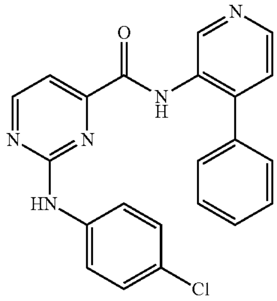

Prepared by Method A (heated at 150° C. for 30 min), obtained 8 mg, 31% yield: $^1$H NMR (500 MHz, DMSO-$d_6$) δ 10.01 (s, 1H), 9.96 (s, 1H), 9.10 (s, 1H), 8.77 (d, J=4.9 Hz, 1H), 8.55 (d, J=4.9 Hz, 1H), 7.57 (t, J=7.3 Hz, 4H), 7.48 (d, J=4.9 Hz, 1H), 7.42-7.29 (m, 4H), 7.21 (d, J=8.9 Hz, 2H); LC/MS (ESI) m/e 402.1 $[(M+H)^+$, calcd for $C_{22}H_{17}ClN_5O$ 402.1]; LC/MS retention time (Method A): $t_R$=2.94 min; (Method B) $t_R$=4.22 min.

Example 11

2-((4-Cyanophenyl)amino)-N-(4-phenylpyridin-3-yl)pyrimidine-4-carboxamide

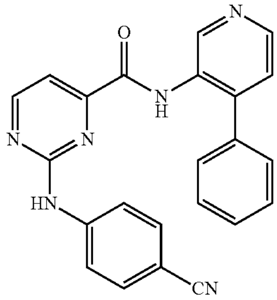 [SMILES: N#Cc1ccc(Nc2nccc(C(=O)Nc3cnccc3-c3ccccc3)n2)cc1]

Prepared by Method B (heated at 100° C. for 2 h), obtained 14.2 mg, 52% yield: $^1$H NMR (500 MHz, DMSO-$d_6$) δ 10.42 (s, 1H), 10.03 (s, 1H), 9.09 (s, 1H), 8.84 (d, J=4.6 Hz, 1H), 8.56 (d, J=5.2 Hz, 1H), 7.77 (d, J=8.9 Hz, 2H), 7.61 (d, J=8.5 Hz, 2H), 7.58-7.55 (m, 2H), 7.49 (d, J=4.9 Hz, 2H), 7.39-7.35 (m, 2H), 7.34-7.29 (m, 1H); LC/MS (ESI) m/e 393.2 $[(M+H)^+$, calcd for $C_{23}H_{17}N_6O$ 393.1]; LC/MS retention time (Method A): $t_R$=2.51 min; (Method B) $t_R$=3.74 min.

Example 12

N-(4-Phenylpyridin-3-yl)-2-((4-(trifluoromethoxy)phenyl)amino)pyrimidine-4-carboxamide

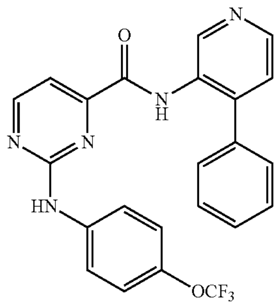 [SMILES: O=C(Nc1cnccc1-c1ccccc1)c1ccnc(Nc2ccc(OC(F)(F)F)cc2)n1]

Prepared by Method A (heated at 150° C. for 30 min), obtained 11 mg, 49% yield: $^1$H NMR (500 MHz, DMSO-$d_6$) δ 10.08 (s, 1H), 9.98 (s, 1H), 9.05 (s, 1H), 8.78 (d, J=4.9 Hz, 1H), 8.56 (d, J=5.2 Hz, 1H), 7.68 (d, J=9.2 Hz, 2H), 7.57 (d, J=6.7 Hz, 2H), 7.48 (d, J=4.9 Hz, 1H), 7.41 (d, J=4.9 Hz, 1H), 7.40-7.33 (m, 3H), 7.19 (d, J=8.9 Hz, 2H); LC/MS (ESI) m/e 452.1 [(M+H)$^+$, calcd for $C_{23}H_{17}F_3N_5O_2$ 452.1]; LC/MS retention time (Method A): $t_R$=3.08 min; (Method B) $t_R$=4.33 min.

Example 13

2-((4-(Difluoromethoxy)phenyl)amino)-N-(4-phenylpyridin-3-yl)pyrimidine-4-carboxamide

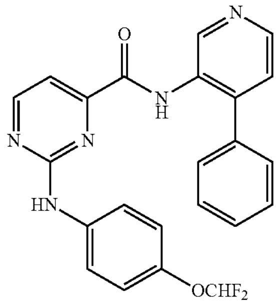 [SMILES: O=C(Nc1cnccc1-c1ccccc1)c1ccnc(Nc2ccc(OC(F)F)cc2)n1]

Prepared by Method A (heated at 150° C. for 30 min), obtained 11.1 mg, 53% yield: $^1$H NMR (500 MHz, DMSO-$d_6$) δ 9.94 (d, J=10.4 Hz, 2H), 9.06 (s, 1H), 8.75 (d, J=4.6 Hz, 1H), 8.55 (d, J=4.9 Hz, 1H), 7.64-7.53 (m, 4H), 7.48 (d, J=4.9 Hz, 1H), 7.43-7.34 (m, 4H), 7.01 (d, J=8.9 Hz, 2H), 7.14 (t, J=74.5 Hz, 1H); LC/MS (ESI) m/e 434.2 [(M+H)$^+$, calcd for $C_{23}H_{18}N_5O_2F_2$ 434.1]; LC/MS retention time (Method A): $t_R$=2.78 min; (Method B) $t_R$=4.01 min.

Example 14

2-((4-(Methylsulfinyl)phenyl)amino)-N-(4-phenylpyridin-3-yl)pyrimidine-4-carboxamide

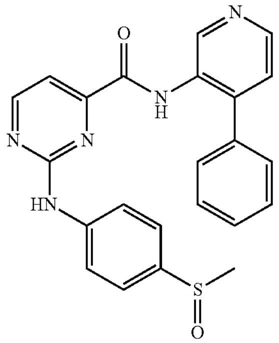 [SMILES: CS(=O)c1ccc(Nc2nccc(C(=O)Nc3cnccc3-c3ccccc3)n2)cc1]

Part A. 2-((4-(Methylthio)phenyl)amino)-N-(4-phenylpyridin-3-yl)pyrimidine-4-carboxamide

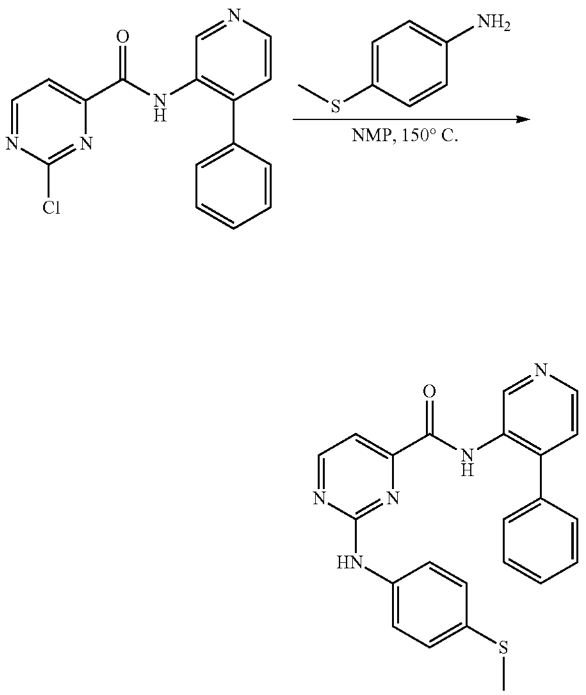

A mixture of 2-chloro-N-(4-phenylpyridin-3-yl)pyrimidine-4-carboxamide (100 mg, 0.322 mmol) and 4-(methylthio)aniline (0.320 mL, 2.57 mmol) in NMP (0.4 mL) was heated at 150° C. for 30 min. The mixture was cooled to room temperature and the residue was purified by column chromatography on silica gel (10% methanol in methylene chloride; 12 g column) to afford 2-((4-(methylthio)phenyl)amino)-N-(4-phenylpyridin-3-yl)pyrimidine-4-carboxamide (60 mg, 0.145 mmol, 45% yield) as a red solid: LC/MS (ESI) m/e 414.1 [(M+H)$^+$, calcd for $C_{23}H_{20}N_5OS$ 414.1].

Part B. 2-((4-(Methylsulfinyl)phenyl)amino)-N-(4-phenylpyridin-3-yl)pyrimidine-4-carboxamide

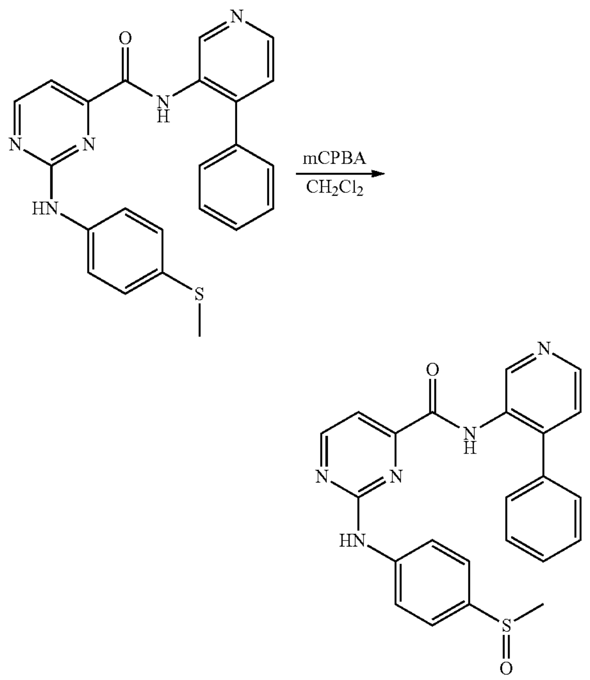

To a mixture of 2-((4-(methylthio)phenyl)amino)-N-(4-phenylpyridin-3-yl)pyrimidine-4-carboxamide (30 mg, 0.073 mmol) in $CH_2Cl_2$ (0.5 mL) at −75° C., was added mCPBA (14.31 mg, 0.058 mmol). The mixture was stirred at −75° C. for 5 min. The mixture was concentrated and the residue was purified by reverse phase HPLC (Method C) to afford 2-((4-(methylsulfinyl)phenyl)amino)-N-(4-phenylpyridin-3-yl)pyrimidine-4-carboxamide, TFA (19 mg, 0.035 mmol, 48% yield) as a yellow solid: $^1$H NMR (400 MHz, DMSO-$d_6$) δ 10.22 (s, 1H), 10.09 (s, 1H), 9.16 (s, 1H), 8.81 (d, J=4.8 Hz, 1H), 8.64 (d, J=5.3 Hz, 1H), 7.77 (d, J=8.8 Hz, 2H), 7.66-7.58 (m, 3H), 7.52 (d, J=8.8 Hz, 2H), 7.46-7.32 (m, 4H), 2.73 (s, 3H); LC/MS (ESI) m/e 430.0 $[(M+H)^+$, calcd for $C_{23}H_{20}N_5O_2S$ 430.1]; HPLC retention time (Method A): $t_R$=8.40 min; (Method B) $t_R$=8.50 min.

Example 15

2-((4-(Methylsulfonyl)phenyl)amino)-N-(4-phenylpyridin-3-yl)pyrimidine-4-carboxamide

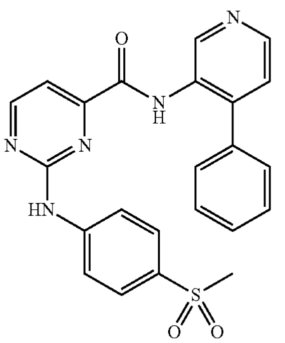 [SMILES: CS(=O)(=O)c1ccc(Nc2nccc(C(=O)Nc3cnccc3-c3ccccc3)n2)cc1]

To a solution of 2-((4-(methylthio)phenyl)amino)-N-(4-phenylpyridin-3-yl)pyrimidine-4-carboxamide (30 mg, 0.073 mmol) (prepared as described in the previous Example) in $CH_2Cl_2$ (0.5 mL) at 0° C. was added mCPBA (35.8 mg, 0.145 mmol). The reaction mixture was stirred at rt for 30 min. The mixture was concentrated and the residue was purified by reverse phase HPLC (Method C) to afford 2-((4-(methylsulfonyl)phenyl)amino)-N-(4-phenylpyridin-3-yl)pyrimidine-4-carboxamide, TFA (9 mg, 0.016 mmol, 22% yield) as an off-white solid: $^1$H NMR (400 MHz, DMSO-$d_6$) δ 10.49 (br. s., 1H), 10.08 (br. s., 1H), 9.04 (s, 1H), 8.84 (d, J=4.8 Hz, 1H), 8.57 (d, J=4.8 Hz, 1H), 7.90-7.80 (m, J=8.8 Hz, 2H), 7.80-7.71 (m, J=8.8 Hz, 2H), 7.58 (d, J=7.0 Hz, 2H), 7.49 (t, J=4.6 Hz, 2H), 7.43-7.34 (m, 3H), 3.18 (s, 3H); LC/MS (ESI) m/e 446.0 $[(M+H)^+$, calcd for $C_{23}H_{20}N_5O_3S$ 446.1]; LC/MS retention time (Method A): $t_R$=2.73 min; (Method B) $t_R$=4.02 min.

Example 16

2-((4-(1H-Imidazol-1-yl)phenyl)amino)-N-(4-phenylpyridin-3-yl)pyrimidine-4-carboxamide

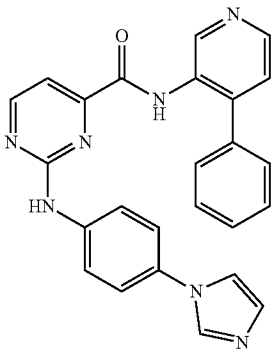 [SMILES: O=C(Nc1cnccc1-c1ccccc1)c1ccnc(Nc2ccc(-n3ccnc3)cc2)n1]

Prepared by Method A (heated at 150° C. for 30 min), obtained 8.8 mg, 42% yield: LC/MS (ESI) m/e 434.2 $[(M+H)^+$, calcd for $C_{25}H_{20}N_7O$ 434.2]; LC/MS retention time (Method A): $t_R$=1.77 min; (Method B) $t_R$=2.73 min.

Example 17

2-((4-Fluoro-3-methylphenyl)amino)-N-(4-phenylpyridin-3-yl)pyrimidine-4-carboxamide

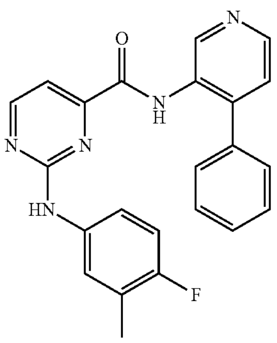 [SMILES: Cc1cc(Nc2nccc(C(=O)Nc3cnccc3-c3ccccc3)n2)ccc1F]

Prepared by Method A (heated at 150° C. for 30 min), obtained 10.2 mg, 79% yield: $^1$H NMR (500 MHz, DMSO-$d_6$) δ 9.98 (s, 1H), 9.76 (s, 1H), 9.08 (s, 1H), 8.73 (d, J=4.6 Hz, 1H), 8.55 (d, J=4.9 Hz, 1H), 7.53 (d, J=7.0 Hz, 2H), 7.47 (d, J=4.9 Hz, 1H), 7.42-7.31 (m, 6H), 6.92 (t, J=9.0 Hz, 1H), 2.17 (s, 3H); LC/MS (ESI) m/e 400.1 [(M+H)$^+$, calcd for $C_{23}H_{19}FN_5O$ 400.2]; LC/MS retention time (Method A): $t_R$=2.89 min; (Method B) $t_R$=4.18 min.

Example 18

2-((3-Chloro-4-methoxyphenyl)amino)-N-(4-phenylpyridin-3-yl)pyrimidine-4-carboxamide

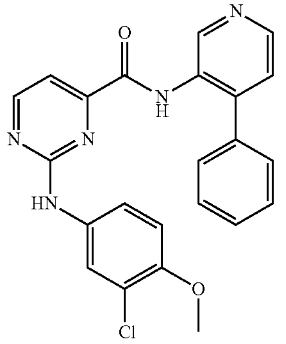 [SMILES: COc1ccc(Nc2nccc(C(=O)Nc3cnccc3-c3ccccc3)n2)cc1Cl]

Prepared by Method A (heated at 150° C. for 30 min), obtained 16.2 mg, 78% yield: $^1$H NMR (500 MHz, DMSO-$d_6$) δ 9.99 (s, 1H), 9.79 (s, 1H), 9.07 (s, 1H), 8.73 (d, J=4.9 Hz, 1H), 8.55 (d, J=4.9 Hz, 1H), 7.64 (br. s., 1H), 7.54 (d, J=6.7 Hz, 2H), 7.50-7.45 (m, 2H), 7.41-7.34 (m, 3H), 7.33 (d, J=4.6 Hz, 1H), 6.92 (d, J=9.2 Hz, 1H), 3.84 (s, 3H); LC/MS (ESI) m/e 432.1 [(M+H)$^+$, calcd for $C_{23}H_{19}ClN_5O_2$ 432.1]; LC/MS retention time (Method A): $t_R$=2.77 min; (Method B) $t_R$=4.03 min.

Example 19

2-((3-Fluoro-4-methoxyphenyl)amino)-N-(4-phenylpyridin-3-yl)pyrimidine-4-carboxamide

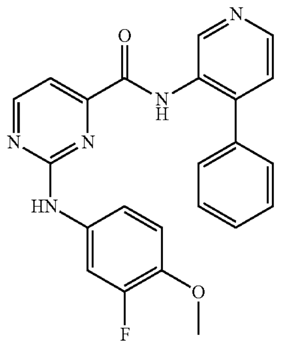 [SMILES: COc1ccc(Nc2nccc(C(=O)Nc3cnccc3-c3ccccc3)n2)cc1F]

Prepared by Method A (heated at 150° C. for 30 min), obtained 13.9 mg, 69% yield: $^1$H NMR (500 MHz, DMSO-$d_6$) δ 10.00 (s, 1H), 9.81 (s, 1H), 9.06 (s, 1H), 8.73 (d, J=4.9 Hz, 1H), 8.55 (d, J=4.9 Hz, 1H), 7.57-7.52 (m, 2H), 7.52-7.44 (m, 2H), 7.41-7.32 (m, 4H), 7.28 (d, J=8.2 Hz, 1H), 6.96 (t, J=9.3 Hz, 1H), 3.83 (s, 3H); LC/MS (ESI) m/e 416.1 [(M+H)$^+$, calcd for $C_{23}H_{19}FN_5O_2$ 416.2]; HPLC (Method B) $t_R$=3.89 min.

Example 20

2-((2-Chloro-4-(trifluoromethyl)phenyl)amino)-N-(4-phenylpyridin-3-yl)pyrimidine-4-carboxamide

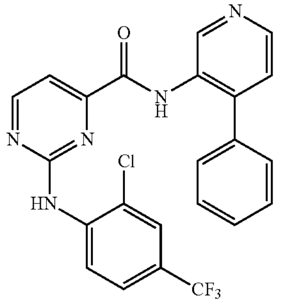 [SMILES: O=C(Nc1cnccc1-c1ccccc1)c1ccnc(Nc2ccc(C(F)(F)F)cc2Cl)n1]

Prepared by Method B (heated at 120° C. for 2 h), obtained 11.2 mg, 49% yield: $^1$H NMR (500 MHz, DMSO-$d_6$) δ 10.06 (s, 1H), 9.13 (s, 1H), 9.09 (s, 1H), 8.84 (d, J=4.6 Hz, 1H), 8.54 (d, J=5.2 Hz, 1H), 8.13 (d, J=8.5 Hz, 1H), 7.92 (d, J=1.5 Hz, 1H), 7.58-7.49 (m, 4H), 7.46 (d, J=4.9 Hz, 1H), 7.42-7.35 (m, 3H); LC/MS (ESI) m/e 470.1 [(M+H)$^+$, calcd for $C_{23}H_{16}ClF_3N_5O$ 470.1]; LC/MS retention time (Method A): $t_R$=3.49 min; (Method B) $t_R$=4.57 min.

Example 21

2-((4-Cyano-2-methylphenyl)amino)-N-(4-phenylpyridin-3-yl)pyrimidine-4-carboxamide

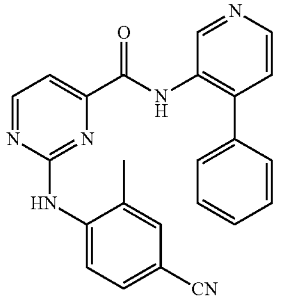 [SMILES: Cc1cc(C#N)ccc1Nc1nccc(C(=O)Nc2cnccc2-c2ccccc2)n1]

Prepared by Method B (heated at 120° C. for 2 h), obtained 2.9 mg, 15% yield: $^1$H NMR (500 MHz, DMSO-$d_6$) δ 9.92 (br. s., 1H), 9.25 (br. s., 1H), 9.17 (s, 1H), 8.79 (d, J=4.9 Hz, 1H), 8.52 (d, J=4.9 Hz, 1H), 7.75 (d, J=8.5 Hz, 1H), 7.68 (s, 1H), 7.51-7.42 (m, 4H), 7.41-7.33 (m, 4H), 2.31 (s, 3H); LC/MS (ESI) m/e 407.2 [(M+H)$^+$, calcd for $C_{24}H_{19}N_6O$ 407.2]; LC/MS retention time (Method A): $t_R$=2.73 min; (Method B) $t_R$=3.80 min.

Example 22

2-((4-Cyano-2-fluorophenyl)amino)-N-(4-phenylpyridin-3-yl)pyrimidine-4-carboxamide

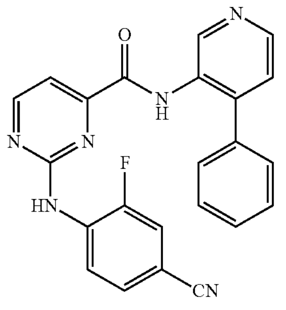 [SMILES: N#Cc1ccc(Nc2nccc(C(=O)Nc3cnccc3-c3ccccc3)n2)c(F)c1]

Prepared by Method B (heated at 100° C. for 2 h), obtained 0.5 mg, 2% yield: LC/MS (ESI) m/e 411.2 [(M+H)$^+$, calcd for $C_{23}H_{16}FN_6O$ 411.1]; LC/MS retention time (Method A): $t_R$=2.81 min; (Method B) $t_R$=3.83 min.

Example 23

2-((2,4-Dichlorophenyl)amino)-N-(4-phenylpyridin-3-yl)pyrimidine-4-carboxamide

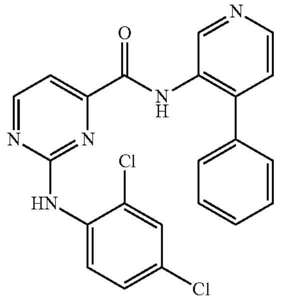 [SMILES: O=C(Nc1cnccc1-c1ccccc1)c1ccnc(Nc2ccc(Cl)cc2Cl)n1]

Prepared by Method B (heated at 120° C. for 2 h), obtained 5 mg, 24% yield: $^1$H NMR (500 MHz, DMSO-$d_6$) δ 9.93 (br. s., 1H), 9.15 (s, 1H), 9.09 (br. s., 1H), 8.76 (d, J=4.9 Hz, 1H), 8.52 (d, J=4.9 Hz, 1H), 7.72 (d, J=8.9 Hz, 1H), 7.64 (d, J=2.4 Hz, 1H), 7.50-7.47 (m, 2H), 7.46-7.37 (m, 5H), 7.25 (dd, J=8.9, 2.4 Hz, 1H); LC/MS (ESI) m/e 436.1 [(M+H)$^+$, calcd for $C_{22}H_{16}Cl_2N_5O$ 436.1]; LC/MS retention time (Method A): $t_R$=3.39 min; (Method B) $t_R$=4.53 min.

Example 24

2-((2-Chloro-4-cyanophenyl)amino)-N-(4-phenylpyridin-3-yl)pyrimidine-4-carboxamide

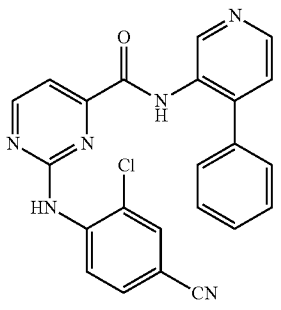 [SMILES: N#Cc1ccc(Nc2nccc(C(=O)Nc3cnccc3-c3ccccc3)n2)c(Cl)c1]

Prepared by Method B (heated at 120° C. for 2 h), obtained 3.1 mg, 15% yield: $^1$H NMR (500 MHz, DMSO-$d_6$) δ 10.05 (br. s., 1H), 9.18 (s, 2H), 8.86 (d, J=4.9 Hz, 1H), 8.54 (d, J=5.2 Hz, 1H), 8.12 (d, J=8.5 Hz, 1H), 8.09 (d, J=1.8 Hz, 1H), 7.61 (dd, J=8.5, 1.8 Hz, 1H), 7.56 (d, J=4.9 Hz, 1H), 7.52 (d, J=6.7 Hz, 2H), 7.46 (d, J=4.9 Hz, 1H), 7.43-7.34 (m, 3H); LC/MS (ESI) m/e 427.1 [(M+H)$^+$, calcd for $C_{23}H_{16}ClN_6O$ 427.1]; LC/MS retention time (Method A): $t_R$=2.96 min; (Method B) $t_R$=4.07 min.

Example 25

2-((2-Fluoro-4-(trifluoromethyl)phenyl)amino)-N-(4-phenylpyridin-3-yl)pyrimidine-4-carboxamide

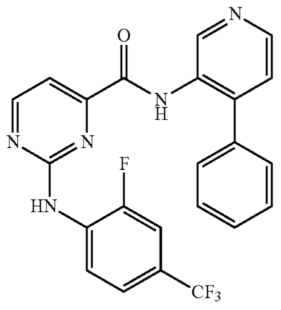 [SMILES: O=C(Nc1cnccc1-c1ccccc1)c1ccnc(Nc2ccc(C(F)(F)F)cc2F)n1]

Prepared by Method C (heated at 100° C. for 2 h), obtained 1.1 mg, 5% yield: $^1$H NMR (400 MHz, METHANOL-$d_4$) δ 9.36 (s, 1H), 8.80 (d, J=4.8 Hz, 1H), 8.48 (d, J=5.0 Hz, 1H), 8.17 (t, J=8.3 Hz, 1H), 7.62 (d, J=4.8 Hz, 1H), 7.56-7.41 (m, 6H), 7.39 (d, J=7.3 Hz, 1H), 7.28 (d, J=8.0 Hz, 1H); LC/MS (ESI) m/e 454.2 [(M+H)$^+$, calcd for $C_{23}H_{16}F_4N_5O$ 454.1]; LC/MS retention time (Method A): $t_R$=3.25 min; (Method B) $t_R$=4.37 min.

Example 26

2-((4-Chloro-2-fluorophenyl)amino)-N-(4-phenylpyridin-3-yl)pyrimidine-4-carboxamide

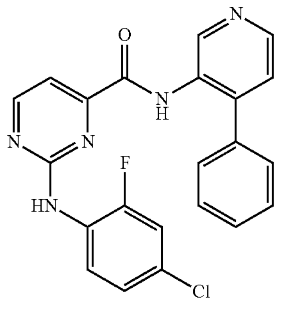 [SMILES: O=C(Nc1cnccc1-c1ccccc1)c1ccnc(Nc2ccc(Cl)cc2F)n1]

Prepared by Method B (heated at 120° C. for 2 h), obtained 2.9 mg, 14% yield: $^1$H NMR (500 MHz, DMSO-$d_6$) δ 9.89 (s, 1H), 9.44 (s, 1H), 9.13 (s, 1H), 8.75 (d, J=4.9 Hz, 1H), 8.53 (d, J=4.6 Hz, 1H), 7.62 (t, J=8.7 Hz, 1H), 7.49 (d, J=6.4 Hz, 2H), 7.45 (d, J=4.9 Hz, 1H), 7.43-7.35 (m, 5H), 7.10 (d, J=8.9 Hz, 1H); LC/MS (ESI) m/e 420.1 [(M+H)$^+$, calcd for $C_{22}H_{16}ClFN_5O$ 420.1]; LC/MS retention time (Method A): $t_R$=3.13 min; (Method B) $t_R$=4.29 min.

Example 27

2-((3-Chloro-4-cyanophenyl)amino)-N-(4-phenylpyridin-3-yl)pyrimidine-4-carboxamide

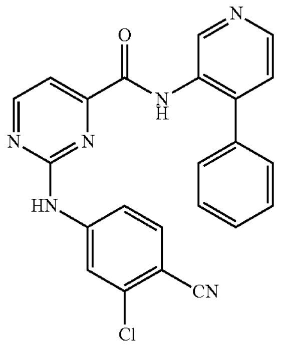 [SMILES: N#Cc1ccc(Nc2nccc(C(=O)Nc3cnccc3-c3ccccc3)n2)cc1Cl]

Prepared by Method B (heated at 100° C. for 2 h), obtained 6.5 mg, 31% yield: $^1$H NMR (500 MHz, DMSO-$d_6$) δ 10.61 (s, 1H), 10.15 (s, 1H), 9.04 (s, 1H), 8.88 (d, J=4.9 Hz, 1H), 8.57 (d, J=4.9 Hz, 1H), 8.01 (s, 1H), 7.73 (s, 2H), 7.56 (d, J=7.3 Hz, 2H), 7.50 (t, J=5.2 Hz, 2H), 7.40-7.35 (m, 2H), 7.33-7.28 (m, 1H); LC/MS (ESI) m/e 427.4 [(M+H)$^+$, calcd for $C_{23}H_{16}ClN_6O$ 427.1]; LC/MS retention time (Method A): $t_R$=2.50 min; (Method B) $t_R$=3.94 min.

Example 28

2-((4-Cyano-3-(trifluoromethyl)phenyl)amino)-N-(4-phenylpyridin-3-yl)pyrimidine-4-carboxamide

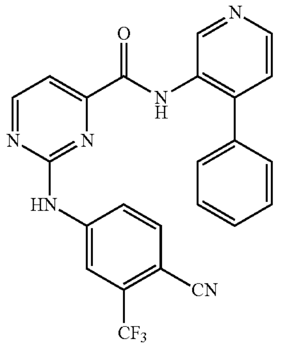 [SMILES: N#Cc1ccc(Nc2nccc(C(=O)Nc3cnccc3-c3ccccc3)n2)cc1C(F)(F)F]

Prepared by Method C (heated at 100° C. for 2 h), obtained 6 mg, 20% yield: $^1$H NMR (500 MHz, DMSO-$d_6$) δ 10.74 (s, 1H), 10.12 (s, 1H), 9.04 (s, 1H), 8.90 (d, J=4.9 Hz, 1H), 8.57 (d, J=4.9 Hz, 1H), 8.20 (s, 1H), 8.12 (d, J=7.0 Hz, 1H), 7.86 (d, J=8.9 Hz, 1H), 7.57-7.52 (m, 3H), 7.49 (d, J=4.9 Hz, 1H), 7.37 (t, J=7.6 Hz, 2H), 7.31-7.25 (m, 1H); LC/MS (ESI) m/e 461.2 [(M+H)$^+$, calcd for $C_{24}H_{16}F_3N_6O$ 461.1]; LC/MS retention time (Method A): $t_R$=2.78 min; (Method B) $t_R$=3.97 min.

Example 29

2-((2-Chloro-4-(difluoromethoxy)phenyl)amino)-N-(4-phenylpyridin-3-yl)pyrimidine-4-carboxamide

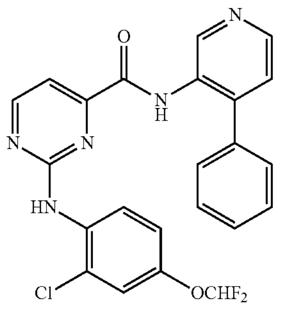 [SMILES: O=C(Nc1cnccc1-c1ccccc1)c1ccnc(Nc2ccc(OC(F)F)cc2Cl)n1]

Prepared by Method B (heated at 100° C. for 2 h), obtained 10.2 mg, 34% yield: $^1$H NMR (500 MHz, DMSO-$d_6$) δ 9.91 (s, 1H), 9.11 (s, 1H), 9.02 (s, 1H), 8.73 (d, J=4.9 Hz, 1H), 8.53 (d, J=5.2 Hz, 1H), 7.70 (d, J=8.9 Hz, 1H), 7.51-7.47 (m, 2H), 7.46-7.36 (m, 6H), 7.41-7.11 (m, 1H), 7.05 (dd, J=8.9, 2.4 Hz, 1H); LC/MS (ESI) m/e 468.1 [(M+H)$^+$, calcd for $C_{23}H_{17}ClF_2N_5O_2$ 468.1]; LC/MS retention time (Method A): $t_R$=3.04 min; (Method B) $t_R$=4.22 min.

Example 30

2-((4-Chloro-2,6-difluorophenyl)amino)-N-(4-phenylpyridin-3-yl)pyrimidine-4-carboxamide

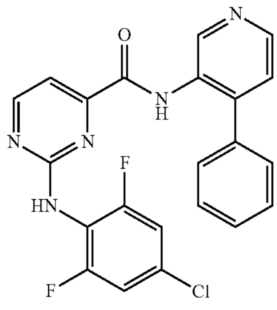 [SMILES: O=C(Nc1cnccc1-c1ccccc1)c1ccnc(Nc2c(F)cc(Cl)cc2F)n1]

Prepared by Method B (heated at 120° C. for 2 h), obtained 5 mg, 17% yield: $^1$H NMR (400 MHz, METHANOL-$d_4$) δ 9.65 (s, 1H), 8.70 (d, J=5.0 Hz, 1H), 8.62 (d, J=5.8 Hz, 1H), 7.84 (d, J=5.8 Hz, 1H), 7.59-7.53 (m, 6H), 7.04 (d, J=7.5 Hz, 2H); LC/MS (ESI) m/e 438.1 [(M+H)$^+$, calcd for $C_{22}H_{15}ClF_2N_5O$ 438.1]; HPLC retention time (Method A): $t_R$=15.07 min; (Method B) $t_R$=10.42 min.

Example 31

2-((4,5-Dichloro-2-fluorophenyl)amino)-N-(4-phenylpyridin-3-yl)pyrimidine-4-carboxamide

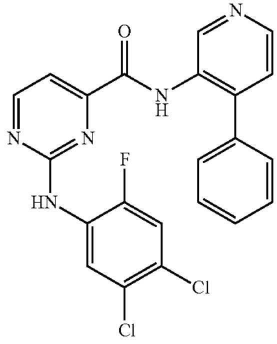 [SMILES: O=C(Nc1cnccc1-c1ccccc1)c1ccnc(Nc2cc(Cl)c(Cl)cc2F)n1]

Prepared by Method C (heated at 100° C. for 2 h), obtained 3.1 mg, 8% yield as the white solid: $^1$H NMR (400 MHz, METHANOL-$d_4$) δ 9.75 (br. s., 1H), 8.80 (d, J=5.0 Hz, 1H), 8.64 (d, J=5.5 Hz, 1H), 7.98 (d, J=7.8 Hz, 1H), 7.89 (d, J=4.0 Hz, 1H), 7.65-7.57 (m, 3H), 7.50 (t, J=7.4 Hz, 2H), 7.44 (d, J=7.5 Hz, 1H), 7.38 (d, J=10.5 Hz, 1H); LC/MS (ESI) m/e 454.06 [(M+H)$^+$, calcd for $C_{22}H_{15}Cl_2FN_5O$ 453.97]; HPLC retention time (Method A): $t_R$=12.94 min; (Method B) $t_R$=13.12 min.

Example 32

2-((4-Chloro-2,5-difluorophenyl)amino)-N-(4-phenylpyridin-3-yl)pyrimidine-4-carboxamide

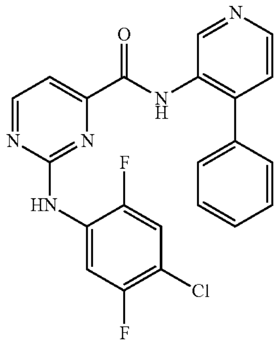 [SMILES: O=C(Nc1cnccc1-c1ccccc1)c1ccnc(Nc2cc(F)c(Cl)cc2F)n1]

Prepared by Method B (heated at 100° C. for 2 h), obtained 8.2 mg, 28% yield: $^1$H NMR (500 MHz, DMSO-$d_6$) δ 10.01 (s, 1H), 9.60 (s, 1H), 9.16 (s, 1H), 8.80 (d, J=4.9 Hz, 1H), 8.54 (d, J=4.9 Hz, 1H), 7.80 (dd, J=10.7, 7.0 Hz, 1H), 7.61 (dd, J=10.2, 6.9 Hz, 1H), 7.49 (d, J=7.3 Hz, 2H), 7.46 (t, J=5.2 Hz, 2H), 7.38 (t, J=7.6 Hz, 2H), 7.34-7.27 (m, 1H); LC/MS (ESI) m/e 438.4 [(M+H)$^+$, calcd for $C_{22}H_{15}ClF_2N_5O$ 438.1]; LC/MS retention time (Method A): $t_R$=3.19 min; (Method B) $t_R$=4.40 min.

Example 33

2-((4-Chloro-5-(difluoromethoxy)-2-fluorophenyl)amino)-N-(4-phenylpyridin-3-yl)pyrimidine-4-carboxamide

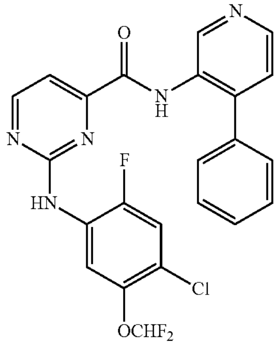 [SMILES: O=C(Nc1cnccc1-c1ccccc1)c1ccnc(Nc2cc(OC(F)F)c(Cl)cc2F)n1]

Prepared by Method B (heated at 100° C. for 2 h), obtained 9.5 mg, 29% yield: $^1$H NMR (500 MHz, DMSO-$d_6$) δ 9.95 (br. s., 1H), 9.62 (br. s., 1H), 9.11 (s, 1H), 8.78 (d, J=4.6 Hz, 1H), 8.53 (d, J=4.9 Hz, 1H), 7.73 (d, J=7.3 Hz, 1H), 7.60 (d, J=10.1 Hz, 1H), 7.49-7.43 (m, 4H), 7.38 (t, J=7.6 Hz, 2H), 7.33 (d, J=7.3 Hz, 1H), 7.31-7.00 (m, 1H); LC/MS (ESI) m/e 486.4 [(M+H)$^+$, calcd for $C_{23}H_{16}ClF_3N_5O_2$ 486.1]; LC/MS retention time (Method A): $t_R$=3.12 min; (Method B) $t_R$=4.26 min.

Example 34

N-(4-Phenylpyridin-3-yl)-2-(pyridin-3-ylamino)pyrimidine-4-carboxamide

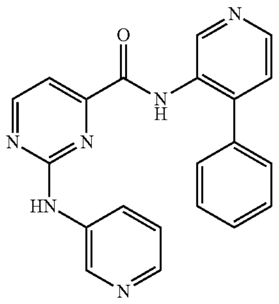 [SMILES: O=C(Nc1cnccc1-c1ccccc1)c1ccnc(Nc2cccnc2)n1]

Prepared by Method B (heated at 100° C. for 4 h), obtained 24.8 mg, 40% yield: $^1$H NMR (400 MHz, DMSO-$d_6$) δ 10.61 (s, 1H), 10.17 (s, 1H), 9.10 (d, J=2.3 Hz, 1H), 9.05 (s, 1H), 8.87 (d, J=4.8 Hz, 1H), 8.62 (d, J=5.0 Hz, 1H), 8.48-8.39 (m, 2H), 7.69 (dd, J=8.5, 5.3 Hz, 1H), 7.60-7.53 (m, 3H), 7.50 (d, J=5.0 Hz, 1H), 7.43-7.35 (m, 2H), 7.34-7.28 (n, 1H); LC/MS (ESI) m/e 369.2 [$(M+H)^+$], calcd for $C_{21}H_{17}N_6O$ 369.1]; HPLC retention time (Method A): $t_R$=6.80 min; (Method B) $t_R$=7.10 min.

Example 35

N-(4-Phenylpyridin-3-yl)-2-(pyridin-4-ylamino)pyrimidine-4-carboxamide

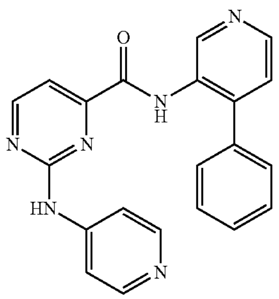 [SMILES: O=C(Nc1cnccc1-c1ccccc1)c1ccnc(Nc2ccncc2)n1]

Prepared by Method B (heated at 100° C. for 3 h), obtained 8.9 mg, 20% yield as a white amorphous solid: $^1$H NMR (500 MHz, DMSO-$d_6$) δ 10.32 (s, 1H), 10.04 (br. s., 1H), 9.02 (s, 1H), 8.84 (d, J=4.9 Hz, 1H), 8.56 (d, J=4.9 Hz, 1H), 8.30-8.25 (m, 2H), 7.61-7.53 (m, 4H), 7.49 (d, J=4.9 Hz, 2H), 7.43-7.37 (m, 2H), 7.36-7.31 (m, 1H); LC/MS (ESI) m/e 369.1 [$(M+H)^+$], calcd for $C_{21}H_{17}N_6O$ 369.1]; HPLC retention time (Method A): $t_R$=6.74 min; (Method B) $t_R$=6.99 min.

Example 36

2-((2-Methylpyridin-4-yl)amino)-N-(4-phenylpyridin-3-yl)pyrimidine-4-carboxamide

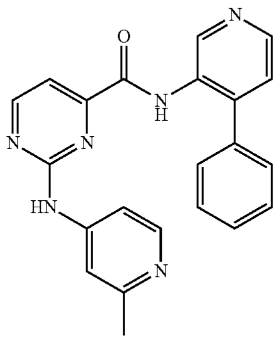 [SMILES: Cc1cc(Nc2nccc(C(=O)Nc3cnccc3-c3ccccc3)n2)ccn1]

Prepared by Method B (heated at 100° C. for 2 h), obtained 27 mg, 71% yield: $^1$H NMR (500 MHz, DMSO-$d_6$) δ 10.22 (s, 1H), 10.10 (br. s., 1H), 9.01 (s, 1H), 8.84 (d, J=4.9 Hz, 1H), 8.57 (d, J=4.9 Hz, 1H), 8.14 (d, J=5.5 Hz, 1H), 7.57 (d, J=7.3 Hz, 2H), 7.50 (d, J=4.9 Hz, 1H), 7.48-7.42 (m, 3H), 7.42-7.38 (m, 2H), 7.37-7.32 (m, 1H), 2.37 (s, 3H); LC/MS (ESI) m/e 383.2 [$(M+H)^+$], calcd for $C_{22}H_{19}N_6O$ 383.2]; LC/MS retention time (Method A): $t_R$=1.74 min; (Method B) $t_R$=3.50 min.

Example 37

2-((2-Methoxypyridin-4-yl)amino)-N-(4-phenylpyridin-3-yl)pyrimidine-4-carboxamide

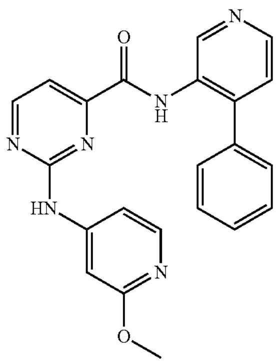 [SMILES: COc1cc(Nc2nccc(C(=O)Nc3cnccc3-c3ccccc3)n2)ccn1]

Prepared by Method B (heated at 100° C. for 2 h), obtained 11.6 mg, 30% yield: $^1$H NMR (500 MHz, DMSO-$d_6$) δ 10.24 (s, 1H), 10.07 (s, 1H), 9.00 (s, 1H), 8.83 (d, J=4.9 Hz, 1H), 8.56 (d, J=5.0 Hz, 1H), 7.89 (d, J=5.8 Hz, 1H), 7.57-7.53 (m, 2H), 7.48 (d, J=5.0 Hz, 1H), 7.45 (d, J=4.7 Hz, 1H), 7.42-7.37 (m, 2H), 7.36-7.31 (m, 1H), 7.18 (dd, J=5.8, 1.8 Hz, 1H), 7.15 (d, J=1.7 Hz, 1H), 3.82 (s, 3H); LC/MS (ESI) m/e 399.2 [$(M+H)^+$], calcd for $C_{22}H_{19}N_6O_2$ 399.2]; LC/MS retention time (Method A): $t_R$=2.10 min; (Method B) $t_R$=3.66 min.

Example 38

2-((6-(Difluoromethoxy)pyridin-3-yl)amino)-N-(4-phenylpyridin-3-yl)pyrimidine-4-carboxamide

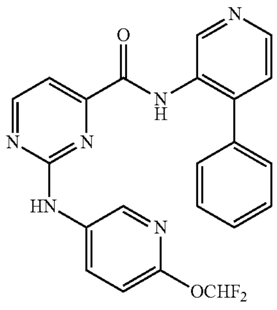 [SMILES: O=C(Nc1cnccc1-c1ccccc1)c1ccnc(Nc2ccc(OC(F)F)nc2)n1]

Prepared by Method C (heated at 100° C. for 2 h), obtained 15.5 mg, 29% yield: $^1$H NMR (500 MHz, DMSO-$d_6$) δ 10.00 (s, 2H), 9.14 (s, 1H), 8.76 (d, J=4.9 Hz, 1H), 8.58 (d, J=5.0 Hz, 1H), 8.38 (d, J=2.6 Hz, 1H), 8.02 (dd, J=8.8, 2.6 Hz, 1H), 7.57-7.52 (m, 3H), 7.65 (t, J=73.4 Hz, 1H), 7.42-7.35 (m, 3H), 7.34-7.28 (m, 1H), 6.86 (d, J=9.0 Hz, 1H); LC/MS (ESI) m/e 435.0 [(M+H)$^+$, calcd for $C_{22}H_{17}F_2N_6O_2$ 435.1]; HPLC retention time (Method A): $t_R$=9.73 min; (Method B) $t_R$=9.98 min.

Example 39

N-(4-Phenylpyridin-3-yl)-2-((6-(trifluoromethyl)pyridin-3-yl)amino)pyrimidine-4-carboxamide

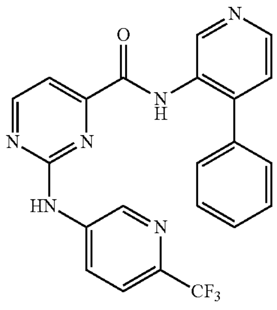 [SMILES: O=C(Nc1cnccc1-c1ccccc1)c1ccnc(Nc2ccc(C(F)(F)F)nc2)n1]

Prepared by Method B (heated at 100° C. for 4 h), obtained 7 mg, 23% yield: $^1$H NMR (400 MHz, CHLOROFORM-d) δ 9.79 (d, J=12.0 Hz, 1H), 8.77 (d, J=5.0 Hz, 1H), 8.60 (d, J=2.5 Hz, 1H), 8.55 (br. s., 1H), 8.17 (d, J=8.3 Hz, 1H), 8.02 (s, 2H), 7.75 (d, J=4.8 Hz, 1H), 7.49 (t, J=6.5 Hz, 5H), 7.31 (d, J=4.8 Hz, 2H); LC/MS (ESI) m/e 437.2 [(M+H)$^+$, calcd for $C_{22}H_{16}F_3N_6O$ 437.2].

Example 40

2-((6-(Difluoromethoxy)-2-methylpyridin-3-yl)amino)-N-(4-phenylpyridin-3-yl)pyrimidine-4-carboxamide

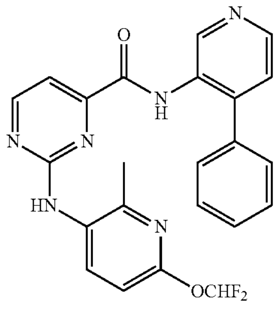 [SMILES: Cc1nc(OC(F)F)ccc1Nc1nccc(C(=O)Nc2cnccc2-c2ccccc2)n1]

Prepared by Method C (heated at 100° C. for 2 h), obtained 4.6 mg, 10% yield: $^1$H NMR (500 MHz, DMSO-$d_6$) δ 9.81 (br. s., 1H), 9.27 (s, 1H), 9.15 (s, 1H), 8.70 (d, J=4.9 Hz, 1H), 8.51 (d, J=4.9 Hz, 1H), 7.78 (d, J=8.5 Hz, 1H), 7.71 (t, J=72.9 Hz, 1H), 7.47-7.41 (m, 3H), 7.40-7.34 (m, J=4.9 Hz, 4H), 6.67 (d, J=9.2 Hz, 1H), 2.37 (s, 3H); LC/MS (ESI) m/e 449.2 [(M+H)$^+$, calcd for $C_{23}H_{19}F_2N_6O_2$ 449.2]; LC/MS retention time (Method A): $t_R$=2.57 min; (Method B) $t_R$=3.95 min.

Example 41

2-((6-(Difluoromethoxy)-2,5-dimethylpyridin-3-yl)amino)-I-(4-phenylpyridin-3-yl)pyrimidine-4-carboxamide

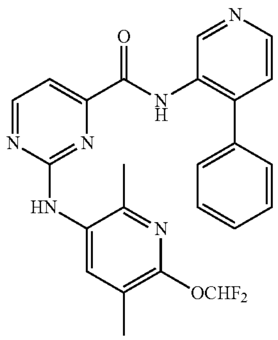 [SMILES: Cc1cc(Nc2nccc(C(=O)Nc3cnccc3-c3ccccc3)n2)c(C)nc1OC(F)F]

Prepared by Method C (heated at 100° C. for 2 h), obtained 18.5 mg, 39% yield: $^1$H NMR (500 MHz, DMSO-$d_6$) δ 9.87 (br. s., 1H), 9.22 (s, 2H), 8.70 (d, J=4.9 Hz, 1H), 8.51 (d, J=4.9 Hz, 1H), 7.64 (s, 1H), 7.74 (t, J=73.5 Hz, 1H), 7.43 (t, J=5.0 Hz, 3H), 7.36 (d, J=4.9 Hz, 1H), 7.34-7.25 (m, 3H), 2.32 (s, 3H), 2.03 (s, 3H); LC/MS (ESI) m/e 463.2 [(M+H)$^+$, calcd for $C_{24}H_{21}F_2N_6O_2$ 463.2]; LC/MS retention time (Method A): $t_R$=2.93 min; (Method B) $t_R$=4.12 min.

Example 42

2-((3-Isopropoxypropyl)amino)-N-(4-phenylpyridin-3-yl)pyrimidine-4-carboxamide

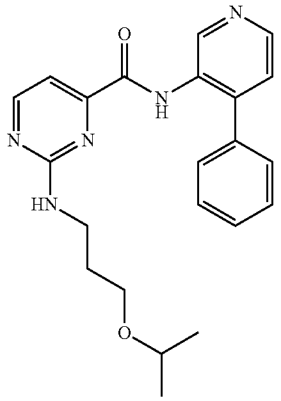 [SMILES: CC(C)OCCCNc1nccc(C(=O)Nc2cnccc2-c2ccccc2)n1]

Prepared by Method A (heated at 150° C. for 60 min), obtained 12.9 mg, 68% yield: $^1$H NMR (500 MHz, DMSO-$d_6$) δ 10.09 (s, 1H), 9.49 (br. s., 1H), 8.52 (dd, J=14.2, 4.7 Hz, 2H), 7.57 (d, J=4.0 Hz, 4H), 7.52 (br. s., 2H), 7.43 (d, J=4.6 Hz, 1H), 7.15 (br. s., 1H), 3.49 (dt, J=12.1, 6.2 Hz, 1H), 3.29 (br. s., 2H), 2.99 (br. s., 2H), 1.58 (br. s., 2H), 1.06 (d, J=6.1 Hz, 6H); LC/MS (ESI) m/e 392.1 [(M+H)$^+$, calcd for $C_{22}H_{26}N_5O_2$ 392.2]; LC/MS retention time (Method A): $t_R$=2.71 min; (Method B) $t_R$=4.00 min.

Example 43

N-(4-(4-Fluorophenyl)pyridin-3-yl)-2-(phenylamino)pyrimidine-4-carboxamide

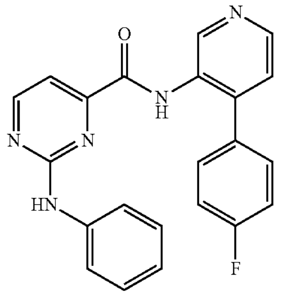 [SMILES: O=C(Nc1cnccc1-c1ccc(F)cc1)c1ccnc(Nc2ccccc2)n1]

Prepared by Method A (heated at 150° C. for 45 min), obtained 16.7 mg, 36% yield as a yellow amorphous solid: $^1$H NMR (500 MHz, DMSO-$d_6$) δ 10.00 (s, 1H), 9.85 (s, 1H), 9.15 (s, 1H), 8.75 (d, J=4.9 Hz, 1H), 8.59 (d, J=5.2 Hz, 1H), 7.65-7.61 (m, 2H), 7.57 (d, J=5.2 Hz, 1H), 7.54 (d, J=7.8 Hz, 2H), 7.36 (d, J=4.9 Hz, 1H), 7.22-7.16 (m, 4H), 6.98 (t, J=7.4 Hz, 1H); LC/MS (ESI) m/e 386.0 [(M+H)$^+$, calcd for $C_{22}H_{17}FN_5O$ 386.1]; HPLC retention time (Method A): $t_R$=10.13 min; (Method B) $t_R$=10.38 min.

Example 44

2-((4-Fluorophenyl)amino)-N-(4-(4-fluorophenyl)pyridin-3-yl)pyrimidine-4-carboxamide

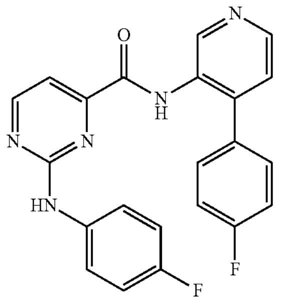 [SMILES: O=C(Nc1cnccc1-c1ccc(F)cc1)c1ccnc(Nc2ccc(F)cc2)n1]

Prepared by Method B (heated at 100° C. for 2 h), obtained 8.8 mg, 34% yield: $^1$H NMR (500 MHz, DMSO-$d_6$) δ 9.95 (s, 1H), 9.89 (s, 1H), 9.12 (s, 1H), 8.74 (d, J=4.9 Hz, 1H), 8.54 (d, J=4.9 Hz, 1H), 7.59 (dd, J=8.5, 5.5 Hz, 2H), 7.53 (dd, J=8.7, 5.0 Hz, 2H), 7.47 (d, J=4.9 Hz, 1H), 7.37 (d, J=4.6 Hz, 1H), 7.18 (t, J=8.7 Hz, 2H), 7.00 (t, J=8.7 Hz, 2H); LC/MS (ESI) m/e 404.1 [(M+H)$^+$, calcd for $C_{22}H_{16}F_2N_5O$ 404.1]; LC/MS retention time (Method A): $t_R$=2.81 min; (Method B) $t_R$=3.97 min.

Example 45

2-((4-Cyanophenyl)amino)-N-(4-(4-fluorophenyl)pyridin-3-yl)pyrimidine-4-carboxamide

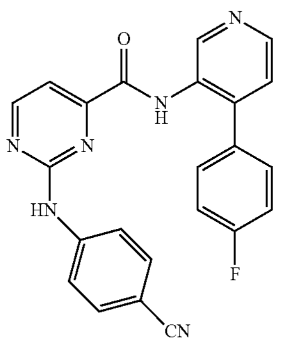 [SMILES: N#Cc1ccc(Nc2nccc(C(=O)Nc3cnccc3-c3ccc(F)cc3)n2)cc1]

Prepared by Method B (heated at 100° C. for 2 h), obtained 6.7 mg, 27% yield: $^1$H NMR (500 MHz, DMSO-$d_6$) δ 10.50 (br. s., 1H), 10.10 (br. s., 1H), 9.11 (s, 1H), 8.84 (d, J=4.9 Hz, 1H), 8.55 (d, J=5.2 Hz, 1H), 7.76 (d, J=8.5 Hz, 2H), 7.66-7.56 (m, 4H), 7.52-7.44 (m, 2H), 7.18 (t, J=8.7 Hz, 2H); LC/MS (ESI) m/e 411.2 [(M+H)$^+$, calcd for $C_{23}H_{16}FN_6O$ 411.1]; LC/MS retention time (Method A): $t_R$=2.62 min; (Method B) $t_R$=3.73 min.

Example 46

2-((4-Chlorophenyl)amino)-N-(4-(4-fluorophenyl)pyridin-3-yl)pyrimidine-4-carboxamide

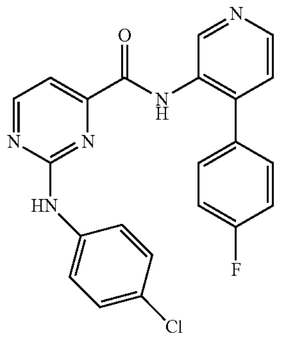 [SMILES: O=C(Nc1cnccc1-c1ccc(F)cc1)c1ccnc(Nc2ccc(Cl)cc2)n1]

Prepared by Method B (heated at 100° C. for 2 h), obtained 9.5 mg, 37% yield: $^1$H NMR (500 MHz, DMSO-$d_6$) δ 10.02 (s, 1H), 9.97 (s, 1H), 9.12 (s, 1H), 8.77 (d, J=4.9 Hz, 1H), 8.54 (d, J=4.9 Hz, 1H), 7.65-7.53 (m, 4H), 7.47 (d, J=5.2 Hz, 1H), 7.40 (d, J=4.6 Hz, 1H), 7.25-7.11 (m, 4H); LC/MS (ESI) m/e 420.1 [$(M+H)^+$], calcd for $C_{22}H_{16}ClFN_5O$ 420.1]; LC/MS retention time (Method A): $t_R$=3.01 min; (Method B) $t_R$=4.19 min.

Example 47

N-(4-(4-Fluorophenyl)pyridin-3-yl)-2-((4-(trifluoromethyl)phenyl)amino)pyrimidine-4-carboxamide

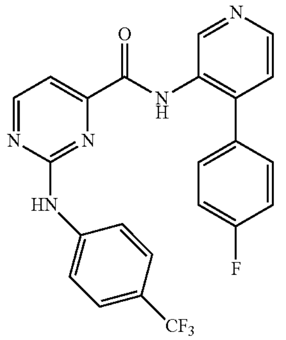 [SMILES: O=C(Nc1cnccc1-c1ccc(F)cc1)c1ccnc(Nc2ccc(C(F)(F)F)cc2)n1]

Prepared by Method B (heated at 100° C. for 2 h), obtained 17 mg, 60% yield: $^1$H NMR (400 MHz, DMSO-$d_6$) δ 10.45 (br. s., 1H), 10.14 (br. s., 1H), 9.06 (s, 1H), 8.82 (d, J=4.8 Hz, 1H), 8.54 (d, J=5.0 Hz, 1H), 7.81 (d, J=8.5 Hz, 2H), 7.63 (dd, J=8.8, 5.5 Hz, 2H), 7.52 (d, J=8.8 Hz, 2H), 7.47 (t, J=5.1 Hz, 2H), 7.16 (t, J=8.8 Hz, 2H); LC/MS (ESI) m/e 454.1 [$(M+H)^+$], calcd for $C_{23}H_{16}F_4N_5O$ 454.1]; HPLC retention time (Method A): $t_R$=11.48 min; (Method B) $t_R$=11.85 min.

Example 48

N-(4-(4-Fluorophenyl)pyridin-3-yl)-2-((4-(trifluoromethoxy)phenyl)amino)pyrimidine-4-carboxamide

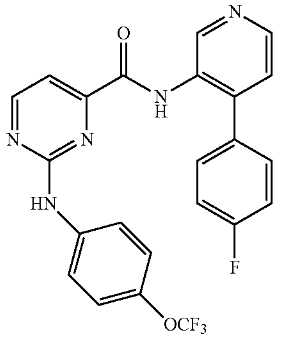

Prepared by Method B (heated at 100° C. for 14 h), obtained 10 mg, 35% yield: $^1$H NMR (500 MHz, DMSO-$d_6$) δ 10.09 (s, 1H), 9.99 (s, 1H), 9.06 (s, 1H), 8.78 (d, J=4.9 Hz, 1H), 8.55 (d, J=4.9 Hz, 1H), 7.69 (d, J=8.9 Hz, 2H), 7.62 (dd, J=8.5, 5.5 Hz, 2H), 7.48 (d, J=4.9 Hz, 1H), 7.41 (d, J=4.6 Hz, 1H), 7.24-7.07 (m, 4H); LC/MS (ESI) m/e 470.2 [$(M+H)^+$], calcd for $C_{23}H_{16}F_4N_5O_2$ 470.1]; LC/MS retention time (Method A): $t_R$=3.15 min; (Method B) $t_R$=4.28 min.

Example 49

2-((4-(Difluoromethoxy)phenyl)amino)-N-(4-(4-fluorophenyl)pyridin-3-yl)pyrimidine-4-carboxamide

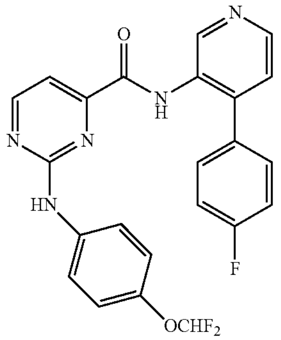 [SMILES: O=C(Nc1cnccc1-c1ccc(F)cc1)c1ccnc(Nc2ccc(OC(F)F)cc2)n1]

Prepared by Method B (heated at 100° C. for 2 h), obtained 6.2 mg, 23% yield: $^1$H NMR (500 MHz, DMSO-$d_6$) δ 9.97 (br. s., 1H), 9.94 (s, 1H), 9.06 (s, 1H), 8.75 (d, J=4.9 Hz, 1H), 8.55 (d, J=4.9 Hz, 1H), 7.65-7.57 (m, 4H), 7.48 (d, J=4.9 Hz, 1H), 7.37 (d, J=4.9 Hz, 1H), 7.19 (t, J=8.9 Hz, 2H), 7.03 (d, J=8.9 Hz, 2H), 7.30-6.96 (m, 1H); LC/MS (ESI) m/e 452.1 [$(M+H)^+$], calcd for $C_{23}H_{17}F_3N_5O_2$ 452.1]; LC/MS retention time (Method A): $t_R$=2.88 min; (Method B) $t_R$=3.98 min.

Example 50

2-((6-(Difluoromethoxy)pyridin-3-yl)amino)-N-(4-(4-fluorophenyl)pyridin-3-yl)pyrimidine-4-carboxamide

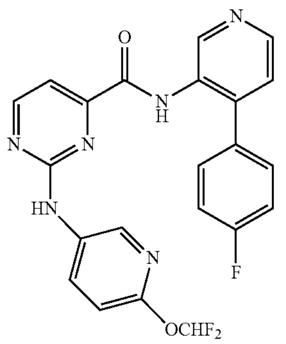 [SMILES: O=C(Nc1cnccc1-c1ccc(F)cc1)c1ccnc(Nc2ccc(OC(F)F)nc2)n1]

Prepared by Method C (heated at 100° C. for 2 h), obtained 6.8 mg, 15% yield as a tan amorphous solid: $^{1}$H NMR (500 MHz, DMSO-$d_6$) δ 10.01 (d, J=2.1 Hz, 2H), 9.11 (s, 1H), 8.77 (d, J=4.9 Hz, 1H), 8.58 (d, J=5.0 Hz, 1H), 8.41 (d, J=2.6 Hz, 1H), 8.05 (dd, J=8.9, 2.6 Hz, 1H), 7.62-7.58 (m, 2H), 7.54 (d, J=5.2 Hz, 1H), 7.62 (t, J=73.2 Hz, 1H), 7.40 (d, J=4.9 Hz, 1H), 7.20 (t, J=8.8 Hz, 2H), 6.89 (d, J=8.7 Hz, 1H); LC/MS (ESI) m/e 453.1 [(M+H)$^+$, calcd for $C_{22}H_{16}F_3N_6O_2$ 453.1]; HPLC retention time (Method A): $t_R$=9.98 min; (Method B) $t_R$=10.12 min.

Example 51

2-(Phenylamino)-N-(4-(2,2,2-trifluoroethoxy)pyridin-3-yl)pyrimidine-4-carboxamide

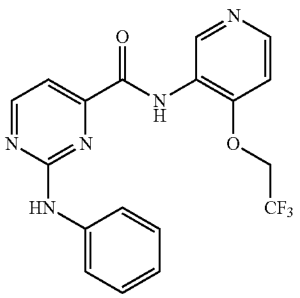 [SMILES: O=C(Nc1cnccc1OCC(F)(F)F)c1ccnc(Nc2ccccc2)n1]

Prepared by Method A (heated at 150° C. for 30 min), obtained 5.3 mg, 30% yield: $^{1}$H NMR (500 MHz, DMSO-$d_6$) δ 9.95 (s, 1H), 9.91 (s, 1H), 9.24 (s, 1H), 8.81 (d, J=4.9 Hz, 1H), 8.41 (d, J=5.8 Hz, 1H), 7.72 (d, J=7.6 Hz, 2H), 7.45 (dd, J=9.3, 5.0 Hz, 2H), 7.36 (t, J=7.9 Hz, 2H), 7.05 (t, J=7.5 Hz, 1H), 5.06 (q, J=8.9 Hz, 2H); LC/MS (ESI) m/e 390.1 [(M+H)$^+$, calcd for $C_{18}H_{15}F_3N_5O_2$ 390.1]; LC/MS retention time (Method A): $t_R$=2.55 min; (Method B) $t_R$=3.78 min.

Example 52

2-((4-Methoxyphenyl)amino)-N-(4-(2,2,2-trifluoroethoxy)pyridin-3-yl)pyrimidine-4-carboxamide

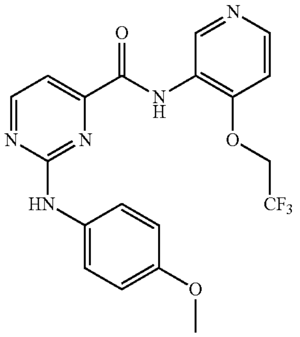 [SMILES: COc1ccc(Nc2nccc(C(=O)Nc3cnccc3OCC(F)(F)F)n2)cc1]

Prepared by Method A (heated at 150° C. for 30 min), obtained 6.5 mg, 52% yield: $^{1}$H NMR (500 MHz, DMSO-$d_6$) δ 9.88 (s, 1H), 9.74 (br. s., 1H), 9.26 (s, 1H), 8.75 (d, J=4.9 Hz, 1H), 8.40 (d, J=5.5 Hz, 1H), 7.60-7.56 (m, J=8.9 Hz, 2H), 7.42 (d, J=5.8 Hz, 1H), 7.39 (d, J=4.9 Hz, 1H), 6.96-6.93 (m, J=9.2 Hz, 2H), 5.04 (q, J=8.9 Hz, 2H), 3.75 (s, 3H); LC/MS (ESI) m/e 420.1 [(M+H)$^+$, calcd for $C_{19}H_{17}F_3N_5O_3$ 420.1]; LC/MS retention time (Method A): $t_R$=2.47 min; (Method B) $t_R$=3.75 min.

Example 53

2-((4-Ethoxyphenyl)amino)-N-(4-(2,2,2-trifluoroethoxy)pyridin-3-yl)pyrimidine-4-carboxamide

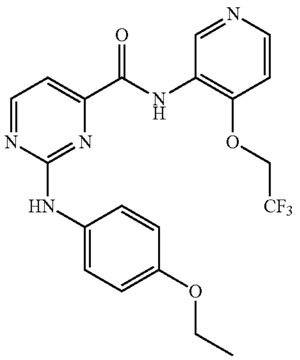 [SMILES: CCOc1ccc(Nc2nccc(C(=O)Nc3cnccc3OCC(F)(F)F)n2)cc1]

Prepared by Method A (heated at 150° C. for 30 min), obtained 6 mg, 31% yield: $^{1}$H NMR (500 MHz, DMSO-$d_6$) δ 9.88 (s, 1H), 9.74 (s, 1H), 9.25 (s, 1H), 8.75 (d, J=4.9 Hz, 1H), 8.40 (d, J=5.8 Hz, 1H), 7.56 (d, J=8.9 Hz, 2H), 7.42 (d, J=5.5 Hz, 1H), 7.39 (d, J=4.9 Hz, 1H), 6.92 (d, J=9.2 Hz, 2H), 5.04 (q, J=8.9 Hz, 2H), 4.01 (q, J=7.0 Hz, 2H), 1.33 (t, J=7.0 Hz, 3H); LC/MS (ESI) m/e 434.2 [(M+H)$^+$, calcd for $C_{20}H_{19}F_3N_5O_3$ 434.1]; LC/MS retention time (Method A): $t_R$=2.63 min; (Method B) $t_R$=3.88 min.

Example 54

2-(p-Tolylamino)-N-(4-(2,2,2-trifluoroethoxy)pyridin-3-yl)pyrimidine-4-carboxamide

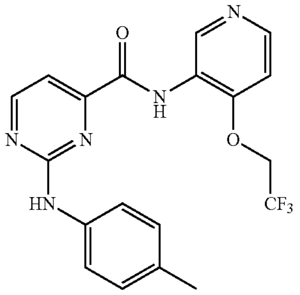 [SMILES: Cc1ccc(Nc2nccc(C(=O)Nc3cnccc3OCC(F)(F)F)n2)cc1]

Prepared by Method A (heated at 150° C. for 30 min), obtained 6.9 mg, 38% yield: $^1$H NMR (500 MHz, DMSO-$d_6$) δ 9.91-9.81 (m, 2H), 9.25 (s, 1H), 8.78 (d, J=4.6 Hz, 1H), 8.41 (d, J=5.8 Hz, 1H), 7.58 (d, J=8.2 Hz, 2H), 7.43 (dd, J=6.9, 5.3 Hz, 2H), 7.16 (d, J=8.2 Hz, 2H), 5.06 (q, J=8.6 Hz, 2H), 2.29 (s, 3H); LC/MS (ESI) m/e 404.1 [(M+H)$^+$, calcd for $C_{19}H_{17}F_3N_5O_2$ 404.1]; LC/MS retention time (Method A): $t_R$=2.70 min; (Method B) $t_R$=3.97 min.

Example 55

2-((4-Fluorophenyl)amino)-N-(4-(2,2,2-trifluoroethoxy)pyridin-3-yl)pyrimidine-4-carboxamide

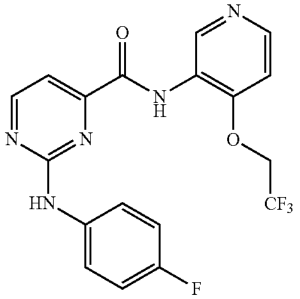 [SMILES: O=C(Nc1cnccc1OCC(F)(F)F)c1ccnc(Nc2ccc(F)cc2)n1]

Prepared by Method A (heated at 150° C. for 30 min), obtained 5.4 mg, 44% yield: $^1$H NMR (500 MHz, DMSO-$d_6$) δ 9.97 (s, 1H), 9.86 (s, 1H), 9.24 (s, 1H), 8.80 (d, J=4.9 Hz, 1H), 8.41 (d, J=5.5 Hz, 1H), 7.74-7.68 (m, 2H), 7.45 (d, J=4.9 Hz, 1H), 7.42 (d, J=5.8 Hz, 1H), 7.19 (t, J=8.9 Hz, 2H), 5.05 (q, J=8.7 Hz, 2H); LC/MS (ESI) m/e 408.1 [(M+H)$^+$, calcd for $C_{18}H_{14}F_4N_5O_2$ 408.2]; LC/MS retention time (Method A): $t_R$=2.58 min; (Method B) $t_R$=3.84 min.

Example 56

2-((4-Chlorophenyl)amino)-N-(4-(2,2,2-trifluoroethoxy)pyridin-3-yl)pyrimidine-4-carboxamide

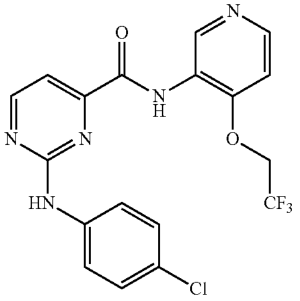 [SMILES: O=C(Nc1cnccc1OCC(F)(F)F)c1ccnc(Nc2ccc(Cl)cc2)n1]

Prepared by Method A (heated at 150° C. for 30 min), obtained 3.4 mg, 17% yield: $^1$H NMR (500 MHz, DMSO-$d_6$) δ 10.11 (s, 1H), 9.88 (s, 1H), 9.22 (s, 1H), 8.82 (d, J=4.6 Hz, 1H), 8.41 (d, J=5.5 Hz, 1H), 7.74 (d, J=8.9 Hz, 2H), 7.48 (d, J=4.6 Hz, 1H), 7.44-7.37 (m, 3H), 5.05 (q, J=8.9 Hz, 2H); LC/MS (ESI) m/e 424.1 [(M+H)$^+$, calcd for $C_{18}H_{14}ClF_3N_5O_2$ 424.1]; LC/MS retention time (Method A): $t_R$=2.78 min; (Method B) $t_R$=4.02 min.

Example 57

2-((4-Cyanophenyl)amino)-N-(4-(2,2,2-trifluoroethoxy)pyridin-3-yl)pyrimidine-4-carboxamide

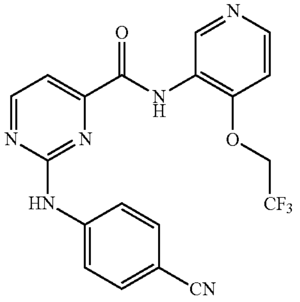 [SMILES: N#Cc1ccc(Nc2nccc(C(=O)Nc3cnccc3OCC(F)(F)F)n2)cc1]

Prepared by Method B (heated at 100° C. for 4 h), obtained 2 mg, 8% yield: $^1$H NMR (500 MHz, DMSO-$d_6$) δ 10.52 (s, 1H), 9.90 (s, 1H), 9.20 (s, 1H), 8.91 (d, J=5.2 Hz, 1H), 8.43 (d, J=5.8 Hz, 1H), 7.94 (d, J=8.9 Hz, 2H), 7.79 (d, J=8.5 Hz, 2H), 7.58 (d, J=4.9 Hz, 1H), 7.43 (d, J=5.8 Hz, 1H), 5.07 (d, J=8.9 Hz, 2H); LC/MS (ESI) m/e 415.1 [(M+H)$^+$, calcd for $C_{19}H_{14}F_3N_6O_2$ 415.1]; LC/MS retention time (Method A): $t_R$=2.40 min; (Method B) $t_R$=3.66 min.

Example 58

N-(4-(2,2,2-Trifluoroethoxy)pyridin-3-yl)-2-((4-(trifluoromethyl)phenyl)amino)pyrimidine-4-carboxamide

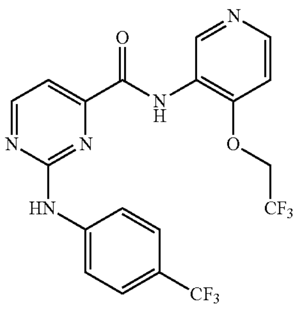 [SMILES: O=C(Nc1cnccc1OCC(F)(F)F)c1ccnc(Nc2ccc(C(F)(F)F)cc2)n1]

Prepared by Method B (heated at 100° C. for 2 h), obtained 5 mg, 18% yield: $^1$H NMR (500 MHz, DMSO-$d_6$) δ 10.41 (s, 1H), 9.90 (s, 1H), 9.24 (s, 1H), 8.89 (d, J=4.9 Hz, 1H), 8.42 (d, J=5.8 Hz, 1H), 7.94 (d, J=8.5 Hz, 2H), 7.70 (d, J=8.5 Hz, 2H), 7.56 (d, J=4.9 Hz, 1H), 7.42 (d, J=5.8 Hz, 1H), 5.03 (q, J=8.9 Hz, 2H); LC/MS (ESI) m/e 458.2 $[(M+H)^+$, calcd for $C_{19}H_{14}F_6N_5O_2$ 458.1]; LC/MS retention time (Method A): $t_R$=2.85 min; (Method B) $t_R$=4.11 min.

Example 59

N-(4-(2,2,2-Trifluoroethoxy)pyridin-3-yl)-2-((4-(trifluoromethoxy)phenyl)amino)pyrimidine-4-carboxamide

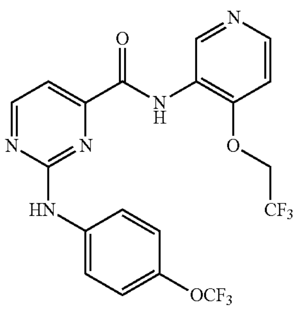 [SMILES: O=C(Nc1cnccc1OCC(F)(F)F)c1ccnc(Nc2ccc(OC(F)(F)F)cc2)n1]

Prepared by Method A (heated at 150° C. for 30 min), obtained 1.8 mg, 8% yield: $^1$H NMR (500 MHz, DMSO-$d_6$) δ 10.18 (s, 1H), 9.89 (s, 1H), 9.24 (s, 1H), 8.84 (d, J=4.9 Hz, 1H), 8.41 (d, J=5.5 Hz, 1H), 7.83 (d, J=9.2 Hz, 2H), 7.50 (d, J=4.6 Hz, 1H), 7.42 (d, J=5.5 Hz, 1H), 7.35 (d, J=8.5 Hz, 2H), 5.03 (q, J=8.7 Hz, 2H); LC/MS (ESI) m/e 474.2 $[(M+H)^+$, calcd for $C_{19}H_{14}F_6N_5O_3$ 474.1]; LC/MS retention time (Method A): $t_R$=2.91 min; (Method B) $t_R$=4.13 min.

Example 60

2-((4-(Difluoromethoxy)phenyl)amino)-N-(4-(2,2,2-trifluoroethoxy)pyridin-3-yl)pyrimidine-4-carboxamide

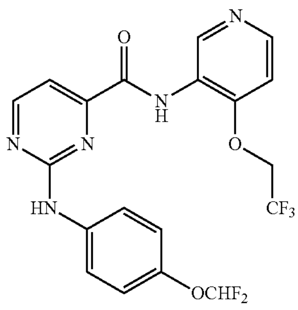 [SMILES: O=C(Nc1cnccc1OCC(F)(F)F)c1ccnc(Nc2ccc(OC(F)F)cc2)n1]

Prepared by Method A (heated at 150° C. for 30 min), obtained 2.8 mg, 20% yield: $^1$H NMR (500 MHz, DMSO-$d_6$) δ 10.03 (s, 1H), 9.88 (s, 1H), 9.23 (s, 1H), 8.81 (d, J=4.9 Hz, 1H), 8.41 (d, J=5.8 Hz, 1H), 7.74 (d, J=8.9 Hz, 2H), 7.46 (d, J=4.9 Hz, 1H), 7.43 (d, J=5.8 Hz, 1H), 7.33-6.98 (m, 3H), 5.04 (q, J=8.7 Hz, 2H); LC/MS (ESI) m/e 456.1 $[(M+H)^+$, calcd for $C_{19}H_{15}F_5N_5O_3$ 456.1].

Example 61

2-((4-Chloro-2-fluorophenyl)amino)-N-(4-(2,2,2-trifluoroethoxy)pyridin-3-yl)pyrimidine-4-carboxamide

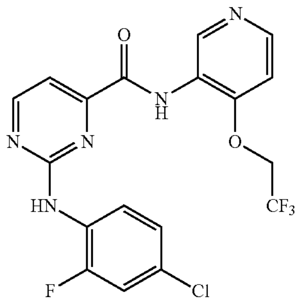 [SMILES: O=C(Nc1cnccc1OCC(F)(F)F)c1ccnc(Nc2ccc(Cl)cc2F)n1]

Prepared by Method B (heated at 100° C. for 2 h), obtained 5 mg, 11% yield: $^1$H NMR (400 MHz, METHANOL-$d_4$) δ 9.72 (s, 1H), 8.78 (d, J=5.0 Hz, 1H), 8.60 (d, J=6.5 Hz, 1H), 7.96 (t, J=8.7 Hz, 1H), 7.77 (d, J=6.5 Hz, 1H), 7.60 (d, J=4.8 Hz, 1H), 7.33 (dd, J=10.8, 2.3 Hz, 1H), 7.28-7.22 (m, 1H), 5.10 (q, J=8.2 Hz, 2H); LC/MS (ESI) m/e 442.1 $[(M+H)^+$, calcd for $C_{18}H_{13}ClF_4N_5O_2$ 442.1]; HPLC retention time (Method A): $t_R$=15.39 min; (Method B) $t_R$=10.53 min.

Example 62

2-((3-Fluoro-4-methoxyphenyl)amino)-N-(4-(2,2,2-trifluoroethoxy)pyridin-3-yl)pyrimidine-4-carboxamide

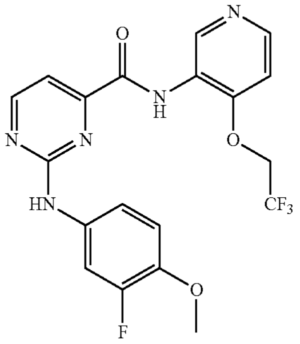 [SMILES: COc1ccc(Nc2nccc(C(=O)Nc3cnccc3OCC(F)(F)F)n2)cc1F]

Prepared by Method A (heated at 150° C. for 30 min), obtained 5.6 mg, 28% yield: $^1$H NMR (500 MHz, DMSO-$d_6$) δ 9.91 (d, J=15.6 Hz, 2H), 9.24 (s, 1H), 8.79 (d, J=4.9 Hz, 1H), 8.41 (d, J=5.8 Hz, 1H), 7.63 (dd, J=13.6, 2.3 Hz, 1H), 7.43 (t, J=5.5 Hz, 3H), 7.15 (t, J=9.3 Hz, 1H), 5.04 (q, J=8.5 Hz, 2H), 3.83 (s, 3H); LC/MS (ESI) m/e 438.1 $[(M+H)^+$, calcd for $C_{19}H_{16}F_4N_5O_3$ 438.1]; LC/MS retention time (Method A): $t_R$=2.48 min; (Method B) $t_R$=3.70 min.

Example 63

2-((6-(Difluoromethoxy)pyridin-3-yl)amino)-N-(4-(2,2,2-trifluoroethoxy)pyridin-3-yl)pyrimidine-4-carboxamide

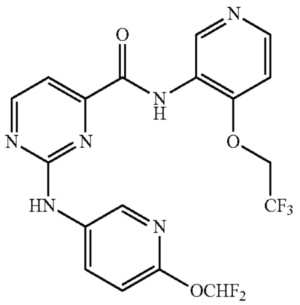 [SMILES: O=C(Nc1cnccc1OCC(F)(F)F)c1ccnc(Nc2ccc(OC(F)F)nc2)n1]

Prepared by Method B (heated at 100° C. for 1 h), obtained 10.3 mg, 15% yield as a yellow solid: $^1$H NMR (400 MHz, METHANOL-$d_4$) δ 9.48 (s, 1H), 8.76 (d, J=4.8 Hz, 1H), 8.68 (d, J=2.5 Hz, 1H), 8.34 (d, J=5.8 Hz, 1H), 8.08 (dd, J=8.7, 2.6 Hz, 1H), 7.58 (d, J=4.8 Hz, 1H), 7.37 (d, J=5.8 Hz, 1H), 7.67-7.26 (m, 1H), 7.02 (d, J=8.8 Hz, 1H), 5.03 (q, J=8.5 Hz, 2H); LC/MS (ESI) m/e 457.0 $[(M+H)^+$, calcd for $C_{18}H_{14}F_5N_6O_3$ 457.1]; HPLC retention time (Method A): $t_R$=9.52 min; (Method B) $t_R$=9.86 min.

Example 64

N-(4-(2,2,2-Trifluoroethoxy)pyridin-3-yl)-2-((6-(trifluoromethyl)pyridin-3-yl)amino)pyrimidine-4-carboxamide

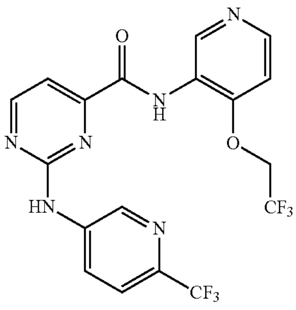 [SMILES: O=C(Nc1cnccc1OCC(F)(F)F)c1ccnc(Nc2ccc(C(F)(F)F)nc2)n1]

Prepared by Method B (heated at 100° C. for 4 h), obtained 10 mg, 29% yield: $^1$H NMR (400 MHz, CHLOROFORM-d) δ 9.75 (br. s., 1H), 9.21 (s, 1H), 8.79 (d, J=4.8 Hz, 1H), 8.40 (br. s., 1H), 8.06 (d, J=7.0 Hz, 1H), 7.75 (d, J=4.8 Hz, 1H), 7.69 (d, J=8.3 Hz, 1H), 7.11 (d, J=8.5 Hz, 1H), 6.97 (d, J=5.0 Hz, 1H), 6.80 (d, J=8.5 Hz, 1H), 4.85 (q, J=7.9 Hz, 2H); LC/MS (ESI) m/e 459.0 $[(M+H)^+$, calcd for $C_{18}H_{13}F_6N_6O_2$ 459.1]; HPLC retention time (Method A): $t_R$=9.53 min; (Method B) $t_R$=9.72 min.

Example 65

2-((3-Isopropoxypropyl)amino)-N-(4-(2,2,2-trifluoroethoxy)pyridin-3-yl)pyrimidine-4-carboxamide

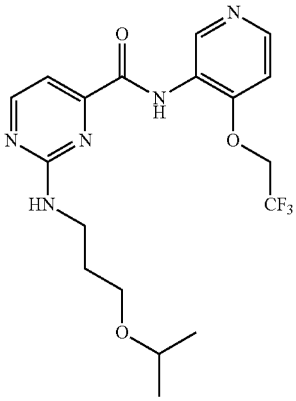 [SMILES: CC(C)OCCCNc1nccc(C(=O)Nc2cnccc2OCC(F)(F)F)n1]

Prepared by Method A (heated at 150° C. for 60 min), obtained 8.8 mg, 94% yield: $^1$H NMR (500 MHz, DMSO-$d_6$) δ 10.20 (br. s., 1H), 9.50 (br. s., 1H), 8.61 (d, J=4.9 Hz, 1H), 8.38 (d, J=5.8 Hz, 1H), 7.68 (br. s., 1H), 7.45-7.10 (m, 2H), 5.11-5.03 (m, 2H), 3.55-3.48 (m, 1H), 3.47-3.40 (m, 4H), 1.80 (t, J=6.6 Hz, 2H), 1.06 (d, J=5.8 Hz, 6H); LC/MS (ESI) m/e 414.1 $[(M+H)^+$, calcd for $C_{18}H_{23}N_5O_3F_3$ 414.2]; LC/MS retention time (Method A): $t_R$=2.54 min; (Method B) $t_R$=3.83 min.

Example 66

2-((4-Cyanophenyl)amino)-N-(4-(2,2,2-trifluoroethoxy)pyrimidin-5-yl)pyrimidine-4-carboxamide

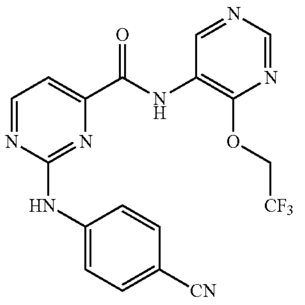 [SMILES: N#Cc1ccc(Nc2nccc(C(=O)Nc3cncnc3OCC(F)(F)F)n2)cc1]

Prepared by Method B (heated at 100° C. for 2 h), obtained 12.2 mg, 46% yield: $^1$H NMR (500 MHz, DMSO-$d_6$) δ 10.57 (s, 1H), 9.92 (s, 1H), 9.34 (s, 1H), 8.91 (d, J=4.9 Hz, 1H), 8.75 (s, 1H), 7.98-7.91 (m, 3H), 7.80 (d, J=8.9 Hz, 2H), 7.58 (d, J=4.9 Hz, 1H), 5.28 (q, J=9.1 Hz, 2H); LC/MS (ESI) m/e 416.1 [(M+H)$^+$, calcd for $C_{18}H_{13}F_3N_7O_2$ 416.1]; LC/MS retention time (Method A): $t_R$=2.59 min; (Method B) $t_R$=3.84 min.

Example 67

2-((4-Chlorophenyl)amino)-N-(4-(2,2,2-trifluoroethoxy)pyrimidin-5-yl)pyrimidine-4-carboxamide

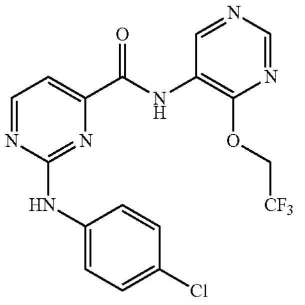 [SMILES: O=C(Nc1cncnc1OCC(F)(F)F)c1ccnc(Nc2ccc(Cl)cc2)n1]

Prepared by Method A (heated at 150° C. for 20 min), obtained 6.3 mg, 33% yield: $^1$H NMR (500 MHz, DMSO-$d_6$) δ 10.16 (s, 1H), 9.89 (br. s., 1H), 9.35 (s, 1H), 8.84 (d, J=4.6 Hz, 1H), 8.74 (s, 1H), 7.75 (d, J=8.9 Hz, 2H), 7.48 (d, J=4.9 Hz, 1H), 7.41 (d, J=8.9 Hz, 2H), 5.25 (q, J=8.9 Hz, 2H); LC/MS (ESI) m/e 425.1 [(M+H)$^+$, calcd for $C_{17}H_{13}ClF_3N_6O_2$ 425.1]; LC/MS retention time (Method A): $t_R$=2.96 min; (Method B) $t_R$=4.25 min.

Example 68

N-(4-(2,2,2-Trifluoroethoxy)pyrimidin-5-yl)-2-((4-(trifluoromethyl)phenyl)amino)pyrimidine-4-carboxamide

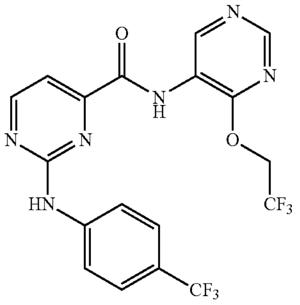 [SMILES: O=C(Nc1cncnc1OCC(F)(F)F)c1ccnc(Nc2ccc(C(F)(F)F)cc2)n1]

Prepared by Method C (heated at 100° C. for 2 h), obtained 19 mg, 20% yield: $^1$H NMR (400 MHz, CHLOROFORM-d) δ 9.99 (br. s., 1H), 9.93 (br. s., 1H), 9.77 (br. s., 2H), 8.93 (d, J=4.8 Hz, 1H), 8.79 (d, J=4.8 Hz, 1H), 8.65 (d, J=2.0 Hz, 2H), 7.96 (d, J=4.8 Hz, 1H), 7.69 (d, J=5.0 Hz, 1H), 4.88 (q, J=8.0 Hz, 2H); LC/MS (ESI) m/e 459.0 [(M+H)$^+$, calcd for $C_{18}H_{13}F_6N_6O_2$ 459.1]; LC/MS retention time (Method A): $t_R$=16.52 min; (Method B) $t_R$=14.60 min.

Example 69

N-(4-(2,2,2-Trifluoroethoxy)pyrimidin-5-yl)-2-((4-(trifluoromethoxy)phenyl)amino)pyrimidine-4-carboxamide

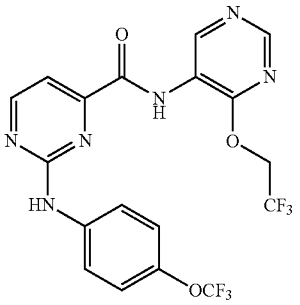 [SMILES: O=C(Nc1cncnc1OCC(F)(F)F)c1ccnc(Nc2ccc(OC(F)(F)F)cc2)n1]

Prepared by Method B (heated at 100° C. for 2 h), obtained 0.7 mg, 2% yield: $^1$H NMR (500 MHz, METHANOL-$d_4$) δ 9.56 (s, 1H), 8.77 (d, J=4.9 Hz, 1H), 8.64 (s, 1H), 7.78 (d, J=9.2 Hz, 2H), 7.56 (d, J=4.9 Hz, 1H), 7.28 (d, J=8.2 Hz, 2H), 5.18 (q, J=8.5 Hz, 2H); LC/MS (ESI) m/e 475.1 [(M+H)$^+$, calcd for $C_{18}H_{13}F_6N_6O_3$ 475.1]; LC/MS retention time (Method A): $t_R$=3.11 min; (Method B) $t_R$=4.34 min.

Example 70

2-((4-(Difluoromethoxy)phenyl)amino)-N-(4-(2,2,2-trifluoroethoxy)pyrimidin-5-yl)pyrimidine-4-carboxamide

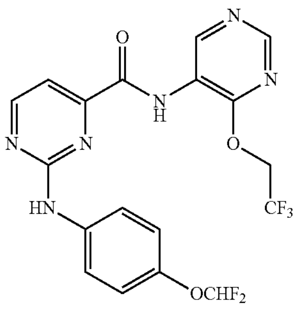 [SMILES: O=C(Nc1cncnc1OCC(F)(F)F)c1ccnc(Nc2ccc(OC(F)F)cc2)n1]

Prepared by Method B (heated at 100° C. for 2 h), obtained 17 mg, 62% yield: $^1$H NMR (500 MHz, DMSO-$d_6$) δ 10.09 (s, 1H), 9.89 (s, 1H), 9.36 (s, 1H), 8.82 (d, J=4.6 Hz, 1H), 8.74 (s, 1H), 7.75 (d, J=8.9 Hz, 2H), 7.46 (d, J=4.9 Hz, 1H), 7.19 (d, J=8.9 Hz, 2H), 7.16 (t, J=74.2 Hz, 1H), 5.24 (q, J=9.1 Hz, 2H); LC/MS (ESI) m/e 457.1 [(M+H)$^+$, calcd for $C_{18}H_{14}F_5N_6O_3$ 457.1]; LC/MS retention time (Method A): $t_R$=2.83 min; (Method B) $t_R$=4.05 min.

Example 71

2-((4-Chloro-2-fluorophenyl)amino)-N-(4-(2,2,2-trifluoroethoxy)pyrimidin-5-yl)pyrimidine-4-carboxamide

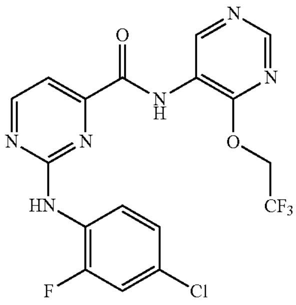 [SMILES: O=C(Nc1cncnc1OCC(F)(F)F)c1ccnc(Nc2ccc(Cl)cc2F)n1]

Prepared by Method B (heated at 100° C. for 2 h), obtained 4 mg, 14% yield: $^1$H NMR (400 MHz, CHLOROFORM-d) δ 9.96 (s, 1H), 9.75 (s, 1H), 8.78 (d, J=4.8 Hz, 1H), 8.63 (s, 1H), 8.27 (t, J=8.8 Hz, 1H), 7.67 (d, J=4.8 Hz, 1H), 7.30 (br. s., 1H), 7.25-7.14 (m, 2H), 5.00 (q, J=8.3 Hz, 2H); LC/MS (ESI) m/e 443.0 [(M+H)$^+$, calcd for $C_{17}H_{12}ClF_4N_6O_2$ 443.1]; HPLC retention time (Method A): $t_R$=15.40 min; (Method B) $t_R$=13.52 min.

Example 72

2-((4-Chloro-2,5-difluorophenyl)amino)-N-(4-(2,2,2-trifluoroethoxy)pyrimidin-5-yl)pyrimidine-4-carboxamide

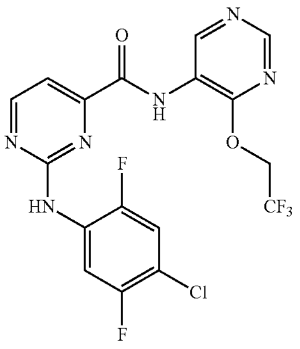 [SMILES: O=C(Nc1cncnc1OCC(F)(F)F)c1ccnc(Nc2cc(F)c(Cl)cc2F)n1]

Prepared by Method B (heated at 100° C. for 2 h), obtained 10.5 mg, 37% yield: $^1$H NMR (400 MHz, CHLOROFORM-d) δ 9.97 (s, 1H), 9.77 (s, 1H), 8.82 (d, J=4.8 Hz, 1H), 8.64 (s, 1H), 8.40 (dd, J=11.0, 7.3 Hz, 1H), 7.73 (d, J=5.0 Hz, 1H), 7.43 (br. s., 1H), 7.26-7.23 (m, 1H), 5.05 (q, J=8.3 Hz, 2H); LC/MS (ESI) m/e 461.0 [(M+H)$^+$, calcd for $C_{17}H_{11}ClF_5N_6O_2$ 461.0]; HPLC retention time (Method A): $t_R$=17.63 min; (Method B) $t_R$=15.82 min.

Example 73

2-((6-(Difluoromethoxy)pyridin-3-yl)amino)-N-(4-(2,2,2-trifluoroethoxy)pyrimidin-5-yl)pyrimidine-4-carboxamide

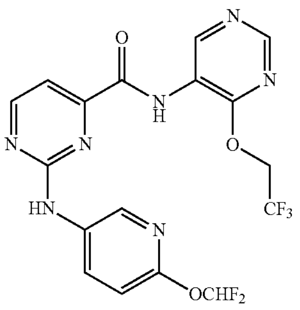

Prepared by Method C (heated at 100° C. for 1 h), obtained 8.1 mg, 15% yield as a tan amorphous solid: $^1$H NMR (500 MHz, DMSO-$d_6$) δ 10.17 (s, 1H), 9.93 (s, 1H), 9.37 (s, 1H), 8.84 (d, J=4.7 Hz, 1H), 8.72 (s, 1H), 8.62 (d, J=2.7 Hz, 1H), 8.18 (dd, J=8.9, 2.7 Hz, 1H), 7.64 (t, J=73.2 Hz, 1H), 7.49 (d, J=4.7 Hz, 1H), 7.13 (d, J=8.8 Hz, 1H), 5.27 (q, J=9.0 Hz, 2H); LC/MS (ESI) m/e 458.0 [(M+H)$^+$, calcd for $C_{17}H_{13}F_5N_7O_3$ 458.1]; HPLC retention time (Method A): $t_R$=14.00 min; (Method B) $t_R$=12.77 min.

Example 74

2-((3-Isopropoxypropyl)amino)-N-(4-(2,2,2-trifluoroethoxy)pyrimidin-5-yl)pyrimidine-4-carboxamide

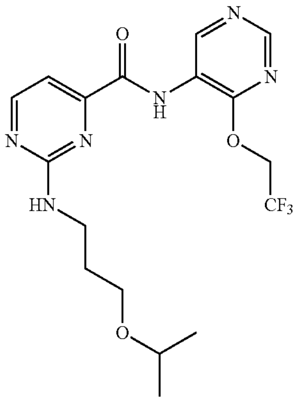 [SMILES: CC(C)OCCCNc1nccc(C(=O)Nc2cncnc2OCC(F)(F)F)n1]

Prepared by Method A (heated at 150° C. for 60 min), obtained 5.6 mg, 30% yield: $^1$H NMR (500 MHz, DMSO-$d_6$) δ 10.17 (br. s., 1H), 9.50 (br. s., 1H), 8.70 (s, 1H), 8.62 (d, J=4.6 Hz, 1H), 7.73 (br. s., 1H), 7.22 (d, J=4.6 Hz, 1H), 5.22 (q, J=8.9 Hz, 2H), 3.56-3.48 (m, 1H), 3.47-3.40 (m, 4H), 1.81 (t, J=6.4 Hz, 2H), 1.07 (d, J=6.1 Hz, 6H); LC/MS (ESI) m/e 415.1 [(M+H)$^+$, calcd for $C_{17}H_{22}F_3N_6O_3$ 415.2]; LC/MS retention time (Method A): $t_R$=2.71 min; (Method B) $t_R$=4.01 min.

Example 75

2-(Phenylamino)-N-(4-(phenylamino)pyrimidin-5-yl)pyrimidine-4-carboxamide

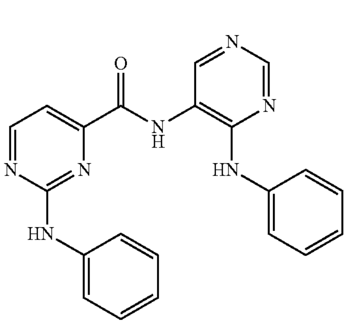 [SMILES: O=C(Nc1cncnc1Nc1ccccc1)c1ccnc(Nc2ccccc2)n1]

Example 76

2-(Phenylamino)-N-(4-(2,2,2-trifluoroethoxy)pyrimidin-5-yl)pyrimidine-4-carboxamide

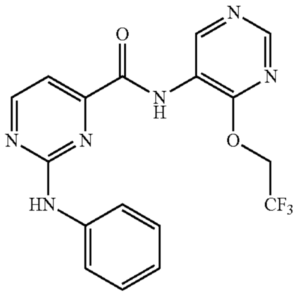

-continued

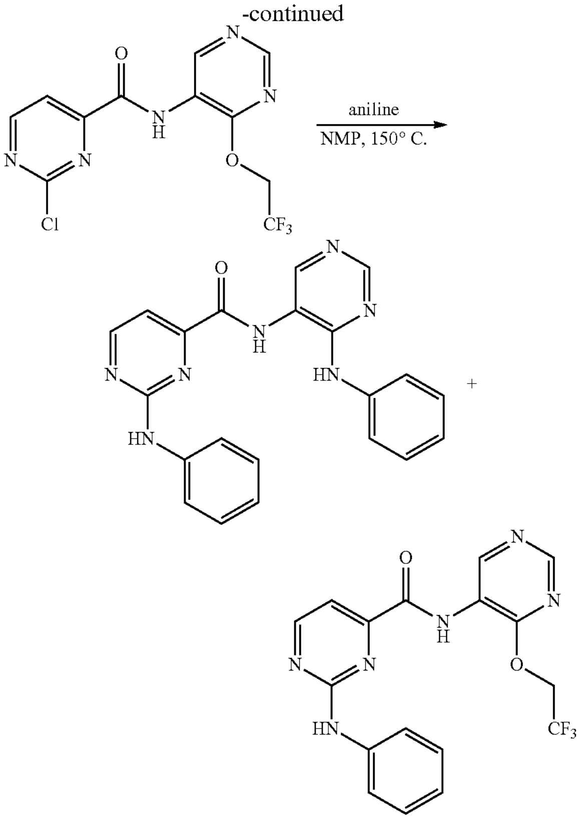

A mixture of 2-chloro-N-(4-(2,2,2-trifluoroethoxy)pyrimidin-5-yl)pyrimidine-4-carboxamide (24 mg, 0.072 mmol) and aniline (0.052 mL, 0.575 mmol) in NMP (0.4 mL) was heated at 150° C. for 45 min. The mixture was cooled to room temperature and was transferred to a separatory funnel containing ethyl acetate (15 mL). The organic layer was washed with water (3×5 mL) and was concentrated. The products were purified by reverse phase HPLC (Method C) to afford 2-(phenylamino)-N-(4-(phenylamino)pyrimidin-5-yl)pyrimidine-4-carboxamide (10.2 mg, 0.026 mmol, 37% yield) as a yellow amorphous solid and 2-(phenylamino)-N-(4-(2,2,2-trifluoroethoxy)pyrimidin-5-yl)pyrimidine-4-carboxamide (15.4 mg, 0.039 mmol, 54% yield) as a pale yellow amorphous solid.

2-(Phenylamino)-N-(4-(phenylamino)pyrimidin-5-yl)pyrimidine-4-carboxamide (Example 75)

$^1$H NMR (400 MHz, DMSO-$d_6$) δ 9.99 (s, 1H), 9.94 (s, 1H), 9.85 (br. s., 1H), 8.81 (d, J=4.8 Hz, 1H), 8.72 (s, 1H), 8.61 (s, 1H), 7.83 (d, J=7.8 Hz, 2H), 7.63-7.57 (m, 2H), 7.46-7.39 (m, 3H), 7.31 (t, J=7.9 Hz, 2H), 7.24-7.18 (m, 1H), 7.02-6.97 (m, 1H); LC/MS (ESI) m/e 384.2 [(M+H)$^+$, calcd for $C_{21}H_{18}N_7O$ 384.2]; HPLC retention time (Method A): $t_R$=9.67 min; (Method B) $t_R$=10.11 min.

2-(Phenylamino)-N-(4-(2,2,2-trifluoroethoxy)pyrimidin-5-yl)pyrimidine-4-carboxamide (Example 76)

$^1$H NMR (400 MHz, DMSO-$d_6$) δ 10.03 (s, 1H), 9.91 (s, 1H), 9.37 (s, 1H), 8.82 (d, J=4.8 Hz, 1H), 8.74 (s, 1H), 7.73 (d, J=7.8 Hz, 2H), 7.46 (d, J=4.8 Hz, 1H), 7.37 (t, J=7.9 Hz, 2H), 7.09-7.01 (m, 1H), 5.27 (q, J=9.0 Hz, 2H); LC/MS (ESI) m/e 391.1 [(M+H)$^+$, calcd for $C_{17}H_{14}F_3N_6O_2$ 391.1]; HPLC retention time (Method A): $t_R$=14.27 min; (Method B) $t_R$=12.93 min.

Example 77

2-((4-Methoxyphenyl)amino)-N-(4-(2,2,2-trifluoroethoxy)pyrimidin-5-yl)pyrimidine-4-carboxamide

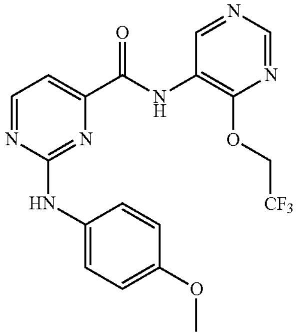 [SMILES: COc1ccc(Nc2nccc(C(=O)Nc3cncnc3OCC(F)(F)F)n2)cc1]

Prepared by Method A (heated at 150° C. for 60 min), obtained 7.1 mg, 27% yield as a yellow amorphous solid: $^1$H NMR (400 MHz, DMSO-$d_6$) δ 9.87 (s, 1H), 9.82 (s, 1H), 9.38 (s, 1H), 8.76 (d, J=4.8 Hz, 1H), 8.73 (s, 1H), 7.59 (d, J=9.0 Hz, 2H), 7.39 (d, J=4.8 Hz, 1H), 6.95 (d, J=9.0 Hz, 2H), 5.24 (q, J=9.0 Hz, 2H), 3.76 (s, 3H); LC/MS (ESI) m/e 421.2 [(M+H)$^+$, calcd for $C_{18}H_{16}F_3N_6O_3$ 421.1]; HPLC retention time (Method A): $t_R$=13.86 min; (Method B) $t_R$=12.62 min.

Example 78

2-Amino-N-(6-methylpyridin-3-yl)pyrimidine-4-carboxamide 2-((4-methoxyphenyl)amino)-N-(4-((4-methoxyphenyl)amino)pyrimidin-5-yl)pyrimidine-4-carboxamide

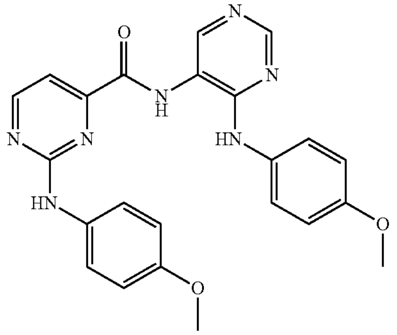

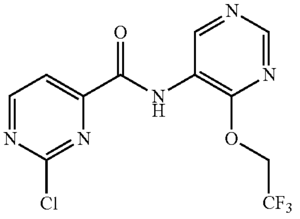

+

-continued

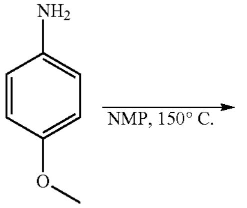

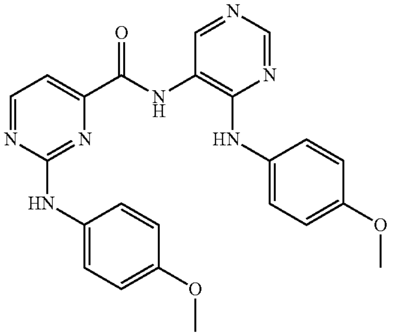

A mixture of 2-chloro-N-(4-(2,2,2-trifluoroethoxy)pyrimidin-5-yl)pyrimidine-4-carboxamide (20 mg, 0.060 mmol) and 4-methoxyaniline (59.1 mg, 0.480 mmol) in NMP (0.2 mL) was heated at 150° C. for 45 min. The mixture was cooled to room temperature and was diluted to 1.5 mL with methanol and was purified by reverse phase HPLC (Gradient: 30-100% B over 20 minutes, then a 5-minute hold at 100% B) to afford 2-amino-N-(6-methylpyridin-3-yl)pyrimidine-4-carboxamide 2-((4-methoxyphenyl)amino)-N-(4-((4-methoxyphenyl)amino)pyrimidin-5-yl)pyrimidine-4-carboxamide (15.1 mg, 56% yield): $^1$H NMR (500 MHz, DMSO-$d_6$) δ 9.72 (br. s., 2H), 8.95 (br. s., 1H), 8.72 (d, J=4.9 Hz, 1H), 8.47-8.42 (m, 2H), 7.70 (d, J=8.9 Hz, 2H), 7.51 (d, J=8.9 Hz, 2H), 7.36 (d, J=4.6 Hz, 1H), 6.95-6.91 (m, 2H), 6.87 (d, J=8.9 Hz, 2H), 3.76 (s, 3H), 3.68 (s, 3H); LC/MS (ESI) m/e 444.3 [(M+H)$^+$, calcd for $C_{23}H_{21}N_7O_3$ 443.2]; LC/MS retention time (Method A): $t_R$=2.35 min; (Method B) $t_R$=3.55 min.

Example 79

N-(4-((Cyclopropylmethyl)amino)pyrimidin-5-yl)-2-(phenylamino)pyrimidine-4-carboxamide

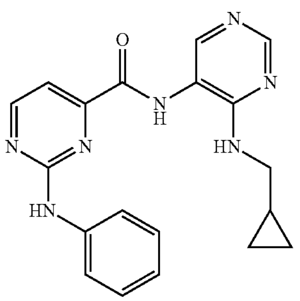

-continued

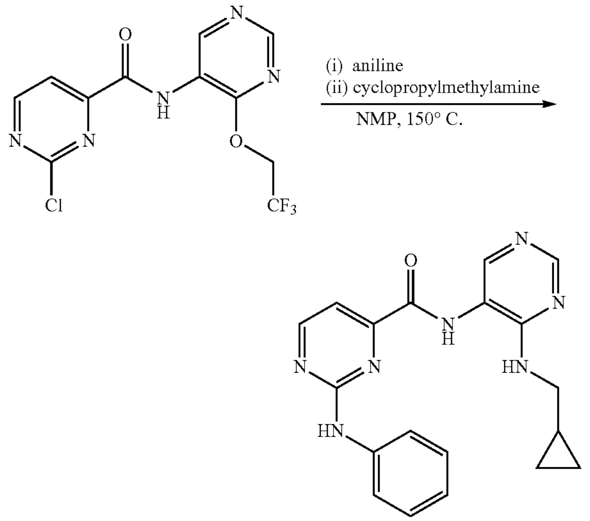

A mixture of 2-chloro-N-(4-(2,2,2-trifluoroethoxy)pyrimidin-5-yl)pyrimidine-4-carboxamide (20 mg, 0.060 mmol) and aniline (0.022 mL, 0.240 mmol) in NMP (0.3 mL) was heated at 150° C. for 30 min. Cyclopropylmethanamine (0.104 mL, 1.199 mmol) was then added and heating was continued for an additional 3.5 h. The mixture was cooled to room temperature and the product was purified by reverse phase HPLC (Method D) to afford N-(4-((cyclopropylmethyl)amino)pyrimidin-5-yl)-2-(phenylamino)pyrimidine-4-carboxamide (8.9 mg, 0.023 mmol, 38% yield) as a pale yellow amorphous solid: $^1$H NMR (500 MHz, DMSO-$d_6$) δ 9.88 (s, 1H), 9.63 (br. s., 1H), 8.76 (d, J=4.9 Hz, 1H), 8.38 (s, 1H), 8.16 (s, 1H), 7.81 (d, J=7.8 Hz, 2H), 7.38 (d, J=4.7 Hz, 1H), 7.35-7.29 (m, 3H), 7.00 (t, J=7.3 Hz, 1H), 3.26 (t, J=6.3 Hz, 2H), 1.14-1.05 (m, 1H), 0.46-0.39 (m, 2H), 0.27-0.21 (m, 2H); LC/MS (ESI) m/e 362.2 $[(M+H)^+$, calcd for $C_{19}H_{20}N_7O$ 362.2]; HPLC retention time (Method A): $t_R$=9.36 min; (Method B) $t_R$=9.79 min.

Example 80

2-((6-(Difluoromethoxy)pyridin-3-yl)amino)-N-(4-(tetrahydro-2H-pyran-4-yl)pyridin-3-yl)pyrimidine-4-carboxamide 94035-081

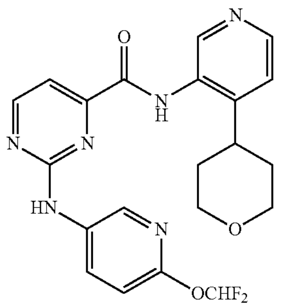

Part A. 4-(3,6-Dihydro-2H-pyran-4-yl)pyridin-3-amine

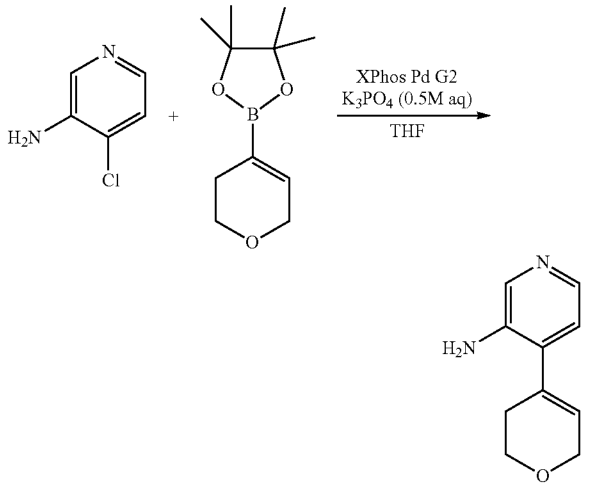

4-Chloropyridin-3-amine (150 mg, 1.167 mmol) and 2-(3,6-dihydro-2H-pyran-4-yl)-4,4,5,5-tetramethyl-1,3,2-dioxaborolane (245 mg, 1.167 mmol) were suspended in dioxane (2.5 mL) in a sealed tube. Phosphoric acid, potassium salt (0.5 M aq) (4.67 mL, 2.334 mmol) was added and the mixture was sonicated under nitrogen for 5 min. XPhos Pd G2 (36.7 mg, 0.047 mmol) was then added and the tube was sealed and the mixture was heated at 80° C. for 2.5 h. The mixture was cooled to room temperature and was transferred to a separatory funnel containing saturated aqueous $NaHCO_3$ solution (10 mL). The aqueous layer was extracted with 5% methanol in dichloromethane (3×20 mL). The combined organic layers were washed with brine (10 mL), dried over $MgSO_4$, filtered, and concentrated. The product was purified by column chromatography on silica gel (2%→6% methanol in $CH_2Cl_2$; 40 g column) to afford 4-(3,6-dihydro-2H-pyran-4-yl)pyridin-3-amine (85 mg, 0.482 mmol, 41% yield) as a purple oil: $^1$H NMR (400 MHz, $CDCl_3$) δ 8.11 (s, 1H), 8.02 (d, J=4.8 Hz, 1H), 6.92 (d, J=4.8 Hz, 1H), 5.98 (tt, J=2.9, 1.5 Hz, 1H), 4.33 (q, J=2.8 Hz, 2H), 3.96 (t, J=5.5 Hz, 2H), 3.83 (br. s., 2H), 2.46-2.38 (m, 2H); LC/MS (ESI) m/e 177.1 $[(M+H)^+$, calcd for $C_{10}H_{13}N_2O$ 177.1].

Part B. 4-(Tetrahydro-2H-pyran-4-yl)pyridin-3-amine

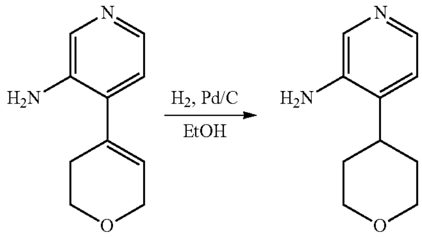 [SMILES: "EtOH" ; Nc1cnccc1C1=CCOCC1 ; Nc1cnccc1C1CCOCC1]

To a solution of 4-(3,6-dihydro-2H-pyran-4-yl)pyridin-3-amine (85 mg, 0.482 mmol) in ethanol (4 mL) was added 10% palladium on carbon (103 mg, 0.048 mmol). The reaction mixture was placed under a hydrogen balloon and was stirred at room temperature for 16 h. The catalyst was removed by filtration and the mixture was concentrated to afford 4-(tetrahydro-2H-pyran-4-yl)pyridin-3-amine (67 mg, 0.376 mmol, 78% yield) as a white solid: $^1$H NMR (400 MHz, CDCl=3) δ 8.08 (s, 1H), 8.06 (d, J=5.0 Hz, 1H), 7.02 (d, J=5.0 Hz, 1H), 4.14 (dt, J=11.1, 3.0 Hz, 2H), 3.68 (br. s., 2H), 3.62-3.54 (m, 2H), 2.82-2.71 (m, 1H), 1.86-1.77 (m, 4H); LC/MS (ESI) m/e 179.1 [(M+H)$^+$, calcd for $C_{10}H_{15}N_2O$ 179.1].

Part C. Methyl 2-((6-(difluoromethoxy)pyridin-3-yl) amino)pyrimidine-4-carboxylate

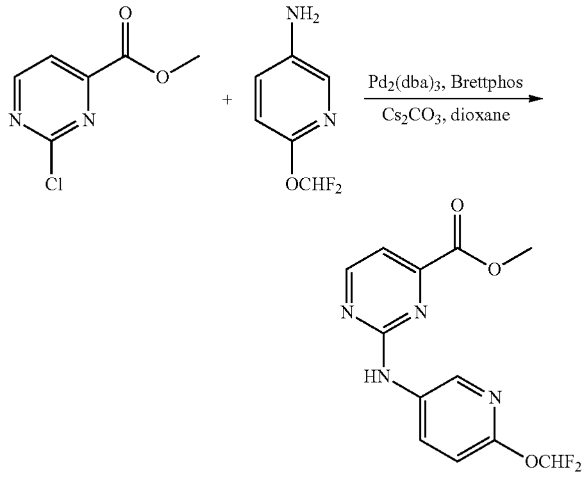

Methyl 2-chloropyrimidine-4-carboxylate (400 mg, 2.318 mmol), 6-(difluoromethoxy)pyridin-3-amine (557 mg, 3.48 mmol), cesium carbonate (1510 mg, 4.64 mmol) and dioxane (10 mL) were combined in a round bottom flask. The mixture was degassed by sonication under nitrogen for 5 min. Tris(dibenzylideneacetone)dipalladium(0) (106 mg, 0.116 mmol) and BrettPhos (124 mg, 0.232 mmol) were added. The vial was placed under nitrogen and the mixture was heated at 100° C. for 1 h. The mixture was cooled to room temperature and was filtered through a pad of Celite and was concentrated. The reaction mixture was transferred to a separatory funnel containing saturated aqueous $NaHCO_3$ solution (15 mL). The aqueous layer was extracted with dichloromethane (3×20 mL). The combined organic layers were washed with brine (15 mL), dried over $MgSO_4$, filtered, and concentrated. The product was purified by column chromatography on silica gel (30%→50% ethyl acetate in hexanes; 90 g column). The product was still contaminated with unreacted 6-(difluoromethoxy)pyridin-3-amine. The product was repurified by column chromatography on silica gel (20%→50% ethyl acetate in hexanes; 90 g column) to give methyl 2-((6-(difluoromethoxy)pyridin-3-yl)amino)pyrimidine-4-carboxylate (136 mg, 0.459 mmol, 20% yield) as a white solid: $^1$H NMR (400 MHz, DMSO-$d_6$) δ 10.29 (s, 1H), 8.78 (d, J=5.0 Hz, 1H), 8.72 (d, J=2.5 Hz, 1H), 8.27 (dd, J=8.9, 2.9 Hz, 1H), 7.66 (t, J=73.3 Hz, 1H), 7.40 (d, J=4.8 Hz, 1H), 7.11 (d, J=8.8 Hz, 1H), 3.93 (s, 3H); LC/MS (ESI) m/e 297.0 [(M+H)$^+$, calcd for $C_{12}H_{11}F_2N_4O_3$ 297.1].

Part D. 2-((6-(Difluoromethoxy)pyridin-3-yl)amino) pyrimidine-4-carboxylic acid

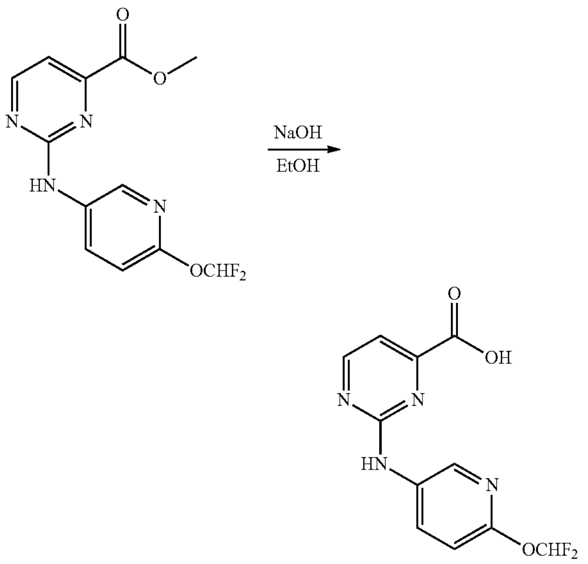

To a solution of methyl 2-((6-(difluoromethoxy)pyridin-3-yl)amino)pyrimidine-4-carboxylate (130 mg, 0.439 mmol) in EtOH (5 mL) was added 5 N sodium hydroxide (0.75 mL, 3.75 mmol) and the mixture was stirred at room temperature for 15 min. The solvent was removed under reduced pressure. The product was taken up in water (1 mL) and the pH was adjusted to pH=3 by the dropwise addition of conc. HCl. The mixture was transferred to a separatory funnel containing water (5 mL). The aqueous layer was extracted with ethyl acetate (3×10 mL). The combined organic layers were washed with brine (5 mL), dried over $MgSO_4$, filtered, and concentrated to afford 2-((6-(difluoromethoxy)pyridin-3-yl)amino)pyrimidine-4-carboxylic acid (100 mg, 0.354 mmol, 81% yield) as a yellow solid: $^1$H NMR (400 MHz, DMSO-$d_6$) δ 10.21 (s, 1H), 8.76 (d, J=2.0 Hz, 1H), 8.75 (d, J=4.8 Hz, 1H), 8.29 (dd, J=8.8, 2.8 Hz, 1H), 7.66 (t, J=73.3 Hz, 1H), 7.37 (d, J=4.8 Hz, 1H), 7.10 (d, J=9.0 Hz, 1H); LC/MS (ESI) m/e 283.0 [(M+H)$^+$, calcd for $C_{11}H_9F_2N_4O_3$ 283.1].

Part E. 2-((6-(Difluoromethoxy)pyridin-3-yl) amino)-N-(4-(tetrahydro-2H-pyran-4-yl)pyridin-3-yl)pyrimidine-4-carboxamide

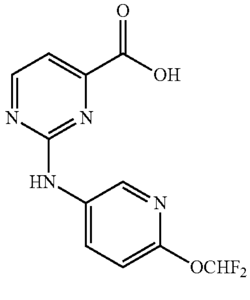

+

-continued

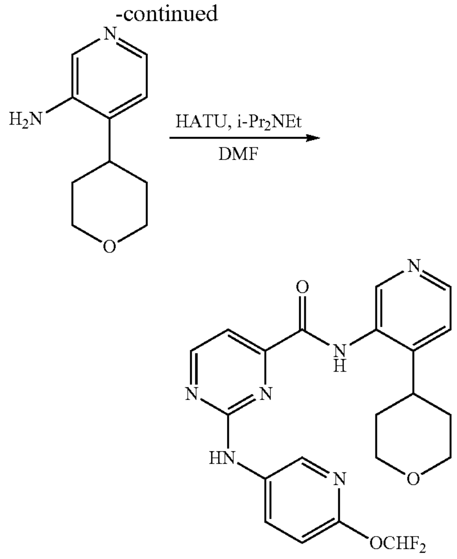

To a solution of 2-((6-(difluoromethoxy)pyridin-3-yl)amino)pyrimidine-4-carboxylic acid (20 mg, 0.071 mmol) and 4-(tetrahydro-2H-pyran-4-yl)pyridin-3-amine (12.63 mg, 0.071 mmol) in DMF (0.8 mL) was added N,N-diisopropylethylamine (0.062 mL, 0.354 mmol) followed by HATU (40.4 mg, 0.106 mmol). The reaction mixture was stirred at rt for 2.5 h. The mixture was concentrated. The product was purified by reverse phase HPLC (Method B, Gradient: 10-100% B over 20 minutes, then a 4-minute hold at 100% B) to afford 2-((6-(difluoromethoxy)pyridin-3-yl)amino)-N-(4-(tetrahydro-2H-pyran-4-yl)pyridin-3-yl)pyrimidine-4-carboxamide (14.7 mg, 45% yield): $^1$H NMR (500 MHz, DMSO-$d_6$) δ 10.14 (s, 1H), 10.12 (s, 1H), 8.81 (d, J=4.9 Hz, 1H), 8.71 (d, J=2.7 Hz, 1H), 8.66 (s, 1H), 8.47 (d, J=5.2 Hz, 1H), 8.29 (dd, J=8.9, 2.7 Hz, 1H), 7.64 (t, J=73.2 Hz, 1H), 7.47-7.43 (m, 2H), 7.10 (d, J=8.9 Hz, 1H), 3.90 (dd, J=10.5, 2.6 Hz, 2H), 3.30 (td, J=11.2, 2.9 Hz, 2H), 3.06-2.96 (m, 1H), 1.72-1.63 (m, 4H); LC/MS (ESI) m/e 443.1 [(M+H)$^+$, calcd for $C_{21}H_{21}F_2N_6O_3$ 443.2]; LC/MS retention time (Method A): $t_R$=2.36 min; (Method B) $t_R$=3.50 min.

Example 81

2-((6-(Difluoromethoxy)pyridin-3-yl)amino)-N-(4-(pyrrolidin-1-ylmethyl)pyridin-3-yl)pyrimidine-4-carboxamide

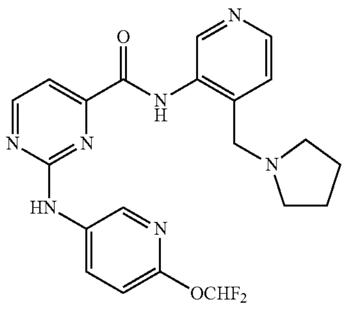 [SMILES: O=C(Nc1cnccc1CN1CCCC1)c1ccnc(Nc2ccc(OC(F)F)nc2)n1]

Part A. 4-(Pyrrolidin-1-ylmethyl)pyridin-3-amine

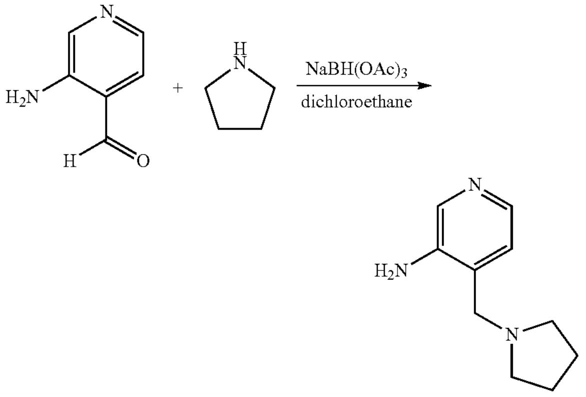

To a mixture of 3-aminoisonicotinaldehyde (515 mg, 4.22 mmol) and pyrrolidine (0.693 mL, 8.43 mmol) in dichloroethane (25 mL) was added sodium triacetoxyborohydride (1788 mg, 8.43 mmol). The resulting mixture was stirred at room temperature for 16 h. The reaction mixture was transferred to a separatory funnel containing saturated aqueous $NaHCO_3$ solution (25 mL). The aqueous layer was extracted with dichloromethane (3×50 mL). The combined organic layers were washed with brine (25 mL), dried over $MgSO_4$, filtered, and concentrated. The product was purified by column chromatography on silica gel (5%→20% methanol in $CH_2Cl_2$; 90 g column) to afford 4-(pyrrolidin-1-ylmethyl)pyridin-3-amine (472 mg, 2.66 mmol, 63% yield) as a yellow oil: $^1$H NMR (400 MHz, $CDCl_3$) δ 8.04 (s, 1H), 7.93 (d, J=4.8 Hz, 1H), 6.99-6.93 (m, 1H), 5.30 (br. s., 2H), 3.67 (s, 2H), 2.58-2.46 (m, 4H), 1.81 (dt, J=6.9, 3.3 Hz, 4H); LC/MS (ESI) m/e 178.2 [(M+H)$^+$, calcd for $C_{10}H_{16}N_3$ 178.1].

Part B. 2-((6-(Difluoromethoxy)pyridin-3-yl)amino)-N-(4-(pyrrolidin-1-ylmethyl)pyridin-3-yl)pyrimidine-4-carboxamide

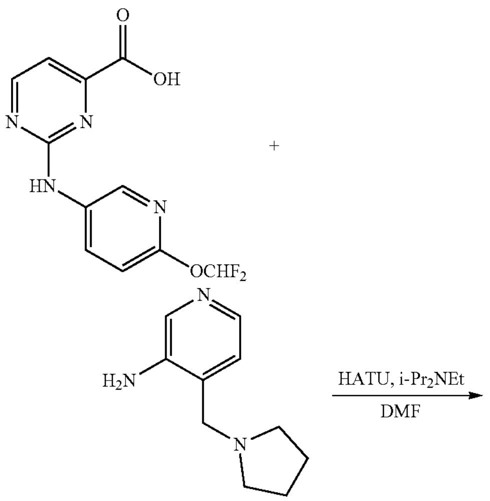

-continued

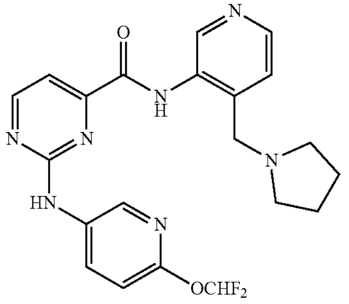

To a solution of 2-((6-(difluoromethoxy)pyridin-3-yl)amino)pyrimidine-4-carboxylic acid (20 mg, 0.071 mmol) (prepared as described in the previous Example) and 4-(pyrrolidin-1-ylmethyl)pyridin-3-amine (18.84 mg, 0.106 mmol) in DMF (0.8 mL) was added N,N-diisopropylethylamine (0.062 mL, 0.354 mmol) followed by HATU (40.4 mg, 0.106 mmol). The reaction mixture was stirred at rt for 2.5 h. The mixture was concentrated. The product was purified by reverse phase HPLC (Method B, Gradient: 40-80% B over 12 minutes, then a 5-minute hold at 100% B) to afford 2-((6-(difluoromethoxy)pyridin-3-yl)amino)-N-(4-(pyrrolidin-1-ylmethyl)pyridin-3-yl)pyrimidine-4-carboxamide (15.1 mg, 44% yield): $^1$H NMR (500 MHz, DMSO-$d_6$) δ 11.67 (s, 1H), 9.92 (s, 1H), 9.41 (s, 1H), 8.80 (d, J=4.9 Hz, 1H), 8.60 (d, J=2.7 Hz, 1H), 8.35 (d, J=4.6 Hz, 1H), 8.20 (dd, J=8.8, 2.7 Hz, 1H), 7.66 (t, J=73.2 Hz, 1H), 7.46 (d, J=4.9 Hz, 1H), 7.37 (d, J=4.9 Hz, 1H), 7.14 (d, J=8.9 Hz, 1H), 3.74 (s, 2H), 2.32 (br. s., 4H), 1.51 (br. s., 4H); LC/MS (ESI) m/e 442.1 [(M+H)$^+$, calcd for $C_{21}H_{22}F_2N_7O_2$ 442.2]; LC/MS retention time (Method A): $t_R$=2.58 min; (Method B) $t_R$=3.94 min.

Example 82

2-((6-Cyanopyridin-3-yl)amino)-N-(4-(2,2,2-trifluoroethoxy)pyridin-3-yl)pyrimidine-4-carboxamide

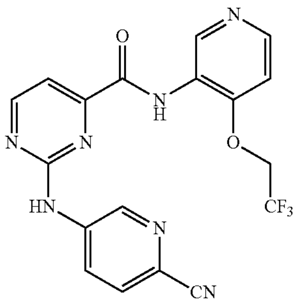 [SMILES: N#Cc1ccc(Nc2nccc(C(=O)Nc3cnccc3OCC(F)(F)F)n2)cn1]

Prepared by Method C (heated at 100° C. for 2 h), obtained 1.2 mg, 5% yield: $^1$H NMR (500 MHz, DMSO-$d_6$) 10.76 (s, 1H), 9.98 (s, 1H), 9.25 (s, 1H), 9.13 (d, J=2.44 Hz, 1H), 8.94 (d, J=4.88 Hz, 1H), 8.43 (d, J=5.49 Hz, 1H), 8.35 (dd, J=8.70, 2.59 Hz, 1H), 8.00 (d, J=8.85 Hz, 1H), 7.64 (d, J=4.88 Hz, 1H), 7.44 (d, J=5.49 Hz, 1H), 5.14 (q, J=8.75 Hz, 2H); MS (ESI) (m/z): 416.4 (M+H)$^+$; LC/MS retention time (Method A): $t_R$=2.30 min; (Method B) $t_R$=3.41 min.

Example 83

2-((6-Methylpyridin-3-yl)amino)-N-(4-(2,2,2-trifluoroethoxy)pyridin-3-yl)pyrimidine-4-carboxamide

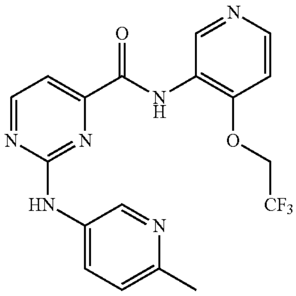 [SMILES: Cc1ccc(Nc2nccc(C(=O)Nc3cnccc3OCC(F)(F)F)n2)cn1]

Prepared by Method C (heated at 100° C. for 2 h), obtained 4.8 mg, 20% yield: $^1$H NMR (500 MHz, DMSO-$d_6$) δ 10.05 (d, J=9.16 Hz, 1H), 9.36 (s, 1H), 8.92 (d, J=2.44 Hz, 1H), 8.83 (d, J=4.88 Hz, 1H), 8.40 (d, J=5.80 Hz, 1H), 7.89 (dd, J=8.24, 2.44 Hz, 1H), 7.47 (dd, J=15.11, 5.34 Hz, 2H), 7.25 (d, J=8.54 Hz, 1H), 5.26 (q, J=8.75 Hz, 2H), 2.45 (s, 3H); MS (ESI) (m/z): 405.0 (M+H)$^+$; LC/MS retention time (Method A): $t_R$=2.09 min; (Method B) $t_R$=3.46 min.

Example 84

2-((6-Fluoropyridin-3-yl)amino)-N-(4-(2,2,2-trifluoroethoxy)pyridin-3-yl)pyrimidine-4-carboxamide

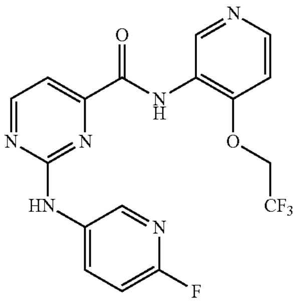 [SMILES: O=C(Nc1cnccc1OCC(F)(F)F)c1ccnc(Nc2ccc(F)nc2)n1]

Prepared by Method C (heated at 100° C. for 2 h), obtained 7.4 mg, 29% yield: $^1$H NMR (500 MHz, DMSO-$d_6$) δ 10.20 (s, 1H), 9.96 (s, 1H), 9.31 (s, 1H), 8.85 (d, J=4.88 Hz, 1H), 8.61 (s, 1H), 8.40 (d, J=5.80 Hz, 1H), 8.15-8.26 (m, 1H), 7.52 (d, J=4.58 Hz, 1H), 7.44 (d, J=5.80 Hz, 1H), 7.21 (dd, J=8.85, 3.05 Hz, 1H), 5.15 (q, J=8.54 Hz, 2H); MS (ESI) (m/z): 409.1 (M+H)$^+$; LC/MS retention time (Method A): $t_R$=2.27 min; (Method B) $t_R$=3.51 min.

Example 85

2-((Tetrahydro-2H-pyran-3-yl)amino)-N-(4-(2,2,2-trifluoroethoxy)pyridin-3-yl)pyrimidine-4-carboxamide

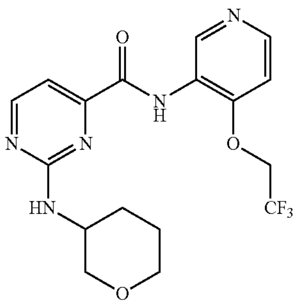 [SMILES: O=C(Nc1cnccc1OCC(F)(F)F)c1ccnc(NC2CCCOC2)n1]

Prepared by Method A (heated at 150° C. for 1.5 h), obtained 23.7 mg, 96% yield: $^1$H NMR (500 MHz, DMSO-$d_6$) δ 10.17 (br. s., 1H), 9.41 (br. s., 1H), 8.62 (d, J=4.58 Hz, 1H), 8.39 (d, J=5.80 Hz, 1H), 7.65 (br. s., 1H), 7.40 (d, J=5.49 Hz, 1H), 7.24 (d, J=4.58 Hz, 1H), 5.00-5.18 (m, 2H), 3.99 (dt, J=8.39, 4.04 Hz, 1H), 3.90 (d, J=10.68 Hz, 1H), 3.64-3.80 (m, 1H), 3.36-3.41 (m, 1H), 3.13-3.25 (m, 1H), 1.93-2.04 (m, 1H), 1.76 (d, J=11.29 Hz, 1H), 1.51-1.68 (m, 2H); MS (ESI) (m/z): 398.2 $(M+H)^+$; LC/MS retention time (Method A): $t_R$=2.36 min; (Method B) $t_R$=3.62 min.

Example 86

2-((6-Fluoropyridin-3-yl)amino)-N-(4-phenylpyridin-3-yl)pyrimidine-4-carboxamide

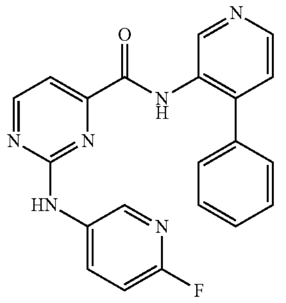 [SMILES: O=C(Nc1cnccc1-c1ccccc1)c1ccnc(Nc2ccc(F)nc2)n1]

Prepared by Method C (heated at 100° C. for 2 h), obtained 6.5 mg, 26% yield: $^1$H NMR (500 MHz, DMSO-$d_6$) δ 10.07 (s, 1H), 10.01 (s, 1H), 9.06 (s, 1H), 8.77 (d, J=4.88 Hz, 1H), 8.56 (d, J=4.88 Hz, 1H), 8.38 (s, 1H), 8.07-8.17 (m, 1H), 7.51-7.56 (m, 2H), 7.48 (d, J=5.19 Hz, 1H), 7.36-7.42 (m, 3H), 7.30-7.34 (m, 1H), 6.96 (dd, J=8.85, 3.05 Hz, 1H); MS (ESI) (m/z): 387.2 $(M+H)^+$; LC/MS retention time (Method A): $t_R$=2.36 min; (Method B) $t_R$=3.61 min.

Example 87

2-((6-Acetamidopyridin-3-yl)amino)-N-(4-phenylpyridin-3-yl)pyrimidine-4-carboxamide

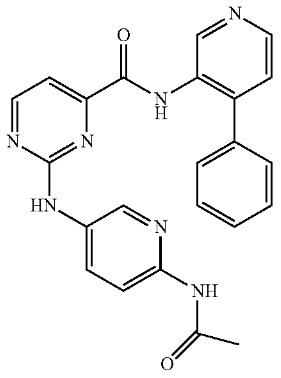 [SMILES: CC(=O)Nc1ccc(Nc2nccc(C(=O)Nc3cnccc3-c3ccccc3)n2)cn1]

Prepared by Method C (heated at 100° C. for 2 h), obtained 8.0 mg, 29% yield: $^1$H NMR (500 MHz, DMSO-$d_6$) δ 10.38 (s, 1H), 9.98 (s, 1H), 9.91 (s, 1H), 9.04 (s, 1H), 8.74 (d, J=4.58 Hz, 1H), 8.55 (d, J=4.88 Hz, 1H), 8.43 (s, 1H), 7.88-7.99 (m, 2H), 7.52 (d, J=7.32 Hz, 2H), 7.47 (d, J=4.88 Hz, 1H), 7.30-7.40 (m, 4H), 2.11 (s, 3H); MS (ESI) (m/z): 426.5 $(M+H)^+$; LC/MS retention time (Method A): $t_R$=1.95 min; (Method B) $t_R$=3.22 min.

Example 88

N-(4-Phenylpyridin-3-yl)-2-((tetrahydro-2H-pyran-4-yl)amino)pyrimidine-4-carboxamide

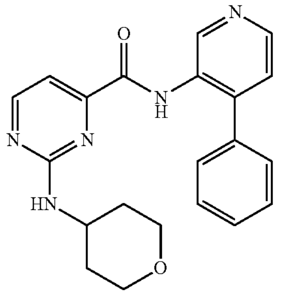 [SMILES: O=C(Nc1cnccc1-c1ccccc1)c1ccnc(NC2CCOCC2)n1]

Prepared by Method A (heated at 150° C. for 1.5 h), obtained 20 mg, 82% yield: $^1$H NMR (500 MHz, DMSO-$d_6$) δ 10.00 (br. s., 1H), 9.26 (br. s., 1H), 8.54 (dd, J=14.34, 4.88 Hz, 2H), 7.48-7.63 (m, 6H), 7.46 (d, J=4.88 Hz, 1H), 7.17 (br. s., 1H), 3.76 (br. s., 2H), 3.59 (br. s., 1H), 3.18 (d, J=5.19 Hz, 2H), 1.63 (br. s., 2H), 1.40 (br. s., 2H); MS (ESI) (m/z): 376.2 $(M+H)^+$; LC/MS retention time (Method A): $t_R$=2.22 min; (Method B) $t_R$=3.51 min.

Example 89

2-((6-Methylpyridin-3-yl)amino)-N-(4-phenylpyridin-3-yl)pyrimidine-4-carboxamide

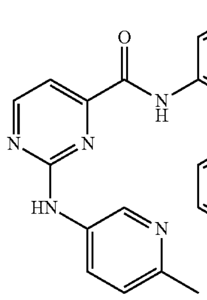

Prepared by Method C (heated at 100° C. for 2 h), obtained 1.1 mg, 4% yield: MS (ESI) (m/z): 383.3 $(M+H)^+$; LC/MS retention time (Method A): $t_R$=2.23 min; (Method B) $t_R$=3.63 min.

Example 90

2-((1-Ethyl-1H-pyrazol-5-yl)amino)-N-(4-phenylpyridin-3-yl)pyrimidine-4-carboxamide

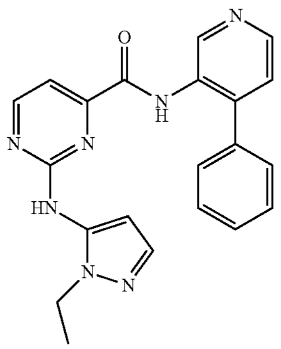 [SMILES: CCn1nccc1Nc1nccc(C(=O)Nc2cnccc2-c2ccccc2)n1]

Prepared by Method C (heated at 100° C. for 2 h), obtained 5.6 mg, 23% yield: $^1$H NMR (500 MHz, DMSO-$d_6$) δ 9.82 (br. s., 1H), 9.65 (br. s., 1H), 9.10 (s, 1H), 8.74 (d, J=4.88 Hz, 1H), 8.53 (d, J=4.88 Hz, 1H), 7.46-7.53 (m, 5H), 7.45 (d, J=4.88 Hz, 1H), 7.41 (d, J=4.88 Hz, 1H), 7.27 (d, J=1.53 Hz, 1H), 5.93 (s, 1H), 4.01 (q, J=7.32 Hz, 2H), 1.26 (t, J=7.17 Hz, 3H); MS (ESI) (m/z): 386.1 $(M+H)^+$; LC/MS retention time (Method A): $t_R$=2.10 min; (Method B) $t_R$=3.39 min.

Example 91

N-(4-Phenylpyridin-3-yl)-2-((5,6,7,8-tetrahydroisoquinolin-4-yl)amino)pyrimidine-4-carboxamide

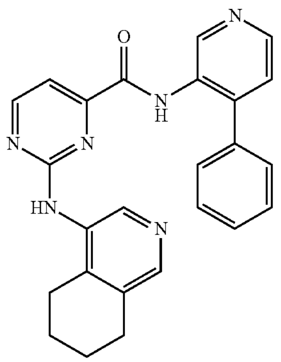 [SMILES: O=C(Nc1cnccc1-c1ccccc1)c1ccnc(Nc2cncc3c2CCCC3)n1]

Prepared by Method C (heated at 100° C. for 2 h), obtained 6.2 mg, 22% yield: $^1$H NMR (500 MHz, DMSO-$d_6$) δ 9.93 (s, 1H), 9.07 (s, 1H), 9.03 (s, 1H), 8.66 (d, J=4.88 Hz, 1H), 8.53 (d, J=4.88 Hz, 1H), 8.38 (s, 1H), 8.10 (s, 1H), 7.37-7.47 (m, 6H), 7.31 (d, J=4.88 Hz, 1H), 2.76 (br. s., 2H), 2.59 (br. s., 2H), 1.72 (br. s., 4H); MS (ESI) (m/z): 423.3 $(M+H)^+$; LC/MS retention time (Method A): $t_R$=2.53 min; (Method B) $t_R$=3.81 min.

Example 92

2-(((3S,4R)-4-Ethoxytetrahydrofuran-3-yl)amino)-N-(4-phenylpyridin-3-yl)pyrimidine-4-carboxamide

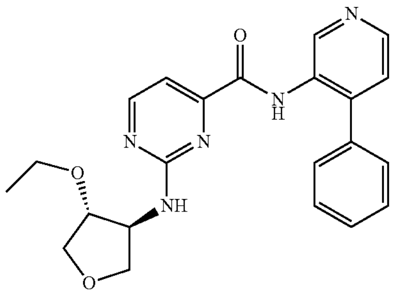 [SMILES: CCO[C@H]1COC[C@@H]1Nc1nccc(C(=O)Nc2cnccc2-c2ccccc2)n1]

Prepared by Method C (heated at 100° C. for 1.5 h), obtained 6.6 mg, 25% yield: $^1$H NMR (500 MHz, DMSO-$d_6$) δ 10.09 (s, 1H), 9.29 (br. s., 1H), 8.58 (d, J=4.88 Hz, 1H), 8.53 (d, J=4.88 Hz, 1H), 7.91 (br. s., 1H), 7.43-7.60 (m, 6H), 7.20 (d, J=4.27 Hz, 1H), 4.09 (br. s., 1H), 3.97 (br. s., 1H), 3.86-3.93 (m, 1H), 3.71 (br. s., 1H), 3.62 (d, J=9.46 Hz, 1H), 3.37-3.49 (m, 3H), 1.10 (t, J=6.87 Hz, 3H); MS (ESI) (m/z): 406.6 $(M+H)^+$; LC/MS retention time (Method A): $t_R$=2.38 min; (Method B) $t_R$=3.52 min.

Example 93

2-((6-(Dimethylamino)pyridin-3-yl)amino)-N-(4-phenylpyridin-3-yl)pyrimidine-4-carboxamide

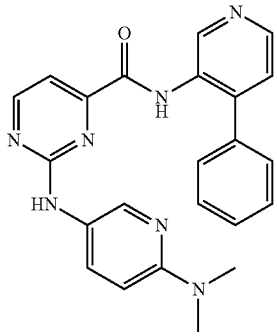 [SMILES: CN(C)c1ccc(Nc2nccc(C(=O)Nc3cnccc3-c3ccccc3)n2)cn1]

Prepared by Method C (heated at 100° C. for 2 h), obtained 4.8 mg, 18% yield: $^{1}$H NMR (500 MHz, DMSO-$d_6$) δ 9.89 (br. s., 1H), 9.47 (br. s., 1H), 9.08 (s, 1H), 8.66 (d, J=4.88 Hz, 1H), 8.53 (d, J=4.88 Hz, 1H), 8.19 (d, J=2.14 Hz, 1H), 7.58 (d, J=8.24 Hz, 1H), 7.52 (d, J=6.71 Hz, 2H), 7.46 (d, J=4.88 Hz, 1H), 7.35-7.44 (m, 3H), 7.27 (d, J=4.58 Hz, 1H), 6.44 (d, J=7.32 Hz, 1H), 3.01 (s, 6H); MS (ESI) (m/z): 412 $(M+H)^+$; LC/MS retention time (Method A): $t_R$=2.44 min; (Method B) $t_R$=3.66 min.

Example 94

N-(4-Phenylpyridin-3-yl)-2-((tetrahydro-2H-pyran-3-yl)amino)pyrimidine-4-carboxamide

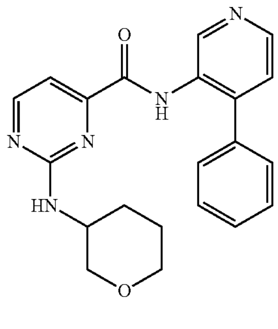 [SMILES: O=C(Nc1cnccc1-c1ccccc1)c1ccnc(NC2CCCOC2)n1]

Prepared by Method A (heated at 150° C. for 1.5 h), obtained 24 mg, 96% yield: $^{1}$H NMR (500 MHz, DMSO-$d_6$) δ 10.08 (br. s., 1H), 9.29 (br. s., 1H), 8.47-8.59 (m, 2H), 7.49-7.62 (m, 6H), 7.45 (d, J=4.88 Hz, 1H), 7.15 (br. s., 1H), 3.72 (d, J=10.68 Hz, 3H), 3.33 (br. s., 1H), 3.15 (br. s., 1H), 1.81 (br. s., 1H), 1.68 (br. s., 1H), 1.49 (br. s., 2H); MS (ESI) (m/z): 376.5 $(M+H)^+$; LC/MS retention time (Method A): $t_R$=2.36 min; (Method B) $t_R$=3.62 min.

Example 95

2-((3-Methylisothiazol-5-yl)amino)-N-(4-phenylpyridin-3-yl)pyrimidine-4-carboxamide

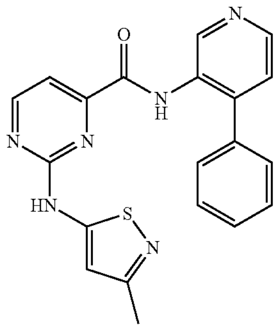 [SMILES: Cc1cc(Nc2nccc(C(=O)Nc3cnccc3-c3ccccc3)n2)sn1]

Prepared by Method C (heated at 100° C. for 2 h), obtained 4.9 mg, 19% yield: MS (ESI) (m/z): 389.5 $(M+H)^+$; LC/MS retention time (Method A): $t_R$=2.30 min; (Method B) $t_R$=3.46 min.

Example 96

2-((6-(2-(Dimethylamino)ethoxy)pyridin-3-yl)amino)-N-(4-phenylpyridin-3-yl)pyrimidine-4-carboxamide

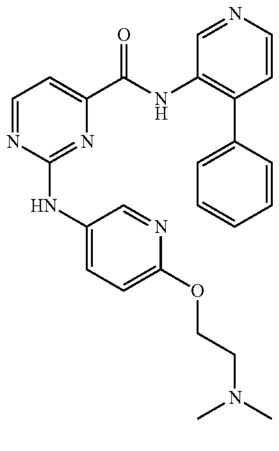 [SMILES: CN(C)CCOc1ccc(Nc2nccc(C(=O)Nc3cnccc3-c3ccccc3)n2)cn1]

Prepared by Method C (heated at 100° C. for 2 h), obtained 24 mg, 83% yield: $^{1}$H NMR (500 MHz, DMSO-$d_6$) δ 9.95 (s, 1H), 9.74 (br. s., 1H), 9.08 (s, 1H), 8.71 (d, J=4.88 Hz, 1H), 8.54 (d, J=4.88 Hz, 1H), 8.29 (d, J=2.75 Hz, 1H), 7.80 (d, J=9.16 Hz, 1H), 7.52 (d, J=7.32 Hz, 2H), 7.47 (d, J=4.88 Hz, 1H), 7.36-7.42 (m, 2H), 7.30-7.35 (m, 2H), 6.62 (d, J=8.55 Hz, 1H), 4.33 (t, J=5.95 Hz, 2H), 2.63 (t, J=5.95 Hz, 2H), 2.22 (s, 6H); MS (ESI) (m/z): 456.4 $(M+H)^+$; LC/MS retention time (Method A): $t_R$=1.87 min; (Method B) $t_R$=3.28 min.

Example 97

2-((3-Cyclopropyl-1-methyl-1H-pyrazol-5-yl)amino)-N-(4-phenylpyridin-3-yl)pyrimidine-4-carboxamide

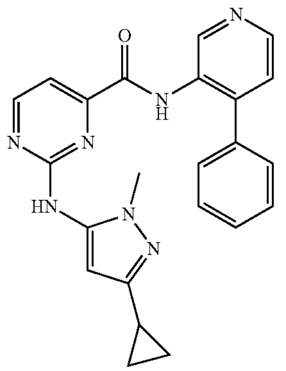 [SMILES: Cn1nc(C2CC2)cc1Nc1nccc(C(=O)Nc2cnccc2-c2ccccc2)n1]

Prepared by Method C (heated at 100° C. for 2 h), obtained 9.4 mg, 36% yield: $^1$H NMR (500 MHz, DMSO-$d_6$) δ 9.98 (s, 1H), 9.52 (br. s., 1H), 9.00 (s, 1H), 8.71 (d, J=4.88 Hz, 1H), 8.55 (d, J=4.88 Hz, 1H), 7.40-7.53 (m, 6H), 7.36 (d, J=4.88 Hz, 1H), 5.90 (s, 1H), 3.56 (s, 3H), 1.73-1.83 (m, 1H), 0.75-0.86 (m, 2H), 0.57-0.63 (m, 2H); MS (ESI) (m/z): 412.3 $(M+H)^+$; LC/MS retention time (Method A): $t_R$=2.33 min; (Method B) $t_R$=3.60 min.

Example 98

2-((1-Methyl-1H-pyrazol-3-yl)amino)-N-(4-phenylpyridin-3-yl)pyrimidine-4-carboxamide

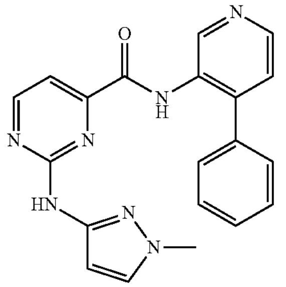 [SMILES: Cn1ccc(Nc2nccc(C(=O)Nc3cnccc3-c3ccccc3)n2)n1]

Prepared by Method C (heated at 100° C. for 2 h), obtained 8.7 mg, 36% yield: $^1$H NMR (500 MHz, DMSO-$d_6$) δ 9.92 (br. s., 1H), 9.85 (br. s., 1H), 9.16 (s, 1H), 8.70 (d, J=4.88 Hz, 1H), 8.53 (d, J=4.88 Hz, 1H), 7.42-7.59 (m, 7H), 7.39 (s, 1H), 7.34 (d, J=4.58 Hz, 1H), 3.74 (s, 3H); MS (ESI) (m/z): 372.3 $(M+H)^+$; LC/MS retention time (Method A): $t_R$=2.13 min; (Method B) $t_R$=3.30 min.

Example 99

2-((1-Methyl-1H-1,2,3-triazol-4-yl)amino)-N-(4-phenylpyridin-3-yl)pyrimidine-4-carboxamide

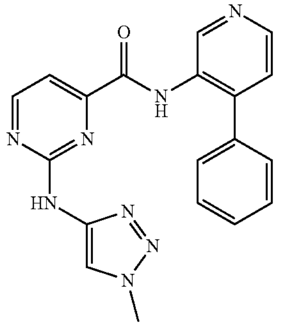 [SMILES: Cn1cc(Nc2nccc(C(=O)Nc3cnccc3-c3ccccc3)n2)nn1]

Prepared by Method C (heated at 100° C. for 2 h), obtained 3.0 mg, 13% yield: $^1$H NMR (500 MHz, DMSO-$d_6$) δ 10.44 (br. s., 1H), 9.97 (br. s., 1H), 9.04 (s, 1H), 8.75 (d, J=4.88 Hz, 1H), 8.57 (d, J=5.19 Hz, 1H), 7.91 (br. s., 1H), 7.56 (d, J=7.02 Hz, 2H), 7.51 (d, J=5.19 Hz, 1H), 7.34-7.45 (m, 4H), 3.94 (s, 3H); MS (ESI) (m/z): 373.1 $(M+H)^+$; LC/MS retention time (Method A): $t_R$=1.90 min; (Method B) $t_R$=3.10 min.

Example 100

2-((6-(Isobutylamino)pyridin-3-yl)amino)-N-(4-phenylpyridin-3-yl)pyrimidine-4-carboxamide

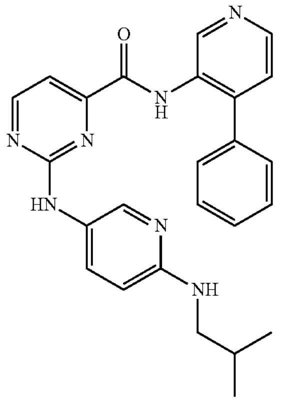 [SMILES: CC(C)CNc1ccc(Nc2nccc(C(=O)Nc3cnccc3-c3ccccc3)n2)cn1]

Prepared by Method C (heated at 100° C. for 2 h), obtained 15 mg, 48% yield: $^1$H NMR (500 MHz, DMSO-$d_6$) δ 9.90 (s, 1H), 9.06 (s, 1H), 8.63 (d, J=4.88 Hz, 1H), 8.53 (d, J=5.19 Hz, 1H), 8.05 (s, 1H), 7.50 (d, J=7.32 Hz, 8H), 7.24 (d, J=4.58 Hz, 1H), 6.33-6.43 (m, 2H), 3.06 (t, J=6.41 Hz, 2H), 1.83-1.90 (m, 1H), 0.92 (d, J=6.41 Hz, 6H); MS (ESI) (m/z): 440.6 $(M+H)^+$; LC/MS retention time (Method A): $t_R$=2.57 min; (Method B) $t_R$=3.86 min.

Example 101

2-((1,2,3-Thiadiazol-5-yl)amino)-N-(4-phenylpyridin-3-yl)pyrimidine-4-carboxamide

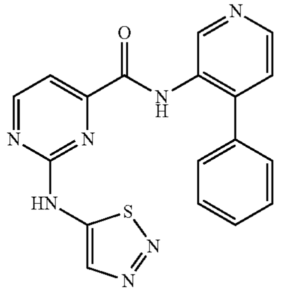 [SMILES: O=C(Nc1cnccc1-c1ccccc1)c1ccnc(Nc2cnns2)n1]

Prepared by Method C (heated at 100° C. for 2 h), obtained 4.4 mg, 18% yield: $^1$H NMR (500 MHz, DMSO-$d_6$) δ 10.29 (s, 1H), 9.10 (s, 1H), 8.84 (d, J=5.19 Hz, 1H), 8.56 (d, J=4.88 Hz, 1H), 8.31 (br. s., 1H), 7.76 (d, J=4.88 Hz, 1H), 7.44-7.62 (m, 7H); MS (ESI) (m/z): 376.2 $(M+H)^+$; LC/MS retention time (Method A): $t_R$=2.08 min; (Method B) $t_R$=3.26 min.

Example 102

2-((1-Methyl-1H-imidazol-4-yl)amino)-N-(4-phenylpyridin-3-yl)pyrimidine-4-carboxamide

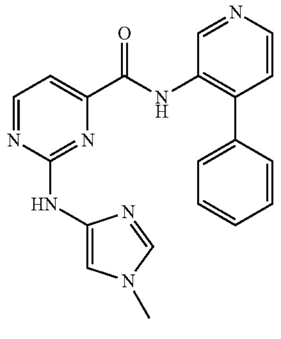 [SMILES: Cn1cnc(Nc2nccc(C(=O)Nc3cnccc3-c3ccccc3)n2)c1]

Prepared by Method C (heated at 100° C. for 2 h), obtained 3.3 mg, 14% yield: $^1$H NMR (500 MHz, DMSO-$d_6$) δ 9.98 (br. s., 1H), 9.71 (br. s., 1H), 9.04 (s, 1H), 8.69 (d, J=4.58 Hz, 1H), 8.56 (d, J=4.88 Hz, 1H), 7.58 (d, J=7.32 Hz, 2H), 7.49 (d, J=5.19 Hz, 1H), 7.40-7.47 (m, 3H), 7.38 (s, 1H), 7.27 (d, J=4.88 Hz, 1H), 7.00 (br. s., 1H), 3.56 (br. s., 3H); MS (ESI) (m/z): 372.3 $(M+H)^+$; LC/MS retention time (Method A): $t_R$=2.03 min; (Method B) $t_R$=3.20 min.

Example 103

N-(5-(2-Fluorophenyl)pyridin-3-yl)-2-((6-methylpyridin-3-yl)amino)pyrimidine-4-carboxamide

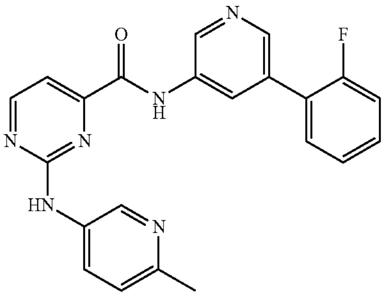 [SMILES: Cc1ccc(Nc2nccc(C(=O)Nc3cncc(-c4ccccc4F)c3)n2)cn1]

Prepared by Method C (heated at 100° C. for 2 h), obtained 10 mg, 39% yield: $^1$H NMR (500 MHz, DMSO-$d_6$) δ 10.70 (s, 1H), 10.02 (s, 1H), 9.02 (d, J=2.44 Hz, 1H), 8.81 (d, J=2.75 Hz, 1H), 8.80 (d, J=4.88 Hz, 1H), 8.58 (t, J=1.68 Hz, 1H), 8.49 (d, J=1.22 Hz, 1H), 8.17 (dd, J=8.39, 2.59 Hz, 1H), 7.66 (td, J=7.86, 1.68 Hz, 1H), 7.51-7.57 (m, 1H), 7.37-7.45 (m, 3H), 7.25 (d, J=8.54 Hz, 1H), 2.44 (s, 3H); MS (ESI) (m/z): 401.3 $(M+H)^+$; LC/MS retention time (Method A): $t_R$=2.55 min; (Method B) $t_R$=3.94 min.

Example 104

N-(5-(2-Fluorophenyl)pyridin-3-yl)-2-((6-fluoropyridin-3-yl)amino)pyrimidine-4-carboxamide

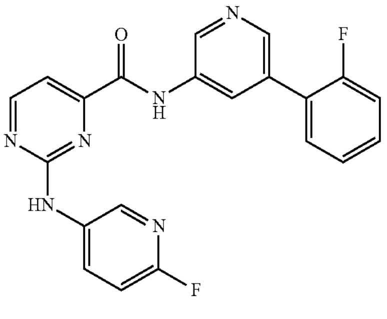 [SMILES: O=C(Nc1cncc(-c2ccccc2F)c1)c1ccnc(Nc2ccc(F)nc2)n1]

Prepared by Method C (heated at 100° C. for 2 h), obtained 7.5 mg, 31% yield: $^1$H NMR (500 MHz, DMSO-$d_6$) δ 10.72 (s, 1H), 10.19 (s, 1H), 9.02 (d, J=2.44 Hz, 1H), 8.82 (d, J=4.88 Hz, 1H), 8.62 (s, 1H), 8.58 (t, J=1.53 Hz, 1H), 8.50 (d, J=1.53 Hz, 1H), 8.38-8.45 (m, 1H), 7.65 (td, J=7.78, 1.83 Hz, 1H), 7.50-7.57 (m, 1H), 7.46 (d, J=4.88 Hz, 1H), 7.37-7.44 (m, 2H), 7.21 (dd, J=8.85, 3.36 Hz, 1H); MS (ESI) (m/z): 405.1 $(M+H)^+$; LC/MS retention time (Method A): $t_R$=2.61 min; (Method B) $t_R$=3.95 min.

Example 105

2-((6-(Difluoromethoxy)pyridin-3-yl)amino)-N-(5-(2-fluorophenyl)pyridin-3-yl)pyrimidine-4-carboxamide

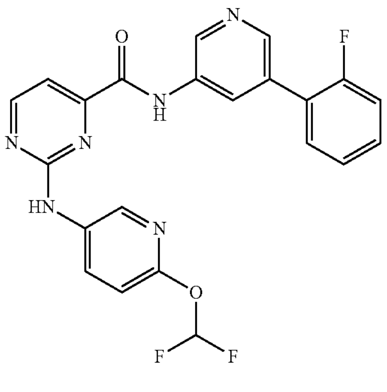 [SMILES: O=C(Nc1cncc(-c2ccccc2F)c1)c1ccnc(Nc2ccc(OC(F)F)nc2)n1]

Prepared by Method C (heated at 100° C. for 2 h), obtained 4.3 mg, 15% yield: $^1$H NMR (500 MHz, DMSO-$d_6$) δ 10.71 (s, 1H), 10.14 (s, 1H), 9.02 (d, J=2.44 Hz, 1H), 8.81 (d, J=4.88 Hz, 1H), 8.68 (d, J=2.75 Hz, 1H), 8.58 (t, J=1.68 Hz, 1H), 8.49 (d, J=1.53 Hz, 1H), 8.35 (dd, J=8.85, 2.75 Hz, 1H), 7.61-7.71 (m, 2H), 7.51-7.57 (m, 1H), 7.37-7.46 (m, 3H), 7.14 (d, J=8.85 Hz, 1H); MS (ESI) (m/z): 453.4 $(M+H)^+$; LC/MS retention time (Method A): $t_R$=2.97 min; (Method B) $t_R$=4.11 min.

Example 106

2-(Isoquinolin-6-ylamino)-N-(4-(2,2,2-trifluoroethoxy)pyridin-3-yl)pyrimidine-4-carboxamide

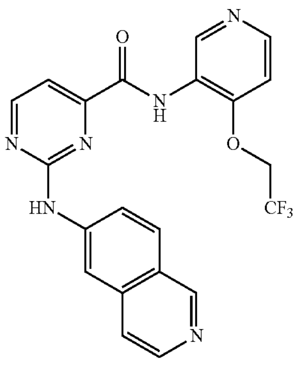 [SMILES: O=C(Nc1cnccc1OCC(F)(F)F)c1ccnc(Nc2ccc3cnccc3c2)n1]

Prepared by Method D (heated at 110° C. for 18 h), obtained 0.6 mg, 1.2% yield: $^1$H NMR (500 MHz, METHANOL-$d_4$) δ 9.41 (s, 1H), 9.10 (s, 1H), 8.87 (d, J=4.9 Hz, 1H), 8.46 (s, 1H), 8.37 (d, J=5.5 Hz, 1H), 8.34 (d, J=5.8 Hz, 1H), 8.08 (d, J=8.9 Hz, 1H), 7.91 (dd, J=9.0, 2.0 Hz, 1H), 7.73 (d, J=5.8 Hz, 1H), 7.65 (d, J=4.6 Hz, 1H), 7.34 (d, J=5.5 Hz, 1H), 4.81 (q, J=8.2 Hz, 2H); LC/MS (ESI) m/e 441.1 $[(M+H)^+$, calcd $C_{21}H_{16}F_3N_6O_2$, 441.1]; LC/MS retention time (Method A): $t_R$=2.32 min.

Example 107

2-(Quinolin-7-ylamino)-N-(4-(2,2,2-trifluoroethoxy)pyridin-3-yl)pyrimidine-4-carboxamide

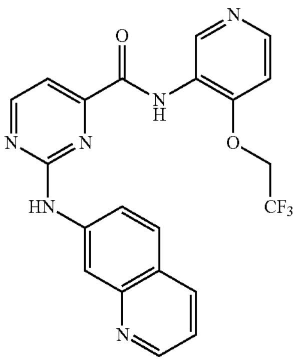 [SMILES: O=C(Nc1cnccc1OCC(F)(F)F)c1ccnc(Nc2ccc3cccnc3c2)n1]

Prepared by Method D (heated at 110° C. for 18 h), obtained 0.7 mg, 3.3% yield: $^1$H NMR (500 MHz, METHANOL-$d_4$) δ 9.41 (s, 1H), 8.85 (d, J=4.9 Hz, 1H), 8.77 (dd, J=4.3, 1.5 Hz, 1H), 8.64 (d, J=1.8 Hz, 1H), 8.35 (d, J=5.8 Hz, 1H), 8.31 (d, J=7.3 Hz, 1H), 7.92 (d, J=8.9 Hz, 1H), 7.81 (dd, J=8.9, 2.1 Hz, 1H), 7.63 (d, J=4.9 Hz, 1H), 7.42 (dd, J=8.2, 4.3 Hz, 1H), 7.32 (d, J=5.8 Hz, 1H), 4.80 (q, J=8.2 Hz, 2H); LC/MS (ESI) m/e 441.1 $[(M+H)^+$, calcd $C_{21}H_{16}F_3N_6O_2$, 441.1]; LC/MS retention time (Method A): $t_R$=2.31 min.

Example 108

2-((1-(2,5-Difluorophenyl)-1H-pyrazol-4-yl)amino)-N-(4-(2,2,2-trifluoroethoxy)pyridin-3-yl)pyrimidine-4-carboxamide

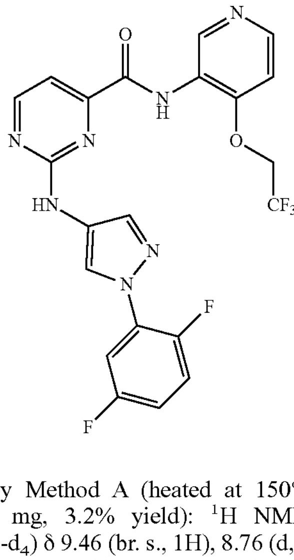

Prepared by Method A (heated at 150° C. for 2 h), obtained 0.5 mg, 3.2% yield: $^1$H NMR (500 MHz, METHANOL-$d_4$) δ 9.46 (br. s., 1H), 8.76 (d, J=4.6 Hz, 1H), 8.48 (br. s., 1H), 8.36 (d, J=5.8 Hz, 1H), 8.09 (br. s., 1H), 7.70 (ddd, J=9.2, 6.2, 3.2 Hz, 1H), 7.50 (d, J=4.6 Hz, 1H), 7.41-7.32 (m, 2H), 7.16-7.07 (m, 1H), 5.00-4.92 (m, 2H); LC/MS (ESI) m/e 492.1 $[(M+H)^+$, calcd $C_{21}H_{15}F_5N_7O_2$, 492.1]; LC/MS retention time (Method A): $t_R$=2.69 min.

Example 109

N-(6-Fluoro-4-(2,2,2-trifluoroethoxy) pyridin-3-yl)-2-((4-(trifluoromethyl)phenyl)amino) pyrimidine-4-carboxamide

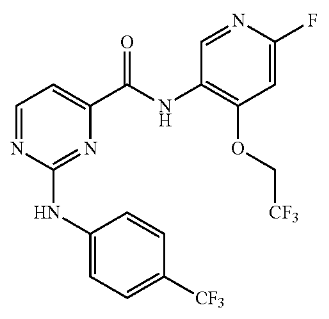 [SMILES: O=C(Nc1cnc(F)cc1OCC(F)(F)F)c1ccnc(Nc2ccc(C(F)(F)F)cc2)n1]

Prepared by Method D (heated at 110° C. for 18 h), obtained 1.1 mg, 7.2% yield: $^1$H NMR (500 MHz, DMSO-$d_6$) δ 10.42 (br. s., 1H), 9.88 (br. s., 1H), 8.88 (d, J=4.6 Hz, 1H), 8.76 (s, 1H), 7.95 (d, J=8.5 Hz, 2H), 7.69 (d, J=8.9 Hz, 2H), 7.53 (d, J=4.9 Hz, 1H), 7.29 (s, 1H), 5.07 (q, J=8.7 Hz, 2H); LC/MS (ESI) m/e 476.1 [(M+H)$^+$, calcd $C_{19}H_{13}F_7N_5O_2$, 476.1]; LC/MS retention time (Method A): $t_R$=3.20 min.

Example 110

2-((4-Chlorophenyl)amino)-N-(6-fluoro-4-(2,2,2-trifluoroethoxy)pyridin-3-yl)pyrimidine-4-carboxamide

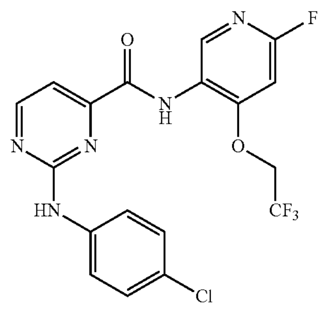 [SMILES: O=C(Nc1cnc(F)cc1OCC(F)(F)F)c1ccnc(Nc2ccc(Cl)cc2)n1]

Prepared by Method D (heated at 110° C. for 18 h), obtained 0.9 mg, 7.4% yield: $^1$H NMR (500 MHz, DMSO-$d_6$) δ 10.12 (s, 1H), 9.84 (s, 1H), 8.82 (d, J=4.9 Hz, 1H), 8.75 (s, 1H), 7.75 (d, J=8.9 Hz, 2H), 7.46 (d, J=4.6 Hz, 1H), 7.39 (d, J=8.9 Hz, 2H), 7.30 (s, 1H), 5.09 (q, J=8.4 Hz, 2H); LC/MS (ESI) m/e 442.3 [(M+H)$^+$, calcd $C_{18}H_{13}F_4Cl_1N_5O_2$, 442.8]; LC/MS retention time (Method A): $t_R$=3.00 min.

Example 111

N-(4-(2,2,2-Trifluoroethoxy)pyridin-3-yl)-2-((5-(trifluoromethyl)pyridin-2-yl)amino)pyrimidine-4-carboxamide

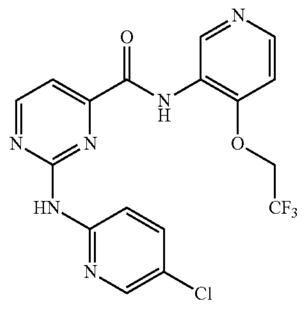 [SMILES: O=C(Nc1cnccc1OCC(F)(F)F)c1ccnc(Nc2ccc(Cl)cn2)n1]

Prepared by Method D (heated at 110° C. for 18 h), obtained 5.9 mg, 34% yield: $^1$H NMR (500 MHz, DMSO-$d_6$) δ 10.75 (s, 1H), 10.00 (s, 1H), 9.27 (s, 1H), 8.97 (d, J=4.6 Hz, 1H), 8.72 (s, 1H), 8.42 (d, J=5.5 Hz, 1H), 8.30 (d, J=8.2 Hz, 1H), 8.16 (d, J=9.2 Hz, 1H), 7.68 (d, J=4.9 Hz, 1H), 7.42 (d, J=5.5 Hz, 1H), 5.05 (q, J=8.5 Hz, 2H); LC/MS (ESI) m/e 459.2 [(M+H)$^+$, calcd $C_{18}H_{13}F_6N_6O_2$, 459.1]; LC/MS retention time (Method A): $t_R$=2.74 min.

Example 112

2-(Naphthalen-1-ylamino)-N-(4-(2,2,2-trifluoroethoxy)pyridin-3-yl)pyrimidine-4-carboxamide

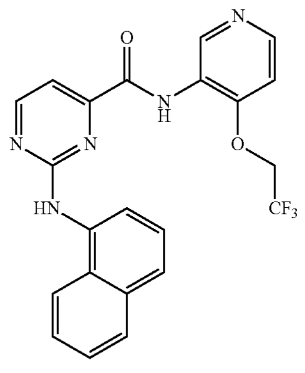 [SMILES: O=C(Nc1cnccc1OCC(F)(F)F)c1ccnc(Nc2cccc3ccccc23)n1]

Prepared by Method A (heated at 150° C. for 1.5 h), obtained 1.0 mg, 6% yield: $^1$H NMR (500 MHz, DMSO-$d_6$) δ 9.83 (s, 1H), 9.27 (s, 1H), 8.74 (d, J=4.6 Hz, 1H), 8.36 (d, J=5.5 Hz, 1H), 8.07 (d, J=7.9 Hz, 1H), 8.00-7.97 (m, 1H), 7.83 (d, J=8.2 Hz, 1H), 7.76 (d, J=7.3 Hz, 1H), 7.61-7.50 (m, 3H), 7.42 (d, J=4.9 Hz, 1H), 7.38 (d, J=5.5 Hz, 1H), 4.92 (q, J=8.7 Hz, 2H); LC/MS (ESI) m/e 440.2 [(M+H)$^+$, calcd $C_{22}H_{17}F_3N_5O_2$, 440.1]; LC/MS retention time (Method A): $t_R$=2.77 min.

Example 113

2-((2,4-Difluorophenyl)amino)-N-(4-(2,2,2-trifluoroethoxy)pyridin-3-yl)pyrimidine-4-carboxamide

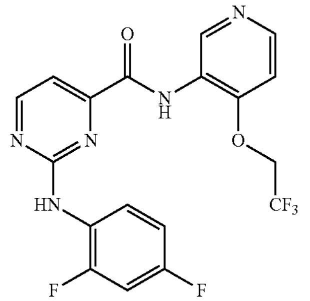 [SMILES: O=C(Nc1cnccc1OCC(F)(F)F)c1ccnc(Nc2ccc(F)cc2F)n1]

Prepared by Method D (heated at 110° C. for 18 h), obtained 11.3 mg, 83% yield: $^1$H NMR (500 MHz, DMSO-$d_6$) δ 9.75 (br. s., 1H), 9.50 (s, 1H), 9.29 (s, 1H), 8.75 (d, J=4.9 Hz, 1H), 8.38 (s, 1H), 7.47 (d, J=4.9 Hz, 1H), 7.41 (d, J=5.8 Hz, 2H), 7.23 (t, J=8.1 Hz, 2H), 4.98 (q, J=8.5 Hz, 2H); LC/MS (ESI) m/e 426.1 [$(M+H)^+$, calcd $C_{18}H_{13}F_5N_5O_2$, 426.1]; LC/MS retention time (Method A): $t_R$=2.40 min.

Example 114

2-(Pyridin-2-ylamino)-N-(4-(2,2,2-trifluoroethoxy)pyridin-3-yl)pyrimidine-4-carboxamide

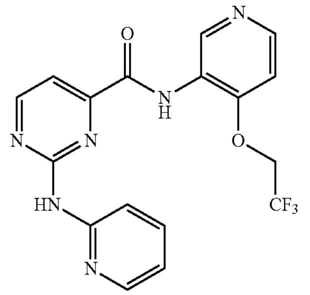 [SMILES: O=C(Nc1cnccc1OCC(F)(F)F)c1ccnc(Nc2ccccn2)n1]

Prepared by Method A (heated at 150° C. for 2 h), obtained 10.4 mg, 63% yield: LC/MS (ESI) m/e 391.1 [$(M+H)^+$, calcd $C_{17}H_{14}F_3N_6O_2$, 391.1]; LC/MS retention time (Method A): $t_R$=2.23 min.

Example 115

2-(Naphthalen-2-ylamino)-N-(4-(2,2,2-trifluoroethoxy)pyridin-3-yl)pyrimidine-4-carboxamide

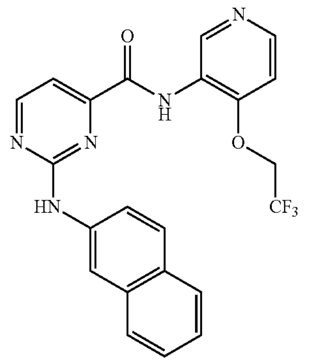 [SMILES: O=C(Nc1cnccc1OCC(F)(F)F)c1ccnc(Nc2ccc3ccccc3c2)n1]

Prepared by Method A (heated at 150° C. for 0.5 h), obtained 2.6 mg, 20% yield: $^1$H NMR (500 MHz, DMSO-$d_6$) δ 10.18 (s, 1H), 10.02 (s, 1H), 9.23 (s, 1H), 8.87 (d, J=4.9 Hz, 1H), 8.41 (d, J=5.5 Hz, 1H), 8.30 (s, 1H), 7.93-7.80 (m, 4H), 7.52-7.45 (m, 2H), 7.43-7.37 (m, 2H), 4.89 (q, J=8.5 Hz, 2H); LC/MS (ESI) m/e 440.2 [$(M+H)^+$, calcd $C_{22}H_{17}F_3N_5O_2$, 440.4]; LC/MS retention time (Method A): $t_R$=2.88 min.

Example 116

2-(Cyclopentylamino)-N-(4-(2,2,2-trifluoroethoxy)pyridin-3-yl)pyrimidine-4-carboxamide

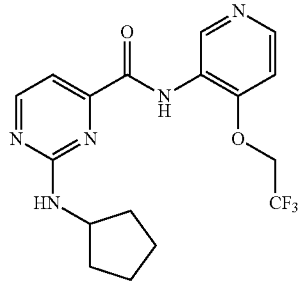 [SMILES: O=C(Nc1cnccc1OCC(F)(F)F)c1ccnc(NC2CCCC2)n1]

Prepared by Method A (heated at 150° C. for 0.5 h), obtained 8.6 mg, 76% yield: $^1$H NMR (500 MHz, DMSO-$d_6$) δ 10.14 (br. s., 1H), 9.51 (br. s., 1H), 8.59 (d, J=4.9 Hz, 1H), 8.38 (d, J=5.5 Hz, 1H), 7.77 (br. s., 1H), 7.37 (d, J=5.5 Hz, 1H), 7.22 (d, J=4.9 Hz, 1H), 5.08 (q, J=8.7 Hz, 2H), 4.31 (d, J=5.8 Hz, 1H), 1.97 (d, J=6.1 Hz, 2H), 1.72 (br. s., 2H), 1.56 (br. s., 4H); LC/MS (ESI) m/e 382.1 [$(M+H)^+$, calcd $C_{17}H_{19}F_3N_5O_2$, 382.2]; LC/MS retention time (Method A): $t_R$=2.62 min.

Example 117

2-(Cyclohexylamino)-N-(4-(2,2,2-trifluoroethoxy)pyridin-3-yl)pyrimidine-4-carboxamide

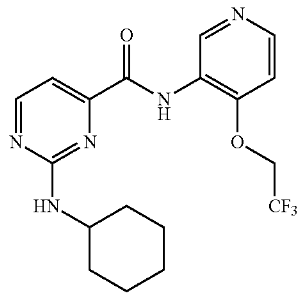 [SMILES: O=C(Nc1cnccc1OCC(F)(F)F)c1ccnc(NC2CCCCC2)n1]

Prepared by Method A (heated at 150° C. for 0.5 h), obtained 10.6 mg, 90% yield: $^1$H NMR (500 MHz, DMSO-$d_6$) δ 9.98 (s, 1H), 9.41 (br. s., 1H), 8.59 (d, J=4.6 Hz, 1H), 8.39 (d, J=5.8 Hz, 1H), 7.59 (br. s., 1H), 7.39 (d, J=5.8 Hz, 1H), 7.20 (d, J=4.9 Hz, 1H), 5.08 (q, J=8.5 Hz, 2H), 3.85 (br. s., 1H), 1.90 (br. s., 2H), 1.77-1.70 (m, 2H), 1.60 (d, J=11.6 Hz, 1H), 1.41-1.28 (m, 4H), 1.21 (br. s., 1H); LC/MS (ESI) m/e 396.2 [$(M+H)^+$, calcd $C_{18}H_{21}F_3N_5O_2$, 396.4]; LC/MS retention time (Method A): $t_R$=2.81 min.

Example 118

2-((Cyclopropylmethyl)amino)-N-(4-(2,2,2-trifluoroethoxy)pyridin-3-yl)pyrimidine-4-carboxamide

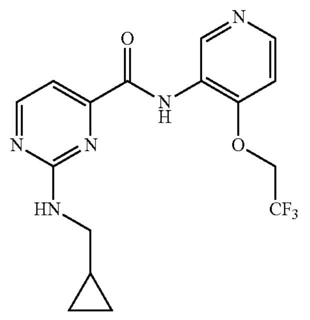

Prepared by Method A (heated at 150° C. for 0.5 h), obtained 8.8 mg, 70% yield: $^1$H NMR (500 MHz, DMSO-$d_6$) δ 10.17 (br. s., 1H), 9.50 (br. s., 1H), 8.61 (d, J=4.9 Hz, 1H), 8.38 (d, J=5.8 Hz, 1H), 7.79 (br. s., 1H), 7.36 (d, J=5.8 Hz, 1H), 7.23 (d, J=4.6 Hz, 1H), 5.07 (q, J=8.5 Hz, 2H), 3.25 (t, J=6.3 Hz, 2H), 1.17-1.06 (m, 1H), 0.51-0.43 (m, 2H), 0.25 (d, J=4.9 Hz, 2H); LC/MS (ESI) m/e 368.1 [(M+H)$^+$, calcd $C_{16}H_{17}F_3N_5O_2$, 368.1]; LC/MS retention time (Method A): $t_R$=2.42 min.

Example 119

2-(Cyclobutylamino)-N-(4-(2,2,2-trifluoroethoxy)pyridin-3-yl)pyrimidine-4-carboxamide

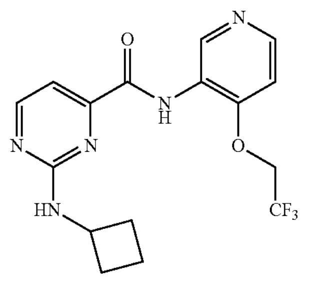 [SMILES: O=C(Nc1cnccc1OCC(F)(F)F)c1ccnc(NC2CCC2)n1]

Prepared by Method A (heated at 110° C. for 1.5 h), obtained 6.0 mg, 53% yield: $^1$H NMR (500 MHz, DMSO-$d_6$) δ 10.12 (br. s., 1H), 9.52 (br. s., 1H), 8.60 (d, J=4.6 Hz, 1H), 8.38 (d, J=5.8 Hz, 1H), 8.04 (br. s., 1H), 7.37 (d, J=5.5 Hz, 1H), 7.23 (d, J=4.6 Hz, 1H), 5.11 (q, J=8.5 Hz, 2H), 4.55-4.45 (m, 1H), 2.35-2.27 (m, 2H), 2.11-1.99 (m, 2H), 1.77-1.63 (m, 2H); LC/MS (ESI) m/e 368.1 [(M+H)$^+$, calcd $C_{16}H_{17}F_3N_5O_2$, 368.1]; LC/MS retention time (Method A): $t_R$=2.43 min.

Example 120

2-(Isopropylamino)-N-(4-(2,2,2-trifluoroethoxy)pyridin-3-yl)pyrimidine-4-carboxamide

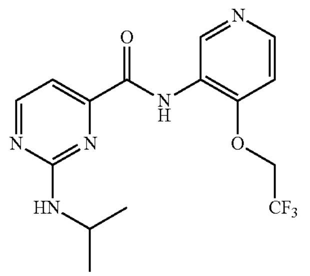 [SMILES: CC(C)Nc1nccc(C(=O)Nc2cnccc2OCC(F)(F)F)n1]

Prepared by Method A (heated at 100° C. for 1.5 h), obtained 6.2 mg, 56% yield: $^1$H NMR (500 MHz, DMSO-$d_6$) δ 10.19 (br. s., 1H), 9.54 (br. s., 1H), 8.60 (d, J=4.6 Hz, 1H), 8.38 (d, J=5.5 Hz, 1H), 7.63 (br. s., 1H), 7.35 (d, J=5.8 Hz, 1H), 7.21 (d, J=4.9 Hz, 1H), 5.08 (q, J=8.9 Hz, 2H), 4.25-4.14 (m, 1H), 1.20 (d, J=6.4 Hz, 6H); LC/MS (ESI) m/e 356.1 [(M+H)$^+$, calcd $C_{15}H_{17}F_3N_5O_2$, 356.1]; LC/MS retention time (Method A): $t_R$=2.49 min.

Example 121

2-((4-(tert-Butyl)cyclohexyl)amino)-N-(4-(2,2,2-trifluoroethoxy)pyridin-3-yl)pyrimidine-4-carboxamide

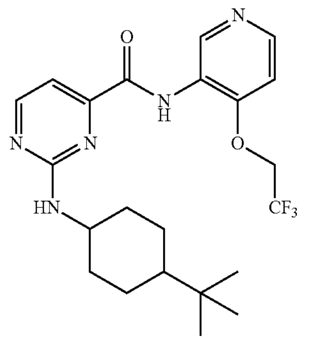

(cis isomer)

Prepared by Method A (heated at 150° C. for 2 h), obtained 2.5 mg, 24% yield: LC/MS (ESI) m/e 452.2 [(M+H)$^+$, calcd $C_{22}H_{29}F_3N_5O_2$, 452.2]; LC/MS retention time (Method A): $t_R$=3.45 min.

Example 122

2-((1S,4S)-4-(tert-Butyl)cyclohexyl)amino)-N-(4-(2,2,2-trifluoroethoxy)pyridin-3-yl)pyrimidine-4-carboxamide

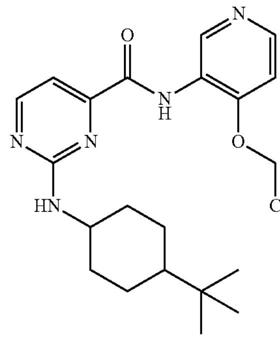

(trans isomer)

Prepared by Method A (heated at 150° C. for 2 h), obtained 2.0 mg, 19% yield: LC/MS (ESI) m/e 452.3 [(M+H)$^+$, calcd $C_{22}H_{29}F_3N_5O_2$, 452.2]; LC/MS retention time (Method A): $t_R$=3.52 min.

Example 123

2-(Ethylamino)-N-(4-(2,2,2-trifluoroethoxy)pyridin-3-yl)pyrimidine-4-carboxamide

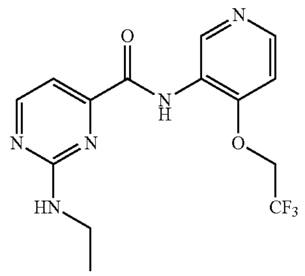 [SMILES: CCNc1nccc(C(=O)Nc2cnccc2OCC(F)(F)F)n1]

Prepared by Method A (heated at 100° C. for 1.5 h), obtained 4.1 mg, 38% yield: $^1$H NMR (500 MHz, DMSO-$d_6$) δ 10.25 (br. s., 1H), 9.54 (br. s., 1H), 8.61 (d, J=4.9 Hz, 1H), 8.38 (d, J=5.5 Hz, 1H), 7.73 (br. s., 1H), 7.35 (d, J=5.2 Hz, 1H), 7.23 (d, J=4.6 Hz, 1H), 5.08 (q, J=8.7 Hz, 2H), 3.45-3.38 (m, 2H), 1.19 (t, J=7.2 Hz, 3H); LC/MS (ESI) m/e 342.1 [(M+H)$^+$, calcd $C_{14}H_{15}F_3N_5O_2$, 342.3]; LC/MS retention time (Method A): $t_R$=2.35 min.

Example 124

2-((Tetrahydro-2H-pyran-4-yl)amino)-N-(4-(2,2,2-trifluoroethoxy)pyridin-3-yl)pyrimidine-4-carboxamide

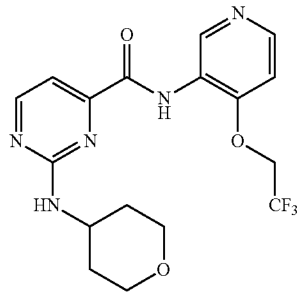 [SMILES: O=C(Nc1cnccc1OCC(F)(F)F)c1ccnc(NC2CCOCC2)n1]

Prepared by Method A (heated at 150° C. for 1.5 h), obtained 2.9 mg, 25% yield: $^1$H NMR (500 MHz, DMSO-$d_6$) δ 9.98 (s, 1H), 8.62 (d, J=4.6 Hz, 1H), 8.39 (d, J=5.8 Hz, 1H), 7.40 (d, J=5.8 Hz, 1H), 7.23 (d, J=4.6 Hz, 1H), 5.10 (q, J=8.7 Hz, 2H), 4.13-4.01 (m, 1H), 3.90 (d, J=11.6 Hz, 2H), 3.43 (t, J=10.4 Hz, 2H), 1.86 (d, J=10.1 Hz, 2H), 1.66-1.53 (m, 2H); LC/MS (ESI) m/e 398.1 [(M+H)$^+$, calcd $C_{17}H_{19}F_3N_5O_2$, 398.1]; LC/MS retention time (Method A): $t_R$=2.04 min.

Example 125

2-((3-Methylbutan-2-yl)amino)-N-(4-(2,2,2-trifluoroethoxy)pyridin-3-yl)pyrimidine-4-carboxamide

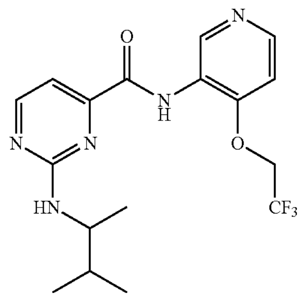 [SMILES: CC(C)C(C)Nc1nccc(C(=O)Nc2cnccc2OCC(F)(F)F)n1]

Prepared by Method A (heated at 150° C. for 1 h), obtained 5 mg, 62% yield: $^1$H NMR (500 MHz, DMSO-$d_6$) δ 10.08 (s, 1H), 9.52 (br. s., 1H), 8.59 (d, J=4.6 Hz, 1H), 8.38 (d, J=5.8 Hz, 1H), 7.55 (br. s., 1H), 7.36 (d, J=5.8 Hz, 1H), 7.20 (d, J=4.9 Hz, 1H), 5.12-5.02 (m, 2H), 3.95 (dt, J=8.9, 6.7 Hz, 1H), 1.84-1.72 (m, 1H), 1.14 (d, J=6.7 Hz, 3H), 0.92 (dd, J=6.6, 5.6 Hz, 6H); LC/MS (ESI) m/e 384.1 [(M+H)$^+$, calcd $C_{17}H_{21}F_3N_5O_2$, 384.1]; LC/MS retention time (Method A): $t_R$=2.70 min.

Example 126

2-((3,3-Dimethylbutan-2-yl)amino)-N-(4-(2,2,2-trifluoroethoxy)pyridin-3-yl)pyrimidine-4-carboxamide

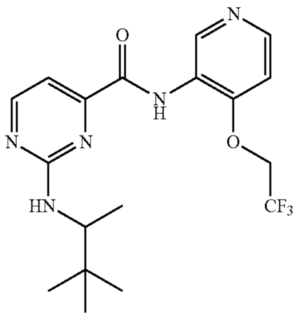 [SMILES: CC(Nc1nccc(C(=O)Nc2cnccc2OCC(F)(F)F)n1)C(C)(C)C]

Prepared by Method A (heated at 150° C. for 1 h), obtained 7.6 mg, 72% yield: $^1$H NMR (500 MHz, DMSO-$d_6$) δ 10.01 (br. s., 1H), 9.45 (br. s., 1H), 8.59 (d, J=4.6 Hz, 1H), 8.39 (d, J=5.8 Hz, 1H), 7.46-7.35 (m, 2H), 7.19 (d, J=4.9 Hz, 1H), 5.07 (qd, J=8.7, 2.6 Hz, 2H), 4.05 (dd, J=9.6, 6.9 Hz, 1H), 1.12 (d, J=6.7 Hz, 3H), 0.93 (s, 9H); LC/MS (ESI) m/e 398.2 [(M+H)$^+$, calcd $C_{18}H_{23}F_3N_5O_2$, 398.2]; LC/MS retention time (Method A): $t_R$=2.85 min.

Example 127

2-(Cyclobutylamino)-N-(6-fluoro-4-(2,2,2-trifluoroethoxy)pyridin-3-yl)pyrimidine-4-carboxamide

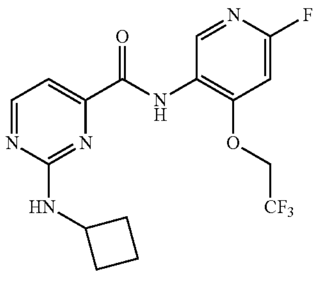 [SMILES: O=C(Nc1cnc(F)cc1OCC(F)(F)F)c1ccnc(NC2CCC2)n1]

Prepared by Method A (heated at 110° C. for 0.5 h), obtained 3.2 mg, 67% yield: $^1$H NMR (500 MHz, DMSO-$d_6$) δ 10.05 (br. s., 1H), 9.08 (br. s., 1H), 8.60 (d, J=4.9 Hz, 1H), 8.05 (br. s., 1H), 7.26 (s, 1H), 7.22 (d, J=4.6 Hz, 1H), 5.14 (q, J=8.6 Hz, 2H), 4.55-4.43 (m, 1H), 2.31 (d, J=8.5 Hz, 2H), 2.12-1.98 (m, 2H), 1.78-1.64 (m, 2H); LC/MS (ESI) m/e 386.4 [(M+H)$^+$, calcd $C_{16}H_{16}F_4N_5O_2$, 386.3]; LC/MS retention time (Method A): $t_R$=2.53 min.

Example 128

2-(Benzylamino)-N-(4-(2,2,2-trifluoroethoxy)pyridin-3-yl)pyrimidine-4-carboxamide

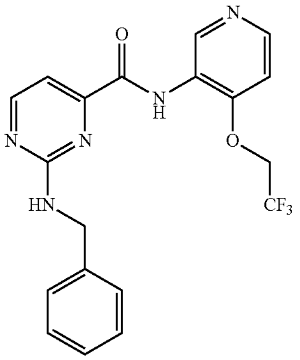 [SMILES: O=C(Nc1cnccc1OCC(F)(F)F)c1ccnc(NCc2ccccc2)n1]

Prepared by Method A (heated at 110° C. for 1.5 h), obtained 8.2 mg, 63% yield: $^1$H NMR (500 MHz, DMSO-$d_6$) δ 10.17 (br. s., 1H), 9.42 (br. s., 1H), 8.64 (d, J=4.9 Hz, 1H), 8.38 (d, J=5.5 Hz, 1H), 8.22 (br. s., 1H), 7.40-7.28 (m, 5H), 7.30-7.18 (m, 2H), 5.09-4.97 (m, 2H), 4.62 (d, J=6.4 Hz, 2H); LC/MS (ESI) m/e 404.1 [(M+H)$^+$, calcd $C_{19}H_{17}F_3N_5O_2$, 404.1]; LC/MS retention time (Method A): $t_R$=2.54 min.

Example 129

2-((2-Fluorobenzyl)amino)-N-(4-(2,2,2-trifluoroethoxy)pyridin-3-yl)pyrimidine-4-carboxamide

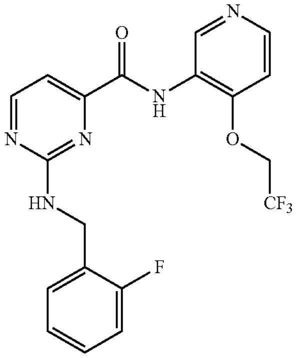 [SMILES: O=C(Nc1cnccc1OCC(F)(F)F)c1ccnc(NCc2ccccc2F)n1]

Prepared by Method A (heated at 110° C. for 1.5 h), obtained 16.4 mg, 81% yield: $^1$H NMR (500 MHz, DMSO-$d_6$) δ 10.19 (br. s., 1H), 9.43 (br. s., 1H), 8.65 (d, J=4.9 Hz, 1H), 8.38 (d, J=5.8 Hz, 1H), 8.16 (br. s., 1H), 7.41 (t, J=7.6 Hz, 1H), 7.37-7.25 (m, 3H), 7.23-7.12 (m, 2H), 5.08-4.93 (m, J=7.6 Hz, 2H), 4.68 (d, J=6.1 Hz, 2H); LC/MS (ESI) m/e 422.1 [(M+H)$^+$, calcd $C_{19}H_{16}F_4N_5O_2$, 422.1]; LC/MS retention time (Method A): $t_R$=2.55 min.

Example 130

2-(Cyclopropylamino)-N-(4-(2,2,2-trifluoroethoxy)pyridin-3-yl)pyrimidine-4-carboxamide

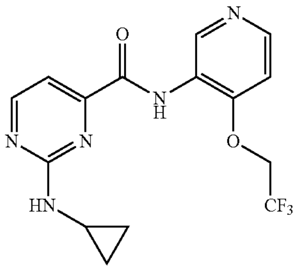 [SMILES: O=C(Nc1cnccc1OCC(F)(F)F)c1ccnc(NC2CC2)n1]

Prepared by Method A (heated at 150° C. for 0.5 h), obtained 7.0 mg, 76% yield: $^{1}$H NMR (500 MHz, DMSO-$d_6$) δ 10.28 (br. s., 1H), 9.52 (br. s., 1H), 8.62 (d, J=4.6 Hz, 1H), 8.38 (d, J=5.8 Hz, 1H), 7.93 (br. s., 1H), 7.37 (d, J=5.8 Hz, 1H), 7.29 (d, J=4.9 Hz, 1H), 5.08 (q, J=8.7 Hz, 2H), 2.85 (dd, J=7.0, 3.4 Hz, 1H), 0.79-0.68 (m, 2H), 0.62-0.50 (m, 2H); LC/MS (ESI) m/e 354.1 [(M+H)$^+$, calcd $C_{15}H_{15}F_3N_5O_2$, 354.1]; LC/MS retention time (Method A): $t_R$=2.20 min.

Example 131

2-((4-Fluorobenzyl)amino)-N-(4-(2,2,2-trifluoroethoxy)pyridin-3-yl)pyrimidine-4-carboxamide

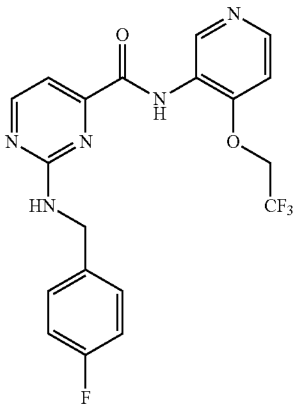 [SMILES: O=C(Nc1cnccc1OCC(F)(F)F)c1ccnc(NCc2ccc(F)cc2)n1]

Prepared by Method A (heated at 110° C. for 1.5 h), obtained 9.6 mg, 78% yield: $^{1}$H NMR (500 MHz, DMSO-$d_6$) δ 10.17 (br. s., 1H), 9.42 (br. s., 1H), 8.64 (d, J=4.6 Hz, 1H), 8.39 (d, J=5.8 Hz, 1H), 8.22 (br. s., 1H), 7.43-7.33 (m, 3H), 7.27 (d, J=4.9 Hz, 1H), 7.15 (t, J=8.9 Hz, 2H), 5.03 (q, J=8.4 Hz, 2H), 4.60 (d, J=6.1 Hz, 2H); LC/MS (ESI) m/e 422.1 [(M+H)$^+$, calcd $C_{19}H_{16}F_4N_5O_2$, 422.1]; LC/MS retention time (Method A): $t_R$=2.57 min.

Example 132

2-((Benzo[d][1,3]dioxol-5-ylmethyl)amino)-N-(4-(2,2,2-trifluoroethoxy)pyridin-3-yl)pyrimidine-4-carboxamide

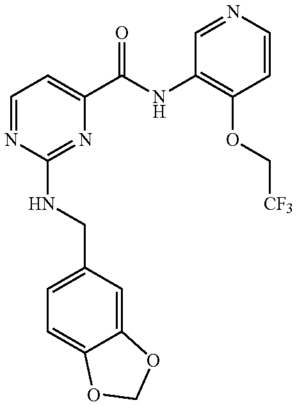 [SMILES: O=C(Nc1cnccc1OCC(F)(F)F)c1ccnc(NCc2ccc3c(c2)OCO3)n1]

Prepared by Method A (heated at 110° C. for 1.5 h), obtained 9.3 mg, 76% yield: $^{1}$H NMR (500 MHz, DMSO-$d_6$) δ 10.18 (br. s., 1H), 9.42 (br. s., 1H), 8.63 (d, J=4.6 Hz, 1H), 8.39 (d, J=5.8 Hz, 1H), 8.14 (br. s., 1H), 7.36 (d, J=5.5 Hz, 1H), 7.26 (d, J=4.6 Hz, 1H), 6.92 (s, 1H), 6.85 (s, 2H), 5.97 (s, 2H), 5.05 (q, J=8.6 Hz, 2H), 4.52 (d, J=6.1 Hz, 2H); LC/MS (ESI) m/e 448.0 [(M+H)$^+$, calcd $C_{20}H_{17}F_3N_5O_4$, 448.1]; LC/MS retention time (Method A): $t_R$=2.48 min.

Example 133

2-((2,6-Dimethyltetrahydro-2H-pyran-4-yl)amino)-N-(4-(2,2,2-trifluoroethoxy)pyridin-3-yl)pyrimidine-4-carboxamide

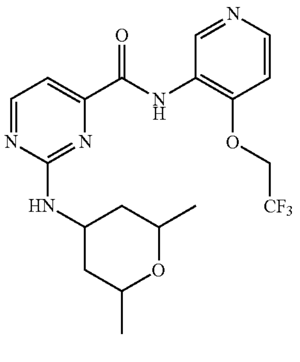 [SMILES: CC1CC(Nc2nccc(C(=O)Nc3cnccc3OCC(F)(F)F)n2)CC(C)O1]

Prepared by Method A (heated at 80° C. for 3 h), obtained 3.9 mg, 24% yield: $^{1}$H NMR (500 MHz, DMSO-$d_6$) δ 10.12 (s, 1H), 9.51 (br. s., 1H), 8.64 (d, J=4.6 Hz, 1H), 8.38 (d, J=5.5 Hz, 1H), 8.00 (br. s., 1H), 7.37 (d, J=5.5 Hz, 1H), 7.26 (d, J=4.6 Hz, 1H), 5.10 (q, J=8.7 Hz, 2H), 4.29 (br. s., 1H), 3.91-3.83 (m, 2H), 1.76 (d, J=12.8 Hz, 2H), 1.45-1.35 (m, 2H), 1.07 (d, J=6.1 Hz, 6H); LC/MS (ESI) m/e 426.2 [(M+H)$^+$, calcd $C_{19}H_{23}F_3N_5O_3$, 426.2]; LC/MS retention time (Method A): $t_R$=2.30 min.

Example 134

N-(4-(2,2,2-Trifluoroethoxy)pyridin-3-yl)-2-((4-(trifluoromethyl)benzyl)amino)pyrimidine-4-carboxamide

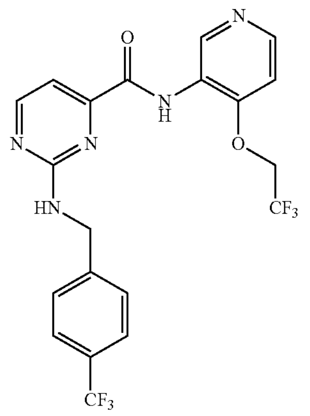 [SMILES: O=C(Nc1cnccc1OCC(F)(F)F)c1ccnc(NCc2ccc(C(F)(F)F)cc2)n1]

Prepared by Method A (heated at 150° C. for 2 h), obtained 6.4 mg, 47% yield: $^1H$ NMR (500 MHz, DMSO-$d_6$) δ 10.12 (br. s., 1H), 9.38 (br. s., 1H), 8.66 (d, J=3.7 Hz, 1H), 8.38 (d, J=5.5 Hz, 1H), 8.33 (br. s., 1H), 7.70 (d, J=8.2 Hz, 2H), 7.57 (d, J=8.2 Hz, 2H), 7.39-7.25 (m, 2H), 5.01 (m, 2H), 4.72 (d, J=6.1 Hz, 2H); LC/MS (ESI) m/e 472.1 $[(M+H)^+$, calcd $C_{20}H_{16}F_6N_5O_2$, 472.1]; LC/MS retention time (Method A): $t_R$=2.81 min.

Example 135

2-(Methylamino)-N-(4-(2,2,2-trifluoroethoxy)pyridin-3-yl)pyrimidine-4-carboxamide

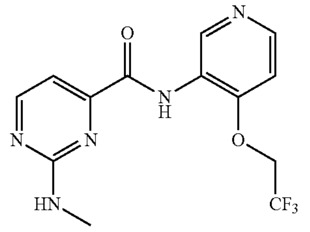 [SMILES: CNc1nccc(C(=O)Nc2cnccc2OCC(F)(F)F)n1]

Prepared by Method A (heated at 80° C. for 1.5 h), obtained 1.0 mg, 7% yield: LC/MS (ESI) m/e 328.1 $[(M+H)^+$, calcd $C_{13}H_{13}F_3N_5O_2$, 328.1]; LC/MS retention time (Method A): $t_R$=1.98 min.

Example 136

N-(6-Fluoro-4-(2,2,2-trifluoroethoxy)pyridin-3-yl)-2-(isopropylamino)pyrimidine-4-carboxamide

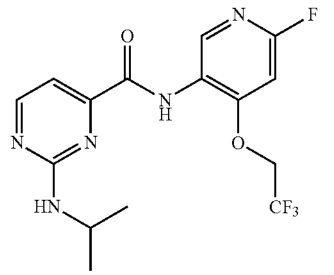 [SMILES: CC(C)Nc1nccc(C(=O)Nc2cnc(F)cc2OCC(F)(F)F)n1]

Prepared by Method A (heated at 110° C. for 0.5 h), obtained 4.6 mg, 83% yield: $^1H$ NMR (500 MHz, DMSO-$d_6$) δ 10.12 (br. s., 1H), 9.11 (br. s., 1H), 8.60 (d, J=4.6 Hz, 1H), 7.64 (br. s., 1H), 7.25 (s, 1H), 7.20 (d, J=4.6 Hz, 1H), 5.12 (q, J=8.7 Hz, 2H), 4.19 (dd, J=13.6, 6.6 Hz, 1H), 1.20 (d, J=6.7 Hz, 6H); LC/MS (ESI) m/e 374.1 $[(M+H)^+$, calcd $C_{15}H_{16}F_4N_5O_2$, 374.1]; LC/MS retention time (Method A): $t_R$=2.62 min.

Example 137

N-(4-(2,2,2-Trifluoroethoxy)pyridin-3-yl)-2-((2-(trifluoromethyl)benzyl)amino)pyrimidine-4-carboxamide

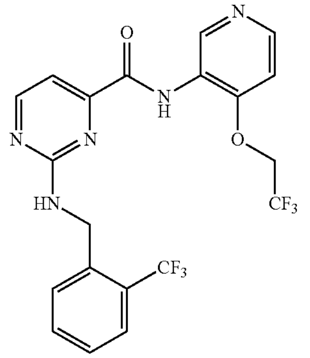 [SMILES: O=C(Nc1cnccc1OCC(F)(F)F)c1ccnc(NCc2ccccc2C(F)(F)F)n1]

Prepared by Method A (heated at 150° C. for 2 h), obtained 2 mg, 17% yield: $^1H$ NMR (500 MHz, DMSO-$d_6$) δ 10.04 (br. s., 1H), 9.36 (br. s., 1H), 8.67 (br. s., 1H), 8.38 (d, J=4.9 Hz, 1H), 8.22 (br. s., 1H), 7.75 (d, J=7.9 Hz, 1H), 7.69-7.61 (m, 1H), 7.58 (br. s., 1H), 7.49 (t, J=7.6 Hz, 1H), 7.32 (br. s., 2H), 5.04-4.87 (m, 2H), 4.81 (d, J=5.5 Hz, 2H); LC/MS (ESI) m/e 472.1 $[(M+H)^+$, calcd $C_{20}H_{16}F_6N_5O_2$, 472.1]; LC/MS retention time (Method A): $t_R$=2.80 min.

Example 138

2-((1-Phenylethyl)amino)-N-(4-(2,2,2-trifluoroethoxy)pyridin-3-yl)pyrimidine-4-carboxamide

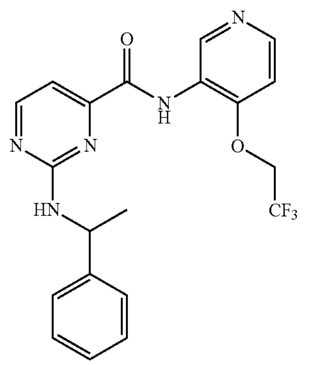 [SMILES: CC(Nc1nccc(C(=O)Nc2cnccc2OCC(F)(F)F)n1)c1ccccc1]

Prepared by Method A (heated at 150° C. for 1 h), obtained 6.9 mg, 68% yield: $^1H$ NMR (500 MHz, DMSO-$d_6$) δ 10.11 (br. s., 1H), 9.40 (br. s., 1H), 8.60 (d, J=4.6 Hz, 1H), 8.40 (d, J=5.5 Hz, 1H), 8.28 (br. s., 1H), 7.45 (d, J=7.6

Hz, 2H), 7.39 (d, J=5.5 Hz, 1H), 7.30 (t, J=7.6 Hz, 2H), 7.25-7.16 (m, 2H), 5.25 (t, J=7.5 Hz, 1H), 5.19-5.04 (m, 2H), 1.52 (d, J=7.0 Hz, 3H); LC/MS (ESI) m/e 418.1 $[(M+H)^+$, calcd $C_{20}H_{19}F_3N_5O_2$, 418.1]; LC/MS retention time (Method A): $t_R$=2.64 min.

Example 139

N-(4-(2,2,2-Trifluoroethoxy)pyridin-3-yl)-2-((3-(trifluoromethyl)benzyl)amino)pyrimidine-4-carboxamide

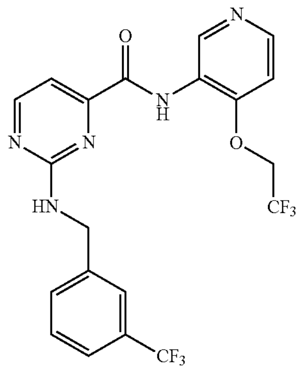 [SMILES: O=C(Nc1cnccc1OCC(F)(F)F)c1ccnc(NCc2cccc(C(F)(F)F)c2)n1]

Prepared by Method A (heated at 150° C. for 2 h), obtained 6.3 mg, 51% yield: $^1H$ NMR (500 MHz, DMSO-$d_6$) δ 10.11 (br. s., 1H), 9.40 (br. s., 1H), 8.60 (d, J=4.6 Hz, 1H), 8.40 (d, J=5.5 Hz, 1H), 8.28 (br. s., 1H), 7.45 (d, J=7.6 Hz, 2H), 7.39 (d, J=5.5 Hz, 1H), 7.30 (t, J=7.6 Hz, 2H), 7.25-7.16 (m, 2H), 5.25 (t, J=7.5 Hz, 1H), 5.19-5.04 (m, 2H), 1.52 (d, J=7.0 Hz, 3H); LC/MS (ESI) m/e 418.1 $[(M+H)^+$, calcd $C_{20}H_{19}F_3N_5O_2$, 418.1]; LC/MS retention time (Method A): $t_R$=2.64 min.

Example 140

2-((3-Fluorobenzyl)amino)-N-(4-(2,2,2-trifluoroethoxy)pyridin-3-yl)pyrimidine-4-carboxamide

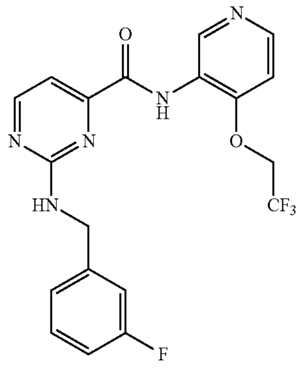 [SMILES: O=C(Nc1cnccc1OCC(F)(F)F)c1ccnc(NCc2cccc(F)c2)n1]

Prepared by Method A (heated at 110° C. for 1.5 h), obtained 8.2 mg, 66% yield: $^1H$ NMR (500 MHz, DMSO-$d_6$) δ 10.13 (br. s., 1H), 9.39 (br. s., 1H), 8.65 (d, J=4.6 Hz, 1H), 8.39 (d, J=5.8 Hz, 1H), 7.36 (t, J=7.0 Hz, 3H), 7.28 (d, J=4.9 Hz, 1H), 7.23-7.13 (m, 2H), 7.11-7.04 (m, 1H), 5.03 (q, J=8.3 Hz, 2H), 4.65 (d, J=6.1 Hz, 2H); LC/MS (ESI) m/e 422.1 $[(M+H)^+$, calcd $C_{19}H_{16}F_4N_5O_2$, 422.1]; LC/MS retention time (Method A): $t_R$=2.56 min.

Example 141

N-(4-(2,2,2-Trifluoroethoxy)pyridin-3-yl)-2-((2,2,2-trifluoroethyl)amino)pyrimidine-4-carboxamide

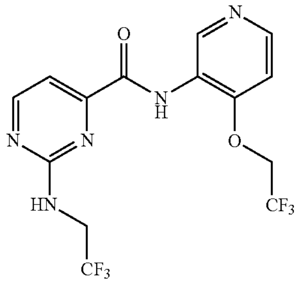 [SMILES: O=C(Nc1cnccc1OCC(F)(F)F)c1ccnc(NCC(F)(F)F)n1]

Prepared by Method A (heated at 100° C. for 1.5 h), obtained 3.3 mg, 20% yield: $^1H$ NMR (500 MHz, DMSO-$d_6$) δ 10.10 (br. s., 1H), 9.32 (br. s., 1H), 8.72 (d, J=4.9 Hz, 1H), 8.40 (d, J=5.5 Hz, 1H), 8.32 (br. s., 1H), 7.40 (d, J=4.9 Hz, 1H), 7.37 (d, J=5.5 Hz, 1H), 5.05 (q, J=8.7 Hz, 2H), 4.32-4.22 (m, 2H); LC/MS (ESI) m/e 396.1 $[(M+H)^+$, calcd $C_{14}H_{12}F_6N_5O_2$, 396.1]; LC/MS retention time (Method A): $t_R$=2.42 min.

Example 142

2-((1-Methylpiperidin-4-yl)amino)-N-(4-(2,2,2-trifluoroethoxy)pyridin-3-yl)pyrimidine-4-carboxamide

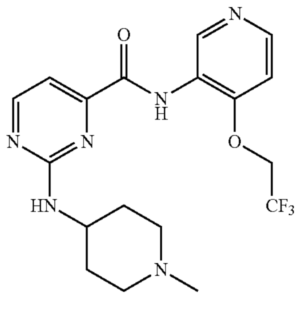 [SMILES: CN1CCC(Nc2nccc(C(=O)Nc3cnccc3OCC(F)(F)F)n2)CC1]

Prepared by Method A (heated at 150° C. for 1.5 h), obtained 9.9 mg, 76% yield: $^1H$ NMR (500 MHz, DMSO-$d_6$) δ 9.97 (s, 1H), 8.60 (d, J=4.6 Hz, 1H), 8.39 (d, J=5.8 Hz, 1H), 7.40 (d, J=5.5 Hz, 1H), 7.22 (d, J=4.9 Hz, 1H), 5.09 (q, J=8.4 Hz, 2H), 3.82 (br. s., 1H), 2.78-2.69 (m, 2H), 2.18 (s, 3H), 2.08-1.99 (m, 2H), 1.91-1.81 (m, 3H), 1.68-1.53 (m, 2H); LC/MS (ESI) m/e 411.1 $[(M+H)^+$, calcd $C_{18}H_{22}F_3N_6O_2$, 411.2]; LC/MS retention time (Method A): $t_R$=1.50 min.

Example 143

2-((1-(Adamantan-1-yl)ethyl)amino)-N-(4-(2,2,2-trifluoroethoxy)pyridin-3-yl)pyrimidine-4-carboxamide

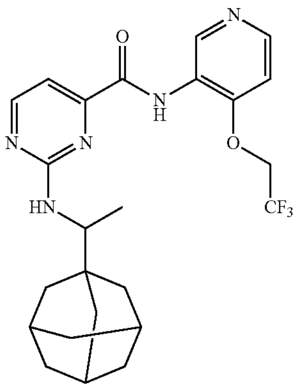 [SMILES: CC(Nc1nccc(C(=O)Nc2cnccc2OCC(F)(F)F)n1)C12CC3CC(CC(C3)C1)C2]

Prepared by Method A (heated at 150° C. for 1 h), obtained 12.0 mg, 74% yield: LC/MS (ESI) m/e 476.3 $[(M+H)^+$, calcd $C_{24}H_{29}F_3N_5O_2$, 476.2]; LC/MS retention time (Method A): $t_R$=3.52 min.

Example 144

2-((3,5-Bis(trifluoromethyl)benzyl)amino)-N-(4-(2,2,2-trifluoroethoxy)pyridin-3-yl)pyrimidine-4-carboxamide

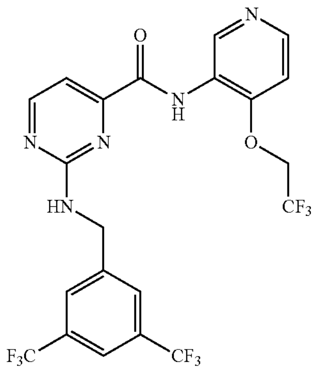 [SMILES: O=C(Nc1cnccc1OCC(F)(F)F)c1ccnc(NCc2cc(C(F)(F)F)cc(C(F)(F)F)c2)n1]

Prepared by Method A (heated at 150° C. for 2 h), obtained 7.1 mg, 49% yield: $^1$H NMR (500 MHz, DMSO-$d_6$) δ 10.11 (br. s., 1H), 9.32 (br. s., 1H), 8.67 (d, J=4.6 Hz, 1H), 8.40 (d, J=5.8 Hz, 2H), 8.06 (s, 2H), 8.00 (s, 1H), 7.35 (d, J=5.5 Hz, 1H), 7.31 (d, J=4.6 Hz, 1H), 5.07-4.97 (m, 2H), 4.82 (d, J=6.1 Hz, 2H); LC/MS (ESI) m/e 540.1 $[(M+H)^+$, calcd $C_{21}H_{15}F_9N_5O_2$, 540.1]; LC/MS retention time (Method A): $t_R$=3.03 min.

Example 145

2-((1,2,2,6,6-Pentamethylpiperidin-4-yl)amino)-N-(4-(2,2,2-trifluoroethoxy)pyridin-3-yl)pyrimidine-4-carboxamide

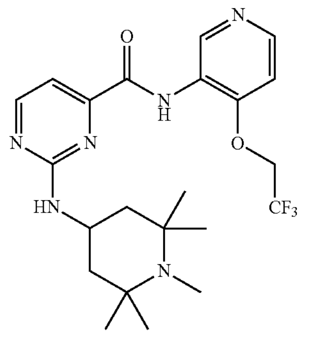 [SMILES: CN1C(C)(C)CC(Nc2nccc(C(=O)Nc3cnccc3OCC(F)(F)F)n2)CC1(C)C]

Prepared by Method A (heated at 150° C. for 2 h), obtained 31.9 mg, 85% yield: $^1$H NMR (500 MHz, DMSO-$d_6$) δ 10.05-9.67 (m, 1H), 9.08 (br. s., 1H), 8.61 (br. s., 1H), 8.41 (d, J=5.5 Hz, 1H), 7.41 (d, J=5.8 Hz, 1H), 7.19 (d, J=4.6 Hz, 1H), 5.12-4.96 (m, 2H), 4.18 (br. s., 1H), 2.20 (s, 3H), 1.89 (s, 1H), 1.80 (d, J=9.5 Hz, 2H), 1.39 (br. s., 2H), 1.13-1.02 (m, 12H); LC/MS (ESI) m/e 467.3 $[(M+H)^+$, calcd $C_{22}H_{30}F_3N_6O_2$, 467.2]; LC/MS retention time (Method A): $t_R$=1.69 min.

Example 146

2-((1-(3,5-Difluorophenyl)ethyl)amino)-N-(4-(2,2,2-trifluoroethoxy)pyridin-3-yl)pyrimidine-4-carboxamide

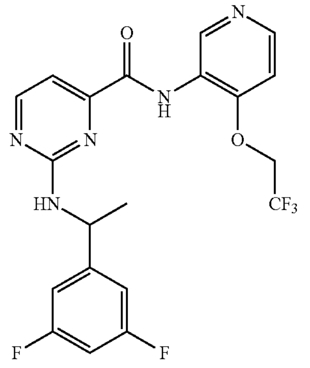 [SMILES: CC(Nc1nccc(C(=O)Nc2cnccc2OCC(F)(F)F)n1)c1cc(F)cc(F)c1]

Prepared by Method A (heated at 150° C. for 1 h), obtained 7.5 mg, 66% yield: $^1$H NMR (500 MHz, DMSO-$d_6$) δ 10.05 (br. s., 1H), 9.31 (br. s., 1H), 8.63 (d, J=4.3 Hz, 1H), 8.41 (d, J=5.8 Hz, 1H), 8.31 (br. s., 1H), 7.39 (d, J=5.5 Hz, 1H), 7.25 (d, J=4.6 Hz, 1H), 7.14 (d, J=6.7 Hz, 2H), 7.11-7.02 (m, 1H), 5.29 (br. s., 1H), 5.19-4.99 (m, 2H), 1.51 (d, J=7.0 Hz, 3H); LC/MS (ESI) m/e 454.1 $[(M+H)^+$, calcd $C_{20}H_{17}F_5N_5O_2$, 454.1]; LC/MS retention time (Method A): $t_R$=2.73 min.

Example 147

2-((Cyclopropylmethyl)amino)-N-(4-phenylpyridin-3-yl)pyrimidine-4-carboxamide

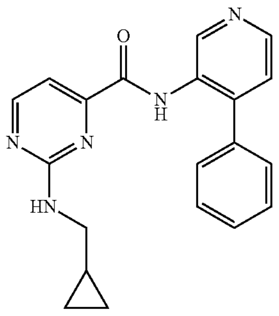 [SMILES: O=C(Nc1cnccc1-c1ccccc1)c1ccnc(NCC2CC2)n1]

Prepared by Method A (heated at 150° C. for 20 min), obtained 4.0 mg, 59% yield: LC/MS (ESI) m/e 346.2 $[(M+H)^+$, calcd $C_{20}H_{20}N_5O_1$, 346.2]; LC/MS retention time (Method A): $t_R$=2.59 min.

Example 148

2-(Cyclopentylamino)-N-(4-(4-fluorophenyl)pyridin-3-yl)pyrimidine-4-carboxamide

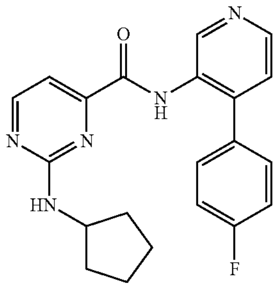 [SMILES: O=C(Nc1cnccc1-c1ccc(F)cc1)c1ccnc(NC2CCCC2)n1]

Prepared by Method A (heated at 150° C. for 0.5 h), obtained 6.2 mg, 94% yield: LC/MS (ESI) m/e 378.1 $[(M+H)^+$, calcd $C_{21}H_{21}F_1N_5O_1$, 378.1]; LC/MS retention time (Method A): $t_R$=2.80 min.

Example 149

N-(4-(2,4-Difluorophenyl)pyridin-3-yl)-2-(naphthalen-2-ylamino)pyrimidine-4-carboxamide

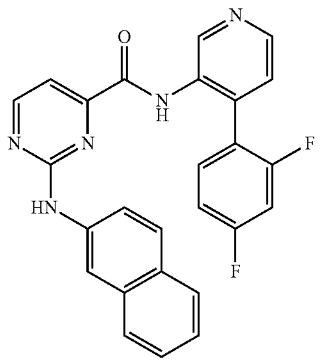 [SMILES: O=C(Nc1cnccc1-c1ccc(F)cc1F)c1ccnc(Nc2ccc3ccccc3c2)n1]

Prepared by Method A (heated at 150° C. for 40 min), obtained 6.3 mg, 36% yield: $^1$H NMR (500 MHz, DMSO-$d_6$) δ 10.09 (s, 1H), 9.99 (br. s., 1H), 9.08 (s, 1H), 8.80 (d, J=4.9 Hz, 1H), 8.57 (d, J=4.9 Hz, 1H), 8.19 (s, 1H), 7.85 (d, J=8.2 Hz, 1H), 7.79 (d, J=8.9 Hz, 1H), 7.72 (d, J=8.2 Hz, 1H), 7.66 (dd, J=8.9, 1.8 Hz, 1H), 7.53-7.44 (m, 3H), 7.43-7.39 (m, 1H), 7.37 (d, J=4.9 Hz, 1H), 7.07 (t, J=8.9 Hz, 1H), 6.89-6.82 (m, 1H); LC/MS (ESI) m/e 454.2 $[(M+H)^+$, calcd $C_{26}H_{18}F_2N_5O_1$, 454.1]; LC/MS retention time (Method A): $t_R$=3.02 min.

Example 150

2-(Cyclohexylamino)-N-(4-(4-fluorophenyl)pyridin-3-yl)pyrimidine-4-carboxamide

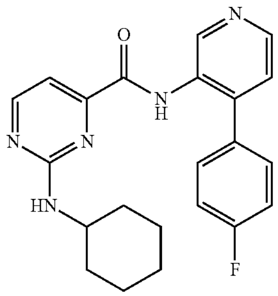 [SMILES: O=C(Nc1cnccc1-c1ccc(F)cc1)c1ccnc(NC2CCCCC2)n1]

Prepared by Method A (heated at 150° C. for 0.5 h), obtained 10.5 mg, 90% yield: LC/MS (ESI) m/e 392.2 $[(M+H)^+$, calcd $C_{22}H_{23}F_1N_5O_1$, 392.2]; LC/MS retention time (Method A): $t_R$=2.95 min.

Example 151

N-(4-(2,4-Difluorophenyl)pyridin-3-yl)-2-(phenylamino)pyrimidine-4-carboxamide

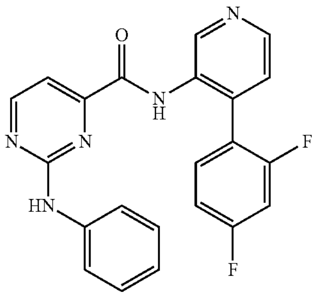 [SMILES: O=C(Nc1cnccc1-c1ccc(F)cc1F)c1ccnc(Nc2ccccc2)n1]

Prepared by Method A (heated at 150° C. for 40 min), obtained 6.3 mg, 36% yield: $^1$H NMR (500 MHz, DMSO-$d_6$) δ 9.87-9.82 (m, 2H), 9.06 (s, 1H), 8.74 (d, J=4.9 Hz, 1H), 8.57 (d, J=4.9 Hz, 1H), 7.61-7.52 (m, 3H), 7.49 (d, J=4.9 Hz, 1H), 7.34 (d, J=4.9 Hz, 1H), 7.32-7.26 (m, 1H), 7.23 (t, J=7.8 Hz, 2H), 7.12 (m, 1H), 7.01 (t, J=7.3 Hz, 1H); LC/MS (ESI) m/e 404.2 $[(M+H)^+$, calcd $C_{22}H_{16}F_2N_5O_1$, 404.1]; LC/MS retention time (Method A): $t_R$=2.69 min.

Example 152

N-(4-(4-Fluorophenyl)pyridin-3-yl)-2-(isopropylamino)pyrimidine-4-carboxamide

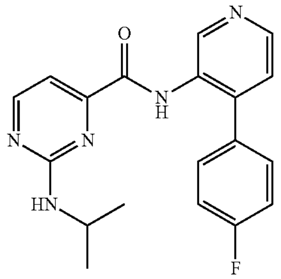 [SMILES: CC(C)Nc1nccc(C(=O)Nc2cnccc2-c2ccc(F)cc2)n1]

Prepared by Method A (heated at 110° C. for 1.5 h), obtained 3.0 mg, 23% yield: LC/MS (ESI) m/e 352.1 $[(M+H)^+$, calcd $C_{19}H_{19}F_1N_5O_1$, 352.1]; LC/MS retention time (Method A): $t_R$=2.55 min.

Example 153

2-(Cyclopropylamino)-N-(4-(4-fluorophenyl)pyridin-3-yl)pyrimidine-4-carboxamide

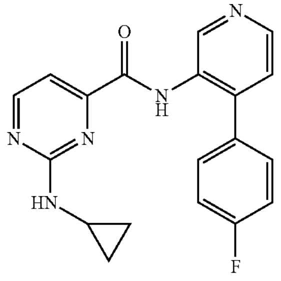 [SMILES: O=C(Nc1cnccc1-c1ccc(F)cc1)c1ccnc(NC2CC2)n1]

Prepared by Method A (heated at 150° C. for 0.5 h), obtained 9.4 mg, 99% yield: LC/MS (ESI) m/e 350.1 $[(M+H)^+$, calcd $C_{19}H_{17}F_1N_5O_1$, 350.1]; LC/MS retention time (Method A): $t_R$=2.43 min.

Example 154

N-(4-(2-Fluorophenyl)pyridin-3-yl)-2-(naphthalen-2-ylamino)pyrimidine-4-carboxamide

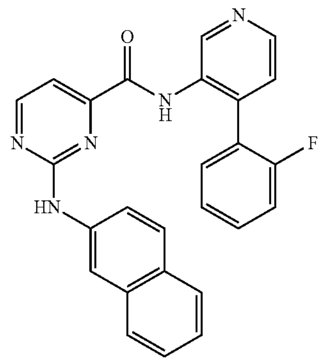 [SMILES: O=C(Nc1cnccc1-c1ccccc1F)c1ccnc(Nc2ccc3ccccc3c2)n1]

Prepared by Method A (heated at 150° C. for 1 h), obtained 4.6 mg, 26% yield: $^1H$ NMR (500 MHz, DMSO-$d_6$) δ 10.08 (s, 1H), 9.96 (s, 1H), 9.06 (s, 1H), 8.79 (d, J=4.9 Hz, 1H), 8.58 (d, J=4.9 Hz, 1H), 8.19 (s, 1H), 7.85 (d, J=8.2 Hz, 1H), 7.79 (d, J=8.9 Hz, 1H), 7.74 (d, J=8.2 Hz, 1H), 7.66 (dd, J=8.9, 1.8 Hz, 1H), 7.52-7.44 (m, 3H), 7.43-7.37 (m, 1H), 7.36 (d, J=4.9 Hz, 1H), 7.19 (d, J=6.4 Hz, 1H), 7.11-6.99 (m, 2H); LC/MS (ESI) m/e 436.2 $[(M+H)^+$, calcd $C_{26}H_{19}F_1N_5O_1$, 436.2]; LC/MS retention time (Method A): $t_R$=2.97 min.

Example 155

2-((2,4-Difluorophenyl)amino)-N-(4-(2-fluorophenyl)pyridin-3-yl)pyrimidine-4-carboxamide

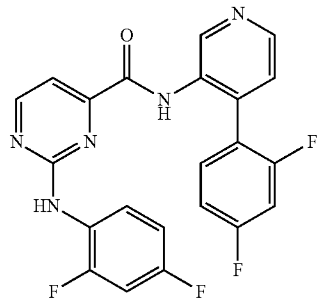 [SMILES: O=C(Nc1cnccc1-c1ccc(F)cc1F)c1ccnc(Nc2ccc(F)cc2F)n1]

Prepared by Method A (heated at 150° C. for 40 min), obtained 2.3 mg, 19% yield: $^1H$ NMR (500 MHz, DMSO-$d_6$) δ 9.87 (br. s., 1H), 9.45 (br. s., 1H), 9.08 (s, 1H), 8.77 (d, J=5.2 Hz, 1H), 8.55 (br. s., 1H), 7.63 (br. s., 1H), 7.55-7.49 (m, 1H), 7.47 (d, J=4.9 Hz, 1H), 7.41 (d, J=4.9 Hz, 1H), 7.32-7.23 (m, 2H), 7.14 (t, J=8.5 Hz, 1H), 6.98 (t, J=8.4 Hz, 1H); LC/MS (ESI) m/e 440.2 $[(M+H)^+$, calcd $C_{22}H_{14}F_4N_5O_1$, 440.1]; LC/MS retention time (Method A): $t_R$=2.83 min.

Example 156

2-(Cyclohexylamino)-N-(4-phenylpyridin-3-yl)pyrimidine-4-carboxamide

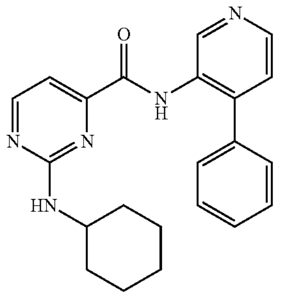

Prepared by Method A (heated at 150° C. for 40 min), obtained 12.5 mg, 85% yield: $^1H$ NMR (500 MHz, DMSO-$d_6$) δ 10.00 (br. s., 1H), 9.31 (br. s., 1H), 8.53 (t, J=4.3 Hz, 2H), 7.63-7.40 (m, 8H), 7.13 (br. s., 1H), 1.77-1.50 (m, 5H), 1.13 (br. s., 5H); LC/MS (ESI) m/e 374.2 $[(M+H)^+$, calcd $C_{22}H_{24}N_5O_1$, 374.2]; LC/MS retention time (Method A): $t_R$=2.96 min.

Example 157

2-((3,3-Dimethylbutan-2-yl)amino)-N-(4-(4-fluorophenyl)pyridin-3-yl)pyrimidine-4-carboxamide

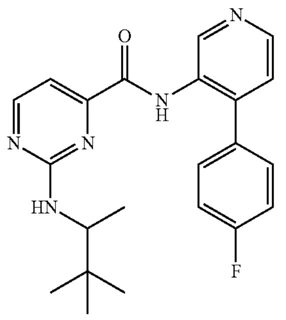 [SMILES: CC(Nc1nccc(C(=O)Nc2cnccc2-c2ccc(F)cc2)n1)C(C)(C)C]

Prepared by Method A (heated at 150° C. for 1 h), obtained 10.8 mg, 79% yield: $^1$H NMR (500 MHz, DMSO-$d_6$) δ 9.97 (br. s., 1H), 9.37 (br. s., 1H), 8.52 (dd, J=7.2, 5.0 Hz, 2H), 7.66 (br. s., 2H), 7.44 (d, J=4.6 Hz, 1H), 7.36 (t, J=8.9 Hz, 3H), 7.12 (br. s., 1H), 3.55 (br. s., 1H), 1.00 (br. s., 3H), 0.75 (br. s., 9H); LC/MS (ESI) m/e 394.2 [$(M+H)^+$, calcd $C_{22}H_{25}N_5O_1$, 394.2]; LC/MS retention time (Method A): $t_R$=3.01 min.

Example 158

N-(4-(2,4-Difluorophenyl)pyridin-3-yl)-2-(methylamino)pyrimidine-4-carboxamide

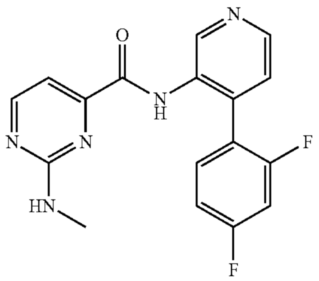

Prepared by Method A (heated at 80° C. for 1.5 h), obtained 2.1 mg, 19% yield: LC/MS (ESI) m/e 342.1 [$(M+H)^+$, calcd $C_{17}H_{14}F_2N_5O_1$, 342.1]; LC/MS retention time (Method A): $t_R$=2.19 min.

Example 159

2-((1-(2,5-Difluorophenyl)-1H-pyrazol-4-yl)amino)-N-(4-phenylpyridin-3-yl)pyrimidine-4-carboxamide

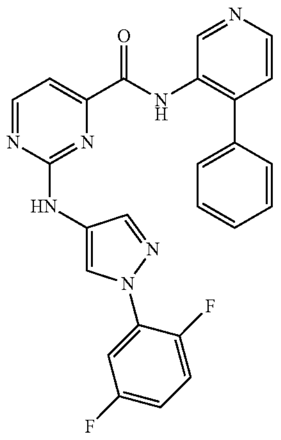 [SMILES: O=C(Nc1cnccc1-c1ccccc1)c1ccnc(Nc2cnn(-c3cc(F)ccc3F)c2)n1]

Prepared by Method A (heated at 150° C. for 1 h), obtained 0.8 mg, 5% yield: LC/MS (ESI) m/e 470.2 [$(M+H)^+$, calcd $C_{25}H_{18}F_2N_7O_1$, 470.1]; LC/MS retention time (Method A): $t_R$=2.78 min.

Example 160

2-((4-(tert-Butyl)cyclohexyl)amino)-N-(4-(2-fluorophenyl)pyridin-3-yl)pyrimidine-4-carboxamide

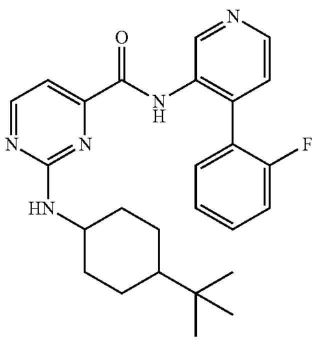 [SMILES: CC(C)(C)C1CCC(Nc2nccc(C(=O)Nc3cnccc3-c3ccccc3F)n2)CC1]

Prepared by Method A (heated at 110° C. for 2 h), obtained 3.2 mg, 16% yield: $^1$H NMR (500 MHz, DMSO-$d_6$) δ 9.83 (br. s., 1H), 9.54 (br. s., 1H), 8.56 (d, J=4.6 Hz, 1H), 8.52 (d, J=4.6 Hz, 1H), 7.69-7.53 (m, 3H), 7.50-7.37 (m, 3H), 7.16 (br. s., 1H), 1.66 (br. s., 2H), 1.44 (br. s., 2H), 1.37-1.17 (m, 4H), 0.99 (br. s., 1H), 0.92-0.77 (m, 9H); LC/MS (ESI) m/e 448.3 [$(M+H)^+$, calcd $C_{26}H_{31}F_1N_5O_1$, 448.2]; LC/MS retention time (Method A): $t_R$=3.64 min.

Example 161

N-(4-(4-Fluorophenyl)pyridin-3-yl)-2-(pyridin-2-ylamino)pyrimidine-4-carboxamide

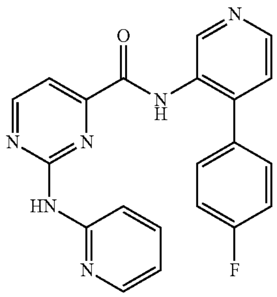 [SMILES: O=C(Nc1cnccc1-c1ccc(F)cc1)c1ccnc(Nc2ccccn2)n1]

Prepared by Method A (heated at 150° C. for 0.5 h), obtained 1.5 mg, 15% yield: LC/MS (ESI) m/e 387.1 $[(M+H)^+$, calcd $C_{21}H_{16}F_1N_6O_1$, 387.1]; LC/MS retention time (Method A): $t_R$=2.38 min.

Example 162

N-(4-(2-Fluorophenyl)pyridin-3-yl)-2-((1-methylpiperidin-4-yl)amino)pyrimidine-4-carboxamide

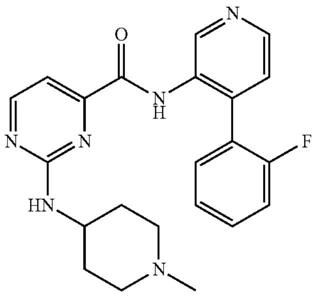 [SMILES: CN1CCC(Nc2nccc(C(=O)Nc3cnccc3-c3ccccc3F)n2)CC1]

Prepared by Method A (heated at 110° C. for 3 h), obtained 7.3 mg, 46% yield: LC/MS (ESI) m/e 407.2 $[(M+H)^+$, calcd $C_{22}H_{24}F_1N_6O_1$, 407.2]; LC/MS retention time (Method A): $t_R$=1.60 min.

Example 163

N-(4-Phenylpyridin-3-yl)-2-(pyridin-2-ylamino)pyrimidine-4-carboxamide

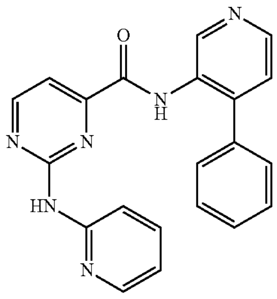 [SMILES: O=C(Nc1cnccc1-c1ccccc1)c1ccnc(Nc2ccccn2)n1]

Prepared by Method A (heated at 150° C. for 20 min), obtained 6.7 mg, 100% yield: LC/MS (ESI) m/e 369.1 $[(M+H)^+$, calcd $C_{21}H_{17}N_6O_1$, 369.1]; LC/MS retention time (Method A): $t_R$=2.35 min.

Example 164

N-(4-(2,4-Difluorophenyl)pyridin-3-yl)-2-(pyridazin-3-ylamino)pyrimidine-4-carboxamide

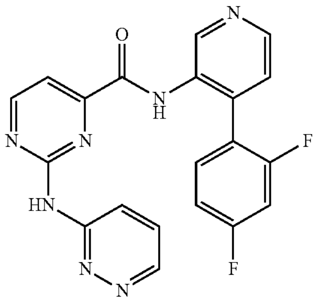 [SMILES: O=C(Nc1cnccc1-c1ccc(F)cc1F)c1ccnc(Nc2cccnn2)n1]

Prepared by Method A (heated at 150° C. for 40 min), obtained 4.6 mg, 62% yield: LC/MS (ESI) m/e 406.2 $[(M+H)^+$, calcd $C_{20}H_{14}F_2N_7O_1$, 406.1]; LC/MS retention time (Method A): $t_R$=1.61 min.

Example 165

2-((1-Methylpiperidin-4-yl)amino)-N-(4-phenylpyridin-3-yl)pyrimidine-4-carboxamide

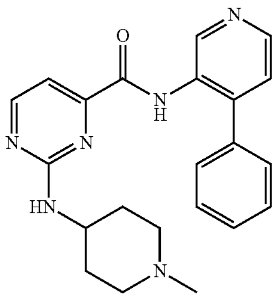 [SMILES: CN1CCC(Nc2nccc(C(=O)Nc3cnccc3-c3ccccc3)n2)CC1]

Prepared by Method A (heated at 150° C. for 1 h), obtained 4.8 mg, 45% yield: LC/MS (ESI) m/e 389.2 $[(M+H)^+$, calcd $C_{22}H_{25}N_6O_1$, 389.2]; LC/MS retention time (Method A): $t_R$=1.62 min.

Example 166

N-(6-Chloro-4-(2-propyl-1,3-dioxolan-2-yl)pyridin-3-yl)-2-(cyclopropylamino)pyrimidine-4-carboxamide

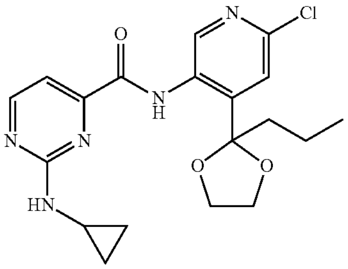 [SMILES: CCCC1(c2cc(Cl)ncc2NC(=O)c2ccnc(NC3CC3)n2)OCCO1]

Prepared by Method A (heated at 100° C. for 2 h), obtained 5.3 mg, 59% yield: $^1$H NMR (500 MHz, DMSO-$d_6$) δ 11.34 (br. s., 1H), 9.42 (br. s., 1H), 8.59 (br. s., 1H), 7.86 (br. s., 1H), 7.43 (s, 1H), 7.28 (d, J=4.3 Hz, 1H), 4.05 (br. s., 2H), 3.84 (br. s., 2H), 2.97 (br. s., 1H), 1.91-1.82 (m, 2H), 1.32-1.20 (m, J=7.6 Hz, 2H), 0.84-0.73 (m, 5H), 0.56 (br. s., 2H); LC/MS (ESI) m/e 404.5 [$(M+H)^+$, calcd $C_{19}H_{23}Cl_1N_5O_3$, 404.1]; LC/MS retention time (Method A): $t_R$=3.00 min.

Example 167

N-(6-Chloro-4-(2-propyl-1,3-dioxolan-2-yl)pyridin-3-yl)-2-((tetrahydro-2H-pyran-4-yl)amino)pyrimidine-4-carboxamide

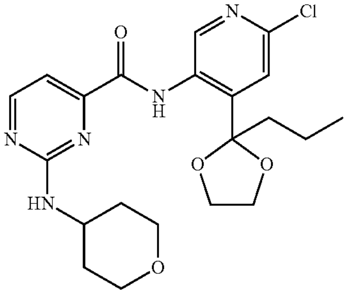 [SMILES: CCCC1(c2cc(Cl)ncc2NC(=O)c2ccnc(NC3CCOCC3)n2)OCCO1]

Prepared by Method A (heated at 100° C. for 2 h), obtained 2.3 mg, 10% yield: LC/MS (ESI) m/e 448.2 [$(M+H)^+$, calcd $C_{21}H_{27}Cl_1N_5O_4$, 448.2]; LC/MS retention time (Method A): $t_R$=2.67 min.

Example 168

2-Morpholino-N-(4-(2,2,2-trifluoroethoxy)pyridin-3-yl)pyrimidine-4-carboxamide

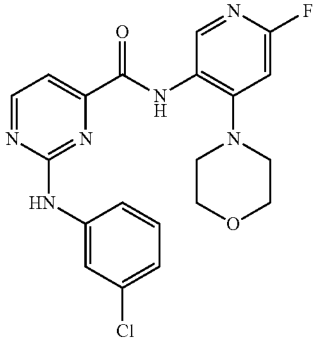 [SMILES: O=C(Nc1cnc(F)cc1N1CCOCC1)c1ccnc(Nc2cccc(Cl)c2)n1]

Prepared by Method A (heated at 140° C. overnight), obtained 7.6 mg, 50% yield: $^1$H NMR (500 MHz, DMSO-d6) δ 10.17 (s, 1H), 9.84 (s, 1H), 8.85 (d, J=4.9 Hz, 1H), 8.66 (s, 1H), 7.89 (t, J=2.2 Hz, 1H), 7.68 (dd, J=8.2, 2.0 Hz, 1H), 7.51 (d, J=4.8 Hz, 1H), 7.39 (t, J=8.1 Hz, 1H), 7.10 (dd, J=7.9, 2.0 Hz, 1H), 6.92 (s, 1H), 3.58 (t, J=4.5 Hz, 4H), 3.05 (t, J=4.5 Hz, 4H); LC/MS (ESI) m/e 429.1 [$(M+H)^+$, calcd $C_{20}H_{19}Cl_1F_1N_6O_2$, 429.1]; LC/MS retention time (Method A): $t_R$=2.67 min.

Example 169

2-((4-Chloro-3-fluorophenyl)amino)-N-(6-fluoro-4-morpholinopyridin-3-yl)pyrimidine-4-carboxamide

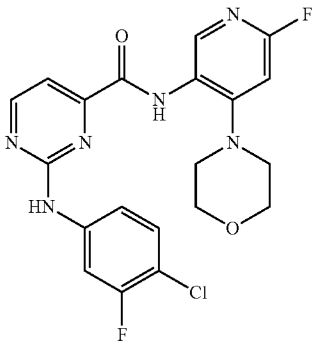 [SMILES: O=C(Nc1cnc(F)cc1N1CCOCC1)c1ccnc(Nc2ccc(Cl)c(F)c2)n1]

Prepared by Method A (heated at 140° C. overnight), obtained 3.2 mg, 19% yield: $^1$H NMR (500 MHz, DMSO-d6) δ 10.31 (s, 1H), 9.82 (s, 1H), 8.86 (d, J=4.8 Hz, 1H), 8.64 (s, 1H), 7.93 (dd, J=12.1, 2.3 Hz, 1H), 7.61-7.48 (m, 3H), 6.91 (s, 1H), 3.58 (t, J=4.5 Hz, 4H), 3.06 (t, J=4.6 Hz, 4H); LC/MS (ESI) m/e 447.2 [$(M+H)^+$, calcd $C_{20}H_{18}Cl_1F_2N_6O_2$, 447.1]; LC/MS retention time (Method A): $t_R$=2.75 min.

Example 170

2-((4-Chloro-3-fluorophenyl)amino)-N-(6-fluoro-4-morpholinopyridin-3-yl)pyrimidine-4-carboxamide

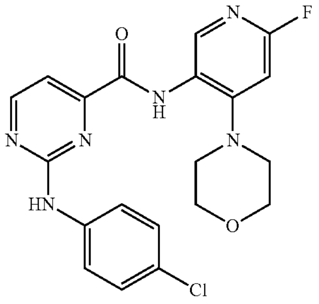 [SMILES: O=C(Nc1cnc(F)cc1N1CCOCC1)c1ccnc(Nc2ccc(Cl)cc2)n1]

Prepared by Method A (heated at 140° C. overnight), obtained 6.4 mg, 39% yield: $^1$H NMR (500 MHz, DMSO-d6) δ 10.10 (s, 1H), 9.77 (s, 1H), 8.82 (d, J=4.8 Hz, 1H), 8.69 (s, 1H), 7.80-7.70 (m, 2H), 7.49 (d, J=4.8 Hz, 1H), 7.47-7.36 (m, 2H), 6.91 (s, 1H), 3.55 (t, J=4.3 Hz, 4H), 3.02 (t, J=4.5 Hz, 4H); LC/MS (ESI) m/e 429.2 [$(M+H)^+$, calcd $C_{20}H_{19}Cl_1F_1N_6O_2$, 429.1]; LC/MS retention time (Method A): $t_R$=2.75 min.

Example 171

2-((4-Chloro-2-fluorophenyl)amino)-N-(6-fluoro-4-morpholinopyridin-3-yl)pyrimidine-4-carboxamide

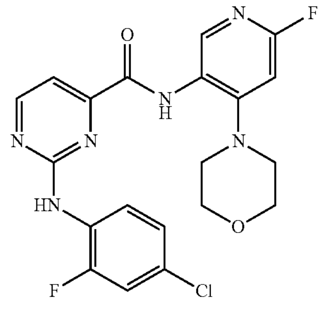 [SMILES: O=C(Nc1cnc(F)cc1N1CCOCC1)c1ccnc(Nc2ccc(Cl)cc2F)n1]

Prepared by Method A (heated at 140° C. overnight), obtained 2.3 mg, 13% yield: $^1$H NMR (500 MHz, DMSO-d6) δ 9.67 (s, 1H), 9.65 (s, 1H), 8.78 (d, J=4.8 Hz, 1H), 8.75 (s, 1H), 7.73 (t, J=8.6 Hz, 1H), 7.57 (dd, J=10.6, 2.4 Hz, 1H), 7.51 (d, J=4.9 Hz, 1H), 7.34 (dd, J=8.8, 2.3 Hz, 1H), 6.89 (s, 1H), 3.52 (t, J=4.4 Hz, 4H), 2.98 (t, J=4.5 Hz, 4H); LC/MS (ESI) m/e 447.0 [(M+H)$^+$, calcd $C_{20}H_{18}Cl_1F_2N_6O_2$, 447.1]; LC/MS retention time (Method A): $t_R$=2.72 min.

Example 172

N-(6-Fluoro-4-morpholinopyridin-3-yl)-2-((3-(trifluoromethoxy)phenyl)amino)pyrimidine-4-carboxamide

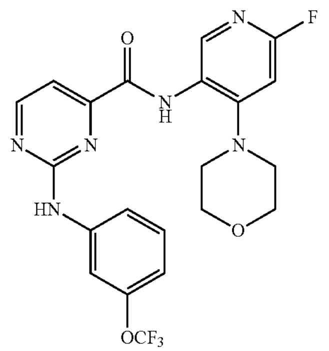 [SMILES: O=C(Nc1cnc(F)cc1N1CCOCC1)c1ccnc(Nc2cccc(OC(F)(F)F)c2)n1]

Prepared by Method A (heated at 140° C. overnight), obtained 4.7 mg, 28% yield: $^1$H NMR (500 MHz, DMSO-d6) δ 10.24 (s, 1H), 9.81 (s, 1H), 8.86 (d, J=4.8 Hz, 1H), 8.64 (s, 1H), 7.80 (s, 1H), 7.75 (dd, J=8.3, 1.9 Hz, 1H), 7.53 (d, J=4.8 Hz, 1H), 7.49 (t, J=8.2 Hz, 1H), 7.06-7.01 (m, 1H), 6.90 (s, 1H), 3.57 (t, J=4.6 Hz, 4H), 3.03 (t, J=4.6 Hz, 4H); LC/MS (ESI) m/e 479.4 [(M+H)$^+$, calcd $C_{21}H_{19}F_4N_6O_3$, 479.1]; LC/MS retention time (Method A): $t_R$=2.93 min.

Example 173

N-(6-Fluoro-4-morpholinopyridin-3-yl)-2-((3-(trifluoromethoxy)phenyl)amino)pyrimidine-4-carboxamide

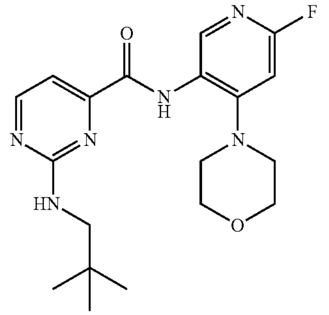 [SMILES: CC(C)(C)CNc1nccc(C(=O)Nc2cnc(F)cc2N2CCOCC2)n1]

Prepared by Method A (heated at 140° C. overnight), obtained 7.8 mg, 67% yield: $^1$H NMR (500 MHz, DMSO-d6) δ 9.94 (s, 1H), 8.68 (s, 1H), 8.59 (d, J=4.8 Hz, 1H), 7.56 (s, 1H), 7.21 (d, J=4.8 Hz, 1H), 6.93 (s, 1H), 3.80 (s, 4H), 3.09 (t, J=4.4 Hz, 4H), 0.97 (s, 9H) (two protons next to t-Bu were likely buried in the solvent peak at 3.33); LC/MS (ESI) m/e 389.5 [(M+H)$^+$, calcd $C_{19}H_{26}F_1N_6O_2$, 389.2]; LC/MS retention time (Method A): $t_R$=2.78 min.

Example 174

2-((4-Cyanophenyl)amino)-N-(6-fluoro-4-morpholinopyridin-3-yl)pyrimidine-4-carboxamide

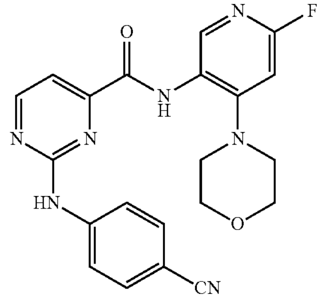 [SMILES: N#Cc1ccc(Nc2nccc(C(=O)Nc3cnc(F)cc3N3CCOCC3)n2)cc1]

Prepared by Method A (heated at 110° C. for 18 h), obtained 3.6 mg, 24% yield: $^1$H NMR (500 MHz, DMSO-d6) δ 10.52 (s, 1H), 9.83 (s, 1H), 8.90 (d, J=4.8 Hz, 1H), 8.64 (s, 1H), 8.00-7.91 (m, 2H), 7.86-7.78 (m, 2H), 7.59 (d, J=4.9 Hz, 1H), 6.92 (s, 1H), 3.57 (t, J=4.6 Hz, 4H), 3.06 (t, J=4.5 Hz, 4H); LC/MS (ESI) m/e 420.2 [(M+H)$^+$, calcd $C_{21}H_{19}F_1N_7O_2$, 420.2]; LC/MS retention time (Method A): $t_R$=2.47 min.

Example 175

N-(6-Fluoro-4-morpholinopyridin-3-yl)-2-(oxetan-3-ylamino)pyrimidine-4-carboxamide

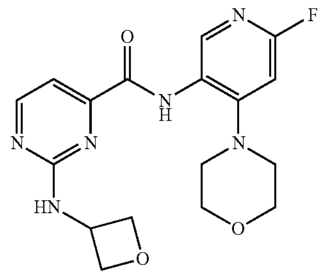 [SMILES: O=C(Nc1cnc(F)cc1N1CCOCC1)c1ccnc(NC2COC2)n1]

Prepared by Method A (heated at 110° C. overnight), obtained 2.8 mg, 32% yield: $^1$H NMR (500 MHz, DMSO-d6) δ 9.95 (s, 1H), 8.64 (d, J=4.8 Hz, 1H), 8.45 (s, 1H), 7.28 (d, J=4.8 Hz, 1H), 6.93 (s, 1H), 5.30 (s, 1H), 4.85 (t, J=6.8 Hz, 2H), 4.62 (t, J=6.4 Hz, 2H), 3.79 (s, 4H), 3.11 (t, J=4.3 Hz, 4H) (one NH was missing); LC/MS (ESI) m/e 375.1 $[(M+H)^+$, calcd $C_{17}H_{20}F_1N_6O_3$, 375.2]; LC/MS retention time (Method A): $t_R$=1.90 min.

Example 176

2-((4-Cyanophenyl)amino)-N-(4-(4,4-difluoropiperidin-1-yl)-6-fluoropyridin-3-yl)pyrimidine-4-carboxamide

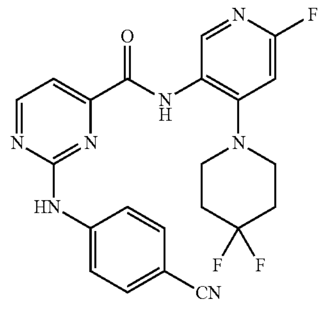 [SMILES: N#Cc1ccc(Nc2nccc(C(=O)Nc3cnc(F)cc3N3CCC(F)(F)CC3)n2)cc1]

Prepared by Method A (heated at 110° C. for 18 h), obtained 2.9 mg, 19% yield: $^1$H NMR (500 MHz, DMSO-d6) δ 10.56 (s, 1H), 9.85 (s, 1H), 8.91 (d, J=4.8 Hz, 1H), 8.68 (s, 1H), 7.93 (d, J=8.5 Hz, 2H), 7.81 (d, J=8.6 Hz, 2H), 7.61 (d, J=4.8 Hz, 1H), 6.99 (s, 1H), 3.18 (t, J=5.6 Hz, 4H), 1.97 (tt, J=12.9, 5.2 Hz, 4H); LC/MS (ESI) m/e 454.2 $[(M+H)^+$, calcd $C_{22}H_{19}F_3N_7O_1$, 454.2]; LC/MS retention time (Method A): $t_R$=2.82 min.

Example 177

N-(4-(4,4-Difluoropiperidin-1-yl)-6-fluoropyridin-3-yl)-2-(phenylamino)pyrimidine-4-carboxamide

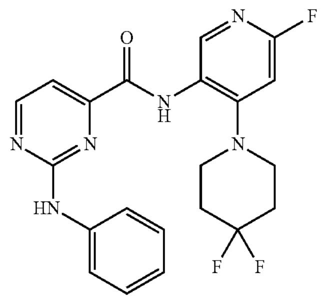 [SMILES: O=C(Nc1cnc(F)cc1N1CCC(F)(F)CC1)c1ccnc(Nc2ccccc2)n1]

Prepared by Method A (heated at 150° C. for 1 h), obtained 2.3 mg, 35% yield: $^1$H NMR (500 MHz, DMSO-d6) δ 9.97 (s, 1H), 9.83 (s, 1H), 8.82 (d, J=4.7 Hz, 1H), 8.72 (s, 1H), 7.76-7.63 (m, 2H), 7.47 (d, J=4.8 Hz, 1H), 7.41-7.30 (m, 2H), 7.05 (dd, J=7.9, 6.7 Hz, 1H), 6.99 (s, 1H), 3.14 (t, J=5.6 Hz, 4H), 1.95 (d, J=6.5 Hz, 4H); LC/MS (ESI) m/e 429.2 $[(M+H)^+$, calcd $C_{21}H_{20}F_3N_6O_1$, 429.2]; LC/MS retention time (Method A): $t_R$=2.87 min.

Example 178

2-((4-Chlorophenyl)amino)-N-(4-(4,4-difluoropiperidin-1-yl)-6-fluoropyridin-3-yl)pyrimidine-4-carboxamide

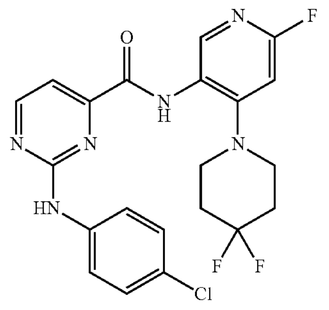

Prepared by Method A (heated at 140° C. for 4 h), obtained 1.3 mg, 20% yield: 1H NMR (500 MHz, DMSO-d6) δ 10.13 (s, 1H), 9.79 (s, 1H), 8.83 (d, J=4.8 Hz, 1H), 8.71 (s, 1H), 7.80-7.66 (m, 2H), 7.51 (d, J=4.8 Hz, 1H), 7.45-7.34 (m, 2H), 6.98 (s, 1H), 3.14 (t, J=5.6 Hz, 4H), 1.94 (d, J=8.5 Hz, 4H); LC/MS (ESI) m/e 463.2 $[(M+H)^+$, calcd $C_{21}H_{19}Cl_1F_3N_6O_1$, 463.1]; LC/MS retention time (Method A): $t_R$=3.04 min.

Example 179

2-((Cyclopropylmethyl)amino)-N-(4-(4,4-difluoropiperidin-1-yl)-6-fluoropyridin-3-yl)pyrimidine-4-carboxamide

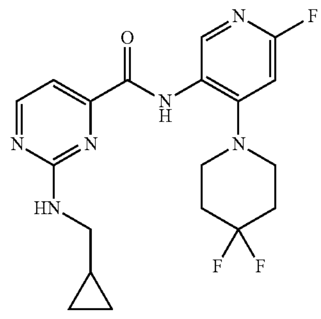 [SMILES: O=C(Nc1cnc(F)cc1N1CCC(F)(F)CC1)c1ccnc(NCC2CC2)n1]

Prepared by Method A (heated at 150° C. for 1 h), obtained 2.5 mg, 40% yield: $^1$H NMR (500 MHz, DMSO-d6) δ 10.01 (s, 1H), 8.72 (s, 1H), 8.61 (d, J=4.6 Hz, 1H), 7.74 (s, 1H), 7.22 (d, J=4.8 Hz, 1H), 7.02 (s, 1H), 3.30 (t, J=6.3 Hz, 2H), 3.20 (t, J=5.7 Hz, 4H), 2.18 (s, 4H), 1.18-1.04 (m, 1H), 0.45 (dt, J=8.9, 3.0 Hz, 2H), 0.33-0.19 (m, 2H); LC/MS (ESI) m/e 407.3 [(M+H)$^+$, calcd $C_{19}H_{22}F_3N_6O_1$, 407.2]; LC/MS retention time (Method A): $t_R$=2.80 min.

Example 180

N-(4-(4,4-Difluoropiperidin-1-yl)-6-fluoropyridin-3-yl)-2-((4-fluorophenyl)amino)pyrimidine-4-carboxamide

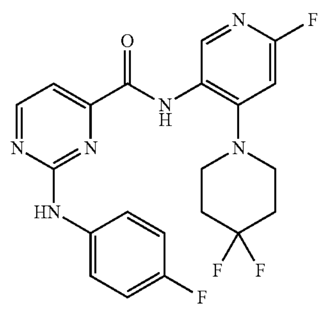 [SMILES: O=C(Nc1cnc(F)cc1N1CCC(F)(F)CC1)c1ccnc(Nc2ccc(F)cc2)n1]

Prepared by Method A (heated at 140° C. for h), obtained 3.8 mg, 52% yield: $^1$H NMR (500 MHz, DMSO-d6) δ 10.00 (s, 1H), 9.77 (s, 1H), 8.80 (d, J=4.8 Hz, 1H), 8.72 (s, 1H), 7.76-7.64 (m, 2H), 7.47 (d, J=4.8 Hz, 1H), 7.27-7.14 (m, 2H), 6.98 (s, 1H), 3.13 (t, J=5.6 Hz, 4H), 1.93 (s, 4H); LC/MS (ESI) m/e 447.2 [(M+H)$^+$, calcd $C_{21}H_{19}F_4N_6O_1$, 447.1]; LC/MS retention time (Method A): $t_R$=2.88 min.

Example 181

2-((4-(Difluoromethoxy)phenyl)amino)-N-(4-(4,4-difluoropiperidin-1-yl)-6-fluoropyridin-3-yl)pyrimidine-4-carboxamide

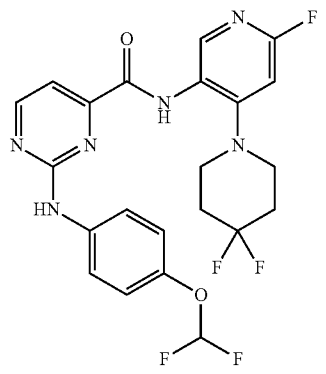 [SMILES: O=C(Nc1cnc(F)cc1N1CCC(F)(F)CC1)c1ccnc(Nc2ccc(OC(F)F)cc2)n1]

Prepared by Method A (heated at 140° C. for 4 h), obtained 2.7 mg, 42% yield: $^1$H NMR (500 MHz, DMSO-d6) δ 10.04 (s, 1H), 9.81 (s, 1H), 8.82 (d, J=4.8 Hz, 1H), 8.70 (s, 1H), 7.77-7.70 (m, 2H), 7.48 (d, J=4.8 Hz, 1H), 7.24-7.16 (m, 2H), 6.98 (s, 1H), 3.14 (t, J=5.6 Hz, 4H), 1.95 (s, 4H); LC/MS (ESI) m/e 495.2 [(M+H)$^+$, calcd $C_{22}H_{20}F_5N_6O_2$, 495.1]; LC/MS retention time (Method A): $t_R$=2.92 min.

Example 182

2-((4-Chlorophenyl)amino)-N-(4-(4,4-difluoropiperidin-1-yl)-6-methylpyridin-3-yl)pyrimidine-4-carboxamide

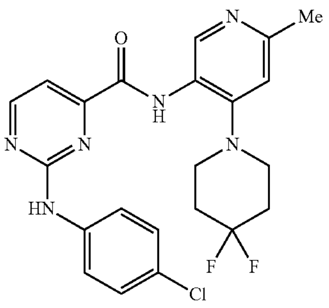 [SMILES: Cc1cc(N2CCC(F)(F)CC2)c(NC(=O)c2ccnc(Nc3ccc(Cl)cc3)n2)cn1]

Prepared by Method A (heated at 140° C. overnight), obtained 2.1 mg, 27% yield: $^1$H NMR (500 MHz, DMSO-d6) δ 10.11 (s, 1H), 9.82 (s, 1H), 9.06 (s, 1H), 8.83 (d, J=5.0 Hz, 1H), 7.76-7.68 (m, 2H), 7.52 (d, J=4.8 Hz, 1H), 7.45-7.37 (m, 2H), 7.10 (s, 1H), 3.04 (t, J=5.6 Hz, 4H), 2.45 (s, 3H), 2.02-1.87 (m, 4H); LC/MS (ESI) m/e 459.2 [(M+H)$^+$, calcd $C_{22}H_{22}Cl_1F_2N_6O_1$, 459.1]; LC/MS retention time (Method A): $t_R$=2.89 min.

Example 183

N-(4-(4,4-Difluoropiperidin-1-yl)-6-fluoropyridin-3-yl)-2-((4-(trifluoromethyl)phenyl)amino)pyrimidine-4-carboxamide

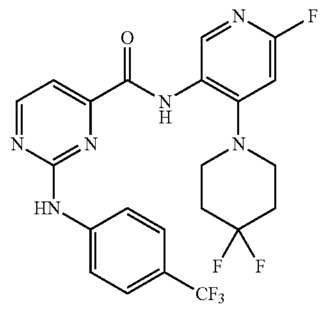 [SMILES: O=C(Nc1cnc(F)cc1N1CCC(F)(F)CC1)c1ccnc(Nc2ccc(C(F)(F)F)cc2)n1]

Prepared by Method A (heated at 140° C. for 4 h), obtained 0.3 mg, 5% yield: $^1$H NMR (500 MHz, Methanol-d4) δ 8.82 (d, J=4.9 Hz, 1H), 8.80 (s, 1H), 7.87 (s, 1H), 7.86 (d, J=2.4 Hz, 1H), 7.70-7.60 (m, 3H), 6.87 (s, 1H), 3.20-3.16 (m, 4H), 1.98 (tt, J=12.9, 5.4 Hz, 4H); LC/MS (ESI) m/e 497.1 [(M+H)$^+$, calcd $C_{22}H_{19}F_6N_6O_1$, 497.1]; LC/MS retention time (Method A): $t_R$=3.13 min.

Example 184

N-(4-(4,4-Difluoropiperidin-1-yl)-6-fluoropyridin-3-yl)-2-((tetrahydro-2H-pyran-4-yl)amino)pyrimidine-4-carboxamide

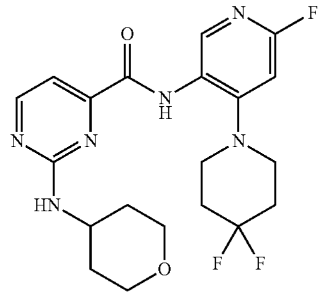 [SMILES: O=C(Nc1cnc(F)cc1N1CCC(F)(F)CC1)c1ccnc(NC2CCOCC2)n1]

Prepared by Method A (heated at 140° C. for 4 h), obtained 3.4 mg, 63% yield: $^1$H NMR (500 MHz, DMSO-d6) δ 9.93 (s, 1H), 8.61 (s, 1H), 8.60-8.40 (m, 1H), 7.64 (s, 1H), 7.22 (d, J=4.7 Hz, 1H), 6.97 (s, 1H), 4.16 (s, 1H), 3.95-3.85 (m, 2H), 3.43 (td, J=11.6, 2.2 Hz, 2H), 3.23 (s, 4H), 2.16 (s, 4H), 1.85 (d, J=12.8 Hz, 2H), 1.57 (qd, J=11.2, 4.3 Hz, 2H); LC/MS (ESI) m/e 437.1 [(M+H)$^+$, calcd $C_{20}H_{24}F_3N_6O_2$, 437.2]; LC/MS retention time (Method A): $t_R$=2.40 min.

Example 185

N-(5-(2-Fluorophenyl)pyridin-3-yl)-2-((3-(trifluoromethyl)phenyl)amino)pyrimidine-4-carboxamide

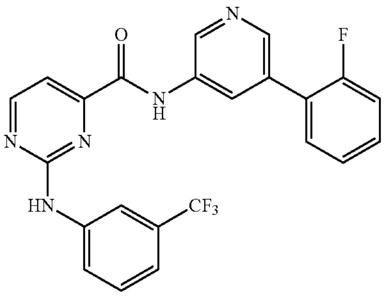 [SMILES: O=C(Nc1cncc(-c2ccccc2F)c1)c1ccnc(Nc2cccc(C(F)(F)F)c2)n1]

Prepared by Method A (heated at 140° C. overnight), obtained 2.7 mg, 16% yield: $^1$H NMR (500 MHz, DMSO-d6) δ 10.75 (s, 1H), 10.35 (s, 1H), 9.04 (d, J=2.4 Hz, 1H), 8.87 (d, J=4.9 Hz, 1H), 8.58 (t, J=1.8 Hz, 1H), 8.51 (q, J=1.9 Hz, 1H), 8.42 (d, J=2.3 Hz, 1H), 8.05-7.97 (m, 1H), 7.65 (td, J=7.8, 1.8 Hz, 1H), 7.59 (t, J=8.0 Hz, 1H), 7.57-7.49 (m, 1H), 7.48 (d, J=4.9 Hz, 1H), 7.45-7.34 (m, 3H); LC/MS (ESI) m/e 454.1 [(M+H)$^+$, calcd $C_{23}H_{16}F_4N_5O_1$, 454.1]; LC/MS retention time (Method A): $t_R$=3.25 min.

Example 186

2-((Cyclopropylmethyl)amino)-N-(5-(2-fluorophenyl)pyridin-3-yl)pyrimidine-4-carboxamide

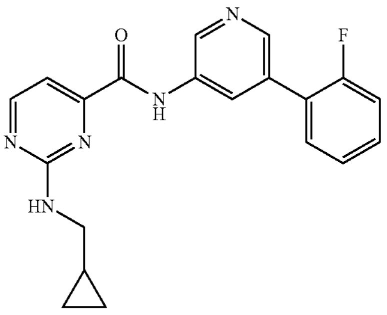 [SMILES: O=C(Nc1cncc(-c2ccccc2F)c1)c1ccnc(NCC2CC2)n1]

Prepared by Method A (heated at 140° C. overnight), obtained 6.5 mg, 74% yield: LC/MS (ESI) m/e 364.2 [(M+H)$^+$, calcd $C_{20}H_{19}F_1N_5O_1$, 364.2]; LC/MS retention time (Method A): $t_R$=2.71 min.

Example 187

N-(5-(2-Fluorophenyl)pyridin-3-yl)-2-((3-(trifluoromethoxy)phenyl)amino)pyrimidine-4-carboxamide

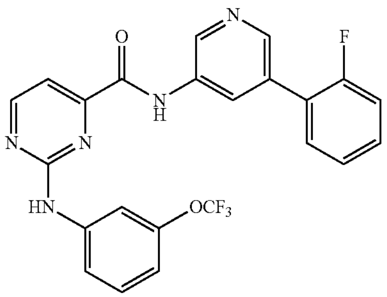 [SMILES: O=C(Nc1cncc(-c2ccccc2F)c1)c1ccnc(Nc2cccc(OC(F)(F)F)c2)n1]

Prepared by Method A (heated at 140° C. overnight), obtained 2.7 mg, 15% yield: $^1$H NMR (500 MHz, DMSO-d6) δ 10.74 (s, 1H), 10.30 (s, 1H), 9.04 (d, J=2.3 Hz, 1H), 8.86 (d, J=4.9 Hz, 1H), 8.58 (t, J=1.8 Hz, 1H), 8.50 (q, J=1.9 Hz, 1H), 8.09 (s, 1H), 7.77-7.72 (m, 1H), 7.65 (td, J=7.9, 1.9 Hz, 1H), 7.57-7.50 (m, 1H), 7.49-7.44 (m, 2H), 7.44-7.36 (m, 3H); LC/MS (ESI) m/e 470.4 $[(M+H)^+$, calcd $C_{23}H_{16}F_4N_5O_2$, 470.1]; LC/MS retention time (Method A): $t_R$=3.24 min.

Example 188

2-((Cyclobutylmethyl)amino)-N-(4-(2,2,2-trifluoroethoxy)pyrimidin-5-yl)pyrimidine-4-carboxamide

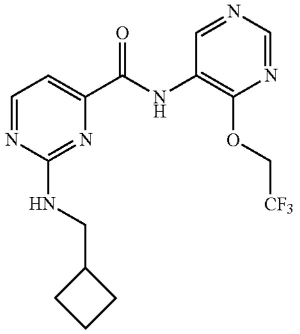 [SMILES: O=C(Nc1cncnc1OCC(F)(F)F)c1ccnc(NCC2CCC2)n1]

Prepared by Method A (heated at 100° C. for 4 h), obtained 5.0 mg, 43% yield: LC/MS (ESI) m/e 383.4 $[(M+H)^+$, calcd $C_{16}H_{18}F_3N_6O_2$, 383.1]; LC/MS retention time (Method A): $t_R$=2.92 min.

Example 189

2-(Neopentylamino)-N-(4-(2,2,2-trifluoroethoxy)pyrimidin-5-yl)pyrimidine-4-carboxamide

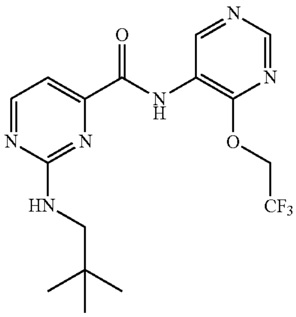 [SMILES: CC(C)(C)CNc1nccc(C(=O)Nc2cncnc2OCC(F)(F)F)n1]

Prepared by Method A (heated at 100° C. for 4 h), obtained 4.6 mg, 35% yield: LC/MS (ESI) m/e 385.5 $[(M+H)^+$, calcd $C_{16}H_{20}F_3N_6O_2$, 385.2]; LC/MS retention time (Method A): $t_R$=2.97 min.

Example 190

2-(((Tetrahydro-2H-pyran-4-yl)methyl)amino)-N-(4-(2,2,2-trifluoroethoxy)pyrimidin-5-yl)pyrimidine-4-carboxamide

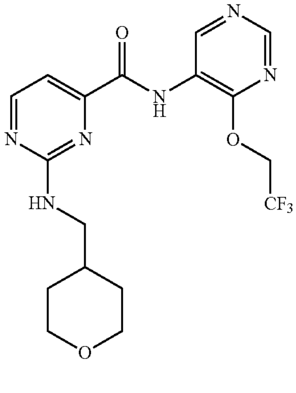 [SMILES: O=C(Nc1cncnc1OCC(F)(F)F)c1ccnc(NCC2CCOCC2)n1]

Prepared by Method A (heated at 100° C. for 2 h), obtained 6.1 mg, 45% yield: $^1$H NMR (500 MHz, DMSO-d6) δ 10.09 (s, 1H), 9.48 (s, 1H), 8.71 (s, 1H), 8.61 (d, J=4.7 Hz, 1H), 7.80 (s, 1H), 7.22 (d, J=4.7 Hz, 1H), 5.23 (q, J=8.8 Hz, 2H), 3.91-3.81 (m, 2H), 3.31-3.24 (m, 4H), 1.84 (s, 1H), 1.69-1.59 (m, 2H), 1.26 (d, J=13.4 Hz, 2H); LC/MS (ESI) m/e 413.4 $[(M+H)^+$, calcd $C_{17}H_{20}F_3N_6O_3$, 413.1]; LC/MS retention time (Method A): $t_R$=2.35 min.

Example 191

2-(((3-Methyloxetan-3-yl)methyl)amino)-N-(4-(2,2,2-trifluoroethoxy)pyrimidin-5-yl)pyrimidine-4-carboxamide

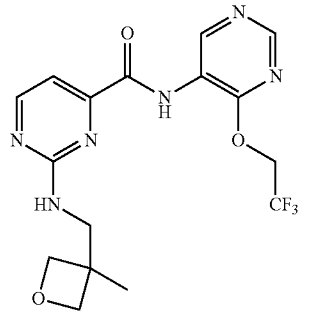 [SMILES: CC1(CNc2nccc(C(=O)Nc3cncnc3OCC(F)(F)F)n2)COC1]

Prepared by Method A (heated at 100° C. for 4 h), obtained 4.7 mg, 38% yield: LC/MS (ESI) m/e 399.2 $[(M+H)^+$, calcd $C_{16}H_{18}F_3N_6O_3$, 399.1]; LC/MS retention time (Method A): $t_R$=2.26 min.

Example 192

2-((Cyclopropylmethyl)amino)-N-(4-(2,2,2-trifluoroethoxy)pyrimidin-5-yl)pyrimidine-4-carboxamide

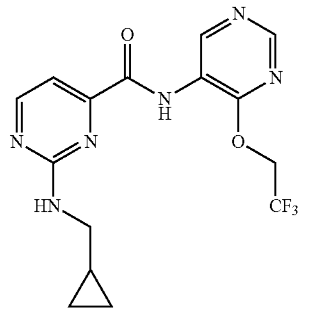 [SMILES: O=C(Nc1cncnc1OCC(F)(F)F)c1ccnc(NCC2CC2)n1]

Prepared by Method A (heated at 100° C. for 4 h), obtained 5.0 mg, 35% yield: LC/MS (ESI) m/e 369.4 $[(M+H)^+$, calcd $C_{15}H_{16}F_3N_6O_2$, 369.1]; LC/MS retention time (Method A): $t_R$=2.64 min.

Example 193

2-((4'-Chloro-[1,1'-biphenyl]-3-yl)amino)-N-(pyrimidin-5-yl)pyrimidine-4-carboxamide

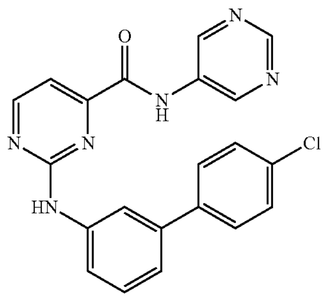 [SMILES: O=C(Nc1cncnc1)c1ccnc(Nc2cccc(-c3ccc(Cl)cc3)c2)n1]

Prepared by Method A (heated at 150° C. for 1 h), obtained 8.0 mg, 67% yield: $^1H$ NMR (500 MHz, DMSO) δ 10.89 (s, 1H), 10.10 (s, 1H), 9.23 (s, 2H), 9.02 (s, 1H), 8.83 (d, J=4.8 Hz, 1H), 8.33 (s, 1H), 7.73 (dd, J=17.1, 8.3 Hz, 3H), 7.48-7.40 (m, 4H), 7.32 (d, J=7.9 Hz, 1H); LC/MS (ESI) m/e 401.1 $[(M-H)^-$, calcd $C_{21}H_{14}Cl_1N_6O_1$, 401.1]; LC/MS retention time (Method A): $t_R$=2.97 min.

Example 194

2-([1,1'-Biphenyl]-3-ylamino)-N-(pyrimidin-5-yl)pyrimidine-4-carboxamide

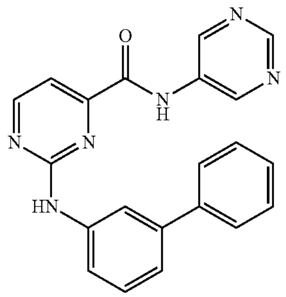 [SMILES: O=C(Nc1cncnc1)c1ccnc(Nc2cccc(-c3ccccc3)c2)n1]

Prepared by Method A (heated at 150° C. for 1 h), obtained 8.8 mg, 79% yield: $^1H$ NMR (500 MHz, DMSO) δ 10.90 (s, 1H), 10.09 (s, 1H), 9.24 (s, 2H), 9.02 (s, 1H), 8.82 (d, J=4.8 Hz, 1H), 8.34 (s, 1H), 7.73 (d, J=9.1 Hz, 1H), 7.69 (d, J=6.7 Hz, 2H), 7.44 (t, J=7.9 Hz, 1H), 7.41 (d, J=4.8 Hz, 1H), 7.40-7.30 (m, 4H); LC/MS (ESI) m/e 367.2 $[(M-H)^-$, calcd $C_{21}H_{15}N_6O_1$, 367.1]; LC/MS retention time (Method A): $t_R$=2.71 min.

Example 195

2-((6-Phenylpyridin-2-yl)amino)-N-(pyrimidin-5-yl)pyrimidine-4-carboxamide

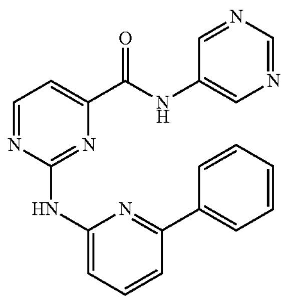 [SMILES: O=C(Nc1cncnc1)c1ccnc(Nc2cccc(-c3ccccc3)n2)n1]

Prepared by Method A (heated at 150° C. for 2 h), obtained 0.3 mg, 5% yield: $^1H$ NMR (400 MHz, Chloroform-d) δ 9.77 (s, 1H), 9.23 (s, 2H), 9.09 (s, 1H), 8.87 (d, J=4.8 Hz, 1H), 8.25 (d, J=8.2 Hz, 1H), 8.14 (s, 1H), 8.08-8.02 (m, 2H), 7.87 (t, J=8.0 Hz, 1H), 7.72 (d, J=4.8 Hz, 1H), 7.57-7.49 (m, 3H), 7.49-7.45 (m, 1H); LC/MS (ESI) m/e 370.1 $[(M+H)^+$, calcd $C_{20}H_{16}N_7O_1$, 370.1]; LC/MS retention time (Method A): $t_R$=2.65 min.

Example 196

2-((2'-Methyl-[1,1'-biphenyl]-3-yl)amino)-N-(pyrimidin-5-yl)pyrimidine-4-carboxamide

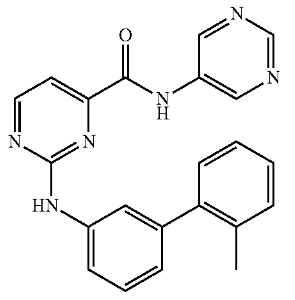 [SMILES: Cc1ccccc1-c1cccc(Nc2nccc(C(=O)Nc3cncnc3)n2)c1]

Prepared by Method A (heated at 150° C. for 1 h), obtained 4.5 mg, 41% yield: $^1$H NMR (500 MHz, DMSO) δ 10.80 (s, 1H), 10.07 (s, 1H), 9.19 (s, 2H), 9.00 (s, 1H), 8.80 (d, J=4.8 Hz, 1H), 7.90 (s, 1H), 7.78 (d, J=8.1 Hz, 1H), 7.41 (dd, J=14.2, 6.3 Hz, 2H), 7.27 (dd, J=15.8, 7.8 Hz, 3H), 7.21 (dd, J=20.1, 13.0 Hz, 1H), 7.00 (d, J=7.6 Hz, 1H), 2.27 (s, 3H); LC/MS (ESI) m/e 383.1 $[(M+H)^+$, calcd $C_{22}H_{19}N_6O_1$, 383.2]; LC/MS retention time (Method A): $t_R$=2.88 min.

Example 197

2-(((2-(2,4-Difluorophenyl)cyclopropyl)methyl)amino)-N-(pyrimidin-5-yl)pyrimidine-4-carboxamide

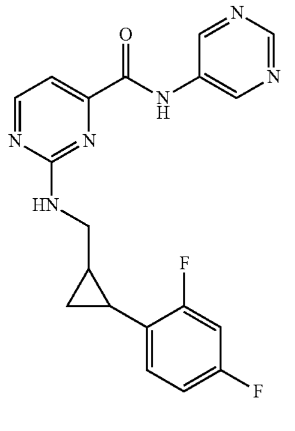 [SMILES: O=C(Nc1cncnc1)c1ccnc(NCC2CC2c2ccc(F)cc2F)n1]

Prepared by Method A (heated at 150° C. for 1 h), obtained 4.1 mg, 67% yield: $^1$H NMR (500 MHz, DMSO-d6) δ 10.69 (s, 1H), 9.21 (s, 2H), 8.99 (s, 1H), 8.59 (s, 1H), 7.80 (s, 1H), 7.23-7.07 (m, 2H), 6.98 (tt, J=7.7, 3.4 Hz, 1H), 6.85 (ddd, J=9.5, 6.0, 3.2 Hz, 1H), 3.73-3.43 (m, 2H), 2.11 (s, 1H), 1.54 (h, J=6.1 Hz, 1H), 1.09 (s, 1H), 1.02 (dt, J=8.6, 5.0 Hz, 1H); LC/MS (ESI) m/e 383.1 $[(M+H)^+$, calcd $C_{19}H_{17}F_2N_6O_1$, 383.1]; LC/MS retention time (Method A): $t_R$=2.51 min.

Example 198

2-(((2-(4-Fluorophenyl)cyclopropyl)methyl)amino)-N-(pyrimidin-5-yl)pyrimidine-4-carboxamide

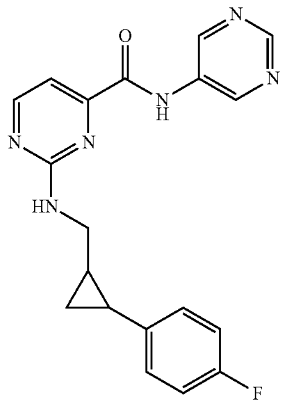 [SMILES: O=C(Nc1cncnc1)c1ccnc(NCC2CC2c2ccc(F)cc2)n1]

Prepared by Method A (heated at 150° C. for 1 h), obtained 4.4 mg, 73% yield: $^1$H NMR (500 MHz, DMSO-d6) δ 10.69 (s, 1H), 9.21 (s, 2H), 8.99 (s, 1H), 8.60 (s, 1H), 7.79 (s, 1H), 7.17 (d, J=4.8 Hz, 1H), 7.12-7.02 (m, 4H), 3.52 (d, J=60.4 Hz, 2H), 1.96 (dt, J=9.2, 4.9 Hz, 1H), 1.40 (q, J=6.5 Hz, 1H), 1.00 (s, 1H), 0.90 (dt, J=9.5, 5.0 Hz, 1H); LC/MS (ESI) m/e 365.1 $[(M+H)^+$, calcd $C_{19}H_{18}F_1N_6O_1$, 365.1]; LC/MS retention time (Method A): $t_R$=2.48 min.

Example 199

2-(((2-(3-Methoxyphenyl)cyclopropyl)methyl)amino)-N-(pyrimidin-5-yl)pyrimidine-4-carboxamide

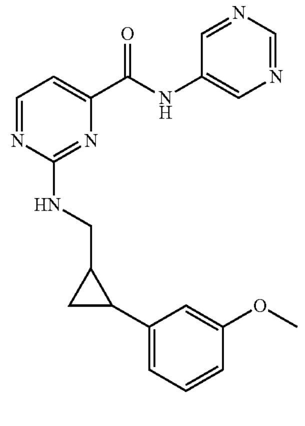 [SMILES: COc1cccc(C2CC2CNc2nccc(C(=O)Nc3cncnc3)n2)c1]

Prepared by Method A (heated at 150° C. for 1 h), obtained 3.4 mg, 63% yield: $^1$H NMR (500 MHz, DMSO-d6) δ 10.70 (s, 1H), 9.21 (s, 2H), 8.98 (s, 1H), 8.60 (s, 1H), 7.79 (s, 1H), 7.17 (d, J=4.8 Hz, 1H), 7.13 (t, J=7.9 Hz, 1H), 6.68 (dd, J=8.2, 2.5 Hz, 1H), 6.64-6.58 (m, 2H), 3.70 (s, 3H), 3.59 (s, 2H), 1.93 (dt, J=9.0, 4.9 Hz, 1H), 1.43 (s, 1H), 0.99 (q, J=5.9, 5.0 Hz, 1H), 0.93 (dt, J=9.5, 4.9 Hz, 1H); LC/MS (ESI) m/e 377.1 $[(M+H)^+$, calcd $C_{20}H_{21}N_6O_2$, 377.2]; LC/MS retention time (Method A): $t_R$=2.41 min.

Example 200

2-(((2-(3-Fluorophenyl)cyclopropyl)methyl)amino)-N-(pyrimidin-5-yl)pyrimidine-4-carboxamide

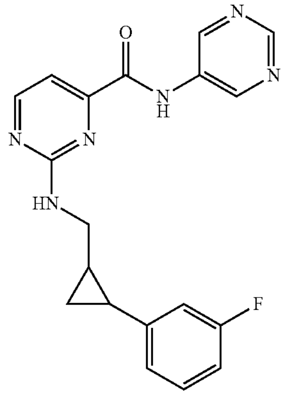 [SMILES: O=C(Nc1cncnc1)c1ccnc(NCC2CC2c2cccc(F)c2)n1]

Prepared by Method A (heated at 150° C. for 1 h), obtained 4.1 mg, 68% yield: $^1$H NMR (500 MHz, DMSO-d6) δ 10.70 (s, 1H), 9.21 (s, 2H), 8.99 (s, 1H), 8.60 (s, 1H), 7.80 (s, 1H), 7.26 (q, J=7.5 Hz, 1H), 7.18 (d, J=4.8 Hz, 1H), 6.96-6.90 (m, 2H), 6.88 (dt, J=10.7, 2.1 Hz, 1H), 3.77-3.42 (m, 2H), 1.99 (dt, J=9.2, 4.9 Hz, 1H), 1.46 (q, J=6.4 Hz, 1H), 1.05 (d, J=6.4 Hz, 1H), 0.98 (dt, J=9.8, 5.0 Hz, 1H); LC/MS (ESI) m/e 365.1 [(M+H)$^+$, calcd $C_{19}H_{18}F_1N_6O_1$, 365.1]; LC/MS retention time (Method A): $t_R$=2.49 min.

Example 201

2-(Phenylamino)-N-(pyrimidin-5-yl)pyrimidine-4-carboxamide

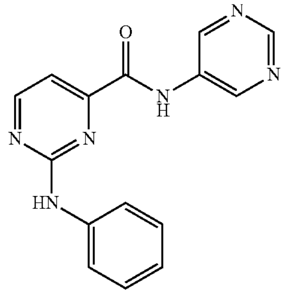 [SMILES: O=C(Nc1cncnc1)c1ccnc(Nc2ccccc2)n1]

Prepared by Method A (heated at 150° C. for 40 min), obtained 4.4 mg, 58% yield: $^1$H NMR (500 MHz, DMSO) δ 10.80 (s, 1H), 9.96 (s, 1H), 9.24 (s, 2H), 9.00 (s, 1H), 8.80 (d, J=4.8 Hz, 1H), 7.83 (d, J=8.0 Hz, 2H), 7.40 (d, J=4.8 Hz, 1H), 7.35 (t, J=7.9 Hz, 2H), 7.03 (t, J=7.3 Hz, 1H); LC/MS (ESI) m/e 292.9 [(M+H)$^+$, calcd $C_{15}H_{22}F_1N_6O_1$, 293.1]; LC/MS retention time (Method A): $t_R$=2.04 min.

Example 202

2-(((1S,2R)-2-Phenylcyclopropyl)amino)-N-(pyrimidin-5-yl)pyrimidine-4-carboxamide

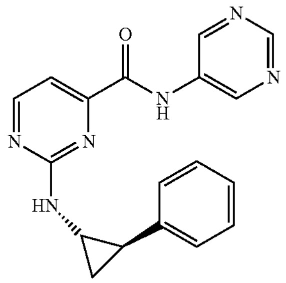

Prepared by Method A (heated at 150° C. for 2 h), obtained 1.8 mg, 31% yield: $^1$H NMR (500 MHz, DMSO-d6) δ 10.25 (s, 1H), 9.18 (s, 1H), 8.97 (s, 1H), 8.75 (s, 1H), 8.64 (d, J=4.8 Hz, 1H), 8.18 (s, 1H), 7.24 (m, 5H), 7.19-7.13 (m, 1H), 3.20 (d, J=18.6 Hz, 1H), 2.03 (ddd, J=9.4, 6.1, 3.2 Hz, 1H), 1.36 (dt, J=9.7, 5.1 Hz, 1H), 1.29 (q, J=6.4 Hz, 1H), 10.54-9.92 (m, 1H); LC/MS (ESI) m/e 333.1 [(M+H)$^+$, calcd $C_{18}H_{17}N_6O_1$, 333.1]; LC/MS retention time (Method A): $t_R$=2.23 min.

Example 203

2-((Cyclobutylmethyl)amino)-N-(4-morpholinopyrimidin-5-yl)pyrimidine-4-carboxamide

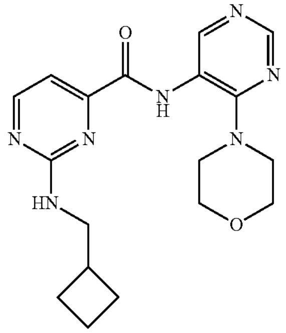 [SMILES: O=C(Nc1cncnc1N1CCOCC1)c1ccnc(NCC2CCC2)n1]

Prepared by Method A (heated at 100° C. for 4 h), obtained 3.1 mg, 29% yield: LC/MS (ESI) m/e 370.5 [(M+H)$^+$, calcd $C_{18}H_{24}N_7O_2$, 370.2]; LC/MS retention time (Method A): $t_R$=2.18 min.

Example 204

2-((Cyclobutylmethyl)amino)-N-(4-morpholinopyrimidin-5-yl)pyrimidine-4-carboxamide

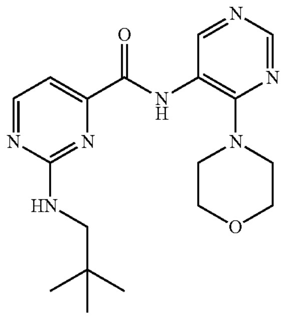 [SMILES: CC(C)(C)CNc1nccc(C(=O)Nc2cncnc2N2CCOCC2)n1]

Prepared by Method A (heated at 100° C. for 4 h), obtained 2.6 mg, 22% yield: LC/MS (ESI) m/e 372.2 $[(M+H)^+$, calcd $C_{18}H_{26}N_7O_2$, 372.2]; LC/MS retention time (Method A): $t_R$=2.28 min.

Example 205

2-((Cyclopropylmethyl)amino)-N-(4-morpholinopyrimidin-5-yl)pyrimidine-4-carboxamide

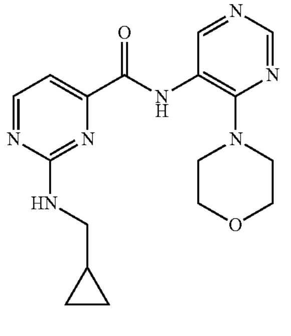 [SMILES: O=C(Nc1cncnc1N1CCOCC1)c1ccnc(NCC2CC2)n1]

Prepared by Method A (heated at 100° C. for 4 h), obtained 2.4 mg, 25% yield: LC/MS (ESI) m/e 356.4 $[(M+H)^+$, calcd $C_{17}H_{22}N_7O_2$, 356.2]; LC/MS retention time (Method A): $t_R$=1.93 min.

Example 206

N-(4-Morpholinopyrimidin-5-yl)-2-(((tetrahydro-2H-pyran-4-yl)methyl)amino)pyrimidine-4-carboxamide

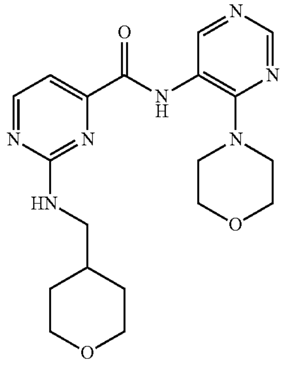 [SMILES: O=C(Nc1cncnc1N1CCOCC1)c1ccnc(NCC2CCOCC2)n1]

Prepared by Method A (heated at 100° C. for 40 min), obtained 3.8 mg, 44% yield: LC/MS (ESI) m/e 400.1 $[(M+H)^+$, calcd $C_{19}H_{26}N_7O_3$, 400.2]; LC/MS retention time (Method A): $t_R$=1.67 min.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

I

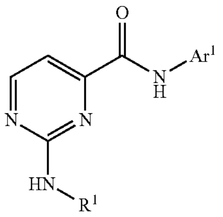

where:

$R^1$ is hydrogen, alkyl, (cycloalkyl)alkyl, alkoxyalkyl, $(Ar^2)$alkyl, $((Ar^2)$cycloalkyl)alkyl, cycloalkyl, (alkyl) cycloalkyl, $Ar^2$, or $Ar^3$;

or $R^1$ is (adamantyl)alkyl, (oxetanyl)alkyl, (tetrahydropyranyl)alkyl, (benzodioxolanyl)alkyl, oxetanyl, (alkyl) piperidinyl, (pentaalkyl)piperidinyl, alkoxytetrahydrofuranyl, tetrahydropyranyl, dialkyltetrahydropyranyl, (dihalophenyl)pyrazolyl, acetamidopyridinyl, (dialkylamino)alkoxypyridinyl, pyridazinyl, (imidizolyl)phenyl, tetrahydroisoquinolinyl, isoquinolinyl, quinolinyl, or naphthyl;

$R^2$ is $N(R^3)(R^4)$, dioxolanyl, (alkyl)dioxolanyl, or tetrahydropyranyl;

$R^3$ is hydrogen, alkyl, (cycloalkyl)alkyl, cycloalkyl, or is $Ar^2$ is phenyl substituted with 0-3 substituents selected from the group consisting of halo, alkyl, haloalkyl, alkoxy, haloalkoxy;

$R^4$ is hydrogen or alkyl;

or $N(R^3)(R^4)$ taken together is azetdinyl, pyrrolidinyl, piperidinyl, piperazinyl, or morpholinyl, and is substituted with 0-4 substituents selected from alkyl and halo;

$Ar^1$ is 3-pyridinyl, 3-pyridazinyl, 4-pyridazinyl, 5-pyrimidinyl, or 2-pyrazinyl, and is substituted with 0-3 substituents selected from the group consisting of cyano, halo, alkyl, haloalkyl, $(R^2)$alkyl, alkoxy, haloalkoxy, $R^2$, and $Ar^2$;

$Ar^2$ is phenyl or pyridinyl and is substituted with 0-3 substituents selected from the group consisting of cyano, halo, alkyl, haloalkyl, alkoxy, haloalkoxy, alkylsulfinyl, alkylsulfonyl, and phenyl that is in turn substituted with 0-3 substituents selected from the group consisting of halo, alkyl, haloalkyl, and alkoxy; and $Ar^3$ is pyrazolyl, isothiazolyl, imidazolyl, thiadiazolyl, or triazolyl, and is substituted with 0-3 substituents selected from the group consisting of cyano, halo, alkyl, cycloalkyl, haloalkyl, alkoxy, and haloalkoxy;

or a pharmaceutically acceptable salt thereof.

2. A compound of claim 1 where $R^1$ is $Ar^2$.

3. A compound of claim 1 where $Ar^1$ is 3-pyridinyl or 5-pyrimidinyl and is substituted with 0-3 substituents selected from the group consisting of cyano, halo, alkyl, haloalkyl, ($R^2$)alkyl, alkoxy, haloalkoxy, $R^2$, and $Ar^2$.

4. A compound of claim 1 where $Ar^1$ is 3-pyridinyl substituted with 0-3 substituents selected from the group consisting of cyano, halo, alkyl, haloalkyl, ($R^2$)alkyl, alkoxy, haloalkoxy, $R^2$, and $Ar^2$.

5. A compound of claim 1 where $Ar^1$ is 5-pyrimidinyl substituted with 0-3 substituents selected from the group consisting of cyano, halo, alkyl, haloalkyl, ($R^2$)alkyl, alkoxy, haloalkoxy, $R^2$, and $Ar^2$.

6. A compound of claim 1 where $Ar^2$ is phenyl substituted with 0-3 substituents selected from the group consisting of cyano, halo, alkyl, haloalkyl, alkoxy, haloalkoxy, alkylsulfinyl, and alkylsulfonyl.

7. A pharmaceutical composition comprising a compound of claim 1 or a pharmaceutically acceptable salt thereof and a pharmaceutically acceptable carrier.

8. A method for the treatment of a disease, disorder, or condition selected from the group consisting of psychiatric disorders and metabolic disorders which comprises administering to a patient a therapeutically affective amount of a compound of claim 1.

9. A method for the treatment of a condition selected from the group consisting of Alzheimer's disease, frontotemporal dementia, progressive supranuclear palsy, argyophilic grain disease, corticobasal degeneration, Pick's disease, Parkinson's disease, amyotrophic lateral sclerosis, stroke, Huntington's disease, peripheral neuropathy, traumatic brain injury, spinal cord trauma, and vascular dementia, which comprises administering to a patient a therapeutically affective amount of a compound of claim 1.

10. The method of claim 9 directed to the treatment of Alzheimer's disease.

* * * * *